(12) United States Patent
Alphey

(10) Patent No.: US 9,487,801 B2
(45) Date of Patent: Nov. 8, 2016

(54) BIOCONTROL

(71) Applicant: Oxitec Limited, Abingdon, Oxfordshire (GB)

(72) Inventor: Luke Alphey, Abingdon (GB)

(73) Assignee: OXITEC LIMITED, Abingdon (GB)

(*) Notice: Subject to any disclaimer, the term of this patent is extended or adjusted under 35 U.S.C. 154(b) by 0 days.

(21) Appl. No.: 14/383,515

(22) PCT Filed: Mar. 5, 2013

(86) PCT No.: PCT/EP2013/054417
§ 371 (c)(1),
(2) Date: Sep. 5, 2014

(87) PCT Pub. No.: WO2013/131920
PCT Pub. Date: Sep. 12, 2013

(65) Prior Publication Data
US 2015/0143552 A1 May 21, 2015

(30) Foreign Application Priority Data
Mar. 5, 2012 (GB) .................... 1203850.1

(51) Int. Cl.
C12N 15/00 (2006.01)
C12N 15/85 (2006.01)
A01K 67/033 (2006.01)
C12N 9/22 (2006.01)

(52) U.S. Cl.
CPC ....... *C12N 15/8509* (2013.01); *A01K 67/0339* (2013.01); *C12N 9/22* (2013.01); *A01K 2217/052* (2013.01); *A01K 2217/203* (2013.01); *A01K 2217/206* (2013.01); *A01K 2227/706* (2013.01); *A01K 2267/02* (2013.01); *A01K 2267/03* (2013.01); *A01K 2267/0393* (2013.01); *C07K 2319/81* (2013.01); *C12N 2800/90* (2013.01); *C12N 2840/002* (2013.01)

(58) Field of Classification Search
None
See application file for complete search history.

(56) References Cited

U.S. PATENT DOCUMENTS

| 5,254,801 | A | 10/1993 | Dotson et al. |
|---|---|---|---|
| 5,278,057 | A | 1/1994 | Jorgensen |
| 5,670,353 | A | 9/1997 | Ahlquist et al. |
| 5,674,747 | A | 10/1997 | Hammock et al. |
| 5,773,697 | A | 6/1998 | Tomes et al. |
| 5,851,796 | A | 12/1998 | Schatz |
| 5,977,441 | A | 11/1999 | Oliver et al. |
| 6,200,800 | B1 | 3/2001 | Choulika et al. |
| 6,235,278 | B1 * | 5/2001 | Miller et al. ............ 424/93.2 |
| 6,338,040 | B1 | 1/2002 | Buman et al. |
| 6,962,810 | B2 | 11/2005 | Fraser et al. |
| 7,998,475 | B2 | 8/2011 | Alphey |
| 8,124,404 | B2 | 2/2012 | Alphey |
| 9,121,036 | B2 | 9/2015 | Alphey |
| 9,125,388 | B2 | 9/2015 | Alphey |
| 9,133,477 | B2 | 9/2015 | Alphey |
| 2003/0150007 | A1 | 8/2003 | Savakis et al. |
| 2003/0213005 | A1 | 11/2003 | Alphey et al. |
| 2004/0082032 | A1 | 4/2004 | Bovi et al. |
| 2005/0221430 | A1 | 10/2005 | Prentice |
| 2006/0212949 | A1 | 9/2006 | Alphey |
| 2006/0242717 | A1 | 10/2006 | Alphey |
| 2006/0275276 | A1 | 12/2006 | Alphey |
| 2007/0056051 | A1 | 3/2007 | Alphey |
| 2008/0115233 | A1 | 5/2008 | Alphey |
| 2009/0170793 | A1 | 7/2009 | Gaur |
| 2009/0183269 | A1 | 7/2009 | Alphey |
| 2013/0298266 | A1 | 11/2013 | Alphey et al. |

FOREIGN PATENT DOCUMENTS

| EP | 0 636 310 | 2/1995 |
|---|---|---|
| EP | 0 955 364 | 11/1999 |
| GB | 2355459 | 4/2001 |
| GB | 2404382 | 2/2005 |
| GB | 2 443 186 | 4/2008 |
| JP | 2008067678 | 3/2008 |
| WO | WO-90/08830 | 8/1990 |
| WO | WO-94/03619 | 2/1994 |
| WO | WO-96/04393 | 2/1996 |
| WO | WO-96/24605 | 8/1996 |

(Continued)

OTHER PUBLICATIONS

Handler et al. Genetics 2002;116:137-49.*

(Continued)

*Primary Examiner* — Janice Li
(74) *Attorney, Agent, or Firm* — Morrison & Foerster LLP

(57) ABSTRACT

Provided is an arthropod male germline gene expression system suitable for conditional expression of an effector gene in an Arthropod male germline. The system comprises a first expression unit comprising an effector gene and a promoter therefor operably linked thereto; and a second expression unit. Said second unit comprises a coding sequence for a transcription factor and an upstream regulatory element operably linked thereto, the transcription factor being capable of acting upon the promoter in the first expression unit to drive expression of the effector gene. The upstream regulatory element includes a promoter for the transcription factor; and a 5' UTR adjacent a start site for the transcription factor coding sequence. The upstream regulatory element driving sufficient expression of the transcription factor such that the transcription factor protein in turn drives transcription of the effector gene before meiosis. Also provided are uses of the system for instance in methods of biocontrol and quality control.

27 Claims, 14 Drawing Sheets

(56) References Cited

FOREIGN PATENT DOCUMENTS

| WO | WO-97/30162 | 8/1997 |
|---|---|---|
| WO | WO-98/08960 | 3/1998 |
| WO | WO-99/10488 | 3/1999 |
| WO | WO-00/73510 | 12/2000 |
| WO | WO-0139599 | 6/2001 |
| WO | WO-0159088 | 8/2001 |
| WO | WO-01/91802 | 12/2001 |
| WO | WO-02/46444 | 6/2002 |
| WO | WO-02/101061 | 12/2002 |
| WO | WO-2004/044150 | 5/2004 |
| WO | WO-2004/098278 | 11/2004 |
| WO | WO-2004/108933 | 12/2004 |
| WO | WO-2005/003364 | 1/2005 |
| WO | WO-2005012534 | 2/2005 |
| WO | WO-2007091099 | 8/2007 |
| WO | WO-2008134068 | 11/2008 |
| WO | WO-2009016627 | 2/2009 |
| WO | WO-2009115569 | 9/2009 |
| WO | WO-2009/157771 | 12/2009 |

OTHER PUBLICATIONS

Beumer et al. Genetics 2006;172:2391-2403.*
Catteruccia et al. Nat Biotech 2005;23:1414-7.*
Webster et al. Cell 1988;52:169-178.*
Han et al. PNAS 2011;108:9673-8.*
Perezgasga et al. Development 2004;131:1691-1702.*
Vivinus et al. Eur J Biochem 2001;268:1908-17.*
Adelman et al., "Formation and loss of large, unstable tandem arrays of the piggyBac transposable element in the yellow fever mosquito, *Aedes aegypti*," Transgenic Res (2004)13(5):411-425.
Alphey et al. (May 2002) "Dominant Lethality and Insect Population Control," Mol. Biochem. Parasitol. 121(2):173-178.
Alphey et al., "Managing Insecticide Resistance by Mass Release of Engineered Insects," J. Econ. Entomol. (2007) 100(5):1642-1649.
Alphey et al., "Modeling resistance to genetic control of insects," Journal of Theoretical Biology (2011) 270:42-55.
Arribas et al., "The ubiquitin genes in *D. melanogaster*: transcription and polymorphism," Biochimica et Biophysica Acta (1986) 868:119-127.
Atkinson et al., "Hermes and Other hAT Elements as Gene Vectors in Insects," in: Insect Transgenesis: Methods and Applications, Hadler et al. (eds.), Boca Raton CRC Press (2000) pp. 219-235.
Atkinson et al., "Genetic transformation systems in insects," Annu Rev Entomol (2001) 46:317-346.
Bello et al., "Spatial and temporal targeting of gene expression in *Drosophila* by means of a tetracycline-dependent transactivator system," Development (1998) 125(12):2193-2202.
Beullens et al., "The isolation of novel inhibitory polypeptides of protein phosphatase 1 from bovine thymus nuclei," J Biol Chem (1992) 267(23):16538-16544.
Beullens et al., "Inactivation of nuclear inhibitory polypeptides of protein phosphatase-1 (NIPP-1) by protein kinase A," J Biol Chem (1993) 268(18):13172-13177.
Beullens et al., "Molecular determinants of nuclear protein phosphatase-1 regulation by NIPP-1," J Biol Chem (1999) 274(20):14053-14061.
Bieschke et al. (Jun. 1998) "Doxycycline-Induced Transgene Expression During *Drosophila* Development and Aging," Mol. Gen Genet. 258(6):571-579.
Blitvich et al., "Developmental- and tissue-specific expression of an inhibitor of apoptosis protein 1 homologue from *Aedes triseriatus* mosquitos," Insect Molecular Biology (2002) 11(5):431-442.
Boudrez et al., "Identification of MYPT1 and NIPP1 as subunits of protein phosphatase 1 in rat liver cytosol," FEBS Letters 455 (1999) 175-178.
Burcin et al., "A regulatory system for target gene expression," Frontiers in Biosc. (1998) 3:c1-7.

Cabrera et al., "Expression Pattern of Gal4 Enhancer Trap Insertions into the bric a brac Locus Generated by P Element Replacement," Genesis (2002) 34:62-65.
Carriere and Tabashnik, "Reversing Insect Adaptation to Transgenic Insecticidal Plants," Proc. R. Soc. Lond. B. (2001) 268:1475-1480.
Chen et al., "Apoptotic Activity of REAPER is Distinct from Signaling by the Tumor Necrosis Factor Receptor 1 Death Domain," The Journal of Biological Chemistry (1996) 271(42):25735-25737.
Chen et al. (Oct. 2000) "The Use of Modified Tetracycline Regulatory Expression System with Reduced Basal Level to Develop and in Vivo Biopesticide Expression System," Food Sci Agricult. Chem. 2(4):220-225.
Davis et al., "Engineered Underdominance Allows Efficient and Economical Introgression of Traits into Pest Populations," J. Theor. Biol. (2001) 212(1):83-98.
Deng et al., "A targeted gene silencing technique shows that *Drosophila* myosin VI is required for egg chamber and imaginal disc morphogenesis," J Cell Science (1999) 112:3677-3690.
Devault et al., "Biotechnology and new integrated pest management approaches," Nature Biotechnology (1996) 14:46-49.
Egloff et al., "Structural basis for the recognition of regulatory subunits by the catalytic subunit of protein phosphatase 1," EMBO J (1997) 16(8):1876-1887.
Elick et al., "Analysis of the Cis-Acting DNA Elements Required for piggyback Transposable Element Excision," Mol. Gen. Genet. (1997) 255:605-610.
Ernst, U. (1991) "Regulation of Sexual Differentiation in *Drosophila*: Alternative Splicing of the Transformer Primary Transcript Requires Masking of the Non-Specific Acceptor Site in Females," Inaugural Dissertation, Aus Frankfurt I Main, BRD.
Fryxell et al., "Autocidal biological control: a general strategy for insect control based on genetic transformation with a highly conserved gene," J Econ Entomol (1995) 88(5):1221-1232.
Funaguma et al., "The Bmdsx transgene including trimmed introns is sex-specifically spliced in tissues of the silkworm, *Bombyx mori*," Journal of Insect Science (online) (2005) 5(17):1-6.
Fussenegger et al., "Autoregulated multicistronic expression vectors provide one-step cloning of regulated product gene expression in mammalian cells," Biotechnol. Prog. (1997) 13:733-740.
Fussenegger et al. (1998) "Regulated Multicistronic Expression Technology for Mammalian Metabolic Engineering," Cytotechnology 28:111-126.
Fux et al. (2003) "Novel Macrolide-Adjustable Bidirectional Expression Modules for Coordinated Expression of Two Different Transgenes in Mice," J Gene Medicine 5:1067-1079.
"Gene Linkage and Genetic Mapping," in Essential Genetics, Daniel L. Hartl and Elizabeth W. Jones (eds.), (1999) Jones and Bartlett Publishers, Sudbury, Massachussetts, pp. 126-127.
Gloor et al., "Targeted Gene Replacement in *Drosophila* Via P Element-Induced Gap Repair," Science (1991) 253:1110-1117.
Golovnin et al., "The su(Hw) insulator can disrupt enhancer-promoter interactions when located more than 20 kilobases away from the *Drosophila* achaete-scute complex," Mol Cell Biol (1999) 19(5):3443-3456.
Gonzy-Treboul et al., "Enhancer-Trap Targeting at the Broad-Complex Locus of *Drosophila melanogaster*," Genes Dev. (1995) 9:1137-1148.
Gossen et al., Tetracycline in Biology, Chemistry and Medicine (2001) pp. 139-157.
Handler et al., "A Current Prospective on Insect Gene Transformation," Insect Biochem. Mol. Biol. (2001) 31(2):111-128.
Handler et al., "Use of piggyback Transposon for Germ-Line Transformation of Insects," Insect Biochem. Mol. Biol. (2002) 32:1211-1220.
Guo et al., "Species-specific signals for the splicing of a short *Drosophila* intron in vitro," Mol Cell Biol (1993) 13(2):1104-1118.
Harris et al., "Field performance of engineered male mosquitoes," Nature Biotechnology (2011) 29(11):1034-1039.
Heinrich et al. (Jul. 18, 2000) "A Repressible Female-Specific Lethal Genetic System for Making Transgenic Insect Strains Suitable for a Sterile-Release Program," Proc. Nat. Acad. Sci. USA 97:8229-8232.

(56) References Cited

OTHER PUBLICATIONS

Heslip et al., "Targeted Transposition at the vestigial Locus of *Drosophila melanogaster*," Genetics (1994) 138:1127-1135.
Hofmann et al. (1996) "Rapid Retroviral Delivery of Tetracycline-Inducible Genes in a Single Autoregulatory Cassette," Proc. Nat. Acad. Sci. USA 93:5185-5190.
Hondred et al., "Use of Ubiquitin Fusions to Augment Protein Expression in Transgenic Plants," Plant Physiology (1999) 119:713-723.
Horn et al., "Highly sensitive, fluorescent transformation marker for *Drosophila* transgenesis," Dev. Genes Evol. (2000) 210:623-629.
Horn et al., "piggyBac-Based Insertional Mutagenesis and Enhancer Detection as a Tool for Functional Insect Genomics," Genetics (2003) 163:647-661.
Horn et al., "Fluorescent transformation markers for insect transgenesis," Insect Biochemistry and Molecular Biology (2002) 32:1221-1235.
Imai, "Control of insecticide resistance in a filed population of houseflies, *Musca domestica*, by releasing susceptible flies," Res. Popul. Ecol. (1987) 29:129-146.
Inoue et al., "Binding of the *Drosophila* Sex-lethal gene product to the alternative splice site of transformer primary transcript," Nature (1990) 344:461-463.
Jagiello et al., "NIPP-1, a nuclear inhibitory subunit of protein phosphatase-1, has RNA-binding properties," J Biol Chem (1997) 272(35):22067-22071.
Jin et al., "Mapping of the RNA-binding and endoribonuclease domains of NIPP1, a nuclear targeting subunit of protein phosphatase 1," Biochem J (1999) 342:13-19.
Jin et al., "Engineered female-specific lethality for control of pest lepidoptera," ACS Synthetic Biology, ACS (2013) 1(3):160-66.
Johnson-Schlitz et al., "P-element-induced interallelic gene conversion of insertions and deletions in *Drosophila melanogaster*," Molecular and Cellular Biology (1993) 13(11):7006-7018.
Krafsur, "Bionomics of the face fly, *Musca autumnalis*," Annu Rev Entomol (1997) 42:503-523 (Abstract).
Lankenau et al., "Comparison of Targeted-Gene Replacement Frequencies in *Drosophila melanogaster* at the forked and white Loci," Molecular and Cellular Biology (1996) 16(7):3535-44.
Loukeris et al., "Introduction of the transposable element Minos into the germ line of *Drosophila melanogaster*," PNAS (1995) 92:9485-9489.
Louis et al. (Nov. 2003) "A Theoretical Model for the Regulation of Sex-Lethal, a Gene That Controls Sex Determination and Dosage Compensation in *Drosophila melanogaster*," Genetics 165:1355-1384.
Munoz, et al., "The AeAct-4 gene is expressed in the developing flight muscles of female *Aedes aegypti*", Insect Molecular Biology, vol. 13, No. 5, Oct. 2004, pp. 563-568.
Namciu et al., "Human matrix attachment regions insulate transgene expression from chromosomal position effects in *Drosophila melanogaster*," Mol Cell Biol (1998) 18(4):2382-2391.
Nitasaka et al., "Repressor of P elements in *Drosophila melanogaster*: Cytotype determination by a defective P element carrying only open reading frames 0 through 2," Proc Natl Acad Sci USA (1987) 84(21):7605-7608.
O'Brochta et al., "Gene vector and transposable element behavior in mosquitos," J Exp Biol (2003) 206(Pt 21):3823-3834.
Oxitec Nov. 2011 Newsletter, http://www.oxitec.com/our-news/newsletters/november-2011-newsletter/, downloaded Dec. 13, 2011, 6 pages.
Pane et al., Development (2002) 129:3715-3725.
Parker et al., "Functional interaction between nuclear inhibitor of protein phosphatase type 1 (NIPP1) and protein phosphatase type 1 (PP1) in *Drosophila*: consequences of over-expression of NIPP1 in flies and suppression by co-expression of PP1," Biochem J (2002) 368:789-797.
PiggyBac website, http://piggybac.bio.nd.edu/, visited Mar. 21, 2006.
Robinson, Mutation Research (2002) 511:113-132.

Ronaldson et al., "Two independent cis-acting elements regulate the sex- and tissue-specific expression of yp3 in *Drosophila melanogaster*," Genet Res. (1995) 66(1):9-17.
Russ et al., "Self-Deleting Retrovirus Vectors for Gene Therapy," Journal of Virology (1996) 70(8):4927-4932.
Saccone et al. (2000) "Sex Determination in Medfly: A Molecular Approach," In: Area-Wide Control of Fruit Flies and Other Pest Insects, Tan, K.H. ed., Penerbit USM, Penag, pp. 491-496.
Saccone et al., "Sex determination in flies, fruit flies and butterflies," Genetica (2002) 116:15-23.
Scali, et al., "Identification of sex-specific transcripts of the *Anopheles gambiae* doublesex gene", Journal of Experimental Biology, vol. 208, No. 19, Oct. 2005, pp. 3701-3709.
Schwechheimer et al. (2000) "Transactivation of a Target Gene Through Feedforward Loop Activation in Plants," Funct Integr Genomics 1 :35-43.
Sepp et al., "Conversion of lacZ Enhancer Trap Lines to GAL4 Lines Using Targeted Transposition in *Drosophila melanogaster*," Genetics (1999) 151:1093-1101.
Shelton et al., "Field tests on managing resistance to Bt-engineered plants," Nature Biotechnology (2000) 18:339-342.
Shockett et al. (Jul. 1995) "A Modified Tetracycline-Regulated System Provides Autoregulatory, Inducible Gene Expression in Cultured Cells and Transgenic Mice," Proc. Nat. Acad. Sci. USA 92:6522-6526.
Simmons et al., "Field Performance of a Genetically Engineered Strain of Pink Bollworm," PLoS ONE (2011) 6(9):1-11.
Sondergaard et al., "Nutritional response in a *Drosophila* yolk protein gene promoter," Mol Gen Genet (1995) 248(1):25-32.
Spradling et al., "Transposition of cloned P elements into *Drosophila* germ line chromosomes," Science (1982) 218(4570):341-347.
Stadtfeld et al., "Without a trace? PiggyBac-ing toward pluripotency," Nat Methods (2009) 6(5):329-330.
Stebbins et al. (2001) "Tetracycline-Inducible Systems for *Drosophila*," Proc. Nat. Acad. Sci. USA. 98:10775-10780.
Stebbins et al. (2001) "Adaptable Doxycycline-Regulated Gene Expression Systems for *Drosophila*," Gene 270: 103-111.
Steiner et al., "Homologous recombination as the main mechanism for DNA integration and cause of rearrangements in the filamentous ascomycete *Ashbya gossypii*." Genetics (1995) 140:973-987.
Van Eynde et al., "Molecular cloning of NIPP-1, a nuclear inhibitor of protein phosphatase-1, reveals homology with polypeptides involved in RNA processing," J Biol Chem (1995) 270(47):28068-28074.
Van Eynde et al., "Organization and alternate splice products of the gene encoding nuclear inhibitor of protein phosphatase-1 (NIPP-1)," Eur J Biochem (1999) 261(1):291-300.
Vulsteke et al., "Properties and phosphorylation sites of baculovirus-expressed nuclear inhibitor of protein phosphatase-1 (NIPP-1)," J Biol Chem (1997) 272(52):32972-32978.
Weinmann et al., "A chimeric transactivator allows tetracycline-responsive gene expression in whole plants," Plant J (1994) 5(4):559-569.
Wera et al., "Inhibition of translation by mRNA encoding NIPP-1, a nuclear inhibitor of protein phosphatase-1," Eur J Biochem (1997) 247(1):411-415.
Wharton et al., "CNS midline enhancers of the *Drosophila* slit and Toll genes," Mech Dev (1993) 40(3):141-154.
Wimmer, "Eco-friendly insect management," Nat Biotechnology (2005) 23(4):432-433.
Wise De Valdez et al., "Genetic elimination of dengue vector mosquitoes," Proc Natl Acad Sci USA (2011) 108(12):4772-4775.
Wobus et al., "A New Transposable Element in Chironomus thummi," Mol. Gen. Genet. (1990) 222:311-316.
Wool et al., "Genetically-Induced Susceptibility to Malathion in *Tribolium castaneum* Despite Selection for Resistance," Ent. Exp. & Appl. (1980) 183-190.
Woltjen et al., "piggyBac transposition reprograms fibroblasts to induced pluripotent stem cells," Nature (2009) 458(7239):766-770.
Wu et al. (Jun. 2000) "Expression of Highly Controllable Genes in Insect Cells Using a Modified Tetracycline-Regulated Gene Expression System," J. Biotechnol. 80(1 ):75-83.

(56) References Cited

OTHER PUBLICATIONS

Alignment of SEQ ID No:22 of D1 (WO 2005/012534) with tTAV, Jul. 4, 2014.
Alphey et al., "Malaria control with genetically manipulated insect vectors," Science (2002) 298:119-21.
Alphey, "Engineering Insects for the Sterile Insect Technique," in: Area-wide Control of Insect Pests: from Research to Field Implementation, Vreysen et al., (eds.), Dordrecht, The Netherlands, Springer (2007) pp. 51-60.
Ant et al., "Control of the olive fruit fly using genetics-enhanced sterile insect technique," BMC Biology (2012) 10:51, 8 pgs.
Arama et al., "Caspase activity and a specific cytochrome C are required for sperm differentiation in *Drosophila*," Dev Cell (2003) 4(5):687-97.
Barreau et al., "Post-meiotic transcription in *Drosophila testes*," Development (2008) 135(11):1897-1902.
Bauer DuMont et al., "Recurrent positive selection at bgcn, a key determinant of germ line differentiation, does not appear to be driven by simple coevolution with its partner protein bam," Mol Biol Evol (2007) 24(1):182-191.
Beall et al., "Discovery of tMAC: a *Drosophila testis*-specific meiotic arrest complex paralogous to Myb-Muv B," Genes Dev (2007) 21(8):904-919.
Beumer et al., "Efficient gene targeting in *Drosophila* with zinc-finger nucleases," Genetics (2006)172(4):2391-2401.
Bibikova et al., "Targeted chromosomal cleavage and mutagenesis in *Drosophila* using zinc-finger nucleases," Genetics (2002)161(3):1169-1175.
Black et al., "Why RIDL is not SIT," Trends Parasitol (2011) 27(8):362-370.
Brand et al., "Ectopic expression in *Drosophila*," Methods Cell Biol (1994)44:635-654.
Brand et al., "Targeted gene expression as a means of altering cell fates and generating dominant phenotypes," Development (1993) 118(2):401-415.
Burt et al., "Site-specific selfish genes as tools for the control and genetic engineering of natural populations," Proc Biol Sci (2003) 270:921-928.
Caceres et al., "Mass rearing of temperature sensitive genetic sexing strains in the Mediterranean fruit fly (*Ceratitis capitata*)," Genetica (2002) 115(1):107-116.
Cagan et al., "Spermatogenesis: Borrowing the Apoptotic Machinery," Curr Biol (2003)13:R600-R602.
Catteruccia et al., "An Anopheles transgenic sexing strain for vector control," Nat Biotechnol, (2005) 23(11):1414-1417.
Catteruccia et al., "Transgenic technologies to induce sterility," Malaria Journal (2009)8 (Supp2)S7.
Cenik et al., "Genome analysis reveals interplay between 5'UTR introns and nuclear mRNA export for secretory and mitochondrial genes," PLoS Genet (2011) 794:e1001366.
Cheng et al., "Cellular transformation by Simian Virus 40 and Murine Polyoma Virus T antigens," Semin Cancer Biol (2009) 19(4):218-228.
Chintapalli et al., "Using FlyAtlas to identify better *Drosophila melanogaster* models of human disease," Nature Genetics (2007) 39(6)715-720.
Deredec et al., "The population genetics of using homing endonuclease genes in vector and pest management," Genetics (2008) 179(4):2013-2026.
Dhillon et al.,"The melon fruit fly, *Bactrocera cucurbitae*: A review of its biology and management," J Insect Sci (2005) 5:40.
Franz, "Genetic sexing strains in the Mediterranean Fruit Fly, an example for other species amenable to large-scale rearing for the sterile insect technique" in:Sterile Insect Technique, Principles and Practice in Area-Wide Integrated Pest Management, Dyck et al., (eds), The Netherlands, Springer (2005) pp. 427-451.
Fu et al., "Female-specific insect lethality engineered using alternative splicing," Nature Biotechnology (2007) 25(3):353-357.
Fu et al., "Female-specific flightless phenotype for mosquito control," Proc Natl Acad Sci USA (2010) 107(10):4550-4554.

Fuller, "Spermatogenesis," in: The Development of *Drosophila Melanogaster*, Bate et al., Cold Spring Harbor Laboratory Press (1993) pp. 71-147.
Fussenegger et al., "The impact of mammalian gene regulation concepts on functional genomic research, metabolic engineering, and advanced gene therapies," Biotechnol Prog (2001) 17(1):1-51.
Fussenegger et al., "Streptogramin-based gene regulation systems for mammalian cells," Nat Biotechnol (2000) 18(11):1203-1208.
Ghosh et al., "Transcription factor binding and induced transcription alter chromosomal c-myc replicator activity," Mol Cell Biol (2004) 24(23):10193-10207.
Gonczy et al., "Bag-of-marbles and benign gonial cell neoplasm act in the germline to restrict proliferation during *Drosophila* spermatogenesis," Development (1997) 124(21):4361-4371.
Gong et al., "A dominant lethal genetic system for autocidal control of the Mediterranean fruit fly," Nat Biotechnol (2005) 23(4):453-456.
Gong et al., "Ends-out, or replacement, gene targeting in *Drosophila*," Proc Natl Acad Sci (USA) (2003) 100(5):2556-2561.
Gossen et al., "Tight control of gene expression in mammalian cells by tetracycline-responsive promoters," Proc Natl Acad Sci (USA) (1992) 89(12):5547-5551.
Gossen et al., "Studying gene function in eukaryotes by conditional gene inactivation," Annu Rev Genet (2002) 36:153-173.
Hiller et al., "Testis-specific TAF homologs collaborate to control a tissue-specific transcription program," Development (2004) 131:5297-5308.
Hockemeyer et al., "Genetic engineering of human pluripotent cells using TALE nucleases," Nat Biotechnol (2011) 29(8):731-734.
Horn et al., "A transgene-based, embryo-specific lethality system for insect pest management," Nat Biotechnol (2003) 1:64-70.
Jattani et al., "Deficiency screen identifies a novel role for beta 2 tubulin in salivary gland and myoblast migration in the *Drosophila* embryo," Dev Dyn (2009) 238(4):853-863.
Jiang et al., "Tombola, a tesmin/TSO1-family protein, regulates transcriptional activation in the *Drosophila* male germline and physically interacts with always early," Development (2007) 134(8):1549-1559.
Jiang et al., "Transcriptional activation in *Drosophila* spermatogenesis involves the mutually dependent function of aly and a novel meiotic arrest gene cookie monster," Development (2003) 130(3):563-573.
Kawase et al., "Gbb/Bmp signaling is essential for maintaining germline stem cells and for repressing bam transcription in the *Drosophila* testis," Development (2004) 131(6):1365-1375.
Kim et al., "Hybrid restriction enzymes: zinc finger fusions to Fok I cleavage domain," Proc Natl Acad Sci (USA) (1996) 93:1156-1160.
Klassen, "History of the Sterile Insect Technique," in: Sterile Insect Technique, Principles and Practice in Area-Wide Integrated Pest Management, Curits et al., (eds) The Netherlands, Springer (2005) pp. 3-36.
Knipling et al., "Possibilities of Insect Control or Eradication Through the Use of Sexually Sterile Males," J Econ Entomol (1955) 48:459-462.
Lycett et al., "Conditional expression in the malaria mosquito *Anopheles stephensi* with Tet-On and Tet-Off systems," Genetics (2004) 167(4):1781-1790.
Mahfouz et al., "De novo-engineered transcription activator-like effector (TALE) hybrid nuclease with novel DNA binding specificity creates double-strand breaks," Proc Natl Acad Sci (USA) (2011) 101(6):2623-2628.
Malacrida et al., "A transgenic sperm marking system in the medfly, as a tool for pest control strategies and sperm use analysis," Entomological Research (2007) 37:A56.
Maynard-Smith et al., "A directed approach for engineering conditional protein stability using biologically silent small molecules," J Biol Chem (2007) 282(34):24866-24872.
Miller., "An improved zinc-finger nuclease architecture for highly specific genome editing," Nat Biotechnol (2007) 25(7):778-785.
Miller et al., "A TALE nuclease architecture for efficient genome editing," Nat Biotechnol (2011) 29(2):143-148.

(56) References Cited

OTHER PUBLICATIONS

Morrison et al., "Genetic Improvements to the sterile insect technique for agricultural pests," Asia Pacific J MOI Biol and Biotechnol (2010) 18(2):275-295.
Nielsen et al., "Axoneme-specific beta-tubulin specialization: a conserved C-terminal motif specifies the central pair," Curr Biol (2001) 11(7):529-533.
Osterwalder et al., "A conditional tissue-specific transgene expression system using inducible GAL4," Proc Natl Acad Sci (USA) (2001) 98(22):12596-12601.
Perezgasga et al., "Regulation of transcription of meiotic cell cycle and terminal differentiation genes by the testis-specific Zn-finger protein matotopetli," Development (2004) 131(8):1691-1702.
Phuc et al., "Late-acting dominant lethal genetic systems and mosquito control," BMC Biol (2007) 5:11.
Raja et al., "Replacement by Drosophila melanogaster Protamines and Mst77F of Histones during Chromatin Condensation in Late Spermatids and Role of Sesame in the Removal of These Proteins from the Male Pronucleus," (2005) Mol Cell Biol 25(14):6165-6177.
Rendon et al., "Medfly (Diptera: Tephritidae) genetic sexing: large-scale field comparison of males-only and bisexual sterile fly releases in Guatemala," J Econ Entomol (2004) 97(5):1547-1553.
Robinson, "Genetic Basis of the Sterile Insect Technique," in: Sterile Insect Technique, Principles and Practice in Area-Wide Integrated Pest Management, Dyck et al., (eds.), The Netherland, Springer (2005) pp. 95-114.
Rong et al., "A targeted gene knockout in Drosophila," Genetics (2001) 157(3):1307-1312.
Rong et al., "Targeted mutagenesis by homologous recombination in D. melanogaster," Genes Dev (2002) 16:1568-1581.
Rong et al., "Gene targeting by homologous recombination in Drosophila," Science (2000) 288(5473):2013-2018.
Santel et al., "The Drosophila don juan (dj) gene encodes a novel sperm specific protein component characterized by an unusual domain of a repetitive amino acid motif," Mech Dev (1997) 64(1-2):19-30.
Schetelig et al., "Strategy for enhanced transgenic strain development for embryonic conditional lethality in Anastrepha suspensa," Pro Natl Acad Sci (USA) (2012) 24: 9348-9353.
Smith et al., "Testis-specific expression of the beta2 tubulin promoter of Aedes aegypti and its application as a genetic sex-separation marker," Insect Mol Biol (2007) 16(1):16-71.
Theodoraki et al., "cDNA cloning, heat shock regulation and developmental expression of the hsp83 gene in the Mediterranean fruit fly Ceratitis capitata," Insect Mol Biol (2006) 15(6):839-852.
Thomas et al., "Insect population control using a dominant, repressible, lethal genetic system," Science (2000) 287(5462):2474-2476.
Urnov et al., "Highly efficient endogenous human gene correction using designed zinc-finger nucleases," Nature (2005) 435:646-651.
Viktorinova et al., "Comparative analysis of binary expression systems for directed gene expression in transgenic insects," Insect Biochem Mol Biol (2007) 37:246-254.
White-Cooper et al., "Transcription of meiotic cell cycle and terminal differentiation genes depends on a conserved chromatin associated protein, whose nuclear localisation is regulated," Development (2000) 127:5463-5473.
Wilson et al., "Position effects on eukaryotic gene expression," Annu Rev Cell Biol (1990) 6:679-714.
Wilson et al., "Sperm plasma membrane breakdown during Drosophila fertilization requires sneaky, an acrosomal membrane protein," Development (2006) 133(24):4871-4879.
Windbichler et al., "A synthetic homing endonuclease-based gene drive system in the human malaria mosquito," Nature (2011) 473(7346):212-215.
Windbichler et al., "Homing endonuclease mediated gene targeting in Anopheles gambiae cells and embryos," Nucleic Acids Res (2007) 35:5922-5933.
Windbichler et al., "Targeting the X chromosome during spermatogenesis induces Y chromosome transmission ratio distortion and early dominant embryo lethality in Anopheles gambiae," PLoS Genet (2008) 4(12):e1000291.
Zhao et al., "Male germ cell specification and differentiation," Dev Cell (2002) 2(5):537-547.
Zimowska et al., "The beta2-tubulin gene from three tephritid fruit fly species and use of its promoter for sperm marking," Insect Biochem Mol Biol (2009) 39(8):508-515.

\* cited by examiner

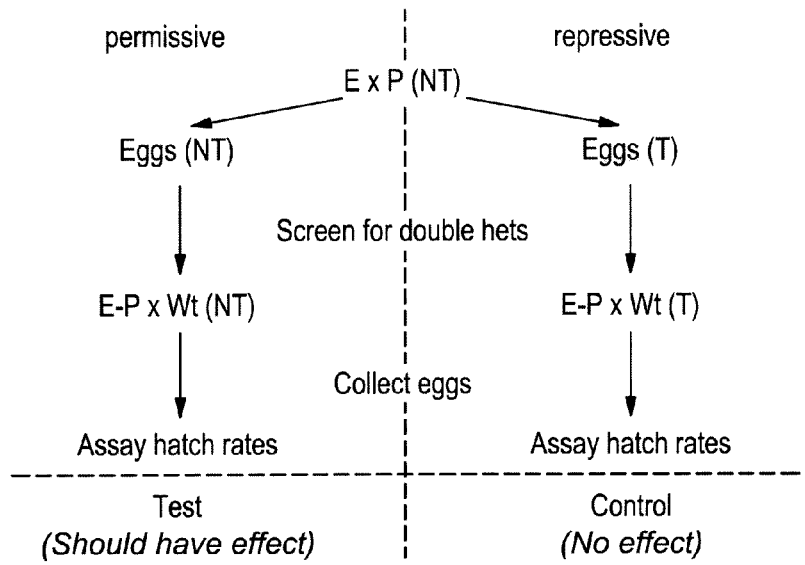
Figure 1. Design of the egg hatch rate assay
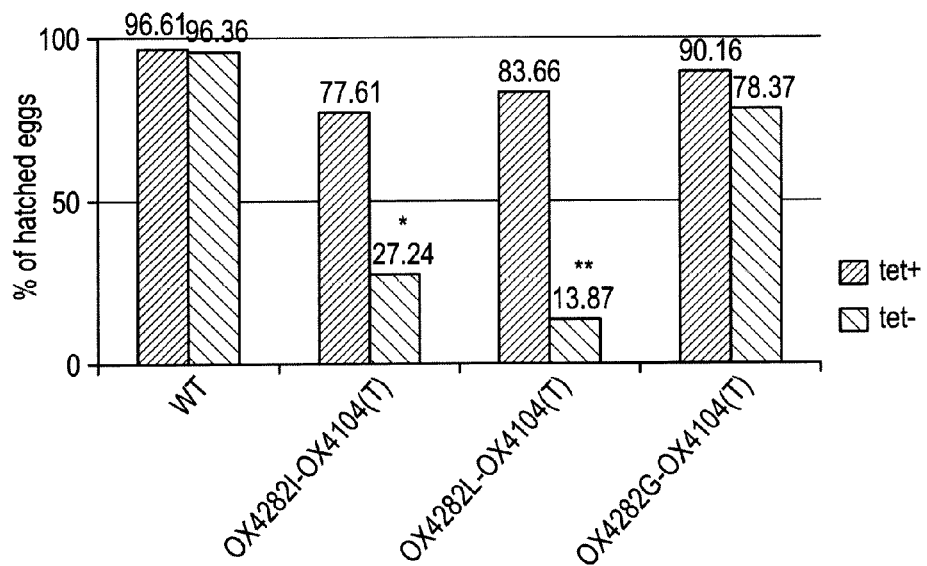
Figure 2. Percentage of OX4282-OX4104 male sterility on and off Tetracycline

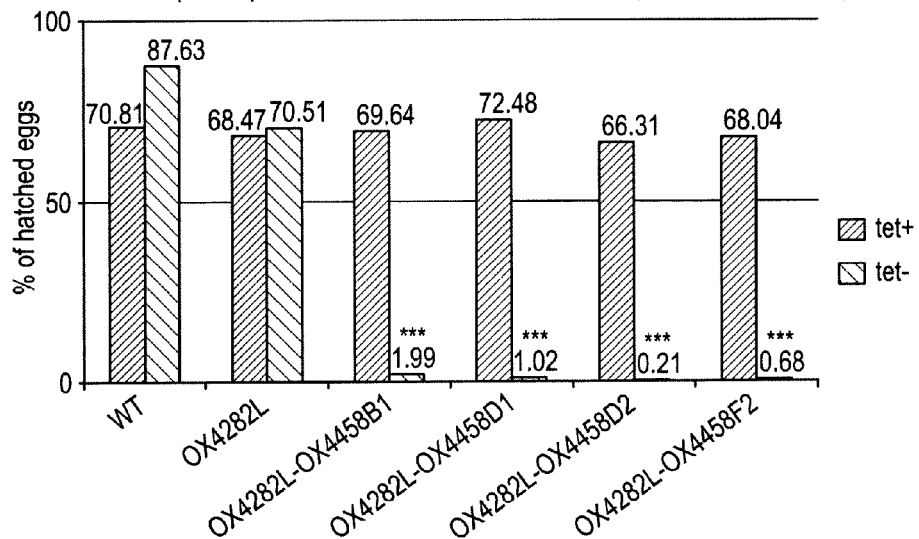
Figure 3. Percentage of OX4282-OX4458 male sterility on and off Tetracycline
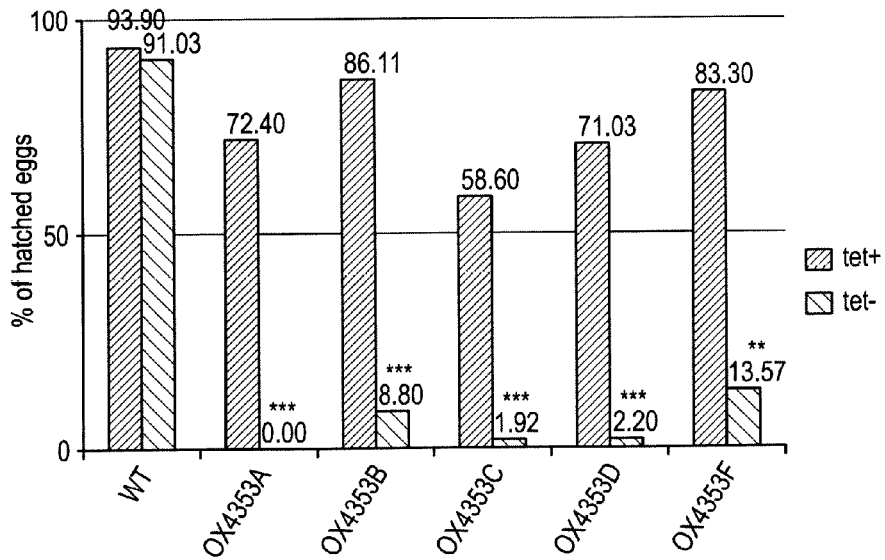
Figure 4. Percentage of OX4353 male sterility on and off Tetracycline

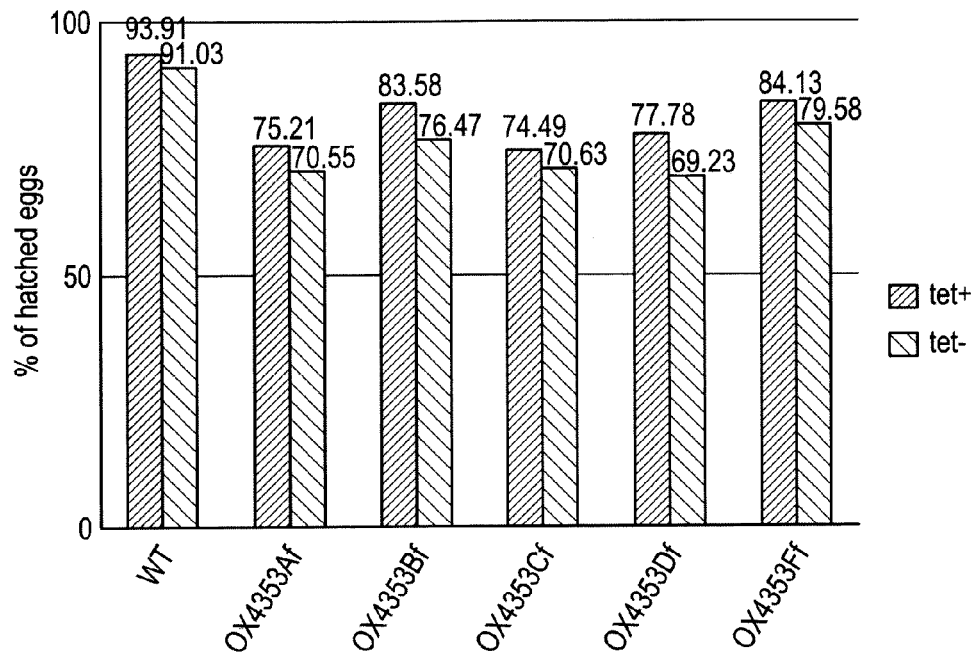
Figure 5. Percentage of OX4353 female sterility on and off Tetracycline
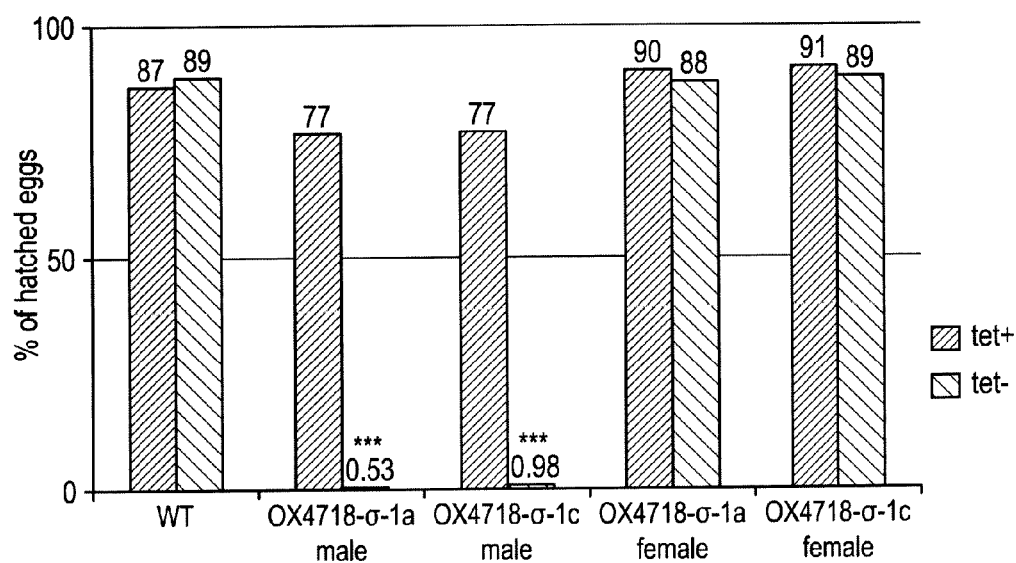
Figure 6. Repressible male-specific sterility in OX4718-σ1 lines

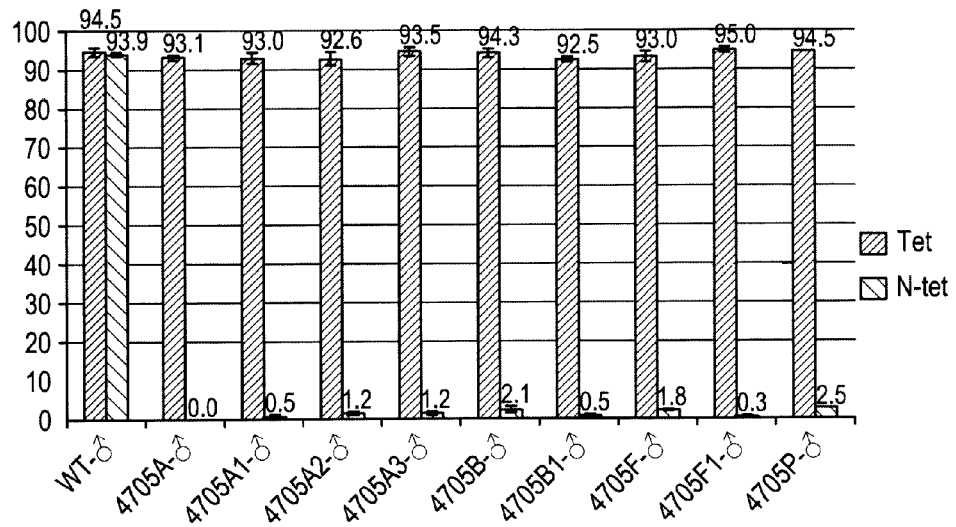
Figure 7. Percentage of OX4705 olive fly male sterility on and off Tetracycline
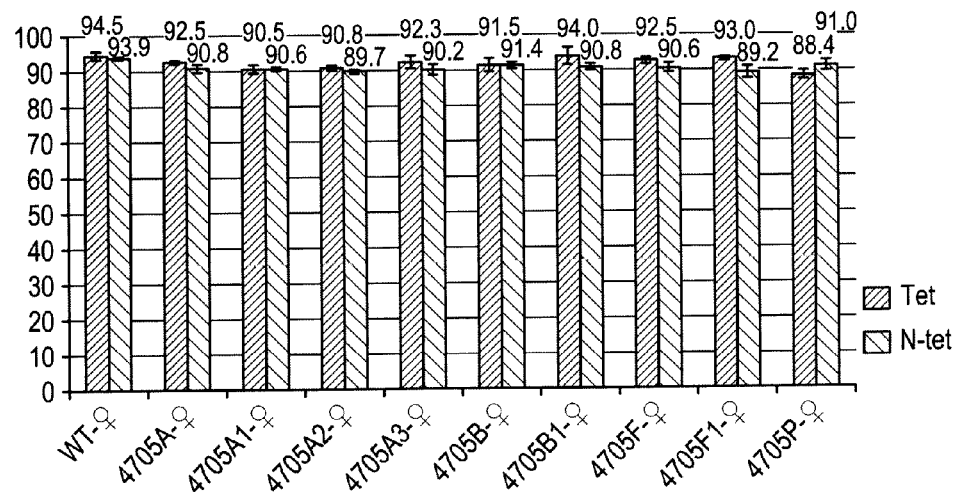
Figure 8. Percentage of OX4705 female sterility on and off Tetracycline

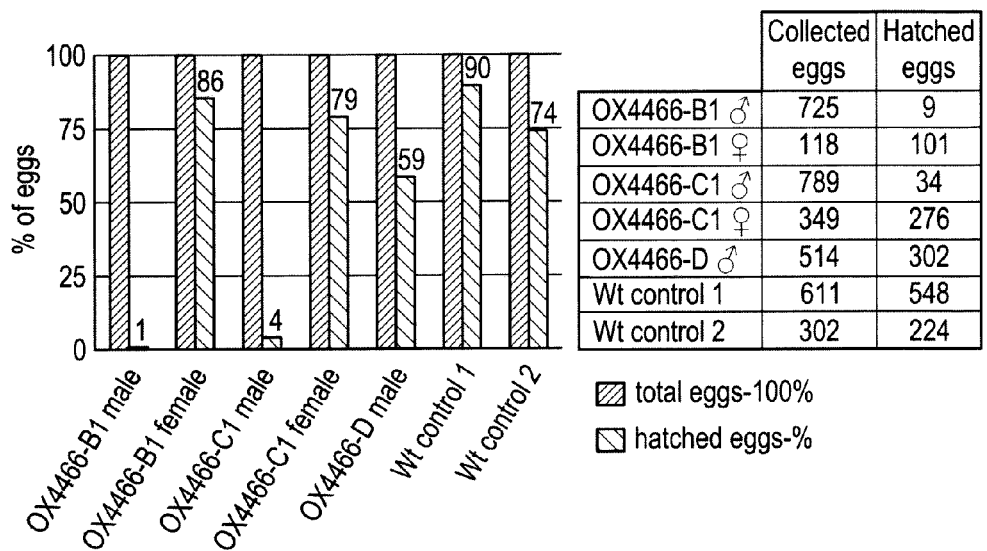
Figure 9. OX4466 strain hatch rate assay
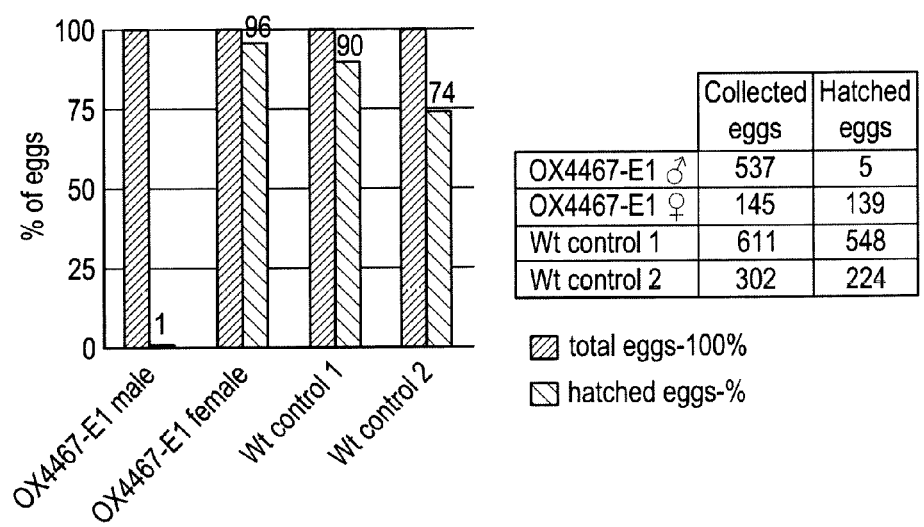
Figure 10. OX4467-E1 strain hatch rate assay

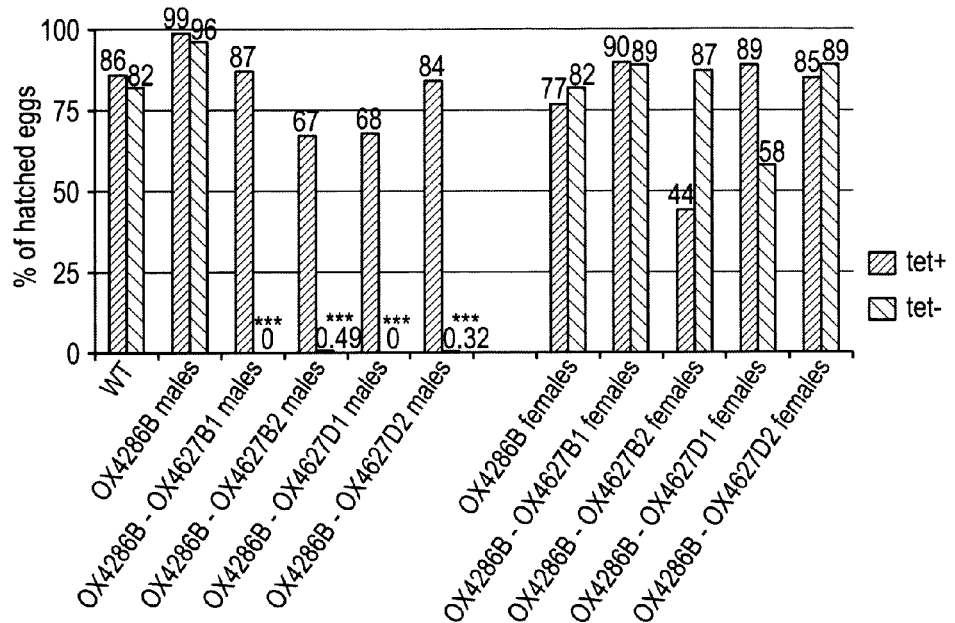
Figure 11. Hatch-rate assay of *Aedes aegypti* lines carrying both topi-tTAV and tetO-Dm-Protamine-FokI alleles
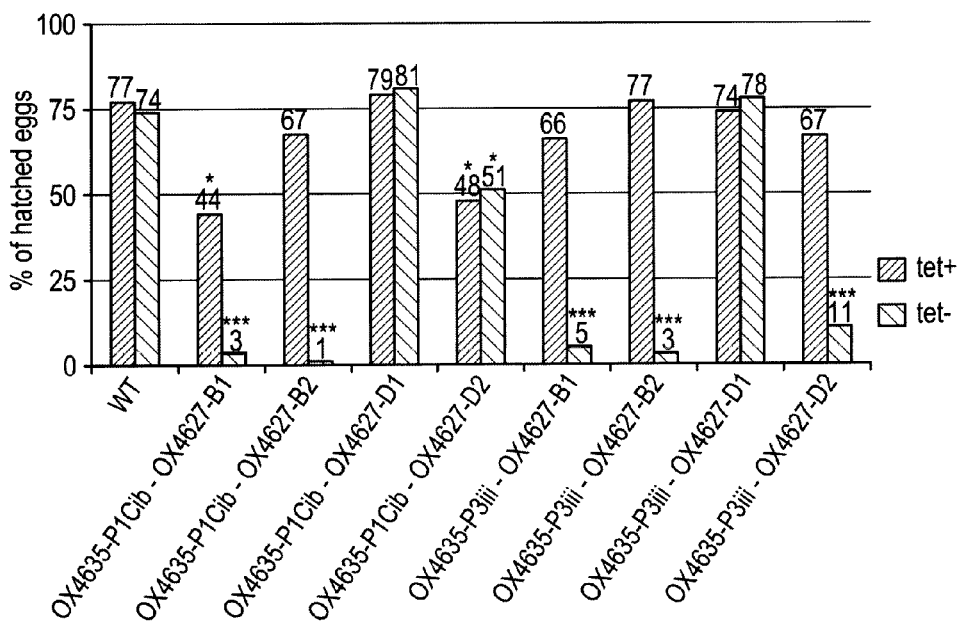
Figure 12. Hatch-rate assay of *Aedes aegypti* lines carrying both β2-tubulin-tTAV and tetO-Ae-Protamine-FokI alleles

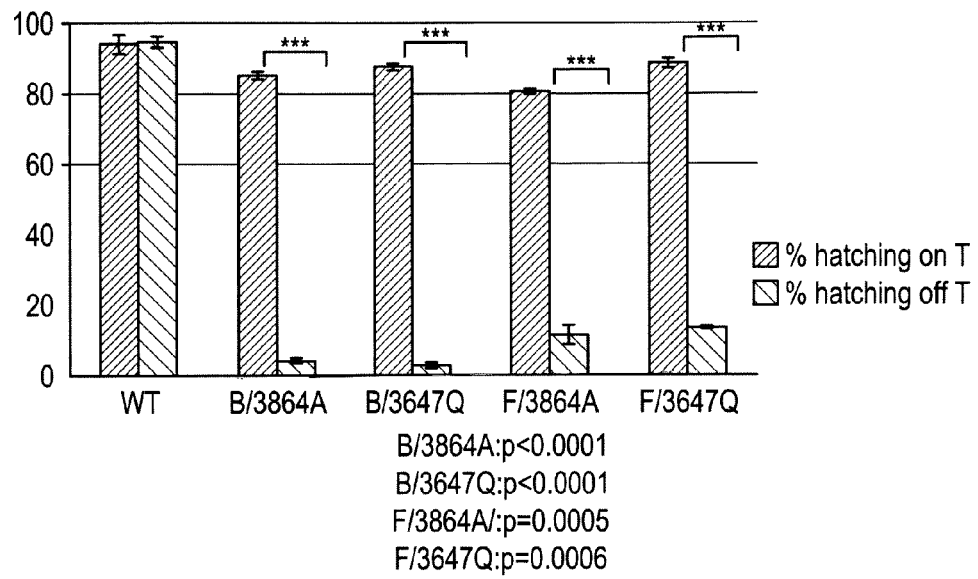
Figure 13. OX4353 strains crossed to two leading RIDL female lethal lines (OX3864A and OX3647Q).
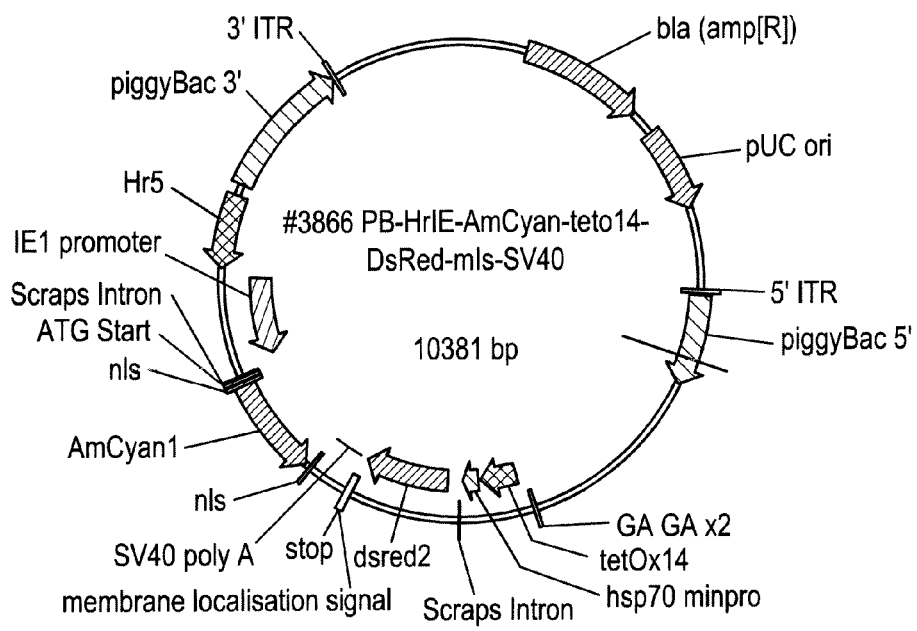
Figure 14. A plasmid map of OX3866

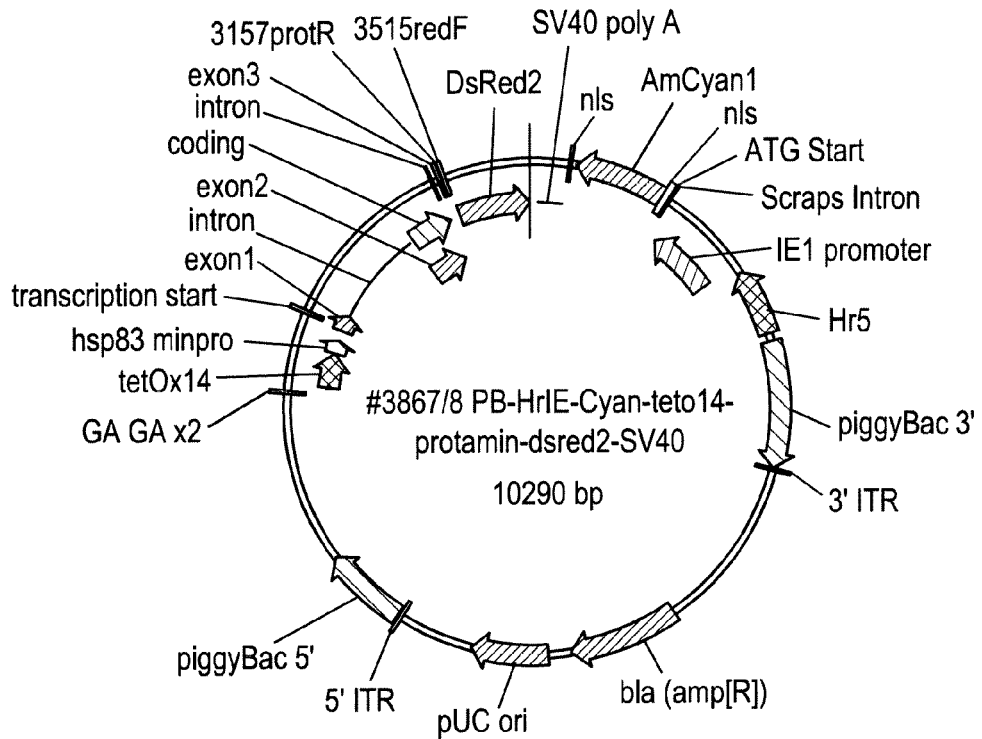
Figure 15. A plasmid map of OX3867
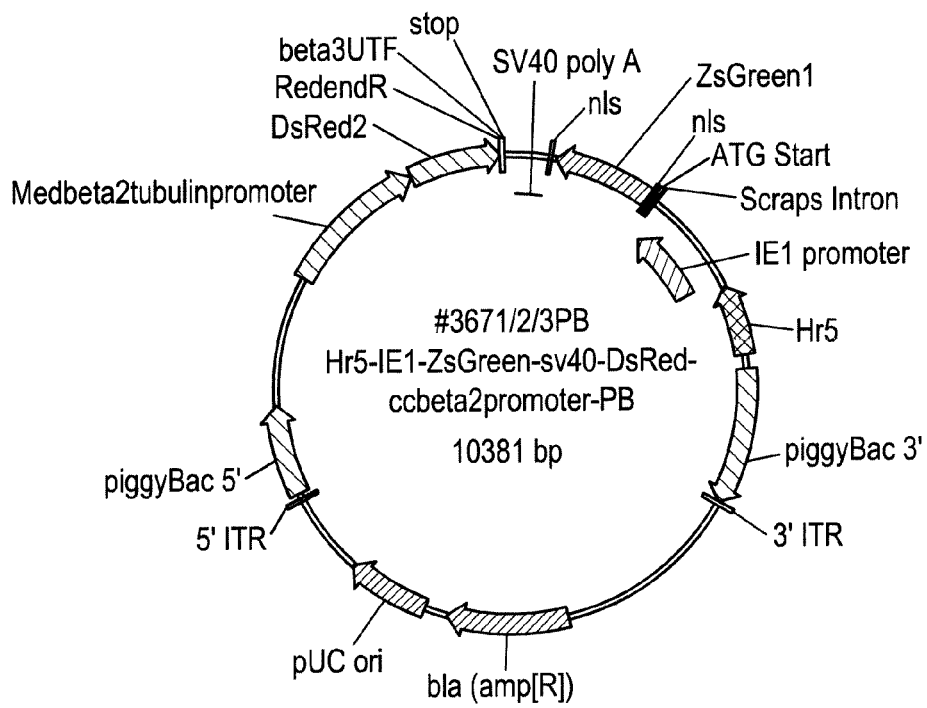
Figure 16. A plasmid map of OX3671

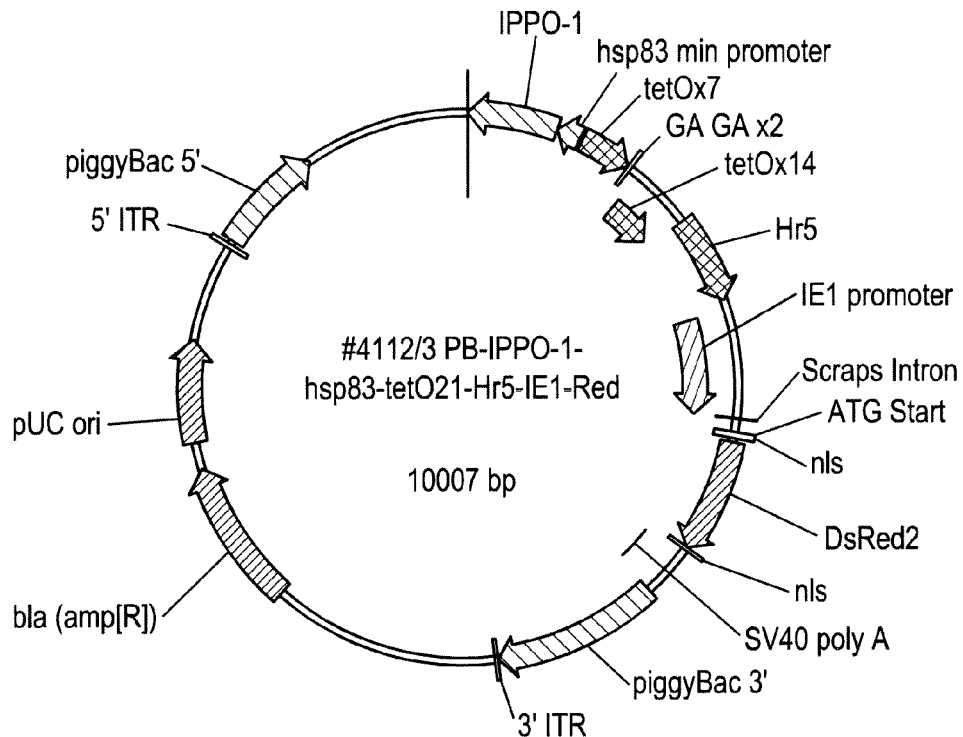
Figure 17. A plasmid map of OX4112
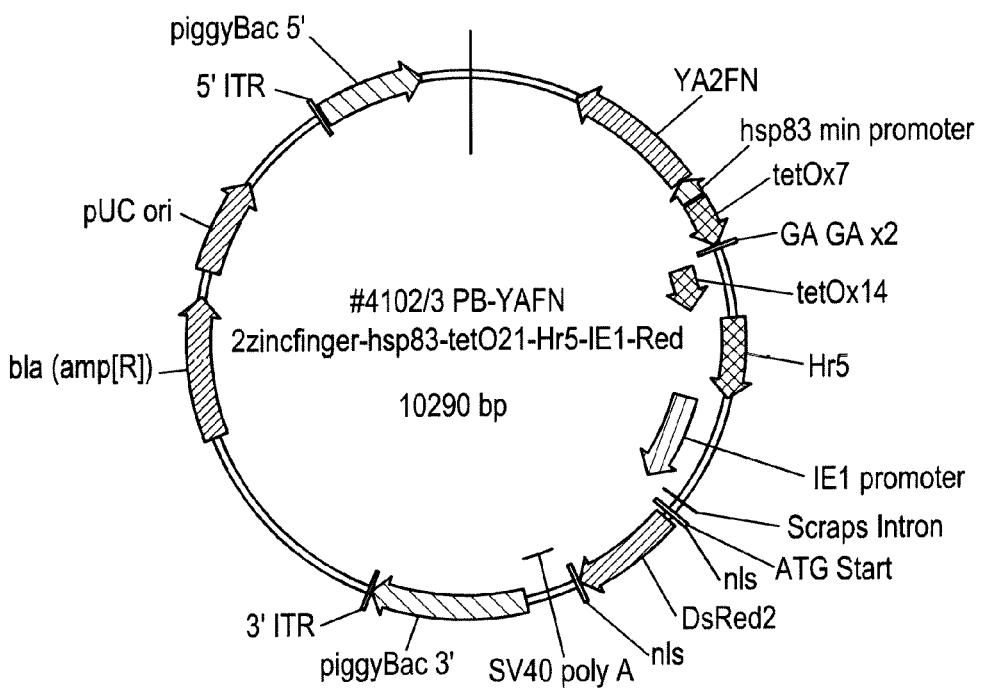
Figure 18. A plasmid map of OX4103

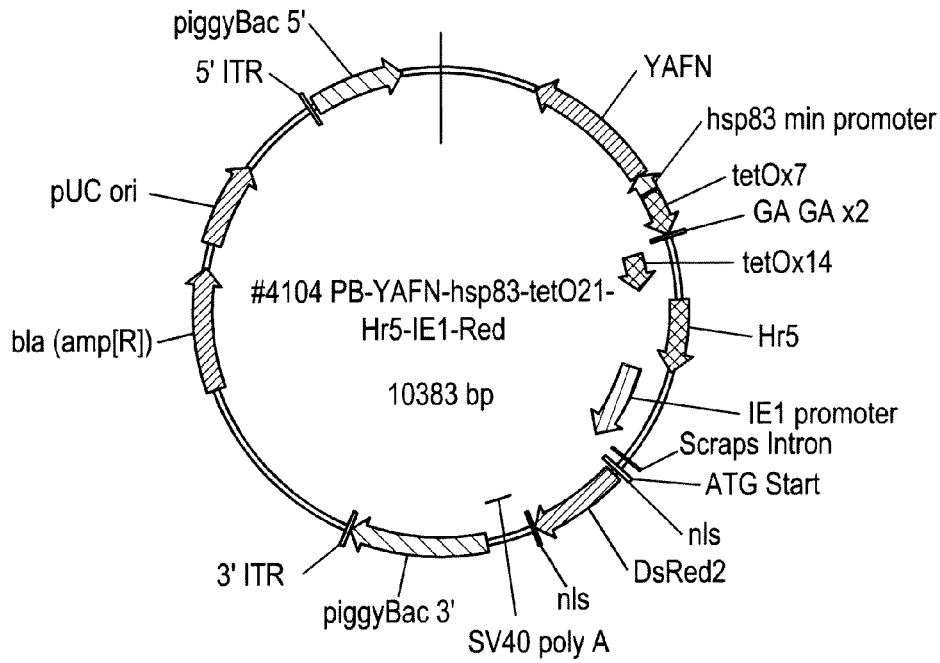
Figure 19. A plasmid map of OX4104
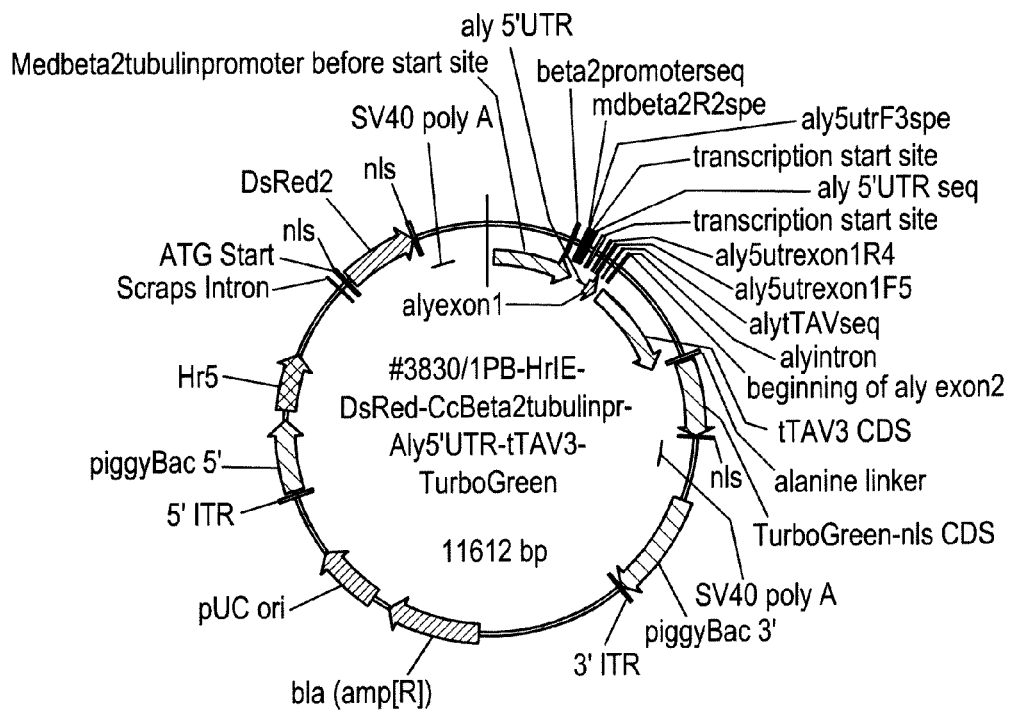
Figure 20. A plasmid map of OX3831

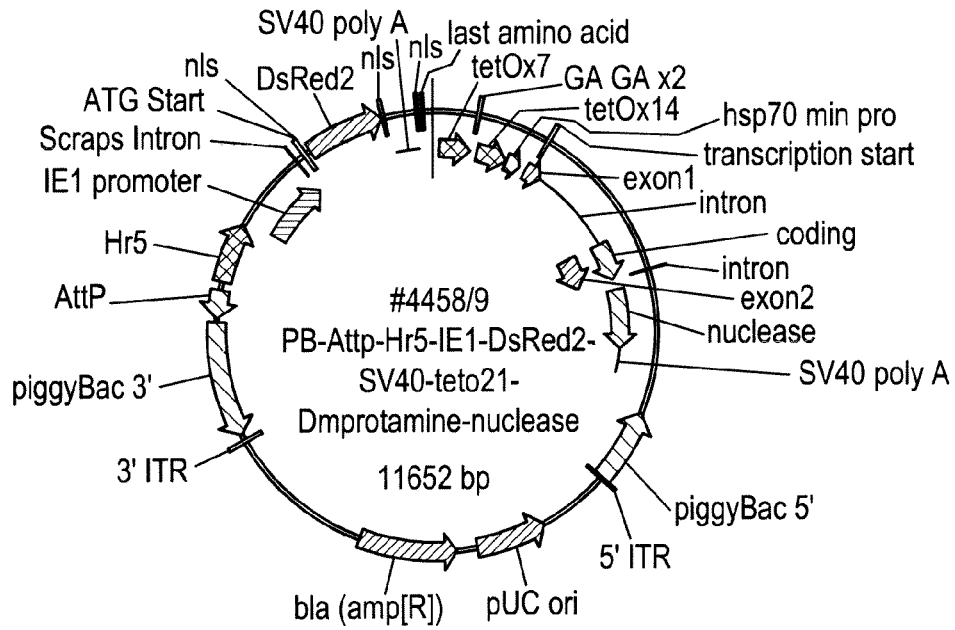
Figure 21. A plasmid map of OX4458
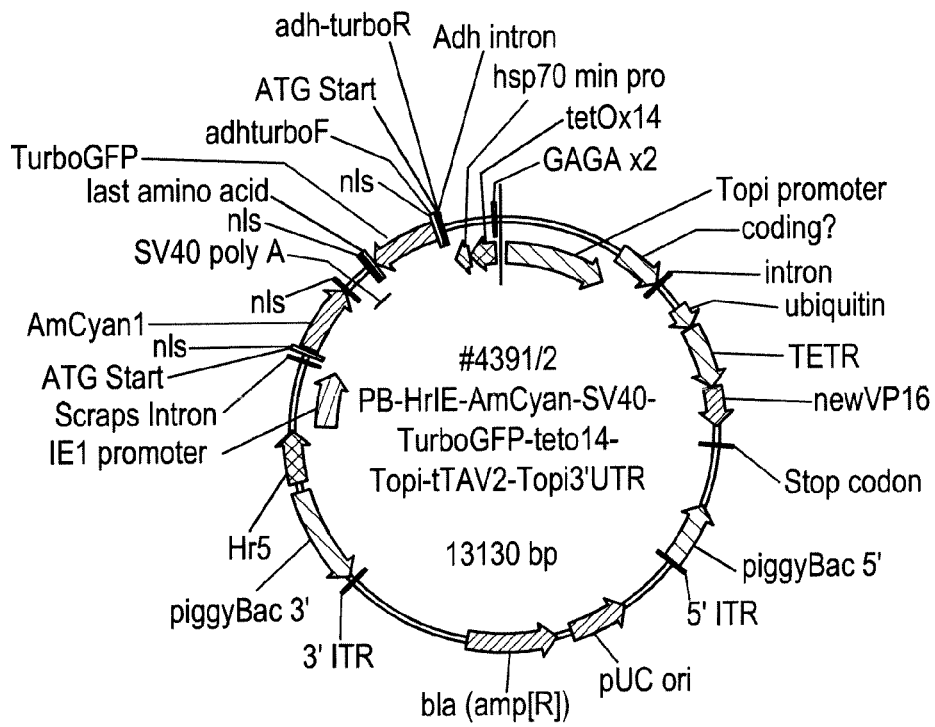
Figure 22. A plasmid map of OX4391

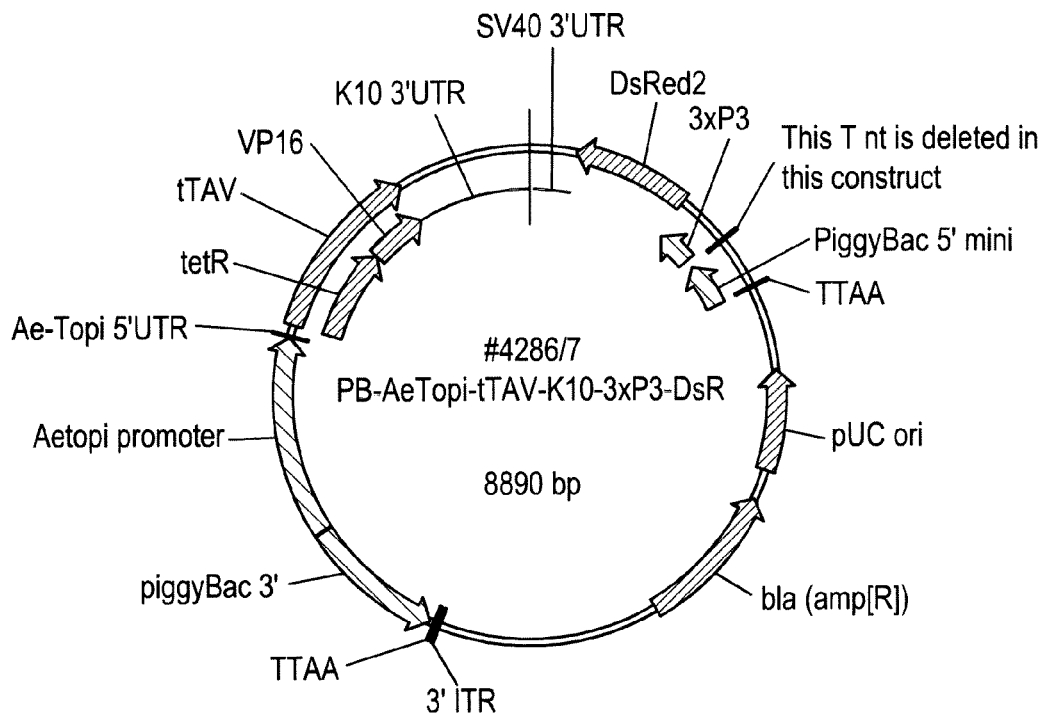
Figure 23. A plasmid map of OX4286
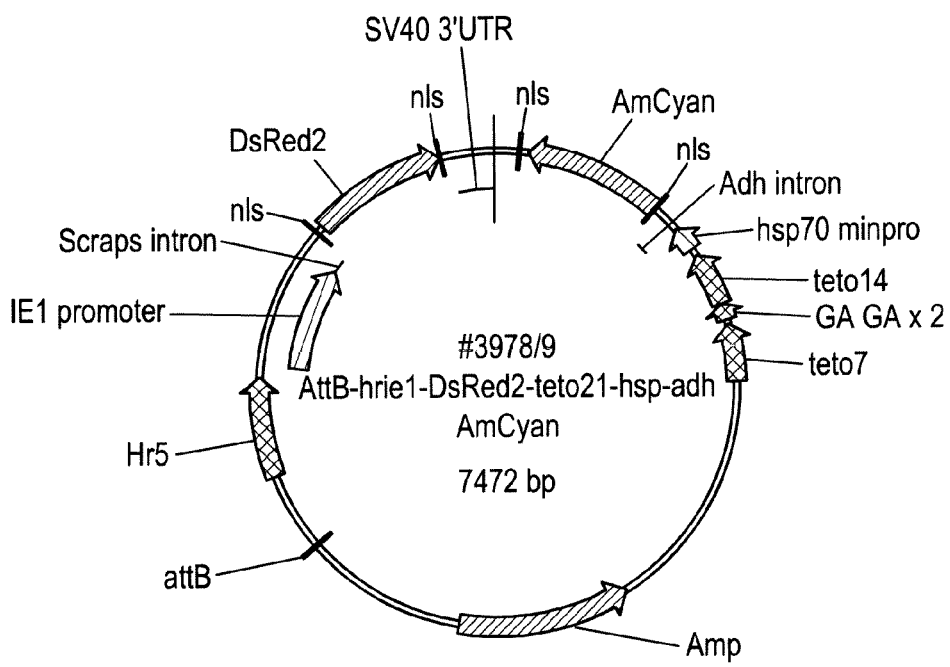
Figure 24. A plasmid map of OX3978

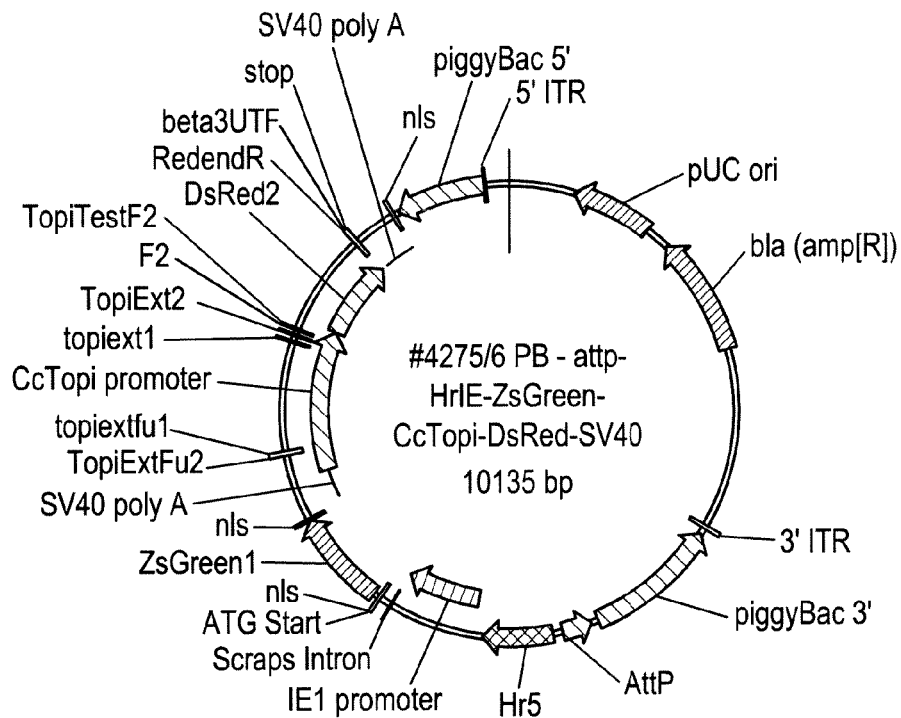
Figure 25. A plasmid map of OX4275
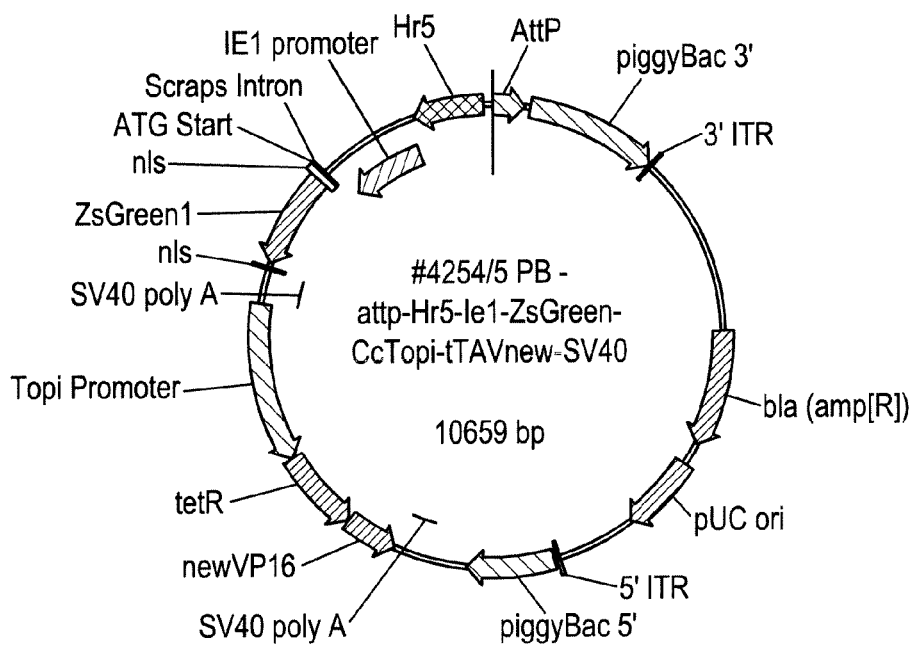
Figure 26. A plasmid map of OX4254

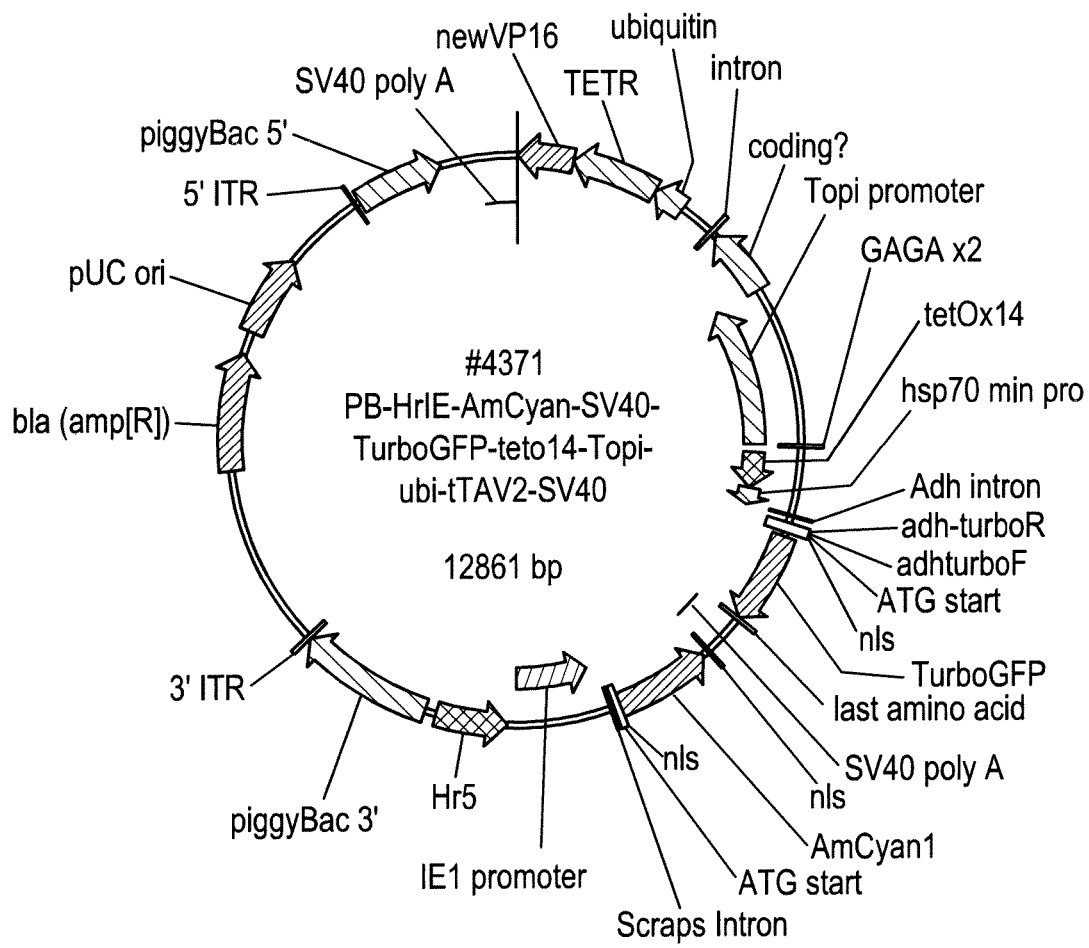
Figure 27. A plasmid map of OX4371

SEQUENCE LISTING

<160> NUMBER OF SEQ ID NOS: 56

<210> SEQ ID NO 1
<211> LENGTH: 1859
<212> TYPE: DNA
<213> ORGANISM: Ceratitis capitata

<400> SEQUENCE: 1

```
atattttgaa aagattttag tcagacggga acgtgttaaa aattagtttt tcaaattgca    60
taacttatcc aaggatcagt aaccaactat aatatttaaa gtgtgaatgg aaattcacag   120
tatcttcgac taaagaactg cagttggatc cgatagtaaa ttgagaagcg gcaaaacctt   180
aagtaaagtc caaacttttt tgttctaaa tacatacaaa ttttttagga catttcatac    240
cagtaggagc aggtaataag atactaacgg cgtatacgta attaaatcgg gagataattt    300
aaaagatgcg cgaaattgtg catattcaag ctggacaatg tggcaaccag attggcggca    360
aattttggga agttatatct gatgaacatt gcatcgatgc cacaggcact tactatggcg    420
atagtgattt gcagctggaa cgtattaatg tatactacaa tgaagcgaca ggtgctaaat    480
atgtacctcg tgctattctg gtggatttag agccaggcac catggactct gtacgttccg    540
gtgcctttgg tcaatttttt cgtcctgata actttgtgtt tggacagtcg ggagcgggta    600
acaattgggc caagggtcat tatactgaag gagctgaatt ggttgactca gtactcgatg    660
ttgtaaggaa agagtctgaa ggatgtgatt gcctacaggg atttcaatta acacattcgc    720
ttggcggcgg tacgggttcc ggcatgggaa cattgttaat atcgaaaatt cgggaggagt    780
```

```
acccggaccg gattatgaat accttttcgg tggtgccctc cccaaaggta tccgacacag    840
tcgtggaacc ttataatgcc acactgagtg tacatcagct ggttgaaaat acggatgaaa    900
catattgcat cgacaatgaa gctctatatg acatatgctt tcgcacattg aaacttacta    960
cccccactta tggcgattta aatcatttag tctctgcaac aatgtccgga gttacgactt   1020
gcttacgatt tccgggtcaa cttaatgcag atttgcgtaa gttggctgtg aatatggtac   1080
catttccacg tttgcatttt tttatgccgg gtttcgctcc actgacttct cgtggctcgc   1140
agcagtatcg cgcacttaca gtgcctgaat tgacacaaca gatgtttgac gccaagaaca   1200
tgatggctgc ttgcgatcct cgtcatggac ggtacttaac agtggcggcc atttttagag   1260
gtcgcatgtc tatgaaggag gttgacgaac aaatgctgaa tattcaaaac aaaaatagca   1320
gtttctttgt tgagtggatt ccaaataact gcaaaactgc tgtttgtgat attcctcctc   1380
gcggtttaaa aatgtcagcg acatttattg gcaattcaac agctatacaa gaattattca   1440
aacgagtttc tgagcagttc acagcaatgt tcaggcgcaa agcttttttg cattggtata   1500
ctggcgaagg tatggatgaa atggagttca ccgaggctga agtaatatg aatgatttag    1560 tatctgaata ccaacagtac caagaagcca ccgccgatga agagggcgag ttcgacgagg   1620
atgaagaagg aggaggggat gaataacagt tcttggtttt tggagatggt aataggaaaa   1680
aatctctata tctttactta attaatatta ttatgcgctc ctcacaattg taaaatccaa   1740
ttgtagcttt ttgttcactt ctcagcaagt attttgtatt atgtactatt tgcttttctt   1800
gtgcgcaagt atacgctttt agtaaaattt aaataaaaa aaaaaaaaaa aaaaaaaaa     1859
```

<210> SEQ ID NO 2
<211> LENGTH: 1870
<212> TYPE: DNA
<213> ORGANISM: Drosophila melanogaster

<400> SEQUENCE: 2

```
ggaaatcgta gtagcctatt tgtgaacatt cggtgtagta atccaagcca ggttcagttc     60
acctcagtat cagctagcac gtacacgact aaaatctaaa cctgaaaaat tatacgttta    120
aatattcagt cttttgccga tttttgcccc actcagactg ttttaaaagc tcgattttt     180 tttgtaccat ttttcggtg tgaaaaaggg ggccctactt tactatcaaa atgcgtgaaa     240
ttgtacacat tcaggccggt caatgcggta accagatcgg tggtaaattc tgggaggtaa    300
tctcggatga gcactgtata gatgcgaccg gaacgtacta cggcgatagt gatctccagc    360
tggagcgcat caatgtatac tacaatgaag ccaccggtgc caagtatgtg ccacgcgcaa    420
ttctcgtgga cctggagccc ggcaccatgg attcggttcg ttctggcgcc tttggccaga    480
tcttccggcc ggacaatttt tgtgtttggcc aatcgggagc aggcaacaac tgggccaagg    540
gtcattacac cgagggtgct gaactggtgg attccgtctt ggatgtggtg cgaaaggagt    600
ccgagggatg cgattgcctt cagggcttcc agtcgaccca ctcgctgggt ggcggcactg    660
gctccggcat gggaaccctg ctgatctcga agatccgcga ggagtacccg gaccgcatca    720
tgaacacctt ctcggtggtg ccctcgccca aggtgtccga tacggtggtg gagccctaca    780
atgccaccct gagtgtgcat cagctggtgg agaacaccga tgagacgtac tgcatcgaca    840
acgaggcgtt gtatgacatc tgcttccgca cactgaagct gaccacgccc acctacggtg    900
acctgaacca tctggtttcg gccaccatgt ctggtgtgac gacctgcctg cgcttccctg    960
gccagctgaa cgctgatctt cgcaagctgg ccgtgaacat ggtacccttc ccccggctgc   1020
```

-continued

| | | |
|---|---|---|
| acttcttcat gcccggattc gcaccgctca cctcgcgagg atcgcaacaa taccgggccc | 1080 | |
| ttaccgttcc ggagctgacc cagcagatgt tcgatgccaa gaacatgatg gctgcgtgcg | 1140 | |
| atccccgaca tggtcgctat ctgaccgtcg ccgccatctt ccgtggccgc atgtccatga | 1200 | |
| aggaggtgga cgagcagatg ctcaacattc agaacaagaa cagcagcttc ttcgtggaat | 1260 | |
| ggatcccgaa taactgcaag acagcggtgt gcgatattcc gcccagaggt ctcaagatgt | 1320 | |
| cggccacctt cattggcaac tccaccgcca ttcaggagct attcaaacgg gtttcggagc | 1380 | |
| agttcaccgc catgttccga aggaaggcct tcttgcattg gtacaccggc gagggaatgg | 1440 | |
| acgaaatgga attcacagag gccgagagca acatgaacga cttggtttct gaatatcaac | 1500 | |
| agtaccagga ggcgactgcc gatgaggagg gcgaattcga tgaagacgaa gagggtggcg | 1560 | |
| gcgatgaata ataggattaa cttcccactc aagatcacac atgaaccaca aaacaggcta | 1620 | |
| gcagggaac ccattaggaa ggcacaatac attggatctt tgggccttag catattgtgc | 1680 | |
| ttcgaggccc gtcggttgta catatttcct atatggattc ttcactgttc gattatttat | 1740 | |
| cattcacaca cgtacagaag aattatgtcc actttgttaa gctcatgttg caattgctgt | 1800 | |
| gatttctggg ttacgaataa atgttgattt ataagcagac aagattacca acagcatttt | 1860 | |
| gcatattttt | 1870 | |

<210> SEQ ID NO 3
<211> LENGTH: 2128
<212> TYPE: DNA
<213> ORGANISM: Aedes aegypti

<400> SEQUENCE: 3

| | | |
|---|---|---|
| cgccaaattt tgatagttta tgcaaaggac ttgcatgttt cccctaatgt gggggtgaat | 60 | |
| cacgctatgt tcttgtggct catatatcgc ttttgtttcg tccataaacc acgtggtcat | 120 | |
| tttttatgaa ttttcacgct tctccttatg atctttcgtc cacacaaaaa ttttcaaatt | 180 | |
| ttgtatgcac cgtgatgctt gagcagtacc cttctccacc cataacgac cacgtggcat | 240 | |
| atggacagcc cccaacgtga caacagactt cgaagcgaat gcatccagta gcacatgttg | 300 | |
| aacgcgtcgc tcccgttttg ggggcccata ctgccgccac aatgtaaatc aatcacagtg | 360 | |
| tgtcatggaa ggccatcctt cttcttgacg acccggagga cgacagttgg aaaaattttc | 420 | |
| acttcgattt tcaccaccga ggaacgcgga cgtgatttgg aaccattctg cttccatctt | 480 | |
| caagcatcgg aagaagcata ttttgaagcc caattttgga accgctagaa gtgctccagg | 540 | |
| atgcgtgaaa tcgttcacat tcaagccggc caatgtggca accagatagg agccaagttc | 600 | |
| tgggaggtaa tatccgacga gcacggaatc gatgccaccg gggcgtattg cggagacagc | 660 | |
| gatttgcagc tggagcggat caacgtgtac tacaacgagg ctaccggagg aaaatacgtc | 720 | |
| ccacgtgccg tgctggtcga tttggaacct ggcactatgg attcggtccg agcgggaccg | 780 | |
| tttggacagc tgttccggcc ggataatttt gtgttcggtc aatctggcgc cggcaacaat | 840 | |
| tgggccaagg acattatac cgaaggggcc gaactggtcg attcggtact cgatgtggtc | 900 | |
| cgtaaagaat ccgaaggctg cgattgtctg cagggcttcc agttgacaca ttcgctgggt | 960 | |
| ggaggaaccg ttctggtaa gattttgggc aggtattagg ttatctttgt attaacggtt | 1020 | |
| gttccttatt caggaatggg aacgctgctg atttcgaaga ttcgagaaga gtatccagat | 1080 | |
| cgtattatga acacattttc tgtcgttcct tcgccgaagg tgtctgacac cgtggttgag | 1140 | |
| ccgtacaacg caacgttaag tgttcaccag ttggttgaga acacgacga atcctactgc | 1200 | |
| atcgacaatg aggccctgta cgacatttgc ttccgaacgt taaaactaac aaccccaact | 1260 | |

```
tacggcgatt tgaaccatct tgtttcggca acgatgtccg gcgttaccac gtgtttgcgt   1320
tttcctggtc agttgaatgc agatctccgt aaattggcag tcaatatggt tccattcccg   1380
cggctgcact ttttcatgac cggcttcgca ccgctgactt cccgaggatc gcagcaatac   1440
cgtgccctta ctgttccgga gctgacccaa cagatgttcg atgcgaagaa catgatggcc   1500
gcatgtgatc cacgacacgg tcgataccta acggtggccg ctatattccg cggacggatg   1560
tccatgaagg aggtcgacga gcagatgttg aacattcaaa gcaaaaatag tagctacttc   1620
gtcgaatgga tcccgaacaa tgtgaagacg gccgtctgcg acattccgcc gcgtggtttg   1680
aaaatgtcgt caacctttat cggtaactcg acggccattc aggagatttt caaacgtatt   1740
gctgaacaat ttaccgctat gttccgaagg aaagctttcc tgcattggta cacgggcgaa   1800
ggcatggacg agatggagtt caccgaagcc gagagcaata tgaatgatct ggtgtcggag   1860
taccagcagt accaggaagc gacggccgac gaggaaggag aattcgacga agaagaggag   1920
ggtggcgagg aatagagaag gaataaaaat ggctgaaatt atccgttatc atactgtgaa   1980
ttgaagatcc tattgttgta attgctgaaa taaaatcttg tttcctaatt tgtatctgta   2040
ttatttttgc aatttctgtt tttcatcacg tcaatcagtc atgaaaattt tactttcctg   2100
cacagaagta tgcagtgtcg taagagtg                                      2128
```

<210> SEQ ID NO 4
<211> LENGTH: 3049
<212> TYPE: DNA
<213> ORGANISM: Bactrocera dorsalis

<400> SEQUENCE: 4

```
acaagacaaa tgctattcca tatacctgca gctattgttc ataataaggg atgcatatag     60
caatacaaat acaacttaat actacttttg taacaatata taaccccttca ccagagtcga    120 ttactttttac cataagtgat acaaacaacc gttaagcgaa caaaactact ctgtagcaac    180
atgttgcaag agtataaaaa tatactaggg ggattatctt gctcttgcaa gattgcagat    240
tccaaaaagc ctatacctaa atatacaagg gcacgggagc acccatagca gaatctagtg    300
atatatgaac gactgattcg gtcaatttat tgtaaatgac taatgtgcat ggctattatg    360
aattggcgaa ccttctgcat tcattctcga caaaaaaaaa ctttaacaaa tctttataat    420
ttaaaaaata aattataaaa tctatttaaa atttaccttc cttcataaaa ttatttacaa    480
cggacatcaa attgttttttc agccgtggta aaagaatcag attatttata accagaaaaa    540
tacttagagt gtgaaatatg attttgtttt tcgtaaaaat aaatgttatt taaataacaa    600
taattacttt gcaaaaaaac actatcttgt ttctactatt ttgtggtagt aacgtatctt    660
ttaaaactca atcaatagat cgttttttca gaattttttc acacaaaaca tattttgaaa    720 agatttagt cagaggagag cgtattaaaa attagatttt tatttaaatt gcgaaactgg    780
tccagtgatc aaatataata tcgaaagtgt actaagaaaa cgtgtactaa gagccctgca    840
attttcactt actaattcat acgctcgtct taaattaaat ctaatcttcg tttccaacca    900
atccaatatt attttgcctct tagtaatttta taattgataa caattaccgt agcagtatag    960
gctcatagtt ttcagacttt aagtgttaaa ggcaatttga aaaatgcgcg aaatcgtaca   1020
tatacaggcc ggacaatgtg gcaatcagat tggcggtaaa ttttgggaag tgatatctga   1080
tgaacattgc attgatgcca ccggcactta ttatggcgat agcgacttac aactagaacg   1140
tattaatgtg tattataatg aagctactgg tgccaaatat gtacctcgtg ccattttggt   1200
```

```
cgatttagaa ccgggcacta tggactcggt acgttctggg gctttcgggc aaatcttccg    1260
tccggataat tttgtatttg gtcagtcagg agcgggtaat aattgggcca agggccatta    1320
tacagaaggc gcagaactgg tcgactccgt acttgatgtt gtacgcaaag agtctgaagg    1380
atgtgattgt ctacaggtgt cgaattaaat gaaccgcata tatttgagta tggtaaagac    1440
gtaacaattt tatttattta tagggatttc agttaacgca ttctcttggt ggcggcacag    1500
gctctggcat gggcacacta ttgatatcga aaattcgtga agaatatcct gatcgtatta    1560
tgaatacatt ttctgtagtg ccctcgccaa agtatccga tactgtggta gagccataca    1620
atgctacgct cagtgtacat cagctggtag aaaacactga cgaaacatac tgcatcgaca    1680
atgaagctct atacgacatc tgtttccgta cattaaagct aactacgcca acctatggtg    1740
acctaaatca tctggtatct gcaacaatgt ctggagtaac aacatgttta cgctttcctg    1800
gtcagctaaa tgcagatctg cgaaagttgg ctgtgaatat ggttccattt cctcgtttac    1860
atttctttat gcctggtttc gctcccttga cctctcgtgg ttcgcaacag tatcgtgcac    1920
ttaccgtacc tgaattaacg caacagatgt ttgacgctaa gaacatgatg gctgcttgcg    1980
atccgcgtca tgggcggtat ttaacggtag ccgctatatt tagagggcgt atgtcaatga    2040
aggaagtgga cgaacaaatg ctgaatattc aaaataaaaa cagcagcttc tttgtggaat    2100
ggatcccaaa taactgcaaa acagctgttt gtgacatacc tccacgtggc ttaaaaatgt    2160
ccgccacatt tattggaaat tcaacagcga ttcaggaatt gtttaaacga gtttccgaac    2220
aattcacggc catgtttagg cgtaaagctt ttttgcattg gtacaccggg gagggtatgg    2280
atgagatgga gtttaccgaa gcagagagca acatgaacga tttggtatcg gaataccaac    2340
aatatcaaga agcgaccgct gatgaagagg gagaattcga cgaggatgaa gaaggaggtg    2400
gagatgaata acagttccat cagacgtaga gatgatagct aatgtgtcta attcatgagt    2460
tttgctaaat tttaactttg ggcgcagaat gcaattgtaa aattggattg tagcatactt    2520
aatttctaat ttaccccctca gtcagcactt tgtgttcata tataatattt gattcctctc    2580
tgctgtatac acgcatttca gtggaattta ttttcttgc aatcttttg aataacttgt    2640 caatagaacg aaactaaata cacaaatatg tctagaccaa attaaaaaaa taaacagatt    2700
ttgaattttg tgagggcaaa cattacttcg tatatagtgg atgtgtatat tgtaaatcaa    2760
aattaccgca atcgaactga attgagtttc tgagtggtgc aacagtttga aacactaact    2820
tacattttat gcggatattg aaccactatt tttgttttag cgccataaaa ttcaataaaa    2880
aacaggaaaa aagtaaactt cgattgcatc aggtaccttt attagctgca tttcttagat    2940
taattttttg tttaactaaa tctgaaaacg taactgagca acgttatata tattatatat    3000
tatgaaggtc tttgtttcaa accttagttt taaatggttg ttttatgcc                3049
```

<210> SEQ ID NO 5
<211> LENGTH: 4476
<212> TYPE: DNA
<213> ORGANISM: Anastrepha suspensa

<400> SEQUENCE: 5

```
cgatcggtga acgtctgaat aaattcgcgt cagtaataat acgtcgcgcg aaacgttata      60
tgcactgcag ccaaaccgag gcaacggaaa tgaatcttat gttggcaacg ggcatgctat     120
catccatcgt tataaccact ggcgcagcag tcttttcacg ctacgagggc tggagttatt     180
tcgacagttt ctattactgc tttgtgacgc tcacaaccat cggcttcggt gactatgtgg     240
cgttgcaaaa cgatcaggcg ctgatcaata aacccggcta tgtggcgctc agtttggtgt     300
```

-continued

```
ttatactatt tgggctggcg gtagttgccg ccagtatcaa tctgctagta ctgcgcttca    360
tgacaatgta atgggaaaga aagttccgca tgcgtgagtc accacatccc taggaagtgg    420
tgaatctgta cagtgacact tgggcgccgt tatgtgatga gcgacaatga cggtcgatga    480
tttataataa cggtgtgcgc gtgtcgagtt gcagcttatt gcattatttt aatcagttat    540
gttttgataa aatactaaat aaacaactac ttatttttta ggcaagccga agacgccaag    600
cgtaacgaac aggatgctca acaagccgca gccgcagctg ctgcgctctc caatcaacaa    660
ctcgcgtatg atgtcgagtc tagtaatttc aatgtgcacg gcaaattgtt ggctaactca    720
cattatacga cagagtacga cgaaaccgta tcaatctgtt catgcacatg cctcggcgga    780
acaaggtgcc tcaatcatga gacgttcgcc gatcctgatt ttcggccaac tgatatcatt    840
gagagtatct cgagtctgaa gcgtgcgtca gtttgatata tgtgtactcc catggtgtag    900
gaaaagaagt gttgctgtga ttgcctgaaa acattgtaaa gcacaattta cccggacaag    960
taaggtgttc gtacgcgcat acatactaac atactggcgt acgtacatat tcatggataa   1020
gtgcattcct tgtacttcca tatttatgca ggtacatact tagtttcata cgagatgtcc   1080
acgctttata gaacttagtt tattgaattg tatacatatt tatggatgtg tgtacgaaca   1140
tgtgcccata aaaagatta atttaaacct ccaaattccg aaatgatggt aagaggaact   1200
tctaatctac acctcgcgtg tataatgatg agaatgattc cgagattggc tattttccaa   1260
cccacaattg gaatcactta gccccctatt gaaaatcaat gtataaggtg taacataaaa   1320
tatgcatgat aaaataaaata ctactccatt ttaaataaaa tactactcca tgcgtatgta   1380
cataaacacc tatagtcgct taccaaaata gtttcacaaa ataatttaaa tacttgaaga   1440
attagaggaa tagattgtag aagttgaagc tactttaaat aaaataagtc aaaagaaaag   1500
tgttcatata aacgctcaag gttttatgca tttactgaaa tacagtaaac tcatatctat   1560
aacttatgta tgtatgtaca tatgtacaac acctatttga aatagtatgtc ttttgaaaga   1620
tatacatatg tacgcgaatg ctgacacagt gcgtaacttc aaaagcaaat caatcagtac   1680
tttgggcccg aagcactccc actctcatac atggttgcta gtcgcagtaa cttagctctg   1740
agaattcaat aaaatttcag aatattttca ccttaaacat atttcgaaaa gattttagtc   1800
agacgattgg attttttaaat tgcaaaaata cggtccaaag ataagttatc aattgttctg   1860
acagtaaatt gctaaacgga aaaagaggtc tagtcgacac gatcgtctgc actagaaatt   1920
ttaatttttct ttgctttaca accaatagaa ttttcagcaa ctgataggtc ctgttttttag   1980
tagcacacac gggtgagcta actctttaat tctaaaaaca gcagcaacag cgacatttttc   2040
aaaccaatcc taaaaaccaa taaattttgg agtgtgtgta gttggcgtgc agtaagcttt   2100
agcgaaaaca ttacaatatg cgcgaaatag tacatattca agctgggcaa tgtggcaatc   2160
agattggtgg aaagttttgg gaagtgatat ctgacgaaca ttgcatcgat gctacaggca   2220
cctattatgg tgatagcgat ttgcaactag aacgcattaa cgtctactat aatgaagcga   2280
ctggtgccaa atatgtacct cgtgccattc ttgtcgactt ggagccgggc accatggact   2340
cggtacgctc tggcgccttc ggacaaatct ttcggccaga caacttcgtg tttggacagt   2400
caggcgcggg caataattgg gctaaaggcc attacacaga aggcgctgaa ttggtcgatt   2460
cagtccttga tgtggtaagg aaagagtctg aaggatgtga ttgcttacag gtgtgtatttt   2520
acatacatat gtattaaaaa aaaaaacact tttttttttt aatttctagg ggtttcagtt   2580
aacgcattcc cttggggggtg gtacgggctc cggcatgggc acgttgttga tatcgaaaat   2640
```

```
tcgagaagag tatccagacc gtattatgaa cacattttca gtggtacctt cgccaaaggt    2700
gtcggatact gtcgtagaac catataatgc cacacttagc gtccatcagc tagtggaaaa    2760
tactgatgag acatactgta tcgacaacga ggctctctat gatatttgct tccgaacact    2820
caaactaact acgcccactt atggcgatct taatcatttg gtttcggcaa caatgtctgg    2880
tgttacgaca tgccttcgct ttcctggcca gcttaatgca gatcttcgga agttggctgt    2940
gaatatggtg ccattcccac gattgcattt ctttatgcct ggattcgctc cgttgacttc    3000
gcgtggttcg caacaatatc gtgcattaac tgtgcccgaa ctaacgcaac aaatgttcga    3060
cgctaaaaat atgatggctg cttgcgaccc acgtcatggt cgttacttga ctgtggcagc    3120
tatctttcga ggacgtatgt ctatgaagga agttgacgaa caaatgctga atatccaaaa    3180
caaaaatagc agtttcttcg tagaatggat cccgaacaat tgcaaaacag cggtatgcga    3240
cattcctccg cgtggcctaa agatgtcagc tacattcatt ggcaattcta ctgcgattca    3300
ggaattattc aaaagagttt cagaacaatt tacggcaatg tttaggcgca agcttttttt    3360
gcattggtac accggtgaag gtatggacga gatggaattc accgaggctg aaagcaatat    3420
gaatgatttg gtatcggaat atcagcagta ccaagaagca actgctgatg aagagggaga    3480
attcgacgag gacgaggaag gaggaggcga cgaataaagc tgcatcatat caactgatac    3540
cagccagacg ctgcatcttg tggccactaa atcgtaaatt tcgattgtag catgattagt    3600
ttttaattta caccacaacg agtaacgtat gttatgctat tgatttcatt cccttctcac    3660
tctatgtaat gcgtacgctt tttagtgaat ttatttttaa aacaaatctt tttgaataga    3720
ttttctataa aaaattaaaa tacaaggaat tgtgtctgga caaaatttgc gatattagaa    3780
aaagttgttt gcttactcga caatttaagt aggacttata acgatataac ttgtcgctat    3840
ctgttgttca tcaaggagca tcaccgagcc caggattac ctcgtatttt atctgtagct    3900
cgcgcattac cgcacgtaat cagagcctaa agctgggact aactctaatt ctcattttgc    3960
aacaacctaa tctacatccc gctctgactc cgtgtgaatt tcaaatagtc gtgtgtcaag    4020
taagataata ccggaatgca accacattca tcaactacaa ctgcatccct acagcagccg    4080
gttctacgtt accggaatgc ctctggtttt tcccgaccaa gggctgccgc cccagtaaac    4140
tagccctgtc tagggagcct gcgcaccacc ggcgagagga caactgactc cgttgccccc    4200
tgctgccgag ccctgcactc gcaaccgacc cctgtggtgc gaccgcccac caccatcaga    4260
ccgcaacaac aacagcggaa cgcacagcag gcccaacgta gacaaccaca cgcgtccctc    4320
acaccccgat ttacaacagy cctaaagaga aacttcaacc aagctgcacg ctagctgttc    4380
cctgataacc agcgatgact ataacatgca cagcgttcat agtccaccac acagtgcagt    4440
atcgtctgat cccgaacaat tgcaaaacag cggtat                              4476
```

<210> SEQ ID NO 6
<211> LENGTH: 309
<212> TYPE: DNA
<213> ORGANISM: Ceratitis capitata
<400> SEQUENCE: 6

```
atattttgaa aagattttag tcagacggga acgtgttaaa aattagtttt tcaaattgca      60
taacttatcc aaggatcagt aaccaactat aatatttaaa gtgtgaatgg aaattcacag     120
tatcttcgac taaagaactg cagttggatc cgatagtaaa ttgagaagcg gcaaaacctt     180
aagtaaagtc caaacttttt ttgttctaaa tacatacaaa tttttttagga catttcatac     240 cagtaggagc aggtaataag atactaacgg cgtatacgta attaaatcgg gagataattt     300
``` aaaagatgc                                                                     309

<210> SEQ ID NO 7
<211> LENGTH: 232
<212> TYPE: DNA
<213> ORGANISM: Drosophila melanogaster

<400> SEQUENCE: 7
ggaaatcgta gtagcctatt tgtgaacatt cggtgtagta atccaagcca ggttcagttc    60
acctcagtat cagctagcac gtacacgact aaaatctaaa cctgaaaaat tatacgttta   120
aatattcagt cttttgccga tttttgcccc actcagactg ttttaaaagc tcgatttttt   180
tttgtaccat ttttcggtg tgaaaaaggg ggccctactt tactatcaaa at            232

<210> SEQ ID NO 8
<211> LENGTH: 1008
<212> TYPE: DNA
<213> ORGANISM: Bactrocera dorsalis

<400> SEQUENCE: 8
acaagacaaa tgctattcca tatacctgca gctattgttc ataataaggg atgcatatag    60
caatacaaat acaacttaat actacttttg taacaatata taaccccttca ccagagtcga   120 ttactttttac cataagtgat acaaacaacc gttaagcgaa caaaactact ctgtagcaac   180
atgttgcaag agtataaaaa tatactaggg ggattatctt gctcttgcaa gattgcagat   240
tccaaaaagc ctatacctaa atatacaagg gcacgggagc acccatagca gaatctagtg   300
atatatgaac gactgattcg gtcaatttat tgtaaatgac taatgtgcat ggctattatg   360
aattggcgaa ccttctgcat tcattctcga caaaaaaaaa ctttaacaaa tctttataat   420
ttaaaaaata aattataaaa tctatttaaa atttaccttc cttcataaaa ttatttacaa   480
cggacatcaa attgttttc agccgtggta aagaatcag attatttata accagaaaaa   540
tacttagagt gtgaaatatg attttgtttt tcgtaaaaat aaatgttatt taaataacaa   600 taattactt gcaaaaaaac actatctgt ttctactatt ttgtggtagt aacgtatctt    660
ttaaaactca atcaatagat cgttttttca gaattttttc acacaaaaca tattttgaaa   720 agatttagt cagaggagag cgtattaaaa attagatttt tatttaaatt gcgaaactgg    780
tccagtgatc aaatataata tcgaaagtgt actaagaaaa cgtgtactaa gagccctgca   840
attttcactt actaattcat acgctcgtct taaattaaat ctaatcttcg tttccaacca   900
atccaatatt atttgcctct tagtaattta taattgataa caattaccgt agcagtatag   960
gctcatagtt ttcagacttt aagtgttaaa ggcaatttga aaaatgcg               1008

<210> SEQ ID NO 9
<211> LENGTH: 541
<212> TYPE: DNA
<213> ORGANISM: Aedes aegypti

<400> SEQUENCE: 9
cgccaaattt tgatagttta tgcaaaggac ttgcatgttt cccctaatgt ggggtgaat    60 cacgctatgt tcttgtggct catatatcgc ttttgtttcg tccataaacc acgtggtcat   120
tttttatgaa ttttcacgct tctccttatg atctttcgtc cacacaaaaa ttttcaaatt   180
ttgtatgcac cgtgatgctt gagcagtacc cttctccacc cataacgac cacgtggcat    240 atggacagcc cccaacgtga caacagactt cgaagcgaat gcatccagta gcacatgttg   300

```
aacgcgtcgc tcccgttttg ggggcccata ctgccgccac aatgtaaatc aatcacagtg    360
tgtcatggaa ggccatcctt cttcttgacg acccggagga cgacagttgg aaaaattttc    420
acttcgattt tcaccaccga ggaacgcgga cgtgatttgg aaccattctg cttccatctt    480
caagcatcgg aagaagcata ttttgaagcc caattttgga accgctagaa gtgctccagg    540
a                                                                   541
```

<210> SEQ ID NO 10
<211> LENGTH: 2118
<212> TYPE: DNA
<213> ORGANISM: Anastrepha suspensa

<400> SEQUENCE: 10

```
cgatcggtga acgtctgaat aaattcgcgt cagtaataat acgtcgcgcg aaacgttata     60
tgcactgcag ccaaaccgag gcaacggaaa tgaatcttat gttggcaacg ggcatgctat    120
catccatcgt tataaccact ggcgcagcag tcttttcacg ctacgagggc tggagttatt    180
tcgacagttt ctattactgc tttgtgacgc tcacaaccat cggcttcggt gactatgtgg    240
cgttgcaaaa cgatcaggcg ctgatcaata aacccggcta tgtggcgctc agtttggtgt    300
ttatactatt tgggctggcg gtagttgccg ccagtatcaa tctgctagta ctgcgcttca    360
tgacaatgta atgggaaaga aagttccgca tgcgtgagtc accacatccc taggaagtgg    420
tgaatctgta cagtgacact tgggcgccgt tatgtgatga cgacaatga cggtcgatga    480 tttataataa cggtgtgcgc gtgtcgagtt gcagcttatt gcattatttt aatcagttat    540
gttttgataa aatactaaat aaacaactac ttatttttta ggcaagccga agacgccaag    600
cgtaacgaac aggatgctca acaagccgca gccgcagctg ctgcgctctc caatcaacaa    660
ctcgcgtatg atgtcgagtc tagtaatttc aatgtgcacg gcaaattgtt ggctaactca    720
cattatacga cagagtacga cgaaaccgta tcaatctgtt catgcacatg cctcggcgga    780
acaaggtgcc tcaatcatga gacgttcgcc gatcctgatt tcggccaac tgatatcatt    840 gagagtatct cgagtctgaa gcgtgcgtca gtttgatata tgtgtactcc catggtgtag    900
gaaaagaagt gttgctgtga ttgcctgaaa acattgtaaa gcacaattta cccggacaag    960
taaggtgttc gtacgcgcat acatactaac atactggcgt acgtacatat tcatggataa   1020
gtgcattcct tgtacttcca tatttatgca ggtacatact tagtttcata cgagatgtcc   1080
acgctttata gaacttagtt tattgaattg tatacatatt tatggatgtg tgtacgaaca   1140
tgtgcccata aaaagatta atttaaacct ccaaattccg aaatgatggt aagaggaact   1200
tctaatctac acctcgcgtg tataatgatg agaatgattc cgagattggc tattttccaa   1260
cccacaattg gaatcactta gccccctatt gaaaatcaat gtataaggtg taacataaaa   1320
tatgcatgat aaataaaata ctactccatt ttaaataaaa tactactcca tgcgtatgta   1380
cataaacacc tatagtcgct taccaaaata gtttcacaaa ataatttaaa tacttgaaga   1440
attagaggaa tagattgtag aagttgaagc tactttaaat aaaataagtc aaaagaaaag   1500
tgttcatata aacgctcaag gttttatgca tttactgaaa tacagtaaac tcatatctat   1560
aacttatgta tgtatgtaca tatgtacaac acctatttga atagtatgtc ttttgaaaga   1620
tatacatatg tacgcgaatg ctgacacagt gcgtaacttc aaaagcaaat caatcagtac   1680
tttgggcccg aagcactccc actctccatac atggttgcta gtcgcagtaa cttagctctg   1740
agaattcaat aaaatttcag aatatttca ccttaaacat atttcgaaaa gattttagtc   1800
agacgattgg attttttaaat tgcaaaaata cggtccaaag ataagttatc aattgttctg   1860
```

```
acagtaaatt gctaaacgga aaaagaggtc tagtcgacac gatcgtctgc actagaaatt     1920
ttaattttct ttgctttaca accaatagaa ttttcagcaa ctgataggtc ctgtttttag     1980
tagcacacac gggtgagcta actctttaat tctaaaaaca gcagcaacag cgacattttc     2040
aaaccaatcc taaaaaccaa taaattttgg agtgtgtgta gttggcgtgc agtaagcttt     2100
agcggaaaca ttacaata                                                  2118

<210> SEQ ID NO 11
<211> LENGTH: 213
<212> TYPE: DNA
<213> ORGANISM: Ceratitis capitata

<400> SEQUENCE: 11
cagttcttgg ttttggaga tggtaatagg aaaaaatctc tatatcttta cttaattaat      60
attattatgc gctcctcaca attgtaaaat ccaattgtag cttttgttc acttctcagc     120 aagtattttg tattatgtac tatttgcttt tcttgtgcgc aagtatacgc ttttagtaaa     180
atttaaaata aaaaaaaaa aaaaaaaaa aaa                                   213

<210> SEQ ID NO 12
<211> LENGTH: 299
<212> TYPE: DNA
<213> ORGANISM: Drosophila melanogaster

<400> SEQUENCE: 12
taggattaac ttcccactca agatcacaca tgaacaccaa acaggctag caggggaacc      60 cattaggaag gcacaataca ttggatcttt gggccttagc atattgtgct tcgaggcccg    120
tcggttgtac atatttccta tatggattct tcactgttcg attatttatc attcacacac    180
gtacagaaga attatgtcca ctttgttaag ctcatgttgc aattgctgtg atttctgggt    240
tacgaataaa tgttgattta taagcagaca agattaccaa cagcattttg catattttt     299

<210> SEQ ID NO 13
<211> LENGTH: 193
<212> TYPE: DNA
<213> ORGANISM: Bactrocera dorsalis

<400> SEQUENCE: 13
agaaggaata aaaatggctg aaattatccg ttatcatact gtgaattgaa gatcctattg      60
ttgtaattgc tgaaataaaa tcttgtttcc taatttgtat ctgtattatt tttgcaattt    120 ctgttttca tcacgtcaat cagtcatgaa aattttactt tcctgcacag aagtatgcag     180
tgtcgtaaga gtg                                                       193

<210> SEQ ID NO 14
<211> LENGTH: 638
<212> TYPE: DNA
<213> ORGANISM: Bactrocera dorsalis

<400> SEQUENCE: 14
cagttccatc agacgtagag atgatagcta atgtgtctaa ttcatgagtt ttgctaaatt      60 ttaacttttgg gcgcagaatg caattgtaaa attggattgt agcatactta atttctaatt    120 taccccctcag tcagcacttt gtgttcatat ataatatttg attcctctct gctgtataca    180
cgcatttcag tggaatttat ttttcttgca atcttttga ataacttgtc aatagaacga     240
aactaaatac acaaatatgt ctagaccaaa ttaaaaaat aaacagattt tgaattttgt     300
```

```
gagggcaaac attacttcgt atatagtgga tgtgtatatt gtaaatcaaa attaccgcaa      360
tcgaactgaa ttgagtttct gagtggtgca acagtttgaa acactaactt acattttatg      420
cggatattga accactattt ttgttttagc gccataaaat tcaataaaaa acaggaaaaa      480
agtaaacttc gattgcatca ggtaccttta ttagctgcat ttcttagatt aattttttgt      540
ttaactaaat ctgaaaacgt aactgagcaa cgttatatat attatatatt atgaaggtct      600
ttgtttcaaa ccttagtttt aaatggttgt tttatgcc                             638
```

<210> SEQ ID NO 15
<211> LENGTH: 959
<212> TYPE: DNA
<213> ORGANISM: Anastrepha suspensa

<400> SEQUENCE: 15

```
agctgcatca tatcaactga taccagccag acgctgcatc ttgtggccac taaatcgtaa       60
atttcgattg tagcatgatt agttttaat ttacaccaca acgagtaacg tatgttatgc       120
tattgatttc attcccttct cactctatgt aatgcgtacg cttttagtg aatttatttt       180 taaaacaaat cttttgaat agattttcta taaaaaatta aaatacaagg aattgtgtct       240
ggacaaaatt tgcgatatta gaaaaagttg tttgcttact cgacaattta agtaggactt       300
ataacgatat aacttgtcgc tatctgttgt tcatcaagga gcatcaccga gccccaggat       360
tacctcgtat tttatctgta gctcgcgcat taccgcacgt aatcagagcc taaagctggg       420
actaactcta attctcattt tgcaacaacc taatctacat cccgctctga ctccgtgtga       480
atttcaaata gtcgtgtgtc aagtaagata taccggaat gcaaccacat tcatcaacta       540
caactgcatc cctacagcag ccggttctac gttaccggaa tgcctctggt ttttcccgac       600
caagggctgc cgccccagta aactagccct gtctagggag cctgcgcacc accggcgaga       660
ggacaactga ctccgttgcc ccctgctgcc gagccctgca ctcgcaaccg acccctgtgg       720
tgcgaccgcc caccaccatc agaccgcaac aacaacagcg gaacgcacag caggcccaac       780
gtagacaacc acacgcgtcc ctcacacccc gatttacaac agycctaaag agaaacttca       840
accaagctgc acgctagctg ttccctgata accagcgatg actataacat gcacagcgtt       900
catagtccac cacacagtgc agtatcgtct gatcccgaac aattgcaaaa cagcggtat       959
```

<210> SEQ ID NO 16
<211> LENGTH: 1014
<212> TYPE: DNA
<213> ORGANISM: artificial
<220> FEATURE:
<223> OTHER INFORMATION: tTAV ORF
<220> FEATURE:
<221> NAME/KEY: CDS
<222> LOCATION: (1)..(1014)

<400> SEQUENCE: 16

```
atg ggc agc cgc ctg gat aag tcc aaa gtc atc aac tcc gcg ttg gag       48
Met Gly Ser Arg Leu Asp Lys Ser Lys Val Ile Asn Ser Ala Leu Glu
1               5                   10                  15 ctg ttg aac gaa gtt ggc att gag gga ctg acg acc cgc aag ttg gcg       96
Leu Leu Asn Glu Val Gly Ile Glu Gly Leu Thr Thr Arg Lys Leu Ala
            20                  25                  30 cag aag ctg ggc gtg gag cag ccc acc ctc tac tgg cac gtg aag aat      144
Gln Lys Leu Gly Val Glu Gln Pro Thr Leu Tyr Trp His Val Lys Asn
        35                  40                  45 aag cgg gcg ctg ctg gat gcc ctg gcc atc gag atg ctc gac cgc cac      192
Lys Arg Ala Leu Leu Asp Ala Leu Ala Ile Glu Met Leu Asp Arg His
```

```
cac acg cat ttt tgc ccg ttg gaa ggc gag tcc tgg cag gac ttc ctc      240
His Thr His Phe Cys Pro Leu Glu Gly Glu Ser Trp Gln Asp Phe Leu
 65                  70                  75                  80 cgc aat aac gcc aag tcg ttc cgc tgc gct ctg ctg tcc cac cga gac      288
Arg Asn Asn Ala Lys Ser Phe Arg Cys Ala Leu Leu Ser His Arg Asp
                 85                  90                  95 ggt gcc aaa gtc cat ctc ggc acg cgc ccg acc gaa aag caa tac gag      336
Gly Ala Lys Val His Leu Gly Thr Arg Pro Thr Glu Lys Gln Tyr Glu
            100                 105                 110 aca ctg gag aac cag ctc gcg ttc ctg tgc cag caa ggc ttc agc ctg      384
Thr Leu Glu Asn Gln Leu Ala Phe Leu Cys Gln Gln Gly Phe Ser Leu
        115                 120                 125 gaa aat gct ctc tac gct ctg agc gcc gtc ggt cac ttt acc ctg ggc      432
Glu Asn Ala Leu Tyr Ala Leu Ser Ala Val Gly His Phe Thr Leu Gly
    130                 135                 140 tgc gtg ctg gag gac caa gag cat caa gtc gca aaa gag gag cgc gag      480
Cys Val Leu Glu Asp Gln Glu His Gln Val Ala Lys Glu Glu Arg Glu
145                 150                 155                 160 acc cca aca acc gat tcg atg ccc cca ctg ctg cgt cag gca atc gag      528
Thr Pro Thr Thr Asp Ser Met Pro Pro Leu Leu Arg Gln Ala Ile Glu
                165                 170                 175 ctg ttc gat cat caa gga gcc gag ccg gca ttc ctg ttc ggc ttg gag      576
Leu Phe Asp His Gln Gly Ala Glu Pro Ala Phe Leu Phe Gly Leu Glu
            180                 185                 190 ctg att atc tgc gga ttg gaa aag caa ctg aaa tgc gag tcg ggc tcg      624
Leu Ile Ile Cys Gly Leu Glu Lys Gln Leu Lys Cys Glu Ser Gly Ser
        195                 200                 205 ggc ccc gcg tac agc cgc gcg cgt acg aaa aac aat tac ggg tct acc      672
Gly Pro Ala Tyr Ser Arg Ala Arg Thr Lys Asn Asn Tyr Gly Ser Thr
    210                 215                 220 atc gag ggc ctg ctc gat ctc ccg gac gac gac gcc ccc gaa gag gcg      720
Ile Glu Gly Leu Leu Asp Leu Pro Asp Asp Asp Ala Pro Glu Glu Ala
225                 230                 235                 240 ggg ctg gcg gct ccg cgc ctg tcc ttt ctc ccc gcg gga cac acg cgc      768
Gly Leu Ala Ala Pro Arg Leu Ser Phe Leu Pro Ala Gly His Thr Arg
                245                 250                 255 aga ctg tcg acg gcc ccc ccg acc gat gtc agc ctg ggg gac gag ctc      816
Arg Leu Ser Thr Ala Pro Pro Thr Asp Val Ser Leu Gly Asp Glu Leu
            260                 265                 270 cac tta gac ggc gag gac gtg gcg atg gcg cat gcc gac gcg cta gac      864
His Leu Asp Gly Glu Asp Val Ala Met Ala His Ala Asp Ala Leu Asp
        275                 280                 285 gat ttc gat ctg gac atg ttg ggg gac ggg gat tcc ccg ggt ccg gga      912
Asp Phe Asp Leu Asp Met Leu Gly Asp Gly Asp Ser Pro Gly Pro Gly
    290                 295                 300 ttt acc ccc cac gac tcc gcc ccc tac ggc gct ctg gat atg gcc gac      960
Phe Thr Pro His Asp Ser Ala Pro Tyr Gly Ala Leu Asp Met Ala Asp
305                 310                 315                 320 ttc gag ttt gag cag atg ttt acc gat gcc ctt gga att gac gag tac     1008
Phe Glu Phe Glu Gln Met Phe Thr Asp Ala Leu Gly Ile Asp Glu Tyr
                325                 330                 335 ggt ggg                                                             1014
Gly Gly <210> SEQ ID NO 17
<211> LENGTH: 338
<212> TYPE: PRT
<213> ORGANISM: artificial
<220> FEATURE:
```

<223> OTHER INFORMATION: Synthetic Construct

<400> SEQUENCE: 17

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Gly Pro Ala Tyr Ser Arg Ala Arg Thr Lys Asn Asn Tyr Gly Ser Thr
    210                 215                 220

Ile Glu Gly Leu Leu Asp Leu Pro Asp Asp Ala Pro Glu Glu Ala
225                 230                 235                 240

Gly Leu Ala Ala Pro Arg Leu Ser Phe Leu Pro Ala Gly His Thr Arg
                245                 250                 255

Arg Leu Ser Thr Ala Pro Pro Thr Asp Val Ser Leu Gly Asp Glu Leu
            260                 265                 270

His Leu Asp Gly Glu Asp Val Ala Met Ala His Ala Asp Ala Leu Asp
        275                 280                 285

Asp Phe Asp Leu Asp Met Leu Gly Asp Gly Asp Ser Pro Gly Pro Gly
    290                 295                 300

Phe Thr Pro His Asp Ser Ala Pro Tyr Gly Ala Leu Asp Met Ala Asp
305                 310                 315                 320

Phe Glu Phe Glu Gln Met Phe Thr Asp Ala Leu Gly Ile Asp Glu Tyr
                325                 330                 335

Gly Gly
```

<210> SEQ ID NO 18
<211> LENGTH: 1014
<212> TYPE: DNA
<213> ORGANISM: artificial
<220> FEATURE:
<223> OTHER INFORMATION: tTAV2 ORF
<220> FEATURE:
<221> NAME/KEY: CDS
<222> LOCATION: (1)..(1014)

<400> SEQUENCE: 18

| | |
|---|---:|
| atg agc cgc ctg gat aag tcc aaa gtc atc aac tcc gcg ttg gag ctg<br>Met Ser Arg Leu Asp Lys Ser Lys Val Ile Asn Ser Ala Leu Glu Leu<br>1                         5                    10                 15 | 48 |
| ttg aac gaa gtt ggc att gag gga ctg acg acc cgc aag ttg gcg cag<br>Leu Asn Glu Val Gly Ile Glu Gly Leu Thr Thr Arg Lys Leu Ala Gln<br>                20                    25                    30 | 96 |
| aag ctg ggc gtg gag cag ccc acc ctc tac tgg cac gtg aag aat aag<br>Lys Leu Gly Val Glu Gln Pro Thr Leu Tyr Trp His Val Lys Asn Lys<br>        35                    40                    45 | 144 |
| cgg gcg ctg ctg gat gcc ctg gcc atc gag atg ctc gac cgc cac cac<br>Arg Ala Leu Leu Asp Ala Leu Ala Ile Glu Met Leu Asp Arg His His<br>50                        55                    60 | 192 |
| acg cat ttt tgc ccg ttg gaa ggc gag tcc tgg cag gac ttc ctc cgc<br>Thr His Phe Cys Pro Leu Glu Gly Glu Ser Trp Gln Asp Phe Leu Arg<br>65                        70                    75                    80 | 240 |
| aat aac gcc aag tcg ttc cgc tgc gct ctg ctg tcc cac cga gac ggt<br>Asn Asn Ala Lys Ser Phe Arg Cys Ala Leu Leu Ser His Arg Asp Gly<br>                85                    90                    95 | 288 |
| gcc aaa gtc cat ctc ggc acg cgc ccg acc gaa aag caa tac gag aca<br>Ala Lys Val His Leu Gly Thr Arg Pro Thr Glu Lys Gln Tyr Glu Thr<br>                  100                   105                  110 | 336 |
| ctg gag aac cag ctc gcg ttc ctg tgc cag caa ggc ttc agc ctg gaa<br>Leu Glu Asn Gln Leu Ala Phe Leu Cys Gln Gln Gly Phe Ser Leu Glu<br>                115                   120                  125 | 384 |
| aat gct ctc tac gct ctg agc gcc gtc ggt cac ttt acc ctg ggc tgc<br>Asn Ala Leu Tyr Ala Leu Ser Ala Val Gly His Phe Thr Leu Gly Cys<br>130                       135                   140 | 432 |
| gtg ctg gag gac caa gag cat caa gtc gca aaa gag gag cgc gag acc<br>Val Leu Glu Asp Gln Glu His Gln Val Ala Lys Glu Glu Arg Glu Thr<br>145                       150                   155                160 | 480 |
| cca aca acc gat tcg atg ccc cca ctg ctg cgt cag gca atc gag ctg<br>Pro Thr Thr Asp Ser Met Pro Pro Leu Leu Arg Gln Ala Ile Glu Leu<br>                         165                   170                  175 | 528 |
| ttc gat cat caa gga gcc gag ccg gca ttc ctg ttc ggc ttg gag ctg<br>Phe Asp His Gln Gly Ala Glu Pro Ala Phe Leu Phe Gly Leu Glu Leu<br>                  180                   185                  190 | 576 |
| att atc tgc gga ttg gaa aag caa ctg aaa tgc gag tcg ggc tcg ggc<br>Ile Ile Cys Gly Leu Glu Lys Gln Leu Lys Cys Glu Ser Gly Ser Gly<br>                195                   200                  205 | 624 |
| ccc gcc tac agc cgc gcc cgc acc aag aac aac tac ggc agc acc atc<br>Pro Ala Tyr Ser Arg Ala Arg Thr Lys Asn Asn Tyr Gly Ser Thr Ile<br>210                     215                   220 | 672 |
| gag ggc ctg ctg gat ctg ccg gat gat gat gcc ccg gag gag gcg ggc<br>Glu Gly Leu Leu Asp Leu Pro Asp Asp Asp Ala Pro Glu Glu Ala Gly<br>225                       230                   235                240 | 720 |
| ctg gcc gcc ccg cgc ctg agc ttc ctg ccg gcc gga cac acc cgc cgc<br>Leu Ala Ala Pro Arg Leu Ser Phe Leu Pro Ala Gly His Thr Arg Arg<br>                    245                   250                  255 | 768 |
| ctg tcg acc gcc ccg ccg acc gac gtg agc ctg ggc gat gag ctg cac<br>Leu Ser Thr Ala Pro Pro Thr Asp Val Ser Leu Gly Asp Glu Leu His<br>                260                   265                  270 | 816 |
| ctg gat ggc gag gat gtg gcg atg gcc cac gcc gat gcc ctg gac gac<br>Leu Asp Gly Glu Asp Val Ala Met Ala His Ala Asp Ala Leu Asp Asp<br>            275                   280                  285 | 864 |
| ttc gac ctg gac atg ctg ggc gat ggc gat agc ccg gga ccg gga ttc<br>Phe Asp Leu Asp Met Leu Gly Asp Gly Asp Ser Pro Gly Pro Gly Phe<br>290                       295                   300 | 912 |

```
acc ccg cac gat agc gcc ccc tac ggc gcc ctg gat atg gcc gat ttc      960
Thr Pro His Asp Ser Ala Pro Tyr Gly Ala Leu Asp Met Ala Asp Phe
305                 310                 315                 320 gag ttc gag cag atg ttc acc gac gcc ctg ggc atc gat gag tac ggc     1008
Glu Phe Glu Gln Met Phe Thr Asp Ala Leu Gly Ile Asp Glu Tyr Gly
                325                 330                 335 ggc taa                                                              1014
Gly
```

<210> SEQ ID NO 19
<211> LENGTH: 337
<212> TYPE: PRT
<213> ORGANISM: artificial
<220> FEATURE:
<223> OTHER INFORMATION: Synthetic Construct

<400> SEQUENCE: 19

```
Met Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Glu Gly Glu Ser Trp Gln Asp Phe Leu Arg
65                  70                  75                  80

Asn Asn Ala Lys Ser Phe Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160

Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Gly
        195                 200                 205

Pro Ala Tyr Ser Arg Ala Arg Thr Lys Asn Asn Tyr Gly Ser Thr Ile
    210                 215                 220

Glu Gly Leu Leu Asp Leu Pro Asp Asp Ala Pro Glu Glu Ala Gly
225                 230                 235                 240

Leu Ala Ala Pro Arg Leu Ser Phe Leu Pro Ala Gly His Thr Arg Arg
                245                 250                 255

Leu Ser Thr Ala Pro Pro Thr Asp Val Ser Leu Gly Asp Glu Leu His
            260                 265                 270

Leu Asp Gly Glu Asp Val Ala Met Ala His Ala Asp Ala Leu Asp Asp
        275                 280                 285

Phe Asp Leu Asp Met Leu Gly Asp Gly Asp Ser Pro Gly Pro Gly Phe
    290                 295                 300

Thr Pro His Asp Ser Ala Pro Tyr Gly Ala Leu Asp Met Ala Asp Phe
```

```
                305                 310                 315                 320
Glu Phe Glu Gln Met Phe Thr Asp Ala Leu Gly Ile Asp Tyr Gly
                    325                 330                 335

Gly

<210> SEQ ID NO 20
<211> LENGTH: 1011
<212> TYPE: DNA
<213> ORGANISM: artificial
<220> FEATURE:
<223> OTHER INFORMATION: tTAV3 ORF
<220> FEATURE:
<221> NAME/KEY: CDS
<222> LOCATION: (1)..(1011)

<400> SEQUENCE: 20 atg ggc agc cgc ctg gac aag agc aag gtg atc aac agc gcc ctg gag      48
Met Gly Ser Arg Leu Asp Lys Ser Lys Val Ile Asn Ser Ala Leu Glu
1               5                   10                  15 ctg ctg aac gaa gtt ggt atc gag ggc ctg acc acc cgc aag ctg gcc      96
Leu Leu Asn Glu Val Gly Ile Glu Gly Leu Thr Thr Arg Lys Leu Ala
            20                  25                  30 cag aag ctg ggc gtg gaa cag ccg acc ctg tac tgg cac gtg aag aac     144
Gln Lys Leu Gly Val Glu Gln Pro Thr Leu Tyr Trp His Val Lys Asn
        35                  40                  45 aag cgc gcc ctg ctg gac gcc ctg gcc atc gaa atg ctg gat cgc cac     192
Lys Arg Ala Leu Leu Asp Ala Leu Ala Ile Glu Met Leu Asp Arg His
    50                  55                  60 cac acc cac ttc tgc ccg ctg gag ggc gag agc tgg cag gat ttc ctg     240
His Thr His Phe Cys Pro Leu Glu Gly Glu Ser Trp Gln Asp Phe Leu
65                  70                  75                  80 cgc aac aac gcc aag agc ttc cgc tgc gcc ctg ctg tcg cac cgc gat     288
Arg Asn Asn Ala Lys Ser Phe Arg Cys Ala Leu Leu Ser His Arg Asp
                85                  90                  95 ggc gcc aag gtg cac ctg ggc acc cgc ccg acc gag aag cag tac gag     336
Gly Ala Lys Val His Leu Gly Thr Arg Pro Thr Glu Lys Gln Tyr Glu
            100                 105                 110 acc ctg gag aac cag ctg gcc ttc ctg tgc cag cag ggc ttc agc ctg     384
Thr Leu Glu Asn Gln Leu Ala Phe Leu Cys Gln Gln Gly Phe Ser Leu
        115                 120                 125 gag aac gcc ctg tac gcc ctg agc gcc gtg ggc cac ttc acc ctg ggc     432
Glu Asn Ala Leu Tyr Ala Leu Ser Ala Val Gly His Phe Thr Leu Gly
    130                 135                 140 tgt gtg ctg gag gat cag gag cac cag gtg gcc aag gag gag cgc gag     480
Cys Val Leu Glu Asp Gln Glu His Gln Val Ala Lys Glu Glu Arg Glu
145                 150                 155                 160 acc ccg acc acc gat agc atg ccg ccg ctg ctg cgc cag gcc atc gag     528
Thr Pro Thr Thr Asp Ser Met Pro Pro Leu Leu Arg Gln Ala Ile Glu
                165                 170                 175 ctg ttc gat cac cag ggc gcc gag ccg gcc ttc ctg ttc ggc ctg gag     576
Leu Phe Asp His Gln Gly Ala Glu Pro Ala Phe Leu Phe Gly Leu Glu
            180                 185                 190 ctg atc atc tgc ggc ctg gaa aag cag ctg aag tgc gag agc ggc agc     624
Leu Ile Ile Cys Gly Leu Glu Lys Gln Leu Lys Cys Glu Ser Gly Ser
        195                 200                 205 gcc tac agc cgc gcc cgt acc aag aac aac tat ggc agc acc atc gag     672
Ala Tyr Ser Arg Ala Arg Thr Lys Asn Asn Tyr Gly Ser Thr Ile Glu
    210                 215                 220 gga ctg ctg gac ctg ccg gat gac gat gcc ccg gag gaa gcc ggc ctg     720
Gly Leu Leu Asp Leu Pro Asp Asp Asp Ala Pro Glu Glu Ala Gly Leu
225                 230                 235                 240
```

```
gcc gcc ccc cgc ctg agc ttc ctg ccc gcc gga cac acg cgc cgc ctg      768
Ala Ala Pro Arg Leu Ser Phe Leu Pro Ala Gly His Thr Arg Arg Leu
            245                 250                 255 agc acc gcc ccg ccg acc gat gtg agc ctg ggc gac gag ctg cac ctg      816
Ser Thr Ala Pro Pro Thr Asp Val Ser Leu Gly Asp Glu Leu His Leu
        260                 265                 270 gat gga gag gat gtg gca atg gcc cac gcc gac gcc ctg gac gat ttc      864
Asp Gly Glu Asp Val Ala Met Ala His Ala Asp Ala Leu Asp Asp Phe
    275                 280                 285 gac ctg gat atg ctg ggc gat gga gat agc ccg gga ccg ggc ttc acg      912
Asp Leu Asp Met Leu Gly Asp Gly Asp Ser Pro Gly Pro Gly Phe Thr
290                 295                 300 ccc cac gat agc gcc ccg tac ggc gcc ctg gac atg gcc gac ttc gag      960
Pro His Asp Ser Ala Pro Tyr Gly Ala Leu Asp Met Ala Asp Phe Glu
305                 310                 315                 320 ttc gag caa atg ttc acc gac gcg ctg ggc atc gat gag tat ggc ggg     1008
Phe Glu Gln Met Phe Thr Asp Ala Leu Gly Ile Asp Glu Tyr Gly Gly
                325                 330                 335 tag                                                                 1011
```

<210> SEQ ID NO 21
<211> LENGTH: 336
<212> TYPE: PRT
<213> ORGANISM: artificial
<220> FEATURE:
<223> OTHER INFORMATION: Synthetic Construct

<400> SEQUENCE: 21

```
Met Gly Ser Arg Leu Asp Lys Ser Lys Val Ile Asn Ser Ala Leu Glu
1               5                   10                  15

Leu Leu Asn Glu Val Gly Ile Glu Gly Leu Thr Thr Arg Lys Leu Ala
            20                  25                  30

Gln Lys Leu Gly Val Glu Gln Pro Thr Leu Tyr Trp His Val Lys Asn
        35                  40                  45

Lys Arg Ala Leu Leu Asp Ala Leu Ala Ile Glu Met Leu Asp Arg His
    50                  55                  60

His Thr His Phe Cys Pro Leu Glu Gly Glu Ser Trp Gln Asp Phe Leu
65                  70                  75                  80

Arg Asn Asn Ala Lys Ser Phe Arg Cys Ala Leu Leu Ser His Arg Asp
                85                  90                  95

Gly Ala Lys Val His Leu Gly Thr Arg Pro Thr Glu Lys Gln Tyr Glu
            100                 105                 110

Thr Leu Glu Asn Gln Leu Ala Phe Leu Cys Gln Gln Gly Phe Ser Leu
        115                 120                 125

Glu Asn Ala Leu Tyr Ala Leu Ser Ala Val Gly His Phe Thr Leu Gly
    130                 135                 140

Cys Val Leu Glu Asp Gln Glu His Gln Val Ala Lys Glu Glu Arg Glu
145                 150                 155                 160

Thr Pro Thr Thr Asp Ser Met Pro Pro Leu Leu Arg Gln Ala Ile Glu
                165                 170                 175

Leu Phe Asp His Gln Gly Ala Glu Pro Ala Phe Leu Phe Gly Leu Glu
            180                 185                 190

Leu Ile Ile Cys Gly Leu Glu Lys Gln Leu Lys Cys Glu Ser Gly Ser
        195                 200                 205

Ala Tyr Ser Arg Ala Arg Thr Lys Asn Asn Tyr Gly Ser Thr Ile Glu
    210                 215                 220
```

```
Gly Leu Leu Asp Leu Pro Asp Asp Asp Ala Pro Glu Glu Ala Gly Leu
225                 230                 235                 240

Ala Ala Pro Arg Leu Ser Phe Leu Pro Ala Gly His Thr Arg Arg Leu
            245                 250                 255

Ser Thr Ala Pro Pro Thr Asp Val Ser Leu Gly Asp Glu Leu His Leu
        260                 265                 270

Asp Gly Glu Asp Val Ala Met Ala His Ala Asp Ala Leu Asp Asp Phe
    275                 280                 285

Asp Leu Asp Met Leu Gly Asp Gly Asp Ser Pro Gly Pro Gly Phe Thr
    290                 295                 300

Pro His Asp Ser Ala Pro Tyr Gly Ala Leu Asp Met Ala Asp Phe Glu
305                 310                 315                 320

Phe Glu Gln Met Phe Thr Asp Ala Leu Gly Ile Asp Glu Tyr Gly Gly
                325                 330                 335

<210> SEQ ID NO 22
<211> LENGTH: 175
<212> TYPE: DNA
<213> ORGANISM: D. melanogaster

<400> SEQUENCE: 22
agttcacctc agtatcagct agcacgtaca cgactaaaat ctaaacctga aaaattatac      60
gtttaaatat tcagtctttt gccgattttt gccccactca gactgtttta aaagctcgat    120
ttttttttgt accattttttt cggtgtgaaa aggggggccc tactttacta tcaaa         175

<210> SEQ ID NO 23
<211> LENGTH: 3960
<212> TYPE: DNA
<213> ORGANISM: Drosophila melanogaster

<400> SEQUENCE: 23
tcctttattg agattaacgg tcaaatcaat agataaaaga aaacttatta catatttaaa      60
gaatgatgaa attttttaaaa ttcattgtat catatgttat tcggccactg taaccgaaat   120
caaccatttt tggcggatgc tgtgtgtttg ttttgctgac aactatcgat tttgtcagac    180
gcagcatctt taactgaacg aaaaaggcgc gtggtgcaaa atatattaat tgattataga    240
tcgtagtgat tatatttgag actatatgat gaagcgacag aatgtccgta ccctttccct    300
ggtggtatgc actttcacct atcttttaat tggagccgcc gtgttcgatt ccctggagtc    360
accaacggag gccaaaagat gggaattcct acagagtgag aagcttgttg atttattaac    420
ctaatttctt agtaatgaat ttatttaatc aattgtagcc gttaagaaca actttgttag    480
aaagtacaat gtgactgacg aggatttccg tgtgatggaa atcgtcatca ttgaaaataa    540
gccccacaag gccggacctc agtggaaatt cgctggagct ttctatttca gcacggttgt    600
actggcaatg ataggtaaat taattatcta ttaaatatga tttattgaat agattataat    660
tctgttgtaa ctttctttag gatatggtca ttctacgcca gttacaattc cgggaaaagc    720
attttgtatg ggctatgcta tggtaagtga acttacaatc ccaatttcca gtcttctaaa    780
gatattccct tattaggtgg gcatcccgct gggtctggtg atgttccagt ctatcggaga    840
acgtctgaat aagtttgcat ccgtgataat aaggcgggca aagagagcca gtggagctcg    900
ctgtacggat gccaccgaaa tgaatctcat gttggccacc ggaatgctct cctccataat    960
aatcaccact ggagcagcag tcttttcccg atacgagggt tggagctact tcgatagctt   1020
ctactattgt tttgtcacct tgacgacaat tggtttcggc gattatgtgg cattgcagaa   1080
```

```
cgaccaagct ctaactaata agcctggcta tgtggcgctg agcttggtct tcatcctatt   1140
cggcttggcc gtggtggccg ccagtatcaa tctattggtg ctccgattca tgaccatgtg   1200
agtccatgtt ctattgcagg aaatatctta tttaatggat ttttaatcac aggcaagcag   1260
aggatgccaa gagagatgag caggatgctc agaacttggc tggaaatgcc cagccggtga   1320
ccttcgatga tgagtccacg tacaatatgc acggcaagct gctggagaac aactacacaa   1380
cggagaacga tgagaccgcc tccctgtgtt cctgcacctg catgggtggc accaggtgcc   1440
tgaatcatga gcagttcgtg gacccggact ttcagcctac cgacattatc gagagcacct   1500
tgtgcctgaa gcgagcctcc gtctgatatc cgtacagcca gctgtgggac tcctcattgt   1560
aggagccaga gccaatggat caccaaatcg tagttacaat cctgtagaga accatccgcc   1620
gccaaaattt ggttgttaga caaaccttcc tccctacgta gattttaaa ccaggatggg    1680
tcataataca tataagtttg gagagcaagg ttaatagtct ttaaaaggca gttttgctt    1740
aagaaataat cgacccatcc cattatacac ccatataaac atttacaaag gagtaaaatc   1800
caggacatcc atgtcaatat caatcgtatc atctggtcgg tagccttgga atcctctatt   1860
gcttccaagg caccgccaaa tccatcccat ctcgaatttt agccgtatat tcgtttatct   1920
atgtaagtac tattaaagtt tgtgctcaaa acggagaact gagttttctg aaatcggggt   1980
gtgtgaaatg tgtcgaagtc ggaaatcgta gtagcctatt tgtgaacatt cggtgtagta   2040
atccaagcca ggttcagttc acctcagtat cagctagcac gtacacgact aaaatctaaa   2100
cctgaaaaat tatacgtttta aatattcagt cttttgccga tttttgcccc actcagactg   2160
ttttaaaagc tcgattttt tttgtaccat ttttttcggtg tgaaaagggg ccctaactt    2220
tactatcaaa atgcgtgaaa ttgtacacat tcaggccggt caatgcggta accagatcgg   2280
tggtaaattc tgggaggtaa tctcggatga gcactgtata gatgcgaccg gaacgtacta   2340
cggcgatagt gatctccagc tggagcgcat caatgtatac tacaatgaag ccaccggtgc   2400
caagtatgtg ccacgcgcaa ttctcgtgga cctggagccc ggcaccatgg attcggttcg   2460
ttctggcgcc tttggccaga tcttccggcc ggacaatttt gtgtttggcc aatcgggagc   2520
aggcaacaac tgggccaagg gtcattacac cgagggtgct gaactggtgg attccgtctt   2580
ggatgtggtg cgaaaggagt ccgagggatg cgattgcctt caggtaagtt ttgggggttt   2640
gggaatttat ctgaaaaagt ttaccctact tttctccaac agggcttcca gctgacccac   2700
tcgctgggtg gcggcactgg ctccggcatg ggaaccctgc tgatctcgaa gatccgcgag   2760
gagtacccgg accgcatcat gaacaccttc tcggtggtgc cctcgcccaa ggtgtccgat   2820
acggtggtgg agccctacaa tgccaccctg agtgtgcatc agctggtgga gaacaccgat   2880
gagacgtact gcatcgacaa cgaggcgttg tatgacatct gcttccgcac actgaagctg   2940
accacgccca cctacggtga cctgaaccat ctggtttcgg ccaccatgtc tggtgtgacg   3000
acctgcctgc gcttccctgg ccagctgaac gctgatcttc gcaagctggc cgtgaacatg   3060
gtacccttcc cccggctgca cttcttcatg cccggattcg caccgctcac ctcgcgagga   3120
tcgcaacaat accgggccct taccgttccg gagctgaccc agcagatgtt cgatgccaag   3180
aacatgatgg ctgcgtgcga tccgcgacat ggtcgctatc tgaccgtcgc cgccatcttc   3240
cgtggccgca tgtccatgaa ggaggtggac gagcagatgc tcaacattca gaacaagaac   3300
agcagcttct tcgtggaatg gatcccgaat aactgcaaga cagcggtgtg cgatattccg   3360
cccagagggtc tcaagatgtc ggccaccttc attggcaact ccaccgccat tcaggagcta   3420
ttcaaacggg tttcggagca gttcaccgcc atgttccgaa ggaaggcctt cttgcattgg   3480
```

```
tacaccggcg agggaatgga cgaaatggaa ttcacagagg ccgagagcaa catgaacgac   3540
ttggtttctg aatatcagca gtaccaggag gcgactgccg atgaggaggg cgaattcgat   3600
gaagacgaag agggtggcgg cgatgaataa taggattaac ttcccactca agatcacaca   3660
tgaacaccaa aacaggctag caggggaacc cattaggaag gcacaacaca ttggatcttt   3720
gggccttagc atattgtgct tcgaggcccg tcggttgtac atatttccta tatggattct   3780
tcactgttcg attatttatc attcacacac gtacagaaga aatatgtcca cctttgttaa   3840
gctcatgttg caattgctgt gatttctggg ttacgaataa atgttgattt ataagcagac   3900
aagattacca acagcatttt gcatattttt ataccgttca aaaggcattg cataaaccta   3960

<210> SEQ ID NO 24
<211> LENGTH: 1870
<212> TYPE: DNA
<213> ORGANISM: Drosophila melanogaster

<400> SEQUENCE: 24
ggaaatcgta gtagcctatt tgtgaacatt cggtgtagta atccaagcca ggttcagttc     60
acctcagtat cagctagcac gtacacgact aaaatctaaa cctgaaaaat tatacgttta    120
aatattcagt cttttgccga tttttgcccc actcagactg ttttaaaagc tcgattttt    180 tttgtaccat ttttcggtg tgaaaaaggg ggccctactt tactatcaaa atgcgtgaaa    240
ttgtacacat tcaggccggt caatgcggta accagatcgg tggtaaattc tgggaggtaa    300
tctcggatga gcactgtata gatgcgaccg gaacgtacta cggcgatagt gatctccagc    360
tggagcgcat caatgtatac tacaatgaag ccaccggtgc caagtatgtg ccacgcgcaa    420
ttctcgtgga cctggagccc ggcaccatgg attcggttcg ttctggcgcc tttggccaga    480
tcttccggcc ggacaatttt gtgtttggcc aatcgggagc aggcaacaac tgggccaagg    540
gtcattacac cgagggtgct gaactggtgg attccgtctt ggatgtggtg cgaaaggagt    600
ccgagggatg cgattgcctt cagggcttcc agtcgaccca ctcgctgggt ggcggcactg    660
gctccggcat gggaaccctg ctgatctcga agatccgcga ggagtacccg gaccgcatca    720
tgaacacctt ctcggtggtg ccctcgccca aggtgtccga tacggtggtg gagccctaca    780
atgccaccct gagtgtgcat cagctggtgg agaacaccga tgagacgtac tgcatcgaca    840
acgaggcgtt gtatgacatc tgcttccgca cactgaagct gaccacgccc acctacggtg    900
acctgaacca tctggtttcg gccaccatgt ctggtgtgac gacctgcctg cgcttccctg    960
gccagctgaa cgctgatctt cgcaagctgg ccgtgaacat ggtacccttc ccccggctgc   1020
acttcttcat gcccggattc gcaccgctca cctcgcgagg atcgcaacaa taccgggccc   1080
ttaccgttcc ggagctgacc cagcagatgt tcgatgccaa gaacatgatg gctgcgtgcg   1140
atccccgaca tggtcgctat ctgaccgtcg ccgccatctt ccgtggccgc atgtccatga   1200
aggaggtgga cgagcagatg ctcaacattc agaacaagaa cagcagcttc ttcgtggaat   1260
ggatcccgaa taactgcaag acagcggtgt gcgatattcc gcccagaggt ctcaagatgt   1320
cggccacctt cattggcaac tccaccgcca ttcaggagct attcaaacgg gtttcggagc   1380
agttcaccgc catgttccga aggaaggcct tcttgcattg gtacaccggc gagggaatgg   1440
acgaaatgga attcacagag gccgagagca acatgaacga cttggtttct gaatatcaac   1500
agtaccagga ggcgactgcc gatgaggagg gcgaattcga tgaagacgaa gagggtggcg   1560
gcgatgaata taggattaac cttcccactc aagatcacac atgaacacca aaacaggcta   1620
```

```
gcaggggaac ccattaggaa ggcacaatac attggatctt tgggccttag catattgtgc    1680
ttcgaggccc gtcggttgta catatttcct atatggattc ttcactgttc gattatttat    1740
cattcacaca cgtacagaag aattatgtcc actttgttaa gctcatgttg caattgctgt    1800
gatttctggg ttacgaataa atgttgattt ataagcagac aagattacca acagcatttt    1860
gcatattttt                                                            1870

<210> SEQ ID NO 25
<211> LENGTH: 516
<212> TYPE: DNA
<213> ORGANISM: Ceratitis capitata

<400> SEQUENCE: 25
atgtctgaag aagtggaaac cttcgctttc caagctgaaa ttgctcagct tatgtcgttg      60
atcatcaaca cattctactc gaacaaagaa attttcttc gtgagttgat ctctaacgct     120
tccgatgcac tcgataaaat ccgttacgag tctttgaccg accccaccaa gttggacagt     180
ggcaaagaat tgtatattaa gcttattccc aataaaacgg caggcacttt gaccattatt     240
gatactggta ttggtatgac taaatccgat ttggtcaaca atttgggtac aattgccaag     300
tccggcacta aagcattcat ggaagcattg caagctggtg ctgatatttc tatgattggt     360
caatttggtg ttggttttcta ctcggcttac ttggttgctg acaaagtaac cgttacgtca     420
aagcacaacg atgacgaaca atacatttgg gaatcgtcgg ccggtggctc gttcacagtt     480
aaaccagaca cacagaacc attgggacgt ggtacc                                516

<210> SEQ ID NO 26
<211> LENGTH: 144
<212> TYPE: DNA
<213> ORGANISM: artificial
<220> FEATURE:
<223> OTHER INFORMATION: artificial sequence

<400> SEQUENCE: 26
atcaattgaa ttggaaaaat acgcttgaaa gcacttttgc gcggagcaac aaagaaagtg      60
ttcttaaact attataattg caagtgatta ataaaggaat tttatatttt gttctacgaa     120
gttgatacat tgaaataaaa caag                                             144

<210> SEQ ID NO 27
<211> LENGTH: 221
<212> TYPE: DNA
<213> ORGANISM: Ceratitis capitata

<400> SEQUENCE: 27
tagaacaatc tcgtagcttc tacacttttg acatttggtt tttgtgcctc tataaatagg      60
gctgttcgct tgcaaccggc atcaattgaa ttggaaaaat acgcttgaaa gcacttttgc     120
gcggagcaac aaagaaagtg ttcttaaact attataattg caagtgatta ataaaggaat     180
tttatatttt gttctacgaa gttgatacat tgaaataaaa c                         221

<210> SEQ ID NO 28
<211> LENGTH: 172
<212> TYPE: PRT
<213> ORGANISM: Ceratitis capitata

<400> SEQUENCE: 28

Met Ser Glu Glu Val Glu Thr Phe Ala Phe Gln Ala Glu Ile Ala Gln
1               5                   10                  15
```

```
Leu Met Ser Leu Ile Ile Asn Thr Phe Tyr Ser Asn Lys Glu Ile Phe
            20                  25                  30

Leu Arg Glu Leu Ile Ser Asn Ala Ser Asp Ala Leu Asp Lys Ile Arg
        35                  40                  45

Tyr Glu Ser Leu Thr Asp Pro Thr Lys Leu Asp Ser Gly Lys Glu Leu
    50                  55                  60

Tyr Ile Lys Leu Ile Pro Asn Lys Thr Ala Gly Thr Leu Thr Ile Ile
65                  70                  75                  80

Asp Thr Gly Ile Gly Met Thr Lys Ser Asp Leu Val Asn Asn Leu Gly
                85                  90                  95

Thr Ile Ala Lys Ser Gly Thr Lys Ala Phe Met Glu Ala Leu Gln Ala
            100                 105                 110

Gly Ala Asp Ile Ser Met Ile Gly Gln Phe Gly Val Gly Phe Tyr Ser
        115                 120                 125

Ala Tyr Leu Val Ala Asp Lys Val Thr Val Thr Ser Lys His Asn Asp
    130                 135                 140

Asp Glu Gln Tyr Ile Trp Glu Ser Ser Ala Gly Gly Ser Phe Thr Val
145                 150                 155                 160

Lys Pro Asp Asn Thr Glu Pro Leu Gly Arg Gly Thr
                165                 170
```

```
<210> SEQ ID NO 29
<211> LENGTH: 97
<212> TYPE: DNA
<213> ORGANISM: Drosophila melanogaster

<400> SEQUENCE: 29
atatgtcaaa tggcgtgaga cttttaacaa aaaaaacatt tggttcagaa aaacttcgct    60
taaattacta aagaaaaact tagtagacca tttcagc                             97

<210> SEQ ID NO 30
<211> LENGTH: 2000
<212> TYPE: DNA
<213> ORGANISM: Drosophila melanogaster

<400> SEQUENCE: 30
aatcgtgctt taaagaccga actctcgaat caattaatgc gctccatggc catgaaagtg    60
gcgagtggcg ataagccagc tccaacccat gtggcccccc aactgggagc tggcgataca   120
aactgcttca attttaatgt cctcaaactg tcataaactg taaatgcaca gtaaaagcca   180
tgagtataag gcgggcaagc tgcgacagat tctgtcgtgt agatggccaa gaagctaaag   240
ctgtcagctc aagagtttaa gttcgacaag ctggtgaaac tattgtatct tacactgaag   300
tccgattttc acttaaatat tatatgtact tcgtttattt aaacctaata taaaagtggg   360
aaattaattg ccccactaag tgttaatcct tttcatacta acgctgtata ccttttgaca   420
ccttcatggt tgacttctga ttcacatacg cccatttaaa acaccectca ctctttgaac   480 tcgattttt aggttcactg agcaaacctt ttttttaac acgcttgcgt gtgccgttca    540
acatttagcc agttttttgg gccagtgcaa agacgacccg caggctgaaa gccaacattc   600
gctatacagg gtacaatata gccgcatgag aatacccatt catatgtata tgtatgtatg   660
tatgaatgaa gtcgtgcaca tgagtaaccc gttggcacga cctatcatcg cccattccgc   720
tggctaaggc ctcctggctg ggcgatgggc ggtgggtggt aggtgggcgt ggcacgtgtc   780
gcctgcagct ttcattagtt caatgtcaat gttttgtttt gtgatcctgg aacacaaaaa   840
ctgaagaaca tgggaaccat ccagctgtct gccttgggtt tttaatttta agcgcatgtt   900
```

```
gctggcctcc agccagccac ctgcatcacc tttgcctgtc tgctgattaa gtgagtacaa      960
gctgcaggtg tcctgcatta ggacatcccg ctgctccttc gaggcgaaag gaatgcaaat     1020
taaaactggt atctcttcct tctgtcaccg attctgcgga agctctgtgt gcacagcaaa     1080
ttgaatgagg tgcacagacg gcaatcgata tctcgatgga ggaagtaatc tttaagttcc     1140
tttaagtctg aatatctgga tatccaattt ccttttccc agaaaacgac cgcaacacat      1200
gtcgaaagtt tgcgggcaca aaccattggc atacactgag gtgtatttat aatttaattt     1260
aatttaattt agaattccgt tttatataat taaatatgga atttggatgt taaaacaagt     1320
gtgtgtttca gcgtttctaa ctaaatactc tcggaatttc attagcaatt ctcttgtctt     1380
tgtacccttt tttttgcag tgcacaggcg tacttaccac atcacagaca tggaaattag      1440
gccaaaagtg cgcaggcaat aatgctgaaa tccatttacg taattcgaaa tccgctggcg     1500
gcgttttagc cacgacaaca gtcgtatgca aactttatta attacgcgcc ccgatgacca     1560
ttaccaccat atcgaccatc tactattgac catgaagcca ttcttgcagt ccggcgaaac     1620
tttggctgtt tactattttg ctaggctgag tttcggccac ccattgttgt gttgcgcaat     1680
tggcaccagc tatgaaaatc acgcaaaagt ttttcaaatt aaaaattcaa cagatttcac     1740
tcggaaaatc aacaaccctg gaaagcggca tataacaaaa aacaaaatca atgaattaaa     1800
aaaaaaaaat tacataattc gattgagcct gctgttcata aaaaatattg atactgttta     1860
ttaaaatcca tgtaagactt tagttgtttt aatttaattt atcagaactg ttactttaat     1920
aatgacttta gttagtacct tagaaaatat ggcaacccctt gacagaattg aaatatgttg     1980
gcaacccaag tttggaggcc                                                 2000
```

<210> SEQ ID NO 31
<211> LENGTH: 624
<212> TYPE: DNA
<213> ORGANISM: artificial
<220> FEATURE:
<223> OTHER INFORMATION: TETR of TTAV sequence

<400> SEQUENCE: 31

```
cgagcccgac tcgcatttca gttgcttttc caatccgcag ataatcagct ccaagccgaa       60
caggaatgcc ggctcggctc cttgatgatc gaacagctcg attgcctgac gcagcagtgg      120
gggcatcgaa tcggttgttg gggtctcgcg ctcctctttt gcgacttgat gctcttggtc      180
ctccagcacg cagcccaggg taaagtgacc gacggcgctc agagcgtaga gagcattttc      240
caggctgaag ccttgctggc acaggaacgc gagctggttc tccagtgtct cgtattgctt      300
ttcggtcggg cgcgtgccga gatggacttt ggcaccgtct cggtgggaca gcagagcgca      360
gcggaacgac ttggcgttat tgcggaggaa gtcctgccag gactcgcctt caacgggca      420 aaaatgcgtg tggtggcggt cgagcatctc gatggccagg catccagca gcgcccgctt      480 attcttcacg tgccagtaga gggtgggctg ctccacgccc agcttctgcg ccaacttgcg      540
ggtcgtcagt ccctcaatgc caacttcgtt caacagctcc aacgcggagt tgatgacttt      600
ggacttatcc aggcggctga ccat                                            624
```

<210> SEQ ID NO 32
<211> LENGTH: 624
<212> TYPE: DNA
<213> ORGANISM: artificial
<220> FEATURE:
<223> OTHER INFORMATION: VP16 of TTAV sequence

<400> SEQUENCE: 32

```
atggtcagcc gcctggataa gtccaaagtc atcaactccg cgttggagct gttgaacgaa      60
gttggcattg agggactgac gacccgcaag ttggcgcaga agctgggcgt ggagcagccc     120
accctctact ggcacgtgaa gaataagcgg gcgctgctgg atgccctggc catcgagatg     180
ctcgaccgcc accacacgca tttttgcccg ttggaaggcg agtcctggca ggacttcctc     240
cgcaataacg ccaagtcgtt ccgctgcgct ctgctgtccc accgagacgg tgccaaagtc     300
catctcggca cgcgcccgac cgaaaagcaa tacgagacac tggagaacca gctcgcgttc     360
ctgtgccagc aaggcttcag cctggaaaat gctctctacg ctctgagcgc cgtcggtcac     420
tttaccctgg gctgcgtgct ggaggaccaa gagcatcaag tcgcaaaaga ggagcgcgag     480
accccaacaa ccgattcgat gcccccactg ctcgtcagg caatcgagct gttcgatcat     540
caaggagccg agccggcatt cctgttcggc ttggagctga ttatctgcgg attggaaaag     600
caactgaaat gcgagtcggg ctcg                                            624
```

<210> SEQ ID NO 33
<211> LENGTH: 2652
<212> TYPE: DNA
<213> ORGANISM: Drosophila melanogaster

<400> SEQUENCE: 33

```
caaacgtttc gttaaaattt ccgaacaaat tattcctgcg atagaaactg tacaaatttg      60
aacttttttc gaattcggcc aactgccatt gagttttaaa aactttgaat cgcttttgag     120
agagagcaat tttctgcgaa agatacgcga tcggactagc gccatgaaag tcaaagtttc     180
gggtgaatat acgctggccg agatcgaagt cgagttggac cagcagttga cgccagacga     240
cctgcaaccc ggagccacag tgctggccac caacagagag actggcggct agagcggat     300
tgtcagccat gaggagctgt ccagattctt cgccgtgggg ccagcgggcg ccttaccaat     360
gcccacggat gttgtagtgg agcgaacatt ggcggatccg gctttcaagc aaatcctgca     420
ggaggccgac ggaaagaaag gcttcgatcc ccaggcggag caaatgaaga ttcgcgactt     480
tttggccggc gtcaccagca gcaagatgac cactgagcaa tcggtctttc atggatctcg     540
ttccaattcc tctgcgtcca ctgtcaaccg tataaagtgt ccaacatgtt tggtccagtt     600
cgatgccgtg gcctttcaaa atcattcctg tgaagcgaag ccgatcgagg tggcggtgcc     660
tcagcaggag aagccacatc ttgtgcctac tgtatctgct cctccggctc cgctaagcaa     720
accggctagc gagcgggtaa ttcgggagaa ccaagtgcgt ctgcgccgtt acatcaaaga     780
tgagatgaag tacgatctgg ccacaggcat cgaaagctcg cgcaaaaacg cggccaaggg     840
tcccaacgag tgcaccatgt gcgaccgcaa atttgtccac gcctctggcc tggtgcgcca     900
catggagaag catgccctgg acttgatccc ttcgcaaacc agcgagcaac acatacgat      960
tccggctgcc ggactgcatg tggtggttaa gtgcaactcg tgtggccgca tcttctatga    1020
tccgcaggtg gcttttagac acggccttat tcacgattcg gagcattcaa cgatgcgtca    1080
aagtccaatg acccaagtac cctccaatag agcagatttc aatgagctgc tgctggatgg    1140
cgagatgctg atagacaacg atcccgcatt tgcaacgagc aatcaaaaca caaacccacc    1200
gaagaaggaa atgtttagca gcctgatctt gggaagtgtt ttgcagtgcg agttttgcga    1260
gtacattttc gctgacatag ccgagctgct tgtccattcc gcttcccatg tggcggagcg    1320
gcgctttgag tgcaccgcct gcgacattca gatgaacacg gccaaggaag ccagcatcca    1380
cttccagacg gactgcattt tcatgcgcga agcaatcagg tccctaaatg tcacgcttag    1440
```

-continued

```
tcgctacttt gtgtgtaatg tgtgcgagct gaagtttgcc aacacggacc tgctccagga      1500
gcatcggtgt acctccttc actactttcc tcgcctcaac gagaatggca agaagctcct       1560
gctgccctgt gacttttgcg acgtcaactt tgagttcgcc cacgattttc tggcgcacag      1620
cgaggagaag catctcaaca aaagaagcg cgaaaaggaa acgcgcaaca cgggcgccgg       1680
ccgaatacgt caatatctct gcgatatctg cggcaaatcg tacacccagt caagccatct     1740
gtggcagcat ctacgctttc accagggtgt gaagcccttc gtttgccagg aggaaaactg      1800
tgatcggaag ttcaccattc gcccagatct gaacgaccac attcgcaagt gccacacggg     1860
cgagcgtcca tatctttgtc tggtgtgtgg aaagcgcttt ctcaccggat ccgtcttcta     1920
tcagcaccgt ctgatccatc gcggcgagcg gcgctatgag tgcgaggagt gtggtaaacg      1980
tttctatcgc gcggacgcgc tcaagaatca ccaacgcatc cacaccggag agaagccgta     2040
cagctgcctc ttctgcacga agacttttcg ccagcgcggc gaccgtgaca agcacatccg      2100
agctcgacac tctcacctgg atgccaactc gcgtctcatg atgcagatgc agaagttcca     2160
actggagacg gccgctgcgc agaaggctca agtcataat cccgagcagc aggataatga      2220
tgttgctggt ggtgccagca cctcagatgt gccctcgggc tcgggattca tgtcgactga     2280
gccaagcgtc gcggagatgc agtactctat tacgccggag cagcaggagg aaatggtgtg     2340
tgtgcccatt gacgaggtca ataacagttt ctttatgtcg cactacatgc aagctgtccc      2400
catggaggag gatggttcgg ggcagcatat cattgtcttc gagcagccag gccagaatat     2460
ggacatgatg tccatttacg atcagcaaca ggttggggaa ccaatgcatg agagcggcgt      2520
gcccaagcgg ccggctgagg aaaatgctag ggtggtggtt gtcaaaaaca atccaactaa     2580
gccgatattt tcggataccc atttgtaaaa atcatattca aattcgaatt taaataaagc     2640
ggcaagatag cg                                                          2652
```

<210> SEQ ID NO 34
<211> LENGTH: 701
<212> TYPE: DNA
<213> ORGANISM: Drosophila melanogaster

<400> SEQUENCE: 34

```
gattaacaac gtcggtgtgc catgttaggc actgcgttta ctcatttcgc gaggcgtctt       60
atctgtaacc gaagtgctga atgcagataa ctggcggcca gtaatcaccct gggccaacta    120 cgacgactcc gactctgaca gcctgagcca aggaaaaaca taaacaaatg gcgttaacta     180
cactttgcgg tctacgatat gcgccttggc tgtcagaagt ctgcaaaatg ttgggtaagt     240
ccaaaattta aaaattagct aatgactaat gtgttgtaga agcggaaacg gctttataaa     300
tcattttatt tttaaagatg aatgcatatg cagggactta aaaacacagt ttcaaaatgt     360
ataactacga acccattggt ttgagttct cattattgag atgtacttta aatcttatgt      420
gatattagaa attaaaattc aaagcaattt aaagactaca tttatattat acatatatat     480
tttacgatat acgtatttat aatattcagt tgattctcag gtcatttaag ttataaacat     540
atcggtaagt tgtcagatgt tttactttag caaacatttt agtattgccg tctttgttag     600 aaaccctta gagttgtcca atgccttgga gccaactgtc agttgagcca attttccagc      660
gacggagaaa gcaaatctca tatccctact tatcagcagt a                          701
```

<210> SEQ ID NO 35
<211> LENGTH: 1178
<212> TYPE: DNA

<213> ORGANISM: Ceratitis capitata

<400> SEQUENCE: 35

| | |
|---|---|
| gccgttcagt caaatgtgat attcacaact attgagcaga gaattccatt aatgtacata | 60 |
| tgtattttga ttgctgcaac aaaaaatatt aaaatggttt agcaaggtta attaagtgta | 120 |
| aatgacagat ttttttttac atacaccacc ttcgccctgt agctagttgc gagtttactt | 180 |
| cagtttctat ctaattcgtt tgaatccata tggcagaatt acagtgtaat ggacgctctc | 240 |
| ttactttttt aggcttaaaa aacacattaa agatcaatta attttaagga ataagcaaat | 300 |
| aaaattactc cggcgttcag atattggaaa tatagaataa tgtaacattt aaaataaggc | 360 |
| ctaatattta tcaattatca agacatatgt atatacatga ttcatgcaaa aggtattcat | 420 |
| ttttaataat gcagggaaaa actacagcta aacaacaacg taatcaattc ctacttggta | 480 |
| tttcttcgtt tcccttttaac attttttcat aacagtaggt tttcaatatt ttagatgtaa | 540 |
| atgaaaaatg tacggtttcc gtggcaagct taacttgcca ttcttctgaa caatttaatc | 600 |
| taataatttt tcattatcta aggcgtcaat ttaaatggca aagtattaat attcttgatg | 660 |
| gttgcctaaa ttttagaaat aaacactgaa tgctattaac taaggaagtt gaggtaaaag | 720 |
| ttttgtttaa attccacata tgttggaata tcgtcatcaa aaataaatgt gtcctgtaat | 780 |
| taatatgttt atcgtttagt tttaaaatta aaattaattt aagttaactg taatgggtgt | 840 |
| actcaatcgt tggattagaa attgaaagcg gaggcaaata taattttcg gtgttgggta | 900 |
| agtgttacaa ttcgaacagt tttaaattag aactaattaa atatatgaaa atgcattaaa | 960 |
| atcaaaaata tccatgatta aatcatattt aaaatgtaga aattaataac actaaaatat | 1020 |
| tttggtaaat taagacacta tcaaaaaact cgaaaaaagt aggctagctt tctatgtcaa | 1080 |
| ggcgccattt tttaaagaac aatagatcta gaaatactgc agagtccgca aaattttgaa | 1140 |
| tttatttta taaatataaa ctaaattaaa tccactag | 1178 |

<210> SEQ ID NO 36
<211> LENGTH: 1178
<212> TYPE: DNA
<213> ORGANISM: Ceratitis capitata

<400> SEQUENCE: 36

| | |
|---|---|
| gccgttcagt caaatgtgat attcacaact attgagcaga gaattccatt aatgtacata | 60 |
| tgtattttga ttgctgcaac aaaaaatatt aaaatggttt agcaaggtta attaagtgta | 120 |
| aatgacagat ttttttttac atacaccacc ttcgccctgt agctagttgc gagtttactt | 180 |
| cagtttctat ctaattcgtt tgaatccata tggcagaatt acagtgtaat ggacgctctc | 240 |
| ttactttttt aggcttaaaa aacacattaa agatcaatta attttaagga ataagcaaat | 300 |
| aaaattactc cggcgttcag atattggaaa tatagaataa tgtaacattt aaaataaggc | 360 |
| ctaatattta tcaattatca agacatatgt atatacatga ttcatgcaaa aggtattcat | 420 |
| ttttaataat gcagggaaaa actacagcta aacaacaacg taatcaattc ctacttggta | 480 |
| tttcttcgtt tcccttttaac attttttcat aacagtaggt tttcaatatt ttagatgtaa | 540 |
| atgaaaaatg tacggtttcc gtggcaagct taacttgcca ttcttctgaa caatttaatc | 600 |
| taataatttt tcattatcta aggcgtcaat ttaaatggca aagtattaat attcttgatg | 660 |
| gttgcctaaa ttttagaaat aaacactgaa tgctattaac taaggaagtt gaggtaaaag | 720 |
| ttttgtttaa attccacata tgttggaata tcgtcatcaa aaataaatgt gtcctgtaat | 780 |
| taatatgttt atcgtttagt tttaaaatta aaattaattt aagttaactg taatgggtgt | 840 |

```
actcaatcgt tggattagaa attgaaagcg aggcaaata taattttttcg gtgttgggta      900 agtgttacaa ttcgaacagt tttaaattag aactaattaa atatatgaaa atgcattaaa      960
atcaaaaata tccatgatta aatcatattt aaaatgtaga aattaataac actaaaatat     1020
tttggtaaat taagcacacta tcaaaaaact cgaaaaaagt aggctagctt tctatgtcaa     1080
ggcgccattt tttaaagaac aatagatcta gaaatactgc agagtccgca aaattttgaa     1140
tttattttta taaatataaa ctaaattaaa tccactag                             1178

<210> SEQ ID NO 37
<211> LENGTH: 1785
<212> TYPE: DNA
<213> ORGANISM: Ceratitis capitata

<400> SEQUENCE: 37
ctaattcgtt tgaatccata tggcagaatt acagtgtaat ggacgctctc ttactttttt       60
aggcttaaaa aacacattaa agatcaatta attttaagga ataagcaaat aaaattactc      120
cggcgttcag atattggaaa tatagaataa tgtaacattt aaaataaggc ctaatattta      180
tcaattatca agacatatgt atatacatga ttcatgcaaa aggtattcat ttttaataat      240
gcagggaaaa actacagcta acaacaacg taatcaattc ctacttggta tttcttcgtt       300
tcccttaaac attttttcat aacagtaggt tttcaatatt ttagatgtaa atgaaaaatg      360
tacggtttcc gtggcaagct taacttgcca ttcttctgaa caatttaatc taataatttt      420
tcattatcta aggcgtcaat ttaaatggca aagtattaat attcttgatg gttgcctaaa      480
ttttagaaat aaacactgaa tgctattaac taaggaagtt gaggtaaaag ttttgtttaa      540
attccacata tgttggaata tcgtcatcaa aaataaatgt gtcctgtaat taatatgttt      600
atcgtttagt tttaaaatta aaattaattt aagttaactg taatgggtgt actcaatcgt      660
tggattagaa attgaaagcg gaggcaaata taattttttcg gtgttgggta agtgttacaa    720
ttcgaacagt tttaaattag aactaattaa atatatgaaa atgcattaaa atcaaaaata     780
tccatgatta aatcatattt aaaatgtaga aattaataac actaaaatat tttggtaaat    840 taagcacta tcaaaaaact cgaaaaaagt aggctagctt tctatgtcaa ggcgccattt     900
tttaaagaac aatagatcta gaaatactgc agagtccgca aaattttgaa tttattttta    960
taaatataaa ctaaattaaa tccactagta tgaatacaag tgaagaagaa ttttcgaatt   1020
ccgatgcgtg gctatccgag caactgtttg ctcmattaaa agaatttaat tcagattata   1080
gagaaaagtc ggttggtgat gcatcgacma catttgtatt tccttccggt agtctcagct    1140
gtttgcctga aggagaacct cacgacttaa caaaatcacg acttgaaaac tacgagcctg    1200
ttttcaaatt atctacacca actaatatat cttctttcga tctgaacgat gtgttggatt   1260
taactaatat tactggcaga tgtaacgatt cagcgctgct ggatttggtt gggacagttc   1320
cattaactcc atttgtaact cccgttcctg agacaacatt aatggtaaat gagacagtga   1380
aacaaacggc tgaatcatcc tttgatgtaa cagaagagga attaaagctt tgaaattttt   1440
tggagtcaca gccaactact aatcagtttg gtgtgtattg tatatcggat atacttaata   1500
atatctaatt tcttgatctt ttcagacaca aaatcatatg ttcaaactga ggtttcaccc   1560
actccatatc gtattgtcaa gtgttcaaat tgcaatgttc tctttgattt aatgtctttc   1620
caaacacata tttgtgatta tgacgaacac cacaatctaa ttgctccacc aataacatca   1680
acacctctca gcaaaccaat aaaagaagaa ccattactac cagtagaacc tgcatgtatt   1740
```

```
cgtttattgc gtgaaaatca aattcgaatc cgacgaccta gctcg            1785
```

<210> SEQ ID NO 38
<211> LENGTH: 1238
<212> TYPE: DNA
<213> ORGANISM: artificial
<220> FEATURE:
<223> OTHER INFORMATION: Plasmid

<400> SEQUENCE: 38

```
gccgttcagt caaatgtgat attcacaact attgagcaga gaattccatt aatgtacata     60
tgtattttga ttgctgcaac aaaaaatatt aaaatggttt agcaaggtta attaagtgta    120
aatgacagat ttttttttac atacaccacc ttcgccctgt agctagttgc gagtttactt    180
cagtttctat ctaattcgtt tgaatccata tggcagaatt acagtgtaat ggacgctctc    240
ttactttttt aggcttaaaa aacacattaa agatcaatta attttaagga ataagcaaat    300
aaaattactc cggcgttcag atattggaaa tatagaataa tgtaacattt aaaataaggc    360
ctaatattta tcaattatca agacatatgt atatacatga ttcatgcaaa aggtattcat    420
ctaatattta tcaattatca agacatatgt atatacatga ttcatgcaaa aggtattcat    480
ttttaataat gcagggaaaa actacagcta aacaacaacg taatcaattc ctacttggta    540
tttcttcgtt tccctttaac attttttcat aacagtaggt tttcaatatt ttagatgtaa    600
atgaaaaatg tacggtttcc gtggcaagct taacttgcca ttcttctgaa caatttaatc    660
taataatttt tcattatcta aggcgtcaat ttaaatggca agtattaat attcttgatg    720
gttgcctaaa ttttagaaat aaacactgaa tgctattaac taaggaagtt gaggtaaaag    780
ttttgtttaa attccacata tgttggaata tcgtcatcaa aaataaatgt gtcctgtaat    840
taatatgttt atcgtttagt tttaaaatta aaattaattt aagttaactg taatgggtgt    900
actcaatcgt tggattagaa attgaaagcg gaggcaaata taattttttcg gtgttgggta    960
agtgttacaa ttcgaacagt tttaaattag aactaattaa atatatgaaa atgcattaaa   1020
atcaaaaata tccatgatta aatcatattt aaaatgtaga aattaataac actaaaatat   1080
tttggtaaat taagacacta tcaaaaaact cgaaaaaagt aggctagctt tctatgtcaa   1140
ggcgccattt tttaaagaac aatagatcta gaaatactgc agagtccgca aaattttgaa   1200
tttatttta taaatataaa ctaaattaaa tccactag                             1238
```

<210> SEQ ID NO 39
<211> LENGTH: 1178
<212> TYPE: DNA
<213> ORGANISM: artificial
<220> FEATURE:
<223> OTHER INFORMATION: plasmid

<400> SEQUENCE: 39

```
gccgttcagt caaatgtgat attcacaact attgagcaga gaattccatt aatgtacata     60
tgtattttga ttgctgcaac aaaaaatatt aaaatggttt agcaaggtta attaagtgta    120
aatgacagat ttttttttac atacaccacc ttcgccctgt agctagttgc gagtttactt    180
cagtttctat ctaattcgtt tgaatccata tggcagaatt acagtgtaat ggacgctctc    240
ttactttttt aggcttaaaa aacacattaa agatcaatta attttaagga ataagcaaat    300
aaaattactc cggcgttcag atattggaaa tatagaataa tgtaacattt aaaataaggc    360
ctaatattta tcaattatca agacatatgt atatacatga ttcatgcaaa aggtattcat    420
ttttaataat gcagggaaaa actacagcta aacaacaacg taatcaattc ctacttggta    480
```

```
tttcttcgtt tcccttttaac atttttcat aacagtaggt tttcaatatt ttagatgtaa    540
atgaaaaatg tacggtttcc gtggcaagct taacttgcca ttcttctgaa caatttaatc    600
taataatttt tcattatcta aggcgtcaat ttaaatggca aagtattaat attcttgatg    660
gttgcctaaa ttttagaaat aaacactgaa tgctattaac taaggaagtt gaggtaaaag    720
ttttgtttaa attccacata tgttggaata tcgtcatcaa aaataaatgt gtcctgtaat    780
taatatgttt atcgtttagt tttaaaatta aaattaattt aagttaactg taatgggtgt    840
actcaatcgt tggattagaa attgaaagcg gaggcaaata taattttcg gtgttgggta    900 agtgttacaa ttcgaacagt tttaaattag aactaattaa atatatgaaa atgcattaaa    960
atcaaaaata tccatgatta aatcatattt aaaatgtaga aattaataac actaaaatat   1020
tttggtaaat taagacacta tcaaaaaact cgaaaaaagt aggctagctt tctatgtcaa   1080
ggcgccattt tttaaagaac aatagatcta gaaatactgc agagtccgca aaattttgaa   1140 tttatttta taaatataaa ctaaattaaa tccactag                            1178

<210> SEQ ID NO 40
<211> LENGTH: 1785
<212> TYPE: DNA
<213> ORGANISM: artificial
<220> FEATURE:
<223> OTHER INFORMATION: plasmid

<400> SEQUENCE: 40
ctaattcgtt tgaatccata tggcagaatt acagtgtaat ggacgctctc ttactttttt     60
aggcttaaaa aacacattaa agatcaatta attttaagga ataagcaaat aaaattactc    120
cggcgttcag atattggaaa tatagaataa tgtaacattt aaaataaggc ctaatatta    180 tcaattatca agacatatgt atatacatga ttcatgcaaa aggtattcat ttttaataat    240
gcagggaaaa actacagcta acaacaacg taatcaattc ctacttggta tttcttcgtt    300 tcccttttaac atttttcat aacagtaggt tttcaatatt ttagatgtaa atgaaaaatg    360
tacggtttcc gtggcaagct taacttgcca ttcttctgaa caatttaatc taataatttt    420
tcattatcta aggcgtcaat ttaaatggca aagtattaat attcttgatg gttgcctaaa    480
ttttagaaat aaacactgaa tgctattaac taaggaagtt gaggtaaaag ttttgtttaa    540
attccacata tgttggaata tcgtcatcaa aaataaatgt gtcctgtaat taatatgttt    600
atcgtttagt tttaaaatta aaattaattt aagttaactg taatgggtgt actcaatcgt    660
tggattagaa attgaaagcg gaggcaaata taattttcg gtgttgggta agtgttacaa    720
ttcgaacagt tttaaattag aactaattaa atatatgaaa atgcattaaa atcaaaaata    780
tccatgatta aatcatattt aaaatgtaga aattaataac actaaaatat tttggtaaat    840
taagacacta tcaaaaaact cgaaaaaagt aggctagctt tctatgtcaa ggcgccattt    900
tttaaagaac aatagatcta gaaatactgc agagtccgca aaattttgaa tttattttta    960
taaatataaa ctaaattaaa tccactagta tgaatacaag tgaagaagaa ttttcgaatt   1020
ccgatgcgtg gctatccgag caactgtttg ctcmattaaa agaatttaat tcagattata   1080
gagaaaagtc ggttggtgat gcatcgacma catttgtatt tccttccggt agtctcagct   1140
gtttgcctga aggagaacct cacgacttaa caaaatcacg acttgaaaac tacgagcctg   1200
ttttcaaatt atctcacacca actaatatat cttctttcga tctgaacgat gtgttggatt   1260
taactaatat tactggcaga tgtaacgatt cagcgctgct ggatttggtt gggacagttc   1320
```

```
cattaactcc atttgtaact cccgttcctg agacaacatt aatggtaaat gagacagtga    1380
aacaaacggc tgaatcatcc tttgatgtaa cagaagagga attaaagctt ttgaaatttt    1440
tggagtcaca gccaactact aatcagtttg gtgtgtattg tatatcggat atacttaata    1500
atatctaatt tcttgatctt ttcagacaca aaatcatatg ttcaaactga ggtttcaccc    1560
actccatatc gtattgtcaa gtgttcaaat tgcaatgttc tctttgattt aatgtctttc    1620
caaacacata tttgtgatta tgacgaacac cacaatctaa ttgctccacc aataacatca    1680
acacctctca gcaaaccaat aaaagaagaa ccattactac cagtagaacc tgcatgtatt    1740
cgtttattgc gtgaaaatca aattcgaatc cgacgaccta gctcg                    1785
```

<210> SEQ ID NO 41
<211> LENGTH: 1168
<212> TYPE: DNA
<213> ORGANISM: Aedes aegypti

<400> SEQUENCE: 41

```
gcgagtaact gtcaaagtgc ttcccgatca gctgatttga gacgtcatgt gaatatattc      60
atatggtttt cggcagatgt tgtttccata atacacctcg aaggaatttc gtaagatgat    120
cttatgaacc agcattgact tgataacaaa atccatagat agtcttatga attatgttct    180
gatccattct tggttccata agactgtctt gtgtaatttg agctttagat tataaatttc    240
aatgaatgaa taatactaat ccgcgttgaa aaataggtta accaacttgg gaaaatcaaa    300
ttttgatcca ttttgtcatg ccgcaattcg attaaagcac tttactgtaa gcattagaat    360
cgatttgcga tacgacaaaa tggatgaaaa ttcgattttc tctagttggc taacctattt    420
tgaacgcgaa gaagtatatt atagcagcga acattattg agaaaagttg tgaagaacgc    480
ctgaattggt gcaggtttac gttaggggcg gattaattga tgggggggggg tttgtgattt    540 cttacgcgtc atacaaattg ttttgaattt tcagtcaaaa atcttattct ttggatccaa    600
ttccttaatc tgatcgaaag aaagttttag ttacagcgga attgatgata aatagaaaat    660
atttacccct tgatgcatta aaaacggagt cagccagcga caaatcagca aacacgtcca    720
tttcggaagc catattgaat ttctgatagt gaaatggctg taccgagaaa atttgcctca    780
cgtggttctt cacaatgatg agcaatgggg ttcataagca ttcttatgac attgacaatt    840
gattgttatg aaaaaattac acttgtctta tgaatctcaa tctcgtcgaa tgaaatacgc    900
aagtgtctta tgaaccaaca aaaaaataat aaaaaacgcg ttcattagtg tgatcttatg    960
aaaatcatgc gagattttg cctcagtgta ggcctatcag ctgttgggag gggtggtggg   1020
tgggtggtag tttcgtctct agtctgagct cacggagctc acattcactg gcgatcgttg   1080
cccttccgtc gctaggcaac ccaacgaaac tagcgctctg cggtcacttc tccgcccaac   1140
caacctctaa acccaagcaa tcggattc                                      1168
```

<210> SEQ ID NO 42
<211> LENGTH: 65
<212> TYPE: DNA
<213> ORGANISM: Aedes aegypti

<400> SEQUENCE: 42

```
acttttttcg caaccggccc cttgtcaaga cctactgctg cccgttttcc gcatcgtaga     60
aaaaa                                                                 65
```

<210> SEQ ID NO 43
<211> LENGTH: 2445

<212> TYPE: DNA
<213> ORGANISM: Drosophila melanogaster

<400> SEQUENCE: 43

| | |
|---|---:|
| atgaaagtca aagtttcggg tgaatatacg ctggccgaga tcgaagtcga gttggaccag | 60 |
| cagttgacgc cagacgacct gcaacccgga gccacagtgc tggccaccaa cgagagtact | 120 |
| ggcggcttag agcggattgt cagccatgag gagctgtcca gattcttcgc cgtggggcca | 180 |
| gcgggcgcct taccaatgcc cacggatgtt gtagtggagc gaacattggc ggatccggct | 240 |
| ttcaagcaaa tcctgcagga ggccgacgga agaaaggct tcgatcccca ggcggagcaa | 300 |
| atgaagattc gcgactttt ggccggcgtc accagcagca agatgaccac tgagcaatcg | 360 |
| gtctttcatg gatctcgttc caattcctct gcgtccactg tcaaccgtat aaagtgtcca | 420 |
| acatgtttgg tccagttcga tgccgtggcc tttcaaaatc attcctgtga agcgaagccg | 480 |
| atcgaggtgg cggtgcctca gcaggagaag ccacatcttg tgcctactgt atctgctcct | 540 |
| ccggctccgc taagcaaacc ggctagcgag cgggtaattc gggagaacca agtgcgtctg | 600 |
| cgccgttaca tcaaagatga gatgaagtac gatctggcca caggcatcga aagctcgcgc | 660 |
| aaaaacgcgg ccaagggtcc caacgagtgc accatgtgcg accgcaaatt tgtccacgcc | 720 |
| tctgggctgg tgcgccacat ggagaagcat gccctggact tgatcccttc gcaaaccagc | 780 |
| gagcaaccac atacgattcc ggctgccgga ctgcatgtgg tggttaagtg caactcgtgt | 840 |
| ggccgcatct tctatgatcc gcaggtggct tttagacacg gccttattca cgattcggag | 900 |
| cattcaacga tgcgtcaaag tccaatgacc caagtaccct ccaatagagc agatttcaat | 960 |
| gagctgctgc tggatggcga gatgctgata gacaacgatc ccgcatttgc aacgagcaat | 1020 |
| caaaacacaa acccaccgaa gaaggaaatg tttagcagcc tgatcttggg aagtgttttg | 1080 |
| cagtgcgagt tttgcgagta cattttcgct gacatagccg agctgcttgt ccattccgct | 1140 |
| tcccatgtgg cggagcggcg ctttgagtgc accgcctgcg acattcagat gaacacggcc | 1200 |
| aaggaagcca gcatccactt ccagacggac tgcattttca tgcgcgaagc aatcaggtcc | 1260 |
| ctaaatgtca cgcttagtcg ctactttgtg tgtaatgtgt gcgagctgaa gtttgccaac | 1320 |
| acggacctgc tccaggagca tcggtgtacc tcctttcact actttcctcg cctcaacgag | 1380 |
| aatggcaaga agctcctgct gccctgtgac ttttgcgacg tcaactttga gttcgcccac | 1440 |
| gattttctgg cgcacagcga ggagaagcat ctcaacaaaa agaagcgcga aaaggaaacg | 1500 |
| cgcaacacgg gcgccggccg aatacgtcaa tatctctgcg atatctgcgg caaatcgtac | 1560 |
| acccagtcaa gccatctgtg gcagcatcta cgctttcacc agggtgtgaa gcccttcgtt | 1620 |
| tgccaggagg aaaactgtga tcggaagttc accattcgcc cagatctgaa cgaccacatt | 1680 |
| cgcaagtgcc acacgggcga gcgtccatat ctttgtctgg tgtgtggaaa gcgctttctc | 1740 |
| accggatccg tcttctatca gcaccgtctg atccatcgcg gcgagcggcg ctatgagtgc | 1800 |
| gaggagtgtg gtaaacgttt ctatcgcgcg gacgcgctca agaatcacca acgcatccac | 1860 |
| accggagaga agccgtacag ctgcctcttc tgcacgaaga cttttcgcca gcgcggcgac | 1920 |
| cgtgacaagc acatccgagc tcgacactct cacctggatg ccaactcgcg tctcatgatg | 1980 |
| cagatgcaga agttccaact ggagacggcc gctgcgcaga aggctcaaag tcataatccc | 2040 |
| gagcagcagg ataatgatgt tgctggtggt gccagcacct cagatgtgcc ctcgggctcg | 2100 |
| ggattcatgt cgactgagcc aagcgtcgcg gagatgcagt actctattac gccgagcag | 2160 |
| caggaggaaa tggtgtgtgt gcccattgac gaggtcaata acagtttctt tatgtcgcac | 2220 |

| tacatgcaag ctgtccccat ggaggaggat ggttcggggc agcatatcat tgtcttcgag | 2280 |
| cagccaggcc agaatatgga catgatgtcc atttacgatc agcaacaggt tggggaacca | 2340 |
| atgcatgaga gcggcgtgcc aagcggccg gctgaggaaa atgctagggt ggtggttgtc | 2400 |
| aaaaacaatc caactaagcc gatattttcg gatacctatt tgtaa | 2445 |

```
<210> SEQ ID NO 44
<211> LENGTH: 1707
<212> TYPE: DNA
<213> ORGANISM: Drosophila melanogaster

<400> SEQUENCE: 44
```

| atgtcagttg atccactatc aatcgataat ttcacaatcc aatctgagat ctgcgaagaa | 60 |
| aacgagtttc tggcaaatat aggattacta tctacgacaa caatgtcgcg tcatcaattg | 120 |
| aagaaaccca gaaagatggt ggcggcatgg caaaacgatg aattatttat taaacgccca | 180 |
| aatttcgccc cgcgtattag gatttccgaa aagccagaga tccagggaag aattaaacca | 240 |
| ggcgtggcgt ccaaaaggac tgagaacttt acaagaagc cgtccaatat atctgtagat | 300 |
| gtttcggagg acgagaaagc gaaggaaaag gaaaaggagc aggatcccta ctccaatgac | 360 |
| tttatacttg gcaagagatt gtacaatttc ctgaagtatc tcagctctca ccgttggatt | 420 |
| tggtgtgagt tcgtcgactc cttcctggac aagccgaccc tgaccatggg ctacgatatg | 480 |
| aagcgcttca tagcggagta ctgtccgctc ctgcactctt gcttcatgcc ccgcagagga | 540 |
| tggcaattgg tacgtcggaa tatggggaag gcgcgtcgat tttcggccgc cttcatcgag | 600 |
| ctggaacgcg aagaattgga gtgccagcgc cgcattgtgc ccagttgca gcagcataag | 660 |
| ttcaatccca aggagaacgt gggctacttg gaccagatac ccaagcgtgt gcccctgcca | 720 |
| ctggccaagg atgccacggt cagcagtttt ctgcacggaa actcctttga gggcatcgtc | 780 |
| aatggcactg tcatgggcta cgatccgcag gactacacct atctggttcg attcaataga | 840 |
| aacgacaatg cagtcgtgct cagtcttccg gattcacagc tctattccga cgaggaaacc | 900 |
| gcggcggttc ccttgtcaat tattatgcgc ggcaacaaat cgtcctcggt tatttcggag | 960 |
| agcgccaaga ccgagaagtt cggaaacaag aggtacacca aggaacttct ggaatcagtg | 1020 |
| ctaagggttg gtaaactaca ggatgtcaag cacaagatcc tcatggactt ggcccgaatg | 1080 |
| aatgaggatt tcgagacatt caaggagatt ggttcttcaa gtagtcgtcg cgatgccaag | 1140 |
| gtcacacctc agcgtgagaa tctccagcgt cgctattcgg ccagcatgat aacgctgcac | 1200 |
| cgagtgaacg ctgatatcct tgaaccgctg cgcatcctgc acgactacct ggtcgagtat | 1260 |
| cagaagcagg acgaggagga ggagtccaaa agaggtcgtc ccgccagcga agtctatcag | 1320 |
| aagtgtcgca tgcaggcgga acaggacctc aagactgccg cggatgagaa attcctgaag | 1380 |
| atagaatcgg atcgcacgca ggagttcgtc cgcaaccttc acaccatact gtatctcaat | 1440 |
| ggaaagctgg ggcgcgagaa cagctccaat ttggagacga ttatcgctga tctggttacc | 1500 |
| cacatggtgg acaacatcca gccatcgctg ggccggaaat taaagatgg cgtcgattcc | 1560 |
| ctggagcctc tgcgtcagca ggtggtgcaa atatttaaag acgtcaaaaa accagagcgc | 1620 |
| ttccaaatca cccagcaggc tccgatgcaa accgaggatg gtatctacaa ctttgtggtc | 1680 |
| gaggcacagc cggatactcc cagctaa | 1707 |

```
<210> SEQ ID NO 45
<211> LENGTH: 1030
<212> TYPE: DNA
<213> ORGANISM: artificial
```

<220> FEATURE:
<223> OTHER INFORMATION: plasmid

<400> SEQUENCE: 45

| | | | | | |
|---|---|---|---|---|---|
| ccccatgtta | caaggctgca | atcctttcga | aaaccaatag | cttcgtttgc | agctgtacgt | 60 |
| agggagtttg | agaagagagc | aggtgtgcaa | aacgagtaga | aaacaacttt | tcaacgtcga | 120 |
| accttccttg | tgtttgttga | cgggcgtttt | tgagtatatt | ccatatgaca | agtttgtgat | 180 |
| ccgggtcgag | tcgaaaatat | cataaaaaca | taatcacaat | catgaaagct | atgcttttgt | 240 |
| acccttttct | ttcgcttgtt | atattcaagg | gaccattatt | aaaaacactt | tctattttga | 300 |
| tctttaaata | acggttgttt | agtgagcagt | tggtcaaaaa | cgttgcttaa | agttattgct | 360 |
| acgtgagaga | taattgtact | gtgatcaact | gaagactgaa | agagaaacat | aataaaatgg | 420 |
| taactaaatt | caccaaaaat | gaatgtgaga | gatttaaaaa | aatatttga | tagtcattta | 480 |
| tactggcata | caagggcgtg | ccttgaaggg | gttcctactg | gacacactgg | tactgggaat | 540 |
| tttaataact | ttgaagctaa | aatactccca | ttttcatttg | tagcttttcg | ttaaagtaac | 600 |
| aatatatata | tatttcaaat | aatgtatcaa | aaattttcca | tataagcata | ttttgaaaag | 660 |
| attttagtca | gacgggaacg | tgttaaaaat | tagttttttca | aattgcataa | cttatccaag | 720 |
| gatcagtaac | caactataat | atttaaagtg | tgaatggaaa | tccgcagtat | cttcgactaa | 780 |
| agaactgcag | ttggatccga | tagtaaattg | agaagcggta | aaaccttaag | taaagtccaa | 840 |
| aacttttttg | ttctaaatac | atacaaatgt | acgtttcaaa | tacttctttt | gaatttctat | 900 |
| cttgcatcaa | ttttctatct | aactcaattt | tggttattg | atttaagttt | ttaggacatt | 960 |
| tcataccagt | aggagcaggt | aataagatac | taacggcgta | tacgtaattg | aatcgggaga | 1020 |
| taatttaaaa | | | | | | 1030 |

<210> SEQ ID NO 46
<211> LENGTH: 795
<212> TYPE: DNA
<213> ORGANISM: artificial
<220> FEATURE:
<223> OTHER INFORMATION: plasmid

<400> SEQUENCE: 46

| | | | | | |
|---|---|---|---|---|---|
| cccatgttac | aaggctgcaa | tccttcgaaa | accaatagct | tcgtttgcag | ctgtacgtag | 60 |
| ggagtttgag | aagagagcag | gtgtgcaaaa | cgagtagaaa | acaacttttc | aacgtcgaac | 120 |
| cttccttgtg | tttgttgacg | ggcgtttttg | agtatattcc | atatgacaag | tttgtgatcc | 180 |
| gggccgagtc | gaaaatatca | taaaaacata | atcacaatca | tgaaagctat | gcttttgtac | 240 |
| cctttctttt | cgcttgttat | attcaaggga | ccattattaa | aaacactttc | tattttgatc | 300 |
| tttaaataac | ggttgtttag | tgagcagttg | gtcaaaacg | ttgcttaaag | ttattgctac | 360 |
| gtgagagata | attgtactgt | gatcaactga | agactgaaag | agaaacataa | taaaatggta | 420 |
| actaaattca | ccaaaaatga | atgtgagaga | tttaaaaaaa | tattttgata | gtcatttata | 480 |
| ctggcataca | agggcgtgcc | ttgaagggggt | tcctactgga | cacactggta | ctgggaattt | 540 |
| taataacttt | gaagctaaaa | tactcccatt | ttcatttgta | gcttttcgtt | aaagtaacaa | 600 |
| tatatatata | tttcaaataa | tgtatcaaaa | attttccata | taagcatatt | ttgaaaagat | 660 |
| tttagtcaga | cgggaacgtg | ttaaaaatta | gttttttcaaa | ttgcataact | tatccaagga | 720 |
| tcagtaacca | actataatat | ttaaagtgtg | aatggaaatc | cgcagtatct | tcgactaaag | 780 |
| aactgcagtt | ggatc | | | | | 795 |

<210> SEQ ID NO 47
<211> LENGTH: 221
<212> TYPE: DNA
<213> ORGANISM: artificial
<220> FEATURE:
<223> OTHER INFORMATION: plasmid

<400> SEQUENCE: 47

```
tagaacaatc tcgtagcttc tacactttt g acatttggtt tttgtgcctc tataaatagg      60
gctgttcgct tgcaaccggc atcaattgaa ttggaaaaat acgcttgaaa gcacttttgc     120
gcggagcaac aaagaaagtg ttcttaaact attataattg caagtgatta ataaaggaat     180
tttatatttt gttctacgaa gttgatacat tgaaataaaa c                         221
```

<210> SEQ ID NO 48
<211> LENGTH: 233
<212> TYPE: DNA
<213> ORGANISM: artificial
<220> FEATURE:
<223> OTHER INFORMATION: plasmid

<400> SEQUENCE: 48

```
cgatagtaaa ttgagaagcg gtaaaacctt aagtaaagtc caaaactttt ttgttctaaa      60
tacatacaaa tgtacgtttc aaatacttct tttgaatttc tatcttgcat caattttcta     120
tctaactcaa ttttt ggtta ttgatttaag ttttttaggac atttcatacc agtaggagca    180
ggtaataaga tactaacggc gtatacgtaa ttgaatcggg agataattta aaa             233
```

<210> SEQ ID NO 49
<211> LENGTH: 324
<212> TYPE: DNA
<213> ORGANISM: Aedes aegypti

<400> SEQUENCE: 49

```
gccaacggat gtccacctcg acgacgacga tcaacctgcc ggcctgggaa gatgtcaaga      60
aatccttaca ttaacttcct ccgggatttc cgtaagaagc attgcggact ccaccccgtg     120
caagtgatcc ggatgggagc ccaagcttgg aactgtctcc gggatcaaga acgtcttccg     180
tacatccgga tggcgttcta caaacccatt cgtaggatgc cgtgcccaac aagaattcgc     240
cgtcagcgtc gtagaccaag ccgtagcagg agccaaagcc gctgcagaat gagctgccct     300
atgccgaaga aacgacgacg atgc                                            324
```

<210> SEQ ID NO 50
<211> LENGTH: 30
<212> TYPE: DNA
<213> ORGANISM: artificial
<220> FEATURE:
<223> OTHER INFORMATION: Spacer sequence

<400> SEQUENCE: 50

```
tctggaggcg gtggctcagg cggtggaggc                                       30
```

<210> SEQ ID NO 51
<211> LENGTH: 591
<212> TYPE: DNA
<213> ORGANISM: Planomicrobium okeanokoites

<400> SEQUENCE: 51

```
cagctggtga agagcgagct ggaggaaaag aagtccgagc tgcgccacaa gctgaagtac      60
gtgccccacg agtacatcga gctgatcgag atcgcccgca atagcaccca ggaccgcatc     120
```

```
ctggagatga aggtgatgga attcttcatg aagtgtacg gctaccgcgg caagcacctg    180
ggcggcagcc gcaagcccga cggagccatc tacaccgtgg cagccccat cgattacggc    240 gtgatcgtgg ataccaaggc ctacagcggc ggctacaacc tgcccattgg acaggccgac    300
gagatgcagc gctacgtgga ggaaaaccag acccgcaaca agcacatcaa ccccaacgag    360
tggtggaagg tgtaccccag cagcgtgacc gagttcaagt tcctgttcgt gagcggccac    420
ttcaagggca actacaaggc ccagctgacc cgcctgaacc acatcaccaa ctgcaacgga    480
gccgtgctgt ccgtggagga actgctgatc ggcggcgaga tgatcaaggc cggcaccctg    540
accctggaag aagtgcgccg caagttcaac aacggcgaga tcaacttcta a            591
```

<210> SEQ ID NO 52
<211> LENGTH: 945
<212> TYPE: DNA
<213> ORGANISM: Artificial
<220> FEATURE:
<223> OTHER INFORMATION: Aeprotamine from Aedes aegypti, Fok1 from
      Planomicrobium okeanokoites <400> SEQUENCE: 52

```
gccaacggat gtccacctcg acgacgacga tcaacctgcc ggcctgggaa gatgtcaaga    60
aatccttaca ttaacttcct ccgggatttc cgtaagaagc attgcggact ccaccccgtg   120
caagtgatcc ggatgggagc ccaagcttgg aactgtctcc gggatcaaga acgtcttccg   180
tacatccgga tggcgttcta caaacccatt cgtaggatgc cgtgcccaac aagaattcgc   240
cgtcagcgtc gtagaccaag ccgtagcagg agccaaagcc gctgcagaat gagctgccct   300
atgccgaaga aacgacgacg atgctctgga ggcggtggct caggcggtgg aggccagctg   360
gtgaagagcg agctggagga aaagaagtcc gagctgcgcc acaagctgaa gtacgtgccc   420
cacgagtaca tcgagctgat cgagatcgcc cgcaatagca cccaggaccg catcctggag   480
atgaaggtga tggaattctt catgaaggtg tacggctacc gcggcaagca cctgggcggc   540
agccgcaagc ccgacggagc catctacacc gtgggcagcc ccatcgatta cggcgtgatc   600
gtggatacca aggcctacag cggcggctac aacctgccca ttggacaggc cgacgagatg   660
cagcgctacg tggaggaaaa ccagacccgc aacaagcaca tcaaccccaa cgagtggtgg   720
aaggtgtacc ccagcagcgt gaccgagttc aagttcctgt tcgtgagcgg ccacttcaag   780
ggcaactaca aggcccagct gacccgcctg aaccacatca ccaactgcaa cggagccgtg   840
ctgtccgtgg aggaactgct gatcggcggc gagatgatca aggccggcac cctgaccctg   900
gaagaagtgc gccgcaagtt caacaacggc gagatcaact tctaa                  945
```

<210> SEQ ID NO 53
<211> LENGTH: 38
<212> TYPE: DNA
<213> ORGANISM: Artificial
<220> FEATURE:
<223> OTHER INFORMATION: Primer
<400> SEQUENCE: 53

```
ctcccgtgcg atatcctagg ccccatgtta caaggctg                            38
```

<210> SEQ ID NO 54
<211> LENGTH: 50
<212> TYPE: DNA
<213> ORGANISM: Artificial
<220> FEATURE:
<223> OTHER INFORMATION: Primer

```
<400> SEQUENCE: 54
agccattttg gttaattgaa atccctaaaa taaatgtaat tcatttttcg                50

<210> SEQ ID NO 55
<211> LENGTH: 24
<212> TYPE: DNA
<213> ORGANISM: Artificial
<220> FEATURE:
<223> OTHER INFORMATION: Primer

<400> SEQUENCE: 55
gtaactcccg ttcctgagac aaca                                            24

<210> SEQ ID NO 56
<211> LENGTH: 24
<212> TYPE: DNA
<213> ORGANISM: Artificial
<220> FEATURE:
<223> OTHER INFORMATION: Primer

<400> SEQUENCE: 56
cgatatggag tgggtgaaac ctca                                            24
```

BIOCONTROL

CROSS REFERENCE TO RELATED APPLICATIONS

This application is a U.S. National Phase of International Application No. PCT/EP2013/054417, filed Mar. 5, 2013, which claims priority to United Kingdom Application No. 1203850.1, filed Mar. 5, 2012, the contents of which are incorporated herein by reference in their entireties.

FIELD OF THE INVENTION

The present invention relates to an expression system capable of providing sterile, but competitive, sperm in arthropods, particularly insects, as well as uses thereof in methods of biocontrol (population control), quality control and sex selection of said arthropods.

INTRODUCTION

Insect pests of economic importance, originally native to certain parts of the world, are nowadays widely distributed through international trade and movement of people. Such pests develop large populations and generate damaging infestations of fruit and vegetables worldwide. Potential control methods are wide ranging, including baited spray, direct insecticide spraying, biological control, Integrated pest management (IPM) approaches and the sterile insect technique (SIT) (Malacrida et al., 2007). Current control methods however, rely overwhelmingly on the use of chemical insecticides. Both direct and baited spray have the potential to cause a reduction in pollination due to a decline in bees, and potential for animal or human intoxication. SIT on the other hand, is an environmentally friendly, species-specific method of pest control. It depends on the mass rearing, sterilisation and release of large numbers of sterile males who mate with wild females, causing a reduction in the wild population in the subsequent generation (Dyck et al., 2005; Knipling, 1955). If enough sterile males are released for a sufficient time, the target population will collapse.

SIT relies on irradiation to sterilise the target pest species but this can have a negative impact on the released insects (Alphey, 2002; Alphey, 2007; Alphey et al., 2007). Radiation affects all cells of the insect, not just the gametes, and so a degree of damage to the released insect is unavoidable, with potentially negative effects on its performance (e.g. longevity or mating competitiveness). Radiation-sterilisation needs to be performed at a late developmental stage, limiting the options for release. Also, irradiation instruments are relatively large and costly (to obtain and to run), and tend to impose a degree of centralisation that may be undesirable for some programs. Finally, the isotope-based irradiators which have been the mainstay of SIT programs to date are becoming less favoured due to security concerns about the presence of substantial amounts of radioisotope in these instruments.

Alternatives to radiation have been tried in the past, particularly for mosquitoes. These include chemo-sterilisation and sterilisation by use of cytoplasmic incompatibility (CI, induced by *Wolbachia*), but each of these has its own disadvantages. Chemosterilants tend to be toxic or mutagenic compounds, leading to concerns over worker and environmental safety. *Wolbachia*-based systems depend on the lack of any equivalent *Wolbachia*-infected females in the wild, which may not be the case and also requires that no such females are released; such stringent sex-separation may be difficult to achieve. This and other problems associated with current SIT programs could be overcome by the use of recombinant DNA methods (Morrison et al., 2010; Franz & Robinson, 2011).

A transgenic alternative to radiation-sterilisation has been suggested, termed Release of Insects carrying Dominant Lethals (RIDL: (Alphey, 2002; Alphey, 2007; Alphey and Andeasen, 2002; Alphey et al., 2010; Alphey et al., 2007; Alphey and Thomas, 1999; Thomas et al., 2000). In this system, insects are engineered to carry a dominant repressible lethal gene or genetic system. These are released into the wild; progeny of matings between wild insects and RIDL insects that inherit a copy of the RIDL gene or construct will tend to die. The RIDL system may be designed to kill all progeny that inherit it, or only one sex. It may also be designed to kill the affected insects at a particular stage in development; this may have significant advantages in some species, e.g. some mosquitoes (Phuc et al., 2007). RIDL systems have been constructed in a number of pest species (e.g. Fu et al., 2007; Gong et al., 2005; Phuc et al., 2007). Further information on the RIDL system may be found in WO 01/39599.

Our female lethal RIDL technology (female-specific RIDL, fsRIDL) is highly, even sometimes as much as 100%, effective in separating sexes and has been successfully tested in laboratory, greenhouse and semi-field experiments. RIDL could be used with or without radiation to produce an effective product.

Despite the fact that this strategy provides a considerable advantage for SIT implementation on a number of pest insects, such as fruit flies; *Ceratitis capitata*, *Bactrocera oleae* and *Anastrepha ludens*, Lepidoptera; *Pectinophora gossypiella* and *Plutella xylostella* and mosquitoes; *Aedes aegypti* and *Aedes albopictus*, and can be employed on its own, irradiation might still be the method of sterilisation in certain markets. This is because, in the female-specific RIDL strains described to date, F1 males are fully viable and females are eliminated at a larval stage (i.e. after egg hatch). Furthermore, regulatory pathways and public acceptance will be significantly eased by providing genetic sterilisation (or a trait that confers this). Genetic sterilisation in males would advantageously augment our current "female lethal" (fs-RIDL) strains.

Thus, there is a need in the art for an expression system that can provide a means of genetic sterilisation in males akin to the effects of radiation in an SIT method, but without the associated reduction in fitness of the irradiated individuals.

Crisanti et al., (Catteruccia et al., 2009; Windbichler et al., 2007; Windbichler et al., 2008) have developed an expression system where an endonuclease (IppO-1, also known as I-PpoI) is linked to the promoter from a constitutive structural gene, Beta-2 Tubulin. There a number of problems with this system, discussed herein, not least of which is that the experiments were largely unsuccessful in achieving their aims. However, it would also be particularly useful to be able to exert a degree of control on the timing of the genetic sterilising effect. This control is missing from the Crisanti system.

For instance, one may want to allow breeding of individuals carrying an expression system in the lab, but also want the system to be activated or triggered when required, such as on or shortly before/after release. In other words, one may want to suppress the effect of the system and/or induce it a particular point.

In short, it is desirable for an expression system of this kind to include a means for exerting control on the effect of the expression system. Such control is often referred to as "conditionality," such that a system including this control is a conditional system. Conditional expression systems are known, for instance in insects, but not in the present context of genetic sterilisation. In any case, these conditional systems are not suitable for male germline expression. In fact, in order to harness existing conditional systems, such as the bipartite tet system, one cannot simply include them in a larger male germline expression system. Doing so, in the male germline, does not serve to control expression of an effector (designed to achieve genetic sterilisation in said germline). The reasons for are complex, but centre around the unusual conditions invoked by meiosis.

Despite this, we have surprisingly developed a suitable system for expression in a male germline. The system is capable of providing genetic sterilisation in the sense that expression of the system in the germline produces sperm that are not capable of forming a viable zygote. We have found that use of a conditional system such as tet can be harnessed, but that a significant overhaul of the entire expression system is required. It is extremely advantageous that the system that we have discovered cleverly replicates the effects of radiation in SIT methods. Indeed, it allows for the production of male sterile insects without resorting to the use of debilitating radiation.

We have, therefore, shown that an arthropod expression system comprising a suitable effector harnessed to a conditional system via other regulatory regions can be made capable of inducing conditional genetic sterility, sometimes referred to herein as "sperm lethality." However, it will be appreciated that the preferred intention is not to kill the sperm per se or even to prevent their production, but instead to produce sperm that cannot pass on their genetic information. However, the sperm are otherwise capable of competing with wildtype sperm or rendering a zygote inviable (i.e. prevent formation of a viable zygote).

This solves the above problems by providing conditional, and preferably repressible, male sterility that works by allowing the production of sperm that are defective, in the sense of being unable to fertilise an egg to give a viable zygote or embryo (one capable of developing to a fertile adult), but are still capable of entering or contacting an egg in such a way as to exclude other sperm.

Further technical background information may be found in GB2404382A, GB2355459A, JP2008067678A, WO2009/016627A, WO2008/134068A, W C Black et al. (Trends in Parasitology, 362-370, Vol 27, 2011), C Barreau et al. (Development, 1897-1902, Vol 135, 2008), G Fu et al (Proc Natl Acad Sci USA, 4550-4554, Vol 107, 2010) and T Ant et al. (BMC Biology, 51, Vol 10, 2012).

SUMMARY OF THE INVENTION

Thus, in a first aspect, the present invention provides an arthropod male germline gene expression system suitable for conditional expression of an effector gene in an Arthropod male germline, the system comprising:
   a first expression unit comprising an effector gene and a promoter therefor operably linked thereto;
   a second expression unit comprising a coding sequence for a transcription factor and an upstream regulatory element operably linked thereto, the transcription factor being capable of acting upon the promoter in the first expression unit to drive expression of the effector gene, the upstream regulatory element including:
      a promoter for the transcription factor; and
      a 5' UTR adjacent a translation start site for the transcription factor coding sequence;
   the upstream regulatory element driving sufficient expression of the transcription factor such that the transcription factor protein in turn drives transcription of the effector gene before meiosis.

The transcription factor is preferably a transcriptional activator, such as tTA, GAL4 or their variants. The effector is preferably an endonuclease, most preferably a 3-Zn finger nuclease. The promoter of the first expression unit is preferably a minimal promoter. The promoter of the upstream regulatory element in the second expression unit is most preferably from topi, aly or Beta-2 Tubulin (B2T) or homologues thereof. The homologue is preferably that found in the target arthropod in which the system is to be expressed. This promoter is a male germline promoter, i.e. it is acted upon or activates transcription in the male germline. The 5' UTR in the upstream regulatory element of the second expression unit is preferably that from hsp83, preferably from Medfly or homologues of hsp83, particularly the homologue of hsp83 found in the target arthropod (i.e. that in which the system is to be expressed). Alternatively, the 5' UTR may be that from B2T or homologues thereof, provided that said 5' UTR has been amended to remove or ameliorate the effects of transcriptional delay signals contained in the wild-type, especially if used in combination with the B2T promoter.

The first or second expression unit may also comprise an enhancer. Either or both of the first and second expression unit promoters, especially a minimal promoter, can be considered to further include an enhancer.

The expression units can be provided separately or together within the same construct. If separately, then the expression system can comprise separate constructs. The construct or constructs are preferably plasmids. The plasmids may comprise transposons. The transposons may in turn comprise transposable elements. Examples of transposons may include the piggyBac transposon.

The conditional nature of the expression of the effector gene is such that it can be controlled by a user or is otherwise influenced by outside factors. Such factors may be environment factors such as temperature (for instance in the case where the Gal4-UAS system is used), but are most preferably chemical entity, such as tetracycline or its analogues. Temperature can be controlled in the lab, and it could be envisaged that temperature changes during the course of the day or season may be harnessed. However, in some embodiments this is not preferred as one may wish to achieve a finer degree of control. In such instances, it is particularly preferred that the system is conditional in the sense of being inducible and most preferably repressible.

Inducible systems are known, for instance a GAL4-UAS set up may be employed where the transcription factor is GAL4 and the first expression comprises (outside of the effector gene coding sequence) the UAS region (CGG-$N_{11}$-CCG, where N can be any base) to which GAL4 binds or preferably an oligomer thereof. If the upstream regulatory element in the second expression unit comprises a suitable promoter and 5'UTR, then transcription of the Gal4 transcription factor may be induced by provision of a peptide or hormone for instance that acts on the promoter of the Gal4 transcription factor (directly or indirectly, i.e. causes transcription to be induced).

In another preferred example, the system may be an inducible system, where induction occurs by provision of a chemical entity, such a tetracycline or one of its analogues including doxycycline. In such a situation, the use of rtTA ("reverse tTA") as the transcription factor may be employed for instance, so that rtTA binds DNA only in the presence of tetracycline an analogue such as doxycycline. rtTA is described in WO 2001/059088 inter alia. In this case, provision of tetracycline (i.e. in the diet) or an analogue such as doxycycline will allow the rtTA transcription factor in the present system to act on the first expression unit and hence induce expression of the present effector gene.

However, it is preferred that the system is repressible. A preferred example is that the transcription factor in the second expression unit is tTA or a variant thereof (tTAV, tTAV2, tTAV3 etc). These bind DNA unless tetracycline (Tc), or an appropriate analogue, is present. Tetracycline will block the DNA-binding of tTA, so there will be no interaction between tTA and an enhancer in the first expression unit and, therefore, no transcription of the effector gene. Thus, as is well known (see for instance our RIDL publication referred to herein), tetracycline can be provided in the diet until such time as it is desired to de-repress (i.e. remove or relieve the repression of) expression of the effector gene. In the absence of tetracycline (or an analogue such as doxycycline), such as after field release or upon a switch of diet in the lab, the effector gene is expressed.

Thus, in some embodiments it is preferred that the system is inducible, but in other embodiments, which are particularly preferred, the system is repressible.

The two expression units are preferably one of the two parts of a bipartite (conditional) expression system. Preferred examples include GAL4:UAS and the various tet systems. In the first case, the transcription factor of the second expression unit is preferably Gal4, whilst the first expression unit preferably comprises the UAS sequence for GAL-4 to bind. Suitable variants of GAL4, such as GAL4-VP16 are also envisaged.

In general, either or both of the expression units may comprise an enhancer. However, it is particularly preferred that the first expression unit comprises an enhancer. It is preferred that the transcription factor of the second expression unit is tTA or a variant (i.e. when the present expression system utilises the tet system to provide conditionality). When this is the case, then the first expression unit preferably includes the tet operator (tetO). The tetO-mini promoter (tRE) element is particularly preferred. It provides together the promoter and enhancer elements of the upstream regulatory element of the second expression unit. The 426-bp TRE promoter contains seven tetO 18-mers fused to a mini-cytomegalo-virus (mini-CMV) promoter (see for instance M. Ghosh et al., Mol. Cell Biol. 2004, 24(23) 10193).

Although bipartite systems are preferred, where the first and second expression units are provided in separate constructs, the first expression unit and the second expression unit may also be provided on the same construct or plasmid. As such, the present system is preferably a plasmid or consists of two plasmids. Most preferably the two expression units are transformed as a single plasmid or a vector such at they are inserted at the same locus in the genome.

The arthropod is preferably an insect, as described further below. Male germline will be understood to include sperm, such that the system is capable of expressing the effector gene in sperm.

The effector confers or imparts paternal effect lethality under at least some circumstances, i.e. is, or is a part of a "paternal effect lethal" genetic system. In such a system, death of the offspring (taken here from the stage at which the sperm enters the egg, which in insects may not be simultaneous with membrane fusion) depends on the genotype of the father rather than of the zygote (or potential zygote). So, for example, in a dominant paternal effect lethal system, at least some of the wild type offspring from a heterozygous male mating a (homozygous) wild type female will be affected. Additional zygotic effects are possible of course, and anticipated within the invention. Several potential modes of action for such an effector are possible and envisioned. For example, in some embodiments, the effector is or comprises a nuclease. As such, sterility is achieved via what we term "paternal effect lethal." Here, the effector is expressed (to provide a functional nuclease protein) in the sperm. This may lead to DNA in sperm being affected such that the fertilised embryo has a reduced survival probability; indeed, this is a preferred example of a mechanism by which the paternal effect lethality may be achieved. It is also possible that the effector protein is passed into the egg where DNA cleavage can also occur. However, it is also envisaged that at least some effector transcript may also be passed into the egg, from the sperm, and translated in the egg. In both instances, the nuclease effector can thereby take its effect in the egg as well as the sperm.

The system is suitable for expression of the effector, but it will be understood that this may also be preferably referred to as 'capable of such expression' or 'adapted to express an effector in the male germline.'

The effector gene will be described further below, but it is preferably a reporter, such as a marker e.g. a fluorescent protein such as GFP, YFP and so forth. More preferably, however, the effector gene is a nuclease, of which suitable examples are provided below. Most preferably it is both a nuclease and a reporter, for example a nuclease-fluorescent protein fusion (preferred examples of which include the well known Green Fluorescent Protein or Yellow Fluorescent Protein).

Where reference is made herein to a gene 'being' a reporter or a nuclease, for instance, it will be appreciated the gene comprises DNA or RNA encoding a protein having that stated function.

The first expression unit comprises the effector gene. It also comprises a promoter therefor and which is operably linked thereto. The promoter is therefore suitable for driving transcription of the effector gene. As mentioned above, the first expression unit may also comprise an enhancer, or at least a binding region or sequence for (i.e. recognised by) the transcription factor of the second expression unit.

The second expression unit comprises a coding sequence for the transcription factor. It also comprises an upstream regulatory element. This in turn is operably linked to the coding sequence for the transcription factor so that it can drive transcription of the transcription factor.

The transcription factor is capable of acting upon the promoter in the first expression unit to drive expression of the effector gene, although this may be via an enhancer of course, i.e. the transcription factor may not act directly on the promoter but via an enhancer instead. Other regulatory elements such as those for a 5' cap, a 5' UTR, 3' UTR and polyA tail are of course envisaged.

To drive transcription of the transcription factor, the upstream regulatory element of the second expression unit comprises a promoter and 5' UTR. Both of these need careful selection in order to provide sufficient expression of the effector. As such, the promoter of the second expression unit (i.e. in the upstream regulatory element) is preferably that from Beta-2 Tubulin (B2T). Alternatively, and more preferably, the promoter is from topi or aly. The 5' UTR in the second expression unit (i.e. in the upstream regulatory element) is preferably that from hsp83, for instance that from Medfly, but it may also be from B2T. If both the 5' UTR and promoter is from B2T, then one or other must be amended to such the translational delay signals removed or ameliorated. Reference to these genes includes their homologues of course.

The 5' UTR is defined herein as the sequence 5' adjacent (i.e. upstream) to the translation start site (i.e. minimally, the ATG start sit for translation). It has a median length of about 150 bases in eukaryotes and preferably extends up to the promoter, for instance around 50-500 bases upstream of the ATG start site.

Although the bulk of the framework in the second expression unit may be from B2T, albeit with the B2T ORF replaced with the transcription factor ORF, it will be appreciated that both the second expression unit's promoter and its 5' UTR cannot be those from B2T: at least one of them needs to be changed to provide sufficient accumulation of the effector transcript to occur before meiosis. If the B2T promoter is to be used, then the B2T 5' UTR must be the amended/ameliorated form described above, or it may be that from hsp83.

Alternatively, if the B2T 5' UTR is used, then the promoter must be another early-acting promoter. What is required is that the choice of the 5' UTR and the promoter for the second expression element must act together to allow for sufficient accumulation of the effector transcript to occur before meiosis.

Preferred examples of alternative promoters are the topi and the aly promoters. These may be used with a range of 5' UTRs. Examples of their sequences are provided below.

When reference is made to a particular genetic element such as a promoter, enhancer, 5' UTR or even an ORF being 'from' a certain a named gene, it will be appreciated that it does not actually mean that the element is removed from the reference gene, it simply means that this is the origin of the element. Another way to describe this would be 'derived from.' It is preferred that the species origin of the gene is the same as that of the target species. In other words, where it is desired to express the present effector in a Medfly, it is preferred that the elements are derived from the Medfly homologues of the mentioned gene. Failing that, however, the *Drosophila* versions are preferred.

In fact, it is preferred that the descending order of preference is:
 (most preferred) from the target species (in which the expression of the effector is envisaged);
 from the target genus (i.e. from another species within the same genus); and finally
 (least preferred) from the target family.

The reason is that the action of the preferred promoters at least may not be very well conserved across species. For instance, a *Drosophila* promoter may not work in Medfly, so a promoter from the Medfly homologue of the same gene is preferred. However, as the coding sequence is well conserved, it is relatively simple to identify the beta-2-tubulin gene (for instance) in a given arthropod and hence identify by routine methods a suitable promoter fragment for the Medfly version.

A suitable promoter is normally identified within 1 to 2 kb upstream of the transcription start of the mRNA. Although this range is preferred in the present invention, some male germline promoters can be short and a 100-200 bp stretch is also preferred, either within the 1-2 kb window upstream of the transcription start of the mRNA, or even a 100-200 bp stretch upstream of the transcription start of the mRNA.

Similar considerations in terms of sequence conservation apply in respect of 5' UTRs, where primary sequence conservation is low. Thus, it is preferred that the 5' UTR is from the same species as the target arthropod, for instance following the above example, if the target is Medfly, then it is preferred that the 5' UTR is a 5' UTR from the Medfly homologue of the same gene (identifiable as discussed above by reference to the more highly conserved ORF). One way to identify and define a 5' UTR is that it is attached (as RNA) to the 5' end of a sequence encoding the respective ORF, for example beta-2 tubulin.

In the case of both the 5' UTR and the promoter, it will be readily identifiable if the sequence used in the present expression is insufficient as there will be no expression of the transcription factor, which can be assayed in usual way or tested via the provision of a fusion protein linking the transcription factor ORF to a fluorescent protein.

Preferably, the promoter in the upstream regulatory element of the second expression unit is the beta-2-tubulin promoter. This is most preferably used in combination (in the upstream regulatory element of the second expression unit) with the hsp83 5' UTR described herein.

It is also preferred that the promoter in the upstream regulatory element is the topi promoter. To assist with identifying a homologue of topi, we hereby provide the topi ORF (see below). Further guidance is provided in Perzgasga et al (2004), for instance, which is hereby incorporated by reference and describes topi orthologues from *Drosophila melanogaster, Drosophila pseudoobscura* and *Anopheles gambiae*, the latter being particularly preferred.

Alternatively, it is preferable that the promoter in the upstream regulatory element is the aly promoter. Aly represents a more recent gene duplication than topi, so is not present as a male-germline-specific gene in as wide a range of species as topi. Nevertheless, where it is present this can be readily identified in the same way as for topi by reference to the conserved ORF. The aly ORF is provided below.

The transcription factor of the second expression unit is preferably tTA or a variant thereof and the first expression unit comprises the tet operator (tetO). The amino acid sequences of tTA, tTAV, tTAV2 and tTAV3 is given below.

It is therefore preferable that the transcription factor of the second expression unit comprises polynucleotides encoding any of the amino acid sequences of tTA or its variants, for instance those given above. As described above, it is also preferred that the transcription factor is GAL4 or a variant thereof and the first expression unit comprises the UAS site for GAL4.

For both tTA and Gal4, this preferably includes any sequences having (or encoding) at least 70%, at least 90% or at least 95% amino acid sequence 'identity' or even the less stringent 'similarity' over at least 50 residues with one of said SEQ ID NOS, including the variants.

It will be understood that the placement of the transcription factor recognition sequence (the DNA, for instance, sequence to which the transcription factor binds), must be within the first expression unit and not within the ORF. For instance, with both tetO and UAS the insertion is within a few thousand bases upstream of the ATG start site, for instance. They are normally placed within a few hundred bases of the promoter, but can act out to a couple of kb.

In any case, it is preferred that the promoter is a minimal promoter. Together with the enhancer, one can refer to the {enhancer+minimal promoter} merely as a promoter for the sake of simplicity. Then the enhancer (transcriptional activator binding site, e.g. tetO or UAS) is part of the promoter by definition.

BRIEF DESCRIPTION OF THE FIGURES

Certain embodiments of the invention will now be described with reference to the following figures, wherein:

FIG. 1 is a schematic drawing representing a design of the egg hatch rate assay;

FIG. 2 shows percentage of OX4282-OX4104 male sterility on and off Tetracycline;

FIG. 3 shows percentage of OX4282-OX4458 male sterility on and off Tetracycline;

FIG. 4 shows percentage of OX4353 male sterility on and off Tetracycline;

FIG. 5 shows percentage of OX4353 female sterility on and off Tetracycline;

FIG. 6 shows repressible male-specific sterility in OX4718-σ1 lines;

FIG. 7 shows percentage of OX4705 olive fly male sterility on and off Tetracycline;

FIG. 8 shows percentage of OX4705 female sterility on and off Tetracycline;

FIG. 9 shows OX4466 strain hatch rate assay;

FIG. 10 shows OX4467-E1 strain hatch rate assay;

FIG. 11 shows hatch-rate assay of *Aedes aegypti* lines carrying both topi-tTAV and tetO-Dm-Protamine-FokI alleles;

FIG. 12 shows hatch-rate assay of *Aedes aegypti* lines carrying both β2-tubulin-tTAV and tetO-Ae-Protamine-FokI alleles;

FIG. 13 shows OX4353 strains crossed to two leading RIDL female lethal lines (OX3864A and OX3647Q);

FIG. 14 is a plasmid map of OX3866;
FIG. 15 is a plasmid map of OX3867;
FIG. 16 is a plasmid map of OX3671;
FIG. 17 is a plasmid map of OX4112;
FIG. 18 is a plasmid map of OX4103;
FIG. 19 is a plasmid map of OX4104;
FIG. 20 is a plasmid map of OX3831;
FIG. 21 is a plasmid map of OX4458;
FIG. 22 is a plasmid map of OX4391;
FIG. 23 is a plasmid map of OX4286;
FIG. 24 is a plasmid map of OX3978;
FIG. 25 is a plasmid map of OX4275;
FIG. 26 is a plasmid map of OX4254;
FIG. 27 is a plasmid map of OX4371.

DETAILED DESCRIPTION OF THE INVENTION

The terms 'coding sequence' and ORF may be used interchangeably herein.

As explained above, in a preferred embodiment, the sperm don't die (as the term 'sperm lethal[ity]' might imply to some). Instead, something in the sperm kills the zygote. When we use a nuclease this is probably genetic damage to the sperm DNA, but it is also possible that RNA or protein carried by the sperm have their effect post-fertilisation (indeed, Burt/Crisanti have suggested this to explain the death of females as well as male embryos from their X-shredder in *An. gambiae*, see Windbichler et al 2008, supra).

The prior art teaches that one should use the B2T gene (promoter and ORF) and replace the ORF with a gene of interest. However, we have found that this does not lend itself to a conditional system of the type described herein. If the system is to be made conditional, we have found that it significant changes have to be made to this setup. One of the problems is that transcription shuts down once the cell enters meiosis. Although translation can still occur in the post-meiotic cell(s), further transcription cannot (post-meiotic transcription of a few exceptional genes has recently been described by Barreau et al (2008), but the general point is valid). Thus, if it is desired to express a protein of interest (from said gene of interest), such as an effector protein, then there must be sufficient expression of the effector gene (to provide a corresponding effector RNA) before meiosis. By "effector RNA" it is meant RNA, e.g. mRNA, coding for (which when translated and optionally post-translationally modified, cleaved if a fusion protein, and/or folded) provides an amino acid sequence that functions as the effector protein.

In the context of the present invention, "sufficient" provision of a transcript or a protein relates to both the quantity and timing of said transcript or protein. Thus, when applied to the effector gene, it means that the present system ensures that at least the transcript for the effector protein is generated before meiosis (timing) and that enough of said transcript is thereby provided to achieve the desired protein function. It will be appreciated that this includes all interim events in protein expression, such as optional processing of the transcript, translation of the transcript into an amino acid sequence having a primary structure and optional modification thereof, and provision of secondary, tertiary and even quaternary structure (say for instance in the case of a dimer).

However, when a conditional system is employed, the prior art systems cannot provide sufficient functional effector protein to be effective. This is primarily thought to be because the such conditional systems require not only transcription and translation of the effector protein, but also transcription and translation of a control factor protein that acts as a transcription factor on (the regulatory units of) the effector protein. There is simply not time for the additional requirements of a full cycle of transcription, translation and protein function, followed by further transcription, all before meiosis. In other words if, as is the case here, the conditional system employs a transcription factor, then that transcription factor needs to be transcribed and translated itself to provide a functional transcription factor protein. That transcription factor protein must then in turn act upon the regulatory elements of the effector gene (encoding the effector protein), such that there is sufficient accumulation of effector transcript in each cell before meiosis to in time allow translation of the effector transcript in each cell following meiosis.

What we have found is that it is not merely sufficient to simply replace the ORF in the prior art systems with an ORF coding for a transcription factor. Instead, the B2T promoter region of the art also has to be either amended or replaced entirely so that the system can produce sufficient effector transcript before meiosis (to then have a functional (translated) protein post-meiosis). Thus, in our new conditional system, new upstream regulatory elements (such as a promoter and/or 5'UTR) are required to drive expression of the transcription factor ORF. The new upstream regulatory elements must act early enough in spermatogenesis to generate sufficient transcription factor functional protein to in turn act upon regulatory elements controlling expression of the effector and thereby generate sufficient effector transcript before meiosis occurs and transcription shuts down. It is a particular advantage of the present invention that it is able to achieve this in the context of a conditional system.

The effector protein (i.e. the functional protein encoded by the effector gene) most preferably has a deleterious effect, post-meiotically, on the ability of the sperm to fertilise an egg to produce a viable zygote.

The system is preferably dominant, in the sense that the sterility it causes in the sperm is dominant. This is where the concept of paternal-effect lethality comes in, see further below. The genetic sterility caused by a preferred effector such as a nuclease is preferably dominant in the male, so that all sperm from a heterozygous male are affected. It will be appreciated that this is not essential, since we expect to release homozygous males, but preferable. This is in contrast to dominant in the zygote, as is the case in conventional RIDL. In these prior art systems, one copy (inherited with the sperm) is enough to kill the zygote, but of course eggs fertilized by sperm (from a heterozygous male) that carry a wild-type allele are not affected.

The arthropod is preferably an insect and suitable examples of both insect and non-insect arthropods are provided herein. However, it is particularly preferred that the arthropod is a mosquito, particularly of a species able to transmit malaria or dengue, or an agricultural pest, such as a fruit fly.

The arthropod in which the present system is expressed is a male arthropod and expression occurs in male germline cells thereof, particularly the gonads, i.e. the testes, where spermatogenesis occurs. In addition, or alternatively, expression may occur in the sperm themselves. Preferably, the expression occurs in the majority of said cells i.e. at least 50% of said cells, but it can be much higher, for instance at least 80%, at least 90%, at least 95% or most preferably 99-100% of said cells.

The expression system is, therefore, capable of, adapted to or suitable for expression of a gene in the male germline of an arthropod. By "gene" here it is meant principally a protein. In other words, the function of this expression system is to express a protein in the male germline (germline cells) of an arthropod. The timing of this expression is crucial and is discussed further elsewhere, but it must be sufficient to render sperm unable to fertilise an egg to give a viable zygote. Ideally, the expression system itself is, or is comprised within, a plasmid, transposon or other transposable genetic element capable of expression in the male germline of the arthropod, i.e. by transformation. The expression system is, therefore, preferably a polynucleotide expression system, preferably DNA, RNA or a mixture of the two.

The expression from the system is preferably conditional. Although it may be inducible, it is particularly preferred that the conditionality is repressible such that expression only occurs in the absence of a repressor. In an inducible system, expression will only occur in the presence of an inducer. A particularly preferred repressible system for inclusion in the present expression system is the tet (tetracycline) system or the GAL4/UAS system, both described further herein.

It will be appreciated that the promoter is capable of expression in the male germline cells of an arthropod, i.e. is capable of initiating transcription therein. It will also be appreciated that the promoter is operably linked to the regulatory elements and coding sequence of the present system.

It may be that the system comprises a single coding sequence or more than one coding sequence. The one or more coding sequences may be joined as a fusion or provided separately. Suitable examples of further coding sequences are markers or reporters such as the fluorescent proteins (e.g. GFP, EFP, YFP, etc), but further effectors are also preferred to provide greater specificity.

Aside from the specifically described upstream regulatory elements of the second expression unit, the present system also may include further regulatory elements as appropriate. These facilitate, i.e. enable, expression in the male germline cells of an arthropod. Furthermore, as described below, the further regulatory elements facilitate pre-meiotic processing and translation of RNA. Thus, the further regulatory elements are not part of the promoter but preferably include the 5'UTR in the first expression unit and/or a 3'UTR in both the first and second expression units. Thus, these further regulatory elements can be considered as untranslated sequences, as is the case with the specified 5' UTR of the second expression unit. They all preferably include at least a substantial part of a 5'UTR or 3'UTR, but most preferably a complete 5'UTR or a complete 3'UTR. Most preferably, at least a substantial part of the 5'UTR and a 3'UTR are provided (and preferably both are complete). The regulatory elements thus may include all or part of a 5'UTR, including the various regulatory sequences, associated or found within the 5'UTR that enable translation of an RNA sequence, for instance one that has recently been transcribed from DNA.

All the promoters described herein should preferably include features such as transcription factor and RNA polymerase binding sites. These are promoter elements (typically) not UTR elements (though there can be an overlap). A 5' UTR generally has some translation start signals, possibly also RNA stability, localisation, translation control and intron sequences (though not necessarily).

The same follows for other further regulatory elements that may include a 5' cap and/or a polyA tail. In other words, ideally all of these elements are present in at least a substantial part, i.e. that sufficient to provide their necessary regulatory function. The skilled person would be able to assess whether or not sufficient expression of the coding sequences was provided in the presence or absence of all or part of these regulatory elements, as the fundamental requirement is the downstream functionality of the sperm. The skilled person is able to assess whether the sperm are able to compete, which is advantageous. He is also able to readily identify and whether the sperm produce viable zygotes, which is not advantageous. If the sperm do not compete, and/or if they do produce viable zygotes, then the expression levels of the effector will need revision. In the present invention, the sperm (by which is meant transformed or GM (genetically modified, i.e. carrying the transgene/the present expression system)) are preferably able to compete with wildtype sperm but do not produce viable zygotes. Thus, if one of these is not achieved, especially if viable zygotes are produced, then the system needs revision.

However, what must be borne in mind is that the processing of the RNA of the effector ORF/coding sequence into said effector transcript occurs pre-meiotically and accumulates in sufficient levels such that the later translated and functional protein has the desired effect on the ability of the sperm to fertilise an egg to produce a viable zygote. This is discussed in further detail elsewhere.

Where the effector encodes the preferred nuclease, for instance, this is a deleterious effect. This occurs at any point (although obviously after the effector transcript has been processed and translated and so forth into a functional protein. The basic requirement is that there must be sufficient transcript of the effector before meiosis as transcription shuts down at that point. However, it is envisioned that the effector protein may be functional post-mitoically (but certainly post-meiotically). T Preferably, all the regulatory elements are homologous to each other, i.e. derived from the same gene. It is particularly preferred that, in order to fine-tune expression levels, that the regulatory elements are heterologous to each other, such that the, for instance, 3'UTR may be derived from a different gene to the chosen 5'UTR. It is preferable that the 5' cap and polyA tail are homologous to the promoter, i.e. from the same gene as the promoter.

As the effector gene is one that is not normally expressed in germline cells of a male arthropod, it will also be appreciated that the regulatory elements are heterologous to the gene (i.e. heterologous to the coding sequence). In all of this, it will be appreciated that heterologous refers to the origin of the genetic element such as the promoter, 5'UTR (or other regulatory element) or coding sequence, such that they may come from different genes from the same organism; from conserved genes from different organisms; or even different (unrelated) genes from different organisms. In other words, said elements can be from (in the sense of derived from, although modification is envisaged) a range of different genes within a single organism or a range of different genes from different organisms, with the proviso that they are sufficient to provide the necessary expression levels in the male germline of the arthropod, i.e. in the gonads or sperm thereof. In particular, the coding sequence may not necessarily be from an arthropod at all whilst for example the regulatory elements may also be preferably derived from bacteria or viruses if this assists with the appropriate degree and timing of protein expression from the coding sequence, particularly in respect of pre-meiotic translation.

The coding sequence encodes an effector protein. As mentioned above, the coding sequence is preferably heterologous to the other elements in the expression system such as the promoter and/or the regulatory elements. Whilst the coding sequence in the expression system will be a polynucleotide, it is capable of being transcribed into a suitable messenger RNA (mRNA) sufficient to be then translated into a functional protein. Alternative splices of the RNA are envisaged, regulated by intronic (splice control) sequences in co-operation with a spliceosome. The advantage of providing or controlling alternative splices is that it adds an additional level of regulation to the protein expression. Further guidance on this is provided in our earlier publication WO 2007/091099.

The timing and location of the expression of the effector protein are critical to this invention and are discussed further below. However, it will be appreciated that the function of the effector is to preferably have a deleterious effect on the ability of the sperm to fertilise an egg to produce a viable zygote.

As described herein, it is important that the female feels as though she has been properly fertilised otherwise she will seek a further mate or, indeed, there may already be other wildtype sperm with which the present sperm needs to compete. However, the sperm will be unable to compete if its general functions are significantly impaired, such as its ability to "swim".

The preferred effector has the deleterious effect on the ability of the sperm to fertilise an egg to produce a viable zygote. Preferably, it induces or directly causes DNA damage. Particular preferred examples of this are nucleases, particularly endonucleases. Further examples of these are provided below.

The promoters drive, i.e. are capable of or adapted to initiate, transcription of the effector coding sequence, as well as the regulatory elements surrounding it, into RNA. The timing of this is crucial and highlighted elsewhere. Translation of the effector can occur before or after meiosis.

The effector protein has a deleterious effect, especially after meiosis (post-meiotically). The sperm are created by spermatogenesis from male germline cells carrying the present expression system. Said sperm therefore preferably carry or comprise at least one copy of the effector protein, but preferably significantly more than one copy. This deleterious effect reduces the ability of the sperm to fertilise an egg. Thus, the present system acts well before the induction of lethality in embryo-specific systems as disclosed in Horn and Schetelig (Horn, C., Wimmer, A. E. 2003, Schetelig, M. F., Handler, M. A. 2012). It is strongly preferred that the effector allows the sperm to have sufficient motility such that they are able to compete with normal (i.e. wildtype or untransformed) sperm in the rush to reach the egg. Again it is noteworthy that it is not essential that the sperm carry a copy of the DNA (gene encoding the effector). Indeed, this is preferred and is a key difference from zygotically active RIDL systems, as the present system can:

ensure that there is no egg hatch;
be used in combination with genetic sexing;
provides conditionality; and
pure-breeding, zygotic lethality and resistance.

Generally, insemination is in the female genital tract. Males transfer sperm during mating which the female stores. Mature eggs passing down the female reproductive tract are exposed to this sperm and fertilised. For some species (Medfly, *Aedes aegypti*), females typically mate only once and use the stored sperm for all their eggs. Some other insects, e.g. some moths, mate rather more often.

However, it is particularly preferred that the effector causes sufficient DNA damage that the formation of a viable zygote is impossible, for instance because the haploid genetic information provided by the sperm is damaged. For instance, it is preferred that the sperm's DNA has a double-strand breakage therein. This preferred embodiment results from the use of endonucleases, examples of which are provided herein. Thus, the present invention prevents the formation of viable zygote in the first place, rather than expressing a further protein in the zygote once formed. This is an important distinction over the prior art, such as the RIDL technique, where functional zygotes are formed and then an effector is expressed to kill the zygote. In the present invention, no viable zygote is ever formed.

Thus, it is preferred that the zygote may never advance beyond the single cell stage. Early insect embryos, for instance, divide their nuclei without cell division, then cellularise, so go from 1 cell to >1000 in one step. However, it is also preferred that the embryo merely fails to hatch as a larva (which is a desirable feature in the field). A minimum requirement is, therefore, preferably that the individual fails to develop into a viable adult.

Thus, it can be seen that the present invention provides, as a solution to the problems with the prior art, a delicate balancing act of pre-meiotic accumulation of transcript of/for a heterologous effector protein, preferably an endonuclease, before meiosis occurs in the spermatogenic process, such that, after meiosis, the resulting sperm carry copies of the translated effector sequence which can then take effect in the sperm. This effect takes place before fertilisation, thus effectively rendering the sperm sterile, such that the sperm are sterile, active sperm. This is the "sperm lethal" effect described herein.

There does not seem to be a strong checkpoint for DNA integrity at meiosis. Therefore pre-meiotic damage to DNA is generally tolerated. Indeed, this is probably what radiation does: radiation leads to variable sperm head size, whilst head size is proportional to DNA content. This variable DNA content may therefore derive from uneven segregation of DNA at meiosis due to DNA damage cause by radiation in pre-meiotic cells. However, there is a strong checkpoint in mitosis (normally), so DNA damage in germline stem cells (GSCs) or spermatogonial cells is likely to prevent development of functional (in the sense of ability to fertilise an egg) sperm.

According to a further aspect of the invention, there is provided a method of expressing the effector protein in a gonad or sperm. Preferably, the method comprises transforming the gonad with the present expression system. This aspect also relates to a method of transformation.

Also provided is a method of population control comprising expressing said protein via the present expression system in the gonads of a male arthropod. The preferred arthropods are described herein.

The invention also provides a method of resistance management. In principle for any zygotically active RIDL system, including an embryo-active one, there is a possibility that something in the zygote's genome (e.g. genetic material inherited from the mother) could prevent or reduce the intended lethal effect. In respect of RIDL this would be an inherited resistance factor. To illustrate, a resistance factor might be something that reduces the level of expression of the lethal effector, or reduces the sensitivity of the target of the lethal effector to that effector. However, for the present invention, when an endonuclease is used, it is hard to envisage how that could happen. The damage is already done—using a nuclease as an example, the DNA of the sperm has already been damaged and it is hard to envision how this might be corrected in the egg, thus making the damage permanent.

With respect to resistance management, one could envision a situation where if we were using female-specific RIDL and saw resistance arise in the field. We could add a system according to the present invention, keep the fsRIDL for sex separation and the present invention for sterility. Alternatively we could simply switch to the present system, however sex-separation has distinct benefits for SIT in some species.

This resistance management is not completely comprehensive—behavioural resistance is still possible (if females can discriminate between fertile and sterile males, there will be strong selection for those that preferentially mate fertile males, thereby avoiding exposure to sperm affected by the invention. Such behavioural resistance has been observed in radation-based SIT programs, but only very rarely (we believe that there is only know of one good example). This argument is closely analogous to one that proponents of radiation-sterilisation have used, arguing for the superiority of radiation damage in the sperm to a zygotic (RIDL) lethal for the reasons outlined above.

In the present methods, it is preferred that the conditional system, preferably the tet system described herein, is used to provide a further degree of control. This allows, for instance, breeding under laboratory conditions, i.e. in the presence of a repressor, such as tetracycline. Upon release, or removal of the tetracycline, the repression of the system is removed and the effector protein is thereby expressed.

Male sterility is useful in the present context in both agriculture, to prevent egg hatch for instance, as well as in disease control, for instance in control of disease vectors such as mosquitoes (those responsible for transmission of malaria and dengue fever, for instance). Thus, the present invention also provides a method of biocontainment comprising expression of the system in a population or release of males (carrying the system) into the field. With a repressible system, which is preferred, the strain becomes dependent on the repressor and cannot establish in the wild.

The invention also provides a method of quality control, for instance, by including a reporter such as a fluorescent protein, preferably Green Fluorescent Protein (GFP) or any of the other coloured fluorescent proteins known in the art. This may be the effector protein per se, acting as a transformation marker. Other examples of flourescent proteins used as transformation markers include DsRed, DsRed2 and AmCyan.

Separate transformation markers may also be used, including those described here. Transcription of these transformation markers may be under the control of a separate promoter to that of the first or second expression unit. Examples of such promoters include muscle actin promoter, 3xP3, hrIE and hr5IE1.

However, more preferably, the flourescent protein can be linked to the effector protein in the present system, so that this reporter protein and expression thereof will allow one to assess the degree of inclusion of a transgene or other effector into the population. This has at least some of the following advantages:

(1) like any such marker it identifies the presence of the transgene, so one can follow inheritance. The more tightly the marker is linked to the trait of interest e.g. the lethal system, the less likely it is that mutations occur which inactivate one but not the other. In practice, though, if they (the marker and transgene) are on the same inserted DNA segment this is extremely unlikely in any case;

(2) if linked in the sense of fused, a marker shows expression of the effector protein. This would allow one to look at actual expression. For example, in a preferred instance of tet-repressible expression of a nuclease, fusion of the nuclease to a fluorescent reporter would allow one to check that insects to be released were expressing the nuclease. Presence of the fluorescent marker would tell you that (i) the male has at least one copy of the transgene; (ii) that the expression system is functioning correctly in the sense of giving expression of effector in the absence of the repressor; (iii) that the insects are expressing the nuclease-FP fusion (and therefore were not, for example, inadvertently reared in the presence of the repressor); [(iv) assuming male-specific expression, are male]; (v) by inference they are indeed sterile. In quality control (QC) terms, this gives you much more certainty over 'they're sterile' than merely knowing that the male possesses a copy of the transgene, which is what you get from using a linked (genetically linked, e.g. adjacent gene) fluorescent marker;

(3) with a higher-powered microscope you can see when the expression comes on and where the protein is localised within the cell. This is a helpful development tool and also for monitoring consistency, for instance in ongoing QC to establish whether the system does today what it did yesterday/last year, but also in the context of sperm-to-sperm consistency of expression; and (4) a further advantage is in respect of fluorescent sperm, discussed below.

There is a clear functional connection for a nuclease to cleave DNA, so if it is not in the nucleus it is unlikely to have the desired DNA-cleaving effect. As such, it is therefore also preferred that a nuclear localisation signal is provided to ensure that the nuclease is localised to the nucleus.

In a further aspect, a method of quality control is hereby provided, comprising inducing or de-repressing expression of the present expression system in a target group of individuals and determining whether those individuals meet expected criteria such as size, number, developmental stage or localisation. For instance, if the system includes means to express a reporter such as a fluorescent protein, either as the effector or as part of a fusion protein for instance, then the individuals where expression from the system has been induced or de-repressed will become visible under suitable wavelengths of light.

It is preferred that the present system includes at least one spacer. Such spacers can advantageously be positioned between any of the present elements of the system. For instance, a spacer may be provided between the promoter and the regulatory elements and/or between the regulatory elements and the coding sequence, to thereby provide a "buffer" between these elements to ensure proper functionality thereof. As such, the spacer has no function in gene expression other than to separate these elements although it may optionally include a number of restriction sites, if this is deemed to be useful. Ideally, it should not include any transcription binding factor sites, etc as these might interfere with expression of the effector.

It is also preferred that the effector may be in the form of a fusion sequence or protein, such that, for instance, a nuclease is fused to a marker such that transcription and translation of the effector also leads to transcription and translation of the marker. This has the advantage of showing exposure of a sperm to a nuclease, the presence of the flourescent protein being indicative that the nuclease has been expressed. The flourescent proteins may be viewed under flourescence microscopy using excitation filters suitable for the particular flourescent protein. Examples of these are our strains LA4466 or LA4467 (LA4466=PB-hr5IE1-DsRed-Aeprot-tGFP-EcoRI and LA4467=PB-hr5IE1-DsRed-Aeprot-tGFP-FokICD). It should be noted that earlier strains were labelled "LA" after the inventor, Luke Alphey, but since then we have adopted the prefix "OX" after the Applicant, Oxitec. As such, prefixes LA and OX may be used interchangeably for an individual strain. LA4466/OX4466 and LA4467/OX4467 are both examples of a nuclease function successfully fused to fluorescent expression.

It is also envisaged that the present system and methods can be used to produce fluorescent sperm. For instance, a reporter such as those mentioned above could be linked to the promoter or, indeed, under a separate promoter, such as tetO promoter enhancer system if the effector is tTA or any of its variants. Fluorescent sperm would be advantageous for visual separation of sperm or gonads, particularly in methods of dissection or sex selection. In particular, it infers the ability to determine with which male individual a female has mated, which is useful in the context of a field release program. Such a method might include, providing (e.g. trapping) wild females; dissecting them; looking for stored sperm and see whether such sperm carry the present system, i.e. are fluorescent. This will very quickly tell you whether a female:

(i) is unmated (has not yet mated);
(ii) mated with a wild type male (as it shows non-fluorescent sperm);
(iii) mated with a transgenic male carrying the present system (which would show fluorescent sperm; or
(iv) mated both types of male (shown by the presence of fluorescent and non-fluorescent sperm).

Since 'who are the females mating?' is a key question in assessing and managing an SIT-type program, this is a useful advantage. There are several papers proposing this, e.g. the Malacrida et al 2007 paper already cited, but not in the context we provide here.

An example of this concept is construct (OX3878), which was designed to fluorescently mark sperm heads, in particular in *Aedes aegypti*. This construct utilised an *Aedes aegypti* tGFP-tagged protamine and its regulatory sequences to express a fluorescent fusion protein in a sperm-specific manner. Strong green fluorescence was detected both in whole dissected testis and in the isolated sperm from OX3878 male mosquitoes. This shows that expression of fluorescent proteins can be driven by the present system to produce fluorescent sperm and, furthermore, that the fluorescence can be usefully detected.

Thus, in a further aspect, the invention provides a method of determining the mating status of a female arthropod, comprising use of a system according to the present invention in a transgenic male (i.e. a released) population, wherein said system comprises a marker such as a fluorescent reporter protein; and where sperm is present, assaying for the presence of said marker in a female; the presence of the marker being indicative that the female has mated with a transgenic male carrying the system. The presence of sperm that does not carry the marker is indicative that the female mated with a wild-type (not a transgenic) individual. Where sperm is not present it is indicative that the female has not yet, or recently, mated. In some embodiments, the method includes releasing the transgenic males carrying the present system and allowing them to mate with females (i.e. wild-type females).

It will be appreciated that in the present invention the expression of the system must be invoked or allowed to occur. In other words, the conditions required to induce expression of the effector (and if separate, an optional marked such as a reporter) are adhered to. In the case of a repressible tet system, for instance, this means removal of tetracycline from the diet of the transgenic males.

The overarching aim of the present invention is to provide male sterility. However, what we have also shown is that it is possible to provide sterile sperm, which are still capable of competing with wildtype sperm. This is advantageous as it leads to a greater degree of population control because if the wildtype sperm is easily capable of outcompeting the transformed sperm, and females likely mate both types of male, then there will be only a marginal reduction in the population at the next generation. Even if females typically only mate once, in such a situation there may be strong selection for increased remating.

An ubiquitin fusion protein may also advantageously be included in the present system. This has the advantages of giving expression of both proteins as a fusion, i.e. single polypeptide, but (co-translational) cleavage into two separate proteins. This is useful if one of the proteins does not tolerate fusions (tTA, for example, tends not to function with N-terminal fusions). You still have co-expression in a compact form, however you lose the ability to use the tag (e.g. fluorescent protein, FP) to determine the sub-cellular location of the fusion protein as it is does not stay fused to it.

It is worth reiterating that the present promoter is an "early acting" germline promoter, thus providing the necessary levels of transcription before meiosis. The promoter is defined further below, but again it is worth bearing in mind that the promoter should preferably not act any earlier than the topi promoter after mitosis and, especially, not in the stem cells (at least where the effector does not damage such cell types, i.e. where the effector is not a nuclease).

The promoter should have a germline effect and it is preferable that expression of the system is conditional. Ideally, spermatogenesis should be substantially completed before any negative effects of the expression of the effector are seen. It is preferred that there is no discernable effect on sperm function until after egg entry. Whilst DNA damage could perhaps be seen as 'a negative effect,' one can view DNA in a sperm merely as "cargo" as there is no transcription in the sperm. Any DNA damage caused by the effector must be sufficient to prevent the production of viable progeny.

Thus, the present invention preferably provides conditional germline specificity (in terms of expression).

In a preferred example, the 'framework' for the second expression unit in particular is based on the B2T wild-type gene from Dm or the target arthropod. The coding sequence is replaced with that for the transcription factor and the promoter and/or 5' UTR sequences are also changed. Indeed, even a heterologous enhancer may be inserted or a heterologous 3' UTR used. Clearly, if all these changes were made, there would be little left of the original sequence, so it will be appreciated that this is one way to build up the second expression unit.

In respect of the regulatory elements, particularly the promoter and/or 5'UTR of the upstream regulatory element in the second expression unit, it is important that there is no delayed translational effect for the present transcription factor. One way to achieve this is to use the regulatory elements from a gene known to transcribe and translate at a sufficient, preferably strong, level before meiosis. Suitable examples would include chaperone genes, preferably the HSP family of genes, in particular hsp83. In another preferred embodiment, the 3'UTR may be derived from a virus, such as SV40.

In a particularly preferred embodiment, the second expression unit of the present system comprises a promoter from Beta 2 tubulin (B2T) combined with an amended B2T 5' UTR or a 5'UTR from hsp83. Optionally, a 3'UTR from SV40 may be used. Either or both of the promoter and the 5' UTR may be from topi. topi refers to the *Drosophila* gene *matotopetli*. However, the present invention includes functional homologues and paralogues from other species. These can be identified by reference to the conserved ORF as described above. In the case of a 5'UTR from topi, the promoter may also be from topi, although it is envisaged that it could be from any other of the promoters disclosed herein, for instance B2T. Again, when the promoter from topi is used and/or the 5'UTR from topi is used, the 3'UTR is preferably also from topi, as are the remaining regulatory elements such as the 5' cap and the polyA tail. The reason for this is that topi has an "early" expression pattern in spermatogenesis, such that it is able to drive suitable transcription and translation after mitotic divisions but prior to meiosis.

In the case of B2T, whilst the promoter is useful, we have found that there does appear to be a delay signal involved with the 5'UTR from B2T, hampering early translation. It was for this reason that the 5'UTR of B2T can be replaced by the 5'UTR from, for instance, a chaperone such as hsp83. Thus, it will be seen that whilst in some instances the promoter and regulatory elements are homologous to each other, or at least preferably from conserved homologues from different species, in some instances it may be necessary to use promoters and regulatory elements that are heterologous to each other in order to fine-tune the expression patterns acquired for the present invention. As seen in the Examples, we provide an example of each scenario.

In another aspect, the present invention also provides an arthropod, preferred examples of which are provided herein, transformed with the present system or by the present methods. In other words, the invention also provides a transformant or a genetically modified arthropod, preferably as further defined herein. It will be appreciated that said arthropod is a male, preferably whose gonads carry the present system, such that expression of the effector occurs during spermatogenesis.

It is an advantage of the present invention that the promoter and the regulatory elements act together in synergy to provide the desired expression pattern.

As mentioned above, the promoter is preferably from a testis-specific gene or at least one sufficient to provide "early" expression during spermatogenesis. Alternatives include more constitutive promoters, such as structural promoters, for instance, the tubulin family, particularly the beta tubulins and most preferably the beta 2 tubulin promoter, and homologues thereof. When this is used, it is necessary to use upstream regulatory element that does not have the translational delay signals seen with at least some instances of beta 2 tubulin's upstream regulatory element. An advantage to using the B2T promoter is that the B2T gene coding sequence is highly conserved and it and a suitable promoter fragment can be readily identified and isolated from a given arthropod species by a skilled person.

An example of the B2T promoter sequence is given below.

An example of the ameliorated B2T promoter sequence is given below.

An example of a 5'UTR from B2T is given below. If B2T promoters from other species are used in the present invention, then a skilled person will be readily able to identify the 5'UTR based on its conserved nature from the above SEQ ID NO. They will then be able to replace it with another 5'UTR. Prepared examples include the 5'UTR from chaperones, particularly the hsp family, particularly hsp83. A suitable example, the 5'UTR from hsp83 is given below.

A suitable example of a 3'UTR that has been used successfully in embodiments of the present invention is that from SV40. This 3'UTR is given below.

The topi coding sequence is largely conserved between mosquitoes such as *Aedes aegypti* and Medfly (*C. capitata*). As for B2T, on can clone the coding region of topi (or part of it) by sequence similarity (lots of methods including molecular and sequence-based ones), then go 5' to the transcription start and take a chunk of DNA 5' to that as your promoter. How much is not always immediately clear; conservatively go 5' until you reach the next transcribed region and take all that, but in practice male germline promoters tend to be pretty short (a few hundred bases), so 1 kb 5' of transcription start should be enough, 2-5 if you are feeling cautious. Trial-and-error testing here is also obvious: hook promoter up to FP, make transgenics, look at expression pattern.

topi is useful because it has early expression and is linked to spermatogenesis. It is also advantageous because it is a relatively "compact" system, i.e. consists of relatively few polynucleotides. Again, it is testes-specific and, indeed, it is expressed earlier than B2T. The expression compared to a B2T promoter is perhaps a little weaker, but this may be advantageous in some respects if the levels of expression need to be ameliorated. Topi is an example of a transcription factor and so promoters and/or regulatory elements from other transcription factors that express in the testes and are preferably testes-specific (i.e. expressed only in the testes) are hereby preferred.

We have found that a stronger overall sterilisation effect was seen in crosses where nuclease expression was driven by Topi promoter, compared to B2-tubulin, particularly in *Aedes aegypti*. Nevertheless, significant male sterility was observed in both cases, rendering both topi and the altered form of B2-tubulin suitable promoters for the "paternal lethality effect" in mosquitoes, especially Aedes aegypti.

Genes whose product (e.g. encoded protein) is required only at or after meiosis are likely to be translated only shortly before, or after, meiosis, even if transcribed earlier. In contrast, transcription factors needed to drive the expression of such genes must be expressed (transcribed and translated) early enough for their protein product to accumulate sufficiently to drive adequate expression of target genes prior to the cessation of transcription before the meiotic divisions. Therefore, where it is desired to express a transcriptional activator such as tTA in the male germline, the regulatory elements of a male germline transcription factor may be suitable with minimal modification.

Suitable endonucleases are described in greater detail below. However, preferred embodiments include zinc-finger endonucleases as seen for instance in LA4104. Other alternatives include IppO1, also referred to as I-PpoI, as used by Crisanti et al (Catteruccia et al., 2009; Windbichler et al., 2011; Windbichler et al., 2007; Windbichler et al., 2008). This has certain advantages such as t it has a very long recognition sequence, which is correspondingly rare in random sequence. However, it does not have high specificity relative to some restriction enzymes, for example, in that it will tolerate (i.e. still cut) sequences with a degree of divergence from the canonical recognition sequences. Windbichler et al 2007 show growth arrest in An. gambiae tissue culture cells, which is reasonable evidence (as they also conclude) that expression would be toxic, but they don't show it directly.

A different result is from Windbichler et al 2008, where expression of I-PpoI—which they think should cut only the X chromosome in An. gambiae as its target site in the rDNA seems only to be on the X chromosome in this species—gave completely sterile males rather than their expectation (no viable daughters due to damage to the paternally-derived X chromosome, but viable sons). Their proposed explanation, for which they provide some supporting data, was that the I-PpoI itself is transmitted in the sperm to the fertilised egg, where it cuts the maternally-derived X chromosome as well (they seem to assume as protein, but could potentially equally be as mRNA). This is more an issue of perdurance, which relates to protein (or mRNA) stability.

An alternative preferred endonuclease is the Fok-1 protamine fusion endonuclease. Further preferred alternatives include the EcoRI protamine fusion endonuclease. Protamine is a DNA binding protein and has a generally a very low sequence specificity. This is combined with Fok-1, a type IIS cleavage domain. This cleavage domain must dimerise in order to cleave its target. This is useful, because the site need to be close enough together in order to give rise to non-linear concentration effects. An effector that acts as a monomer is expected to have its effect (here, DNA cleavage) in proportion to its concentration. For many applications one would prefer a non-linear dose-response curve, so that the effect is near zero up to a certain point, but then increases to full effectiveness relatively quickly above that point, the limit of this being a binary 'threshold' effect. A nuclease such as protamine-FokI is predicted to have a degree of this non-linearity. Protamine binds DNA but has little or no sequence specificity. Therefore at low concentration (e.g. molecules per nucleus) the protamine-FokI proteins will tend to be scattered randomly around the chromatin, rarely being in sufficiently close proximity/orientation to dimerise and cut a chromosome.

However, as the concentration increases the probability of such proximity greatly increases, leading to a non-linear relationship between concentration and cutting. This facilitates the selection of a promoter (and specific transgene insertion), as the system is relatively inert even with low-but non-zero levels of off-target (basal) expression, while still having the desired effect at higher expression (in the intended expression domain, de-repressed in the case of a repressible expression system). A similar effect can be achieved where the effector must dimerise (or form a larger complex, e.g. tetramer) prior to binding to DNA. Where a more linear effect is desired, this may readily be accomplished within the method of the invention, by using a nuclease domain that does not need to dimerise, or where the necessary subunits are provided in a single polypeptide (e.g. two copies of the FokI domain rather than one). Additional manipulation of the system can be achieved by using nucleases of greater or lesser sequence specificity, as the available protein molecules will be 'focused' by the specificity and affinity of the DNA binding domain to a larger or smaller number of sites, leading to a greater or lesser degree of concentration at those sites.

It is preferred that the Protamine gene (or protein coding sequence) is obtained from the same species as that of the target species. It is preferable that the Protamine gene is derived from D. melanogaster. It is also preferable that the Protamine gene is derived from Aedes aegypti.

The examples relating to the constitutively expressed constructs OX4466 and OX4467 were designed to investigate the functionality of the effector proteins Aeprotamin-EcoR1 and Aeprotamin-Fok1, respectively. These examples show that both these effector proteins should certainly work when used in a sperm lethal system, i.e. under the control of the early acting promoter (second expression unit). In fact, we have also gone on to show this for the Aeprotamin-Fok1 binary construct. Having proved the functionality for both effector proteins, we developed and injected the Aeprotamin-Fok1 binary construct (see the example "OX4282-OX4627 Topi-tTAV-driven expression of tetO-Ae-Protamine-FokI-CD"), which confirmed the positive outcome of the previous (constitutively expressed) system. It is, therefore, entirely reasonable to expect that an EcoR1 system will also work in the Sperm Lethal setting. Accordingly, the effector gene is preferably Aeprotamin-EcoR1 or Aeprotamin-Fok1. These are most preferably for use in mosquitoes and in particular Aedes, especially Aedes aegypti.

Other type II endonucleases include Eco32I, BfiI, and MboII, for instance. These endonucleases are homodimeric. In general, dimeric endonucleases are advantageous. They are dimeric because they only cleave DNA when dimerised. When they are suitably dimerised, they lead to double stranded DNA breaks.

Other endonucleases may include HEG's (Homing Endonucleases). These HEG's can be monomers or dimers but generally have low specificity (in the sense that they don't require perfect matches to their (very long) recognition sequences, but they certainly don't just cut random sequence). Other alternatives include restriction endonucleases from bacteria. These also have low specificity.

Accordingly, the skilled person can choose the level of specificity required. It will be appreciated that low specificity endonucleases will break or damage the DNA on a greater number of occasions than high specificity endonucleases, for a given recognition sequence. HEGs have very long recognition sequences that would occur by chance at a frequency often less than one per genome. So despite their imperfect specificity for that sequence they may not cut at all (e.g. I-SceI in Windbichler et al., 2011 only cuts the engineered site, not the rest of the genome—at least not at a high enough frequency to cause evident trouble in their experiment).

Thus, a further level of fine-tuning is possible by appropriate selection of endonucleases as the effector. The nuclease effector fusion protein has been found to be fully functional in three different diptera species tested so far, namely *C. capita*, *B. oleae* and *Aedes aegypti*. These species are particularly preferred as are other species in the same genus.

It is particularly preferred that the arthropod (the host organism in which the present system is expressed) is an insect, preferably a tephritid. In particular, it is preferred that the insect is from the Order Diptera, especially higher Diptera and particularly that it is a tephritid fruit fly, preferably Medfly (*Ceratitis capitata*), preferably Mexfly (*Anastrepha ludens*), preferably Oriental fruit fly (*Bactrocera dorsalis*), Olive fruit fly (*Bactrocera oleae*), Melon fly (*Bactrocera cucurbitae*), Natal fruit fly (*Ceratitis rosa*), Cherry fruit fly (*Rhagoletis cerasi*), Queensland fruit fly (*Bactrocera tyroni*), Peach fruit fly (*Bactrocera zonata*) Caribbean fruit fly (*Anastrepha suspensa*) or West Indian fruit fly (*Anastrepha obliqua*). It is also particularly preferred that the host organism is a mosquito, preferably from the genera *Stegomyia*, *Aedes*, *Anopheles* or *Culex*. Particularly preferred are *Stegomyia aegyptae*, also known as *Aedes aegypti*, *Stegomyia albopicta* (also known as *Aedes albopictus*), *Anopheles stephensi*, *Anopheles albimanus* and *Anopheles gambiae*.

Within Diptera, another preferred group is *Calliphoridae*, particularly the New World screwworm (*Cochliomyia hominivorax*), Old World screwworm (*Chrysomya bezziana*) and Australian sheep blowfly (*Lucilia cuprina*). *Lepidoptera* and *Coleoptera* are also preferred, especially moths, including codling moth (*Cydia pomonella*), and the silk worm (*Bombyx mori*), the pink bollworm (*Pectinophora gossypiella*), the diamondback moth (*Plutella xylostella*), the Gypsy moth (*Lymantria dispar*), the Navel Orange Worm (*Amyelois transitella*), the Peach Twig Borer (*Anarsia lineatella*) and the rice stem borer (*Tryporyza incertulas*), also the noctuid moths, especially *Heliothinae*. Among *Coleoptera*, Japanese beetle (*Popilla japonica*), White-fringed beetle (*Graphognatus* spp.), Boll weevil (*Anthonomous grandis*), corn root worm (*Diabrotica* spp) and Colorado potato beetle (*Leptinotarsa decemlineata*) are particularly preferred.

However, as we have shown in the Examples, the present system and methods can be implemented across Diptera, including higher and lower Diptera. Higher Diptera are therefore preferred. Lower Diptera are also preferred.

In some embodiments, it is preferred that the insect is not a Drosphilid. Thus, in some embodiments, expression in Drosophilids, especially *Drosophila melanogaster*, is excluded.

It is preferred that the expression of the effector protein leads to a phenotypic consequence in the organism, namely sterility. It is particularly preferred that the functional protein can be associated with visible markers (including fluorescence).

Where reference to a particular nucleotide or protein sequence is made, it will be understood that this includes reference to any mutant or variant thereof, having substantially equivalent biological activity thereto. Preferably, the mutant or variant has at least 85%, preferably at least 90%, preferably at least 95%, preferably at least 99%, preferably at least 99.9%, and most preferably at least 99.99% sequence identity with the reference sequences.

We anticipate that:

a) the present sterility is dominant, so that all sperm of a heterozygous male would be affected (not necessarily all defective, as the system might be selective for some type of sperm, or less than 100% effective against those sperm that should be affected); and b) the mechanism is not dependent on inheritance by the zygote of a dominant lethal gene via these sperm.

The present system is therefore not a RIDL system, as both a) and b) distinguish from RIDL.

One potential advantage of radiation had been that it is difficult to see what heritable or genetic change in the wild target population could overcome the sterilising effect of radiation. Thus it is difficult to imagine resistance arising in the wild population to this aspect of radiation-based SIT (other types of resistance, such as behavioural resistance e.g. assortative mating (Dhillon et al., 2005), might nonetheless arise). In contrast, genes or alleles conferring resistance to the killing or incapacitating action of RIDL genes might conceivably arise. Similarly, though the precise biochemical basis of CI is not known, embryos infected with suitable strains of *Wolbachia* are able to reverse CI-induced male sterility, therefore a biochemical/genetic resistance to CI-induced sterility seems conceivable.

The present invention overcomes these difficulties. The sterilising mechanisms are designed to act prior to zygotic gene expression, so that the possibility of heritable resistance is severely restricted. For example, consider the use of a nuclease expressed in spermatogenesis. Under restrictive conditions (for fertility, permissive for expression of the nuclease), this will tend to damage the DNA in much the same way as does radiation, e.g. inducing double-strand breaks. Therefore it is equally difficult to imagine how a wild target population could develop resistance to such sterility or paternal-effect lethality. It may be that the artificial mass-rearing population could develop resistance, however use of a suitable conditional expression system, so that little damage is done to the sperm (or other cells or tissues) under permissive (for fertility) conditions, will minimise the selective pressure for such alleles. Though similar in this respect to radiation, the method of the present invention has several advantages. The sterilising effect is restricted to the gonads or gametes, and so is less likely to reduce the performance of the insects. By selection of a suitable repressible expression system, sterility may be achieved simply by removal of the repressor. In this version, the system also provides biocontainment, in that insects released into the wild (deliberately or inadvertently) are sterile, or some or all of their progeny are sterile.

We intend to combine the female lethal (or flightless) RIDL technology with the present "sperm lethal" invention to develop insect products suitable for implementation in an SIT program. We show in the examples that the present "sperm lethal" system is viable in combination with RIDL technology. Of course there will be also species where sex separation is not desirable, and others where it is desirable but can be achieved by other means (e.g. physical size-based sex separation, as is suitable for *Aedes aegypti*). Thus, preferably, the present expression system can also be combined with existing female lethal (or flightless) technology to develop further arthropod, and particularly insect, products suitable for implementation in an SIT-type program. Male-only release is considered desirable for SIT for several species, for example where adult females are actually or potentially harmful even if sterile (e.g. mosquitoes, by biting, or Medfly, by oviposition into unripe fruit), also for Medfly co-released sterile females appear to 'distract' sterile males from seeking out wild females (Rendón et al., 2004).

Suitable sex separation systems include separation based on natural sexual dimorphism (e.g. size for *Aedes aegypti*, pupation time for tsetse fly); induced sexual dimorphism (e.g. Catteruccia et al., 2005). Alternatively, one sex may be eliminated by use of a lethal genetic sexing system; such systems have been constructed by classical genetics (e.g. Franz, 2005; Klassen and Curtis, 2005) and also by recombinant DNA methods, including embodiments of RIDL (Fu et al., 2007; Thomas et al., 2000). Both conditional expression systems may use the same condition, so that control of each of the two phenotypes is co-ordinately controlled. So, for example, if each system were repressed by tetracycline (or suitable analogues thereof, such as chlortetracycline), rearing in the presence of a suitable concentration of tetracycline would allow the strain to be grown to adequate numbers. In the last generation before release, rearing without tetracycline would lead to derepression of both the female-specific lethal system and the proposed sperm lethal system. Therefore, females would die and the remaining males would be sterile.

A degree of cross-talk between the two tet-repressible systems may be anticipated, such that both effectors will be expressed by both systems. Expression of the sperm lethal effector in females is unlikely to have any undesirable consequences, since it is intended that these females die. Cross-talk the other way, i.e. expression of the female-lethal effector in spermatogenesis may be more problematic, depending on the nature of the female-lethal effector and its effect on spermatogenesis. Such cross-talk, if deemed undesirable, may readily be avoided restricting expression of the female-lethal effector to females, for example by use of sex-specific alternative splicing to regulate the production of functional effector (Fu et al., 2007).

The combined technologies can be achieved in two ways:
the proposed invention can be inserted separately into the insect's genome by transposon mediated transformation. Thorough analysis of the strains generated will lead to candidate strains with the desired features. These can be back crossed to lead female lethal (preferably fs-RIDL) strains to generate double homozygotes for the two insertions.

In a particularly preferred embodiment, the two systems may be combined on a single DNA construct, with a conditional female-specific lethal construct. This construct would therefore provide both genetic sexing and male sterility.

Spermatogenesis is a highly specialized process of cellular differentiation resulting in the formation of functional spermatozoa for successful reproduction. In principle, the process of spermatogenesis is well conserved in all sexually proliferating organisms although the size and shape of the mature sperm vary considerably among different species. Many details are comparable between mammals and *Drosophila* making the fly a very good model system to study fertility defects. *Drosophila* germ cells, like those of mammals, are set aside early in embryonic development and migrate through the primordium of the hindgut into the interior of the embryo where they join the somatic parts of the embryonic gonads (Zhao and Garbers, 2002). At the end of the third larval instar and the onset of pupariation, the first germ cells have entered meiosis. Spermatogenesis is a continuous process during adult life and, thus, the adult testes contain all stages from stem cells to mature sperm.

In general, for male (insect) germline cells in spermatogenesis, transcription shuts down shortly before meiosis (Fuller, 1993). There may be a few genes transcribed later (Barreau et al., 2008), but these are exceptional. In general, genes whose products are required at or after meiosis are nonetheless transcribed before meiosis; the mRNA is stored and translated later, i.e. when required, e.g. post meiotically. The mRNA is then typically degraded after translation. Many genes follow this pattern; examples included β2-tubulin and protamines, also the meiotic regulator twine. Of these, twine protein is required for entry into meiosis, β2-tubulin is required for the meiotic spindle and post-meiotically for the flagellum; protamines are required strictly post-meiotically. Thus, suitable control of timing can be afforded.

In principle it should be possible to disrupt sperm production by affecting (e.g. killing) somatic cells in the testis (e.g. cyst cells) that are required for spermatogenesis, or by affecting hormone production etc in the male or (slightly more promising) expressing or abrogating factors in the seminal fluid. However, such methods would at almost certainly produce, at best, males with no sperm, or obviously aberrant sperm. For this reason, we have sought to focus on male-germline expression.

Germ Line Promoter Sequences

Therefore, a single-gene expression construct can be readily made which will express the gene of interest ("effector") in the male germline. Many genes have been identified in *Drosophila* which express during spermatogenesis and many of these are specific to the germline, or to the male germline. Such expression data are readily obtainable directly from the literature; there are also large-scale projects (Chintapalli et al., 2007) and http://www.flyatlas.org/) which have performed expression analysis on many of the genes in the *Drosophila* genome (e.g. FlyAtlas (Chintapalli et al., 2007) and http://www.flyatlas.org/, *Drosophila* testis expression database (www.fly-ted.org) and data collated on FlyBase e.g. http://flybase.bio.indiana.edu/). An expression construct can therefore be made as follows:

(1) identify a suitable testis-expressed gene, e.g. β2-tubulin, which encodes a male-germline-specific isoform of β-tubulin (Nielsen et al., 2001) (a recent report (Jattani et al., 2009) indicates that the expression and function of β2-tubulin may not be strictly confined to the male germline in *Drosophila*, nonetheless a promoter fragment from *An. gambiae* β2-tubulin was used to express a potent nuclease, known to cut sequences in the *An. gambiae* genome, without obvious effects other than in the male germline and in embryos fertilised by sperm from such males);

(2) isolate a wild type copy of the gene;

(3) replace the coding region of the gene with the effector gene; and 4) make transgenic insects carrying this gene.

Male-germline-specific expression of fluorescent protein reporters has been achieved by this method in *Drosophila* using a range of genes involved in spermatogenesis such as protamine, don juan and sneaky, for example (Raja and Renkawitz-Pohl, 2005; Santel et al., 1997; Wilson et al., 2006). β2-tubulin is a well-conserved gene, so an extension to this method, in step 2 isolating the appropriate gene from the species of interest (or a related species, such as *Anopheles gambiae* for use in *Anopheles stephensi* (Catteruccia et al., 2005)) will allow use in an arbitrarily selected arthropod species. This approach has indeed been successfully used for male-germline-specific expression of a fluorescent protein reporter in several species including the Mediterranean fruit fly (Malacrida et al., 2007), *Aedes aegypti* (Maynard-Smith et al., 2007) and *Anopheles gambiae* (Catteruccia et al., 2005), all of which used promoter fragments from the β2-tubulin of the target species, except for Catteruccia et al. who used a promoter fragment from *Anopheles gambiae* β2-tubulin to drive spermatogenesis-specific expression of a fluorescent protein in *Anopheles stephensi*.

"Sperm lethality" will be used in conjunction with a conditional expression system to ensure transition through generations under permissive conditions. This condition can be temperature, for example working through a temperature-sensitive protein effector. However, temperature based conditional systems tend to be "leaky", for example. The TSL sexing medfly strain (Casares, 2002), a system based on the presence/absence of an externally applied molecule (e.g. RU486/mifepristone (Osterwalder et al., 2001)) could be an alternative. However, it is not suitable for a bipartite expression system (Brand et al., 1994; Brand and Perrimon, 1993; Fussenegger, 2001; Fussenegger et al., 2000; Gossen and Bujard, 1992; Gossen and Bujard, 2002; Victorinová and Wimmer, 2007).

On the other hand, the Tet-off or Tet-on system is the scheme of choice (Gossen and Bujard, 1992; Gossen and Bujard, 2002). This system depends on the expression of a transcription factor which conditionally drives expression of a suitable gene (the effector). In the tet systems, binding of the synthetic transcription factor tTA (or its variants, including rtTA) is affected by the concentration of tetracycline and/or related compounds such as chlortetracycline or doxycycline. In the tet-off expression system, binding of tTA to tetO is inhibited by tetracycline, therefore expression of the effector is inhibited by tetracycline, hence "Tet-off". A similar expression system regulated by streptogramin is also known (Fussenegger et al., 2000). However, expression of tTA under the control of β2-tubulin, for example, will not lead to significant expression of the effector, even in the absence of tetracycline. This is because expression of tTA will be substantially post-meiotic (more precisely, substantially after the shut-down of transcription prior to meiosis), and therefore too late to drive expression of the effector, even in the absence of tetracycline.

The key is to understand the timing of gene expression in spermatogenesis in arthropods and in particular in insects. There is essentially no gene expression after initiation of meiosis. Therefore, to use a bipartite expression system such as tet-off (or tet-on), transcription of the sequence-specific transcription factor (tTA) has to be sufficiently far in advance of meiosis to allow accumulation of tTA mRNA, translation of tTA protein and tTA-dependent transcription of the effector all before meiosis. Most genes expressed during spermatogenesis are transcribed in spermatocytes (i.e. before meiosis) but then translated later, when the protein product is actually required. For most proteins involved in sperm differentiation or function (and therefore most sperm proteins), this means translation after meiosis. Therefore, suitable expression for our purposes means early transcription AND early translation of the tTA. This is not widely recognised and also not easy to achieve. Thus, we were the first to identity that there was a problem here.

A suitable 3'UTR, can be constructed using heterologous sequence, rather than sequence derived from the testis-expressed gene, also all or part of the coding region of the testis-expressed gene may be retained, for example. Male-germline-specific expression of fluorescent protein reporters has been achieved by this method in *Drosophila* using a range of genes involved in spermatogenesis such as protamine, don Juan and sneaky, for example (Raja and Renkawitz-Pohl, 2005; Santel et al., 1997; Wilson et al., 2006). Similarly, 5' UTR can be substituted with a heterologous sequence to avoid translation after meiosis. The five prime untranslated region (5' UTR), can contain sequences for controlling gene expression by way of regulatory elements for example. sequences that promote or inhibit translation initiation or introns within 5' UTRs have been linked to regulation of gene expression and mRNA export (Cenic et al., 2011). It begins at the transcription start site and ends one nucleotide (nt) before the start codon (usually AUG) of the coding region.

In order to obtain adequate expression of tTAV and respectively of the effector gene, in other words in order to obtain "sperm lethality," we have substituted (in the upstream regulatory element of the second expression unit) the 5' UTR, and in some cases the 3' UTR, of the β2-tubulin gene with the corresponding sequence(s) from hsp83 (Theodoraki & Mintzas, 2006) and SV40 (Simian vacuolating virus 40 or Simian virus 40) (Cheng et al., 2009), respectively, see the discussion herein and the present Examples.

In other words, the preferred 5' UTR is from hsp83. This is preferably from Medfly as that is what we used in specific examples, but homologues from other species are also preferred. The preferred 3' UTR is from SV40, but could also be from hsp83 (species as above for the 5' UTR). We have found the choice of the 5' UTR to be more important however than that of the 3' UTR.

Earlier expression of a transactivator, exemplified here as tTA may be also achieved by any of the following methods. One example is by identifying promoters acting earlier in spermatogenesis. This means promoters acting such that a transcription factor, e.g.

tTA, expressed under the control of this promoter, will be able to drive the expression of a tTA-responsive effector construct. We prefer this not to be a promoter substantially active in the germline stem cells, as such genes (e.g. vasa) are expressed in immature stages; this will tend to lead to expression of the effector (in induced or de-repressed conditions) to be expressed very early in development, possibly leading to damage to or loss of the germline and hence the production of no or fewer gametes. If the expression system were induced (or derepressed) later in development, the time course of spermatogenesis, i.e. the time between stem cell division and the production of mature sperm (several days in *Drosophila*), would lead to a slow response (e.g. sterility) to the induction (or derepression); this effect is compounded by the ability of males to store sperm.

We therefore prefer to use promoter elements from genes expressed in spermatogonia or primary spermatocytes. As discussed above, many genes expressed in primary spermatocytes are involved in later functions and are translated post-meiotically, therefore we prefer genes (and promoters from genes) with pre-meiotic functions. A particularly preferred class of genes are those encoding transcription factors, or components of transcriptional complexes, which are involved in the expression of spermatogenesis genes, e.g. later-acting genes. A key reason for preferring such genes is that they are, almost by definition, expressed (at the protein level) early enough in spermatogenesis to be able to drive the pre-meiotic expression of other genes (of course negative regulatory elements of such complexes are also preferred, it is the timing of expression rather than the specific function of the translated protein that is important).

Several classes of such genes are known. However, as discussed below, not all are suitable and some are preferred over others. Classes include the can-class of meiotic arrest genes. This class comprises can, mia, sa, nht and rye; these encode testis specific paralogues of broadly expressed TATA-binding protein associated factors (TAFs) (Hiller et al., 2004). Another class is the aly-class of meiotic arrest genes. These include aly, comr, achi/vis, topi and tomb which encode components of a complex of sequence specific DNA binding proteins and associated factors paralogous to a broadly expressed transcriptional regulatory complex known as dREAM or Myb-MuvB (Beall et al., 2007; Jiang et al., 2007; Jiang and White-Cooper, 2003; White-Cooper et al., 2000). Most of these genes appear to have arisen by duplication of conserved 'somatic' genes, e.g. ancestral TAFs or Myb-MuvB components that functioned in both soma and germline, followed by specialisation of these versions to a germline- or male-germline-specific expression and role. Several of these duplications appear to have occurred relatively recently in evolution, meaning that the germline-specific paralogs exist in a variable, and in some cases quite narrow, phylogenetic/taxonomic range. We prefer to use the promoter(s) of gene(s) conserved from *Drosophila* to the species of interest, and particularly prefer promoters of genes conserved across a wide phylogenetic/taxonomic range; this conservation both makes the identification of homologues easier, and makes the specific gene more generally useful.

Such (conserved early acting) genes can be identified in one of two ways:

1. By Homology with Genes Known, e.g. from *Drosophila*, to have Suitable Patterns and Levels of Expression.

This is achieved by homology searches in sequence databases. However, some spermatogenesis genes are rapidly evolving, and specific homologues may not be readily identifiable across a wide phylogenetic range. For example, bag-of-marbles (bam) meets the criteria above of early expression—bam is expressed in spermatogonia (and also in oogenesis) and early function—it is involved in regulating the number of mitotic divisions of spermatogonia (Gonczy et al., 1997; Kawase et al., 2004). Furthermore, a fragment of the bam promoter has been used successfully in a bipartite expression system (GAL4/UAS) in spermatogenesis (and also oogenesis) in *Drosophila* (Jiang et al., 2007). However, bam is recognisable only in Drosophilids. Another gene with a similar expression pattern, whose gene product is thought to interact with that of bam, is benign gonial cell neoplasm (bgcn). Unfortunately, this gene is also not well conserved across insects; both genes show signs of positive selection and rapid evolution (Bauer DuMont et al., 2007).

Difficulties also arise with several members of the can-class and aly-class meiotic arrest genes. Many of them appear to have derived from a duplication of an ancestral gene presumably used in both somatic and germline cells. The germline versions tend to be rapidly evolving, so that the somatic paralogue is more easily identified than the germline paralogue. Furthermore, the series of duplications leading to these somatic/germline gene pairs in *Drosophila* seems to post-date the divergence of Diptera from other orders of insects, so germline-specific paralogs of most of these genes do not exist outside Diptera, and several of them only in higher Diptera.

However, exceptions do exist; these are readily identified by sequence comparisons with insects from other orders (e.g. *Apis mellifera*, *Tribolium castaneum*, *Bombyx mori*—the list of insects for which a significant fraction of the genome has been sequenced is rapidly increasing and readily accessed by a person skilled in the art). One example of such a gene is *matotopetli* (topi), an aly-class gene which encodes a putative sequence-specific DNA binding protein identified in a two-hybrid screen as binding to another aly-class protein (Comr) and is therefore presumably a component of a testis-specific Myb-MuvB complex. Topi homologues were identified in *Drosophila* and *Anopheles gambiae* (Perezgasga et al., 2004); by sequence similarity searches of public sequence databases we have also identified homologues in several other orders of insects including *Coleoptera* (*Tribolium castaneum*, NW_001092862.1), Hymenoptera (*Apis mellifera*, NW_001253507.1). Topi is therefore an example of a well-conserved gene with a suitable expression pattern (based on (i) quantitative rtPCR data on FlyAtlas and elsewhere; (ii) developmental expression pattern shown by RNA in situ hybridisation to be in primary spermatocytes, especially early primary spermatocytes (Perezgasga et al., 2004); (iii) predicted function as part of a male germline-specific transcription complex (Beall et al., 2007; Perezgasga et al., 2004); (iv) actual function, by phenotypic analysis of mutants, affects expression of a number of other spermatogenesis genes (Perezgasga et al., 2004)).

Genes with early acting promoters can also be identified by:

2. Homoloq Identification of the Selected Gene(s) from the Target Species

Alignments of relevant sequences from species of greater or lesser phylogenetic distance from the species of interest will identify regions likely to be conserved in gene of interest in the target species. Preferably, to enrich for the gene of interest and to avoid problems with introns, cDNA from RNA extracted from males will be used, most preferably from dissected testes. From a cloned fragment of the transcribed region of the gene of interest, a suitable promoter fragment may be obtained.

A candidate for a suitable promoter fragment comprises at least 50 nucleotide bases of genomic DNA 5' to the transcription start, and, preferably, the transcription start itself and at least 1 nucleotides of transcribed region. This will comprise the promoter fragment and an open reading frame for the reporter. It may also contain 5' and 3' UTR sequences, either from the same gene as the promoter fragment, or another region. Those from the same gene are likely to function in spermatogenesis, if the gene has been correctly identified as active in spermatogenesis, however they may also contain signals, e.g. for delayed translation, that would be undesirable for expression of a protein, such as tTA, that must function pre-meiotically. Regulatory sequences from the same gene as the promoter fragment are therefore preferred for genes whose function is known or thought (e.g. by homology) to be pre-meiotic (e.g. topi), but heterologous regulatory sequences are preferred for genes whose function is known or thought to be meiotic or post-meiotic.

For the purposes of our work we have isolated and tested topi promoter sequences from *C. capitata* and *A. aegypti* with various effector proteins, the present Examples.

Protein Effectors to Give a Late Sperm Phenotype

'Late' here means after the point to which sperm function is required, e.g. transfer to the female or entry into the egg. The objective is to produce sperm that are transferred to the female and will induce refractoriness to remating in the female, and will do well in sperm competition if the female does remate. Sperm competition occurs, or can occur, when a female mates more than one male; in this circumstance the question arises of which males sire what proportion of the female's embryos. It is likely that males transferring no sperm will do badly in this instance. Because of the likelihood or possibility of evolutionary responses to the use of males with no sperm, or sperm incapable of being transferred to a female, or incapable of competing with other sperm after transfer to a female, it is desirable for biological control purposes to engineer sterile males that do produce sperm, that these sperm are capable of being transferred to a female and are capable of competing with other sperm after transfer to a female.

Paternal-Effect Lethals

Our approach, which is our favoured method to achieve "sterility" is to this is to construct paternal-effect lethals, whereby the sperm enter an egg but no viable zygote (capable of developing to a fertile adult) is formed. Preferably, this effect is generated by males with a single copy of the paternal-effect lethal, though the use of multiple copies is also envisioned. The release into the environment of males homozygous for a conditional paternal-effect lethal is particularly preferred, as such a strain is substantially stable during rearing. Paternal-effect lethals (Pals) of the invention characteristically affect all or most of the sperm produced by a male carrying at least one copy of the Pal. In particular, the zygote may be adversely affected, e.g. killed, sterilised or its development (e.g. sexual phenotype(s)) changed, based on the genotype of the parent. This is in contrast to RIDL, wherein the effect on the zygote is based on the genotype of the embryo. Thus, progeny of mating between a wild type female and a male heterozygous for a RIDL construct at a single locus will typically give ~50% normal progeny and ~50% which inherit the RIDL construct and may be affected by it. In contrast, all of the progeny of a male heterozygous for a Pal may be affected.

Several types of protein-based effector are envisioned. Protein or RNA effectors may be transmitted with the sperm to affect the egg or developing zygote. These may be on the surface of the sperm (e.g. as *Drosophila* sex peptide, SP), or produced and stored within it. Sperm, and cells in other stages in spermatogenesis, are remarkably resistant to some types of protein, for example pro-apoptotic proteins, presumably because the apoptotic pathway has been co-opted for other purposes in spermatogenesis (Arama et al., 2003; Cagan, 2003).

It is preferred that the effector have a direct biochemical effect on the sperm, rather than merely using the sperm as a vehicle via which to enter the egg (and then to have an effect there). This is due to considerations of potential resistance. In an SIT-type program, the released males have been produced in an artificial rearing facility, so they and their genotype is to some extent under control, or at least variations can potentially be identified and eliminated more easily than they could be from a wild population of the same species. A biochemical effect acting in the egg (or developing zygote) may potentially be altered or mitigated by changes in that egg; if these are heritable then there is at least the basis for potential heritable resistance to a toxin producing this biochemical effect. In contrast, it is difficult to see how the maternal or zygotic genotype could compensate for at least some types of damage that has already been done to the sperm before it enters the egg (or before it enters the female). One example of such damage is damage to the genetic information contained by the sperm, other examples, though perhaps with less certainty about the ability of the maternal/zygotic genome to compensate, include loss or damage to essential components of early processes such as sperm membrane breakdown or sperm nucleus decondensation, for example, or centrosome function.

One preferred class of paternal effect lethals are nucleases. Though sperm contribute several things to the zygote, one key one is genetic information. If this genetic information is damaged to the extent that some or (preferably) substantially all of the zygotes are non-viable, then this forms the basis for a suitable form of sterility through paternal-effect lethality. Radiation-sterilisation, as used for example in conventional Sterile Insect Technique, is an example of conditional (in this case inducible by irradiation) paternal-effect lethality; sterilisation with chemosterilants, e.g. thiotepa, is another. Each of these approaches work by damaging the DNA in the sperm, thus degrading the genetic information that it carries to the point that many zygotes die (Robinson, 2005). Chemosterilants such as thiotepa and bisazir, for example, may leave toxic residues and are generally regarded as unacceptable for widespread use.

Suitable expression of a suitable nuclease in the sperm, or during spermatogenesis, will have the effect of damaging the genetic information of the gamete, or resulting gamete, without similarly damaging the genetic information of somatic cells of the male. This will reduce the degree of incapacitation of the male associated with the sterilisation process. In contrast, the use of radiation or chemosterilants typically exposes all cells approximately equally to the sterilising agent.

A suitable nuclease is one that cuts DNA, preferably generating double-stranded breaks. DNA-modifying enzymes which affect the storage or interpretation of genetic information, or which lead to indirect cutting or modification of the DNA, e.g. by cellular DNA repair machinery, are also here classed as nucleases; it will be understood that references to 'cutting' DNA, for example, therefore include 'modifying' DNA, as appropriate.

Suitable expression is conditional expression, such that under restrictive conditions (for fertility, obviously these are permissive conditions for expression of the nuclease) at least 30%, preferably more than 50% and most preferably >90% of the sperm from a male with at least one copy of the nuclease-comprising paternal-effect lethal system (a 'PAL male') are incapable of fertilising an egg to form a viable zygote capable of surviving to give a fertile adult under typical rearing conditions, e.g. as found in the wild, or laboratory conditions approximating those found in the wild. Conversely, under permissive conditions (for fertility), equivalent PAL males should give significantly more viable zygotes than under restrictive conditions; preferably at least 50% of the zygotes should survive.

Preferably, expression of the nuclease in males is substantially restricted to the germline. While this may mean that expression is substantially restricted to the male germline, this is not essential. For some applications, elimination of females is desirable (e.g. genetic sexing in SIT (Alphey, 2007; Franz, 2005)). Under circumstances where females are to be eliminated anyway, expression of the nuclease in females may not be undesirable. Indeed it may be desirable, if used to eliminate, or assist in the elimination of, females. This would be an example of potential 'dual use'—using the nuclease both as a PAL and as (zygotic) dominant lethal to kill some or all of the females. Many nucleases are known. Relevant classes include restriction endonucleases and zinc finger nucleases and transcription activator-like effector (TALE) nucleases (Hockemeyer et al., 2011; Mahfouz et al., 2011; Miller et al., 2011) and homing endonucleases. Different classes and different members within a class, show different levels of sequence specificity at or near the site at which they cut. In principle, an enzyme with a very high degree of sequence specificity will cut at a relatively small number of sites per genome, perhaps only one. This is not preferred, as it allows the possibility of resistance by mutation or variation of the target site. Where a specific sequence is repeated many times, so that there are multiple sites in the genome despite a relatively high degree of specificity for a relatively long recognition sequence, this is more acceptable. However, we prefer that the nuclease has multiple target sites per genome. This means recognising a relatively long sequence that is nonetheless present in multiple copies in the genome or a relatively short recognition sequence or a significant degree of redundancy within the target sequence, of incomplete specificity for the nominal target sequence, or indeed a nuclease with little or no sequence specificity at all. I-PpoI is of this type, having a long recognition sequence but it's in a highly conserved section of rDNA, which is present in multiple copies per genome. I-PpoI is further discussed elsewhere.

Zinc finger nucleases (ZFNs) have been described, wherein each zinc finger provides sequence-specific binding to a short nucleotide sequence, e.g. 3 nucleotides. Higher affinity and greater sequence specificity can therefore be provided by combining multiple such zinc fingers into a single protein. If this is combined with a nuclease, e.g. the nuclease domain of the restriction endonuclease FokI, an artificial sequence-specific nuclease can be constructed, with arbitrary sequence specificity (Kim et al., 1996). Such synthetic zinc finger nucleases have been developed for gene therapy purposes, for example (Urnov et al., 2005). Considerable effort has gone into improving their specificity, to reduce cutting to a single site in the genome, e.g. (Miller et al., 2007). In an example in *Drosophila*, zinc-finger nucleases have been produced which, when expressed in transgenic flies, specifically damage the target locus, e.g. the yellow and later also rosy and bw loci (Beumer et al., 2006; Bibikova et al., 2002). An unwanted side-effect was observed, which was that high level expression of some of the ZFNs used was toxic. It was further shown that this toxicity depended on the nuclease, rather than the DNA binding activity, of the toxic ZFNs (Beumer et al., 2006). Though undesirable for gene targeting, this broader specificity is attractive for our purpose of generating damage at several or many sites.

The use of homing endonucleases (HEGs) is generally not preferred, as they tend to recognise relatively long (15-40 bp, though often accepting some mismatches to the nominal target sequence) nucleotide sequences which therefore occur rarely, if at all, in any given insect genome. The minimum number of acceptable recognition/cutting sites is one per diploid genome; one per haploid genome is preferred and recognising/cutting multiple sites per haploid genome is particularly preferred. An example of a HEG likely to be inappropriate is I-SceI. Originally isolated from yeast (*Saccharomyces cerevisiae*) mitochondria, I-SceI has been used in *Drosophila* as part of a system allowing or promoting targeted homologous recombination (Gong and Golic, 2003; Rong and Golic, 2000; 2001; Rong et al., 2002). One attractive feature of I-SceI for that homologous recombination system was precisely that I-SceI does not readily cut any endogenous sequences in the *Drosophila melanogaster* genome, and will therefore tend to cut specifically at engineered sites inserted on transgenes. Though some other insect genomes may by chance have one or more sites recognised by I-SceI, this enzyme is not generally preferred for use in the present invention. One example of a homing endonuclease that cuts multiple sites per genome is PpoI. Though this has a rather specific, long recognition site, it corresponds to a highly conserved sequence in an rDNA gene. Since multiple copies of this rDNA gene are present in all eukaryotic genomes, multiple target sites are available. There are potential mechanisms, such as gene conversion, whereby a 'resistant', i.e. resistant to PpoI-mediated cutting, mutation of such a gene could spread through the rDNA sequences, however there are sufficient copies of this sequence that the risk of resistant genomes, where all or almost all of these sites have become resistant, seems rather low. I-SceI and PpoI have both been shown to function in mosquito (*Anopheles gambiae*) tissue culture cells (Windbichler et al., 2007); as one might expect expression of PpoI was deleterious to the cells, leading to cell proliferation arrest, whereas I-SceI was relatively innocuous. Homing endonucleases are a class of selfish DNA element which can spread through populations of the fungi wherein they have been identified. No homing endonucleases are known in animals, but it has been proposed that their unusual properties (cutting a homologous non-HEG-bearing chromosome and being copied into it by the cell's DNA repair machinery (Burt and Trivers, 2006)) could be used to construct a 'gene drive' system (Burt, 2003); proof-of-principle has been accomplished using I-SceI and an artificial target site (Windbichler et al., 2011). A gene drive system is a system for spreading genes through a target, e.g. wild, population where the gene to be spread does not confer a simple selective advantage (e.g. Alphey et al., 2002).

In addition to the 'conventional' use of HEGs as gene drive systems, which resembles their natural spreading mechanism and involves copying the HEG into cut DNA, it has also been proposed that a HEG located on the Y chromosome that specifically cuts the X chromosome might lead to males from whom the only viable gametes are Y-bearing (Deredec et al., 2008).

HEGs typically recognise a target site of 15-40 bp. ZFNs recognise approximately 3 bp per zinc finger. In the typical configuration, ZFNs need to dimerise to cut DNA; this means an effective recognition sequence of 18 bp. A specific 18 nt sequence will typically occur once in $4^{18}$ nucleotides, which is approx $7 \times 10^{10}$ nucleotides or 7000 Mb. For comparison, insect genomes are typically a few hundred Mbp, and the human genome about 3000 Mbp, so such sequences will typically occur 0-1 times per genome. Of course this is a simplified calculation, and ignores the effects of GC content, repetitive DNA, etc, but the general point still holds, that the specificity of such long recognition sequences is desirable for purposes that need specificity, such as gene therapy and gene targeting, but molecules with a shorter recognition sequence are generally preferred for the purpose of cutting the genome two or more times.

One such class of enzymes are restriction endonucleases. These typically have recognition sites of 4-10 bp, which will typically cut a eukaryotic genome many times ($4^{10}$ is approximately $1 \times 10^6$). Some restriction endonucleases are sensitive to the methylation state of the substrate DNA; enzymes which are insensitive to methylation, or which cut DNA modified in a why characteristic of the target genome, are preferred. For example, *Drosophila melanogaster* genomic DNA is substantially unmethylated, therefore an enzyme such as DpnI, which cuts only adenomethylated DNA, is not preferred. In contrast, to cut the same sequence (GATC), alternative enzymes such as DpnII, MboI or Sau3AI would be preferred. FokI, which is not methylation sensitive and for which the nuclease domain is known to function in a range of cell types as well as in vitro, is particularly preferred.

The nuclease need not have any substantial sequence specificity. Another preferred class of nuclease is one in which a nuclease domain, for example from FokI, is combined with a DNA binding domain, said DNA binding domain having little or no sequence specificity (though a general preference for some types of DNA over others, for example for GC-rich or AT-rich regions or sequences, is acceptable). Particularly preferred examples of this class of effector are protamine-nuclease and histone-nuclease fusions. Some of the advantages of protamine-nuclease fusions are described above. Two types of nuclease domain are envisioned. Firstly, one which requires to bind at least one other protein ('dimerise'; it will be understood that a requirement to form larger complexes, e.g. trimers, tetramers, etc are included in this term), either with itself (homodimer) or with at least one different protein (heterodimer) in order to cut DNA; secondly one which does not need to so dimerise.

The key difference between these two types is their concentration/function relationships. An enzyme that does not need to dimerise will, broadly, function in proportion to its concentration. Therefore very low concentrations will produce some DNA damage or modification; higher concentrations will produce more. This is advantageous when the conditional expression system produces relatively low amounts of effector. The time course of spermatogenesis is likely to give the effector at least some hours to act, and probably rather longer. In contrast, an enzyme that does need to dimerise will typically have a non-linear dose-response function. Particularly for an enzyme that can bind at many sites in the genome, at low concentration it is unlikely that two enzyme molecules will meet in such a way as to be able to cut. At higher concentrations, it is much more than proportionately likely (typically increasing as the square of concentration for homodimers, cube for homotrimers, etc). This may be advantageous where, for example, the conditional expression system is somewhat leaky, producing a low, non-zero level of effector in at least some cells other than the intended cells (e.g. other than in the male germline, or, as another example, in male germline cells where intended expression is in spermatogonia or later stages of spermatogenesis only). Then this low 'basal' expression should be relatively harmless, or at least show a more-than-linear difference in its activity in the non-target cell relative to its activity in the target cell(s).

Another relevant type of leaky activity relates to the conditionality of the conditional expression system—it is unlikely that the supposedly 'off' condition will in fact give zero expression, therefore an additional system, such as this, which exaggerates the phenotypic difference between the 'on' and 'off' states is desirable. Note that these arguments and potential benefits apply to other classes of effector. Within nuclease effectors, they apply to zinc finger nucleases as well as to protamine-nucleases, etc. In particular, the FokI nuclease domain needs to dimerise to cut DNA. Normally this is by homodimerisation. However, variants are known which alter this. The two nuclease domains can be included in the same protein, connected by a suitable linker, so that dimerisation is not required (i.e. intramolecular, rather than intermolecular dimerisation is sufficient for). Also, mutants of FokI are known where heterodimerisation is required (Miller et al., 2007). Note that it is not required that each of the two dimerisation domains have nuclease activity. This permits another method of achieving greater specificity. The two (or more) proteins which need to heterodimerise may be expressed under separate control (e.g. transcriptional control, but also translational or degradation control, for example). Only cells expressing both domains will have significant activity. Therefore, leaky expression of one protein in a cell that does not also suffer leaky expression of the other protein will have little or no adverse effect.

EXAMPLES

Example 1

Germ Line Specific Promoters

In order to test the suitability of an isolated promoter region, a fluorescent protein can be used as a reporter, and particularly a fusion between a tetracycline-responsive transcriptional activator (tTA) and a fluorescent protein. This allows both direct visualisation of protein expression, and also further testing of the suitability of the timing and level of expression directed by the candidate suitable promoter fragment for the specific purpose of use as a part of a conditional bipartite expression system functional in spermatogenesis. Expression of the reporter from such insertions illustrates the activity of the candidate suitable promoter fragment. Assessment of several such insertion lines allows a determination as to the likely suitability of the promoter fragment. Several insertion lines should be examined due to 'position effect'; a well-known phenomenon whereby the expression of an inserted gene is influence by the chromatin context into which it is inserted (Wilson et al., 1990).

The actual ability of the candidate suitable promoter fragment to function as part of a conditional expression system in the male germline can be tested as above but including a suitable expression system, or relevant component thereof, e.g. encoding tTA or a related sequence. Use of a tTA-fluorescent protein (tTA-FP) fusion in the reporter test above allows the same insertion line, or set of insertion lines, to be used for both tests. Crossing to a suitable line, e.g. tRE-X, where X may be an effector or reporter, under conditions permissive for expression from the expression system, will allow a determination of whether the expression system (promoter-tTA, tRE-X) is functional in spermatogenesis and, e.g. by fluorescence microscopy on dissected testes, where, when and how much X and/or tTA-FP is expressed. Similar experiments under conditions repressive for expression will allow a determination as to whether the expression system is conditional.

If expression studies indicate that the candidate suitable promoter fragment is not in fact suitable, one can take a different promoter fragment from the same gene. Such a revised fragment is typically longer, as the original fragment may have omitted some important regulatory elements, however in the case of expression being specific but too late in development, e.g. post-meiotic, even though the gene from which the promoter fragment was derived is thought (e.g. based on RNA in situ data) to be transcribed sufficiently early, it may be desirable to eliminate some elements, especially UTR elements, to remove signals for translational delay. It may also be desirable to test longer and shorter fragments to identify regions of the promoter necessary for or influencing gene expression levels and temporal and tissue specificity; this approach has been widely used to analyse promoters and can be achieved simply by iterations of the above procedure with variants of the original candidate promoter fragment.

RNA in situ hybridisation experiments demonstrated that that the Medfly β2-tubulin transcription is at an early-to-late stage in Medfly spermatogenesis. It is assumed that the Medfly β2-tubulin transcript starts at a similar stage as Dmβ2-tubulin, which is before meiosis and is synthesised from the late third instar larval stage, before there is significant meiosis in the developing testes. Sperm marking systems using this gene promoter have been developed for the mosquitoes *Anopheles stephensi* (Catteruccia, Benton et al. 2005) and *Ae. aegypti* (Smith, Walter et al. 2007), for Medfly (Scolari, Schetelig et al. 2008) during the period of our research towards sperm lethality and later the Caribbean fruit fly, *Anastrepha suspensa* (Zimowska, Nirmala et al., 2009). According to this, we have amplified the β2-tubulin promoter from the medfly genome using the following primers:

```
Forward:
                                          (SEQ ID NO: 53)
CTCCCGTGCGATATCCTAGGCCCCATGTTACAAGGCTG Reverse:
                                          (SEQ ID NO: 54)
AGCCATTTTGGTTAATTGAAATCCCTAAAATAAATGTAATTCATTTTCG
```

Construct OX3671 (FIG. 16) contains the Medfly β2-tubulin promoter (the 1556 bp promoter fragment was amplified from Medfly genomic DNA) fused to the DsRed2 sequence. Most of the Ccβ2-tubulin 3'-UTR sequence was omitted and replaced by a commonly used 3'-UTR-SV40—known to express in a variety of species. Expression of the transgene should result in sperm fluorescing red under the appropriate excitation filter. DsRed2 expression was clearly visible in the abdomen of transgenic males in all three lines obtained, with two areas of more intense fluorescence, seemingly the testes (data not shown).

To further assess whether the DsRed2 marker expresses in sperm, sexually mature transformed male's testis were dissected. Results demonstrate that mature sperm exhibits strong DsRed2 expression compared with sperm from a wild type male. In alignment with B2-tubulin expression pattern, early spermatocytes do not exhibit fluorescence, which starts to be clearly visible in the spermatid stages of spermatogenesis.

In order to test whether we would obtain similar patterns of fluorescence expression using the bipartite "tet-off system", two fluorescent reporter constructs were built; OX3866 (FIG. 14) (tetO-mini promoter-DsRed2-mls) and OX3867 (FIG. 15) (tetO-mini promoter-protamine fused with DsRed2). The tetO-mini promoter element is known as tRE and is preferred. In OX3866 (FIG. 14) the DsRed2 reporter is fused to a membrane localisation signal (mls) which is predicted to lead to any expressed fluorescent protein being membrane-bound or -associated after expression, whereas in OX3867 (FIG. 15) the DsRed2 is fused to a *Drosophila* protamine. Both reporter genes were tested with promoters driving expression of tTAV in somatic cells and found to be functional.

Following the finding that the β2-tubulin promoter drives expression of DsRed2 in sperm, albeit too late for our purposes, construct OX3831 (FIG. 20) was designed and modified from OX3671 (FIG. 16), with Medfly β2-tubulin promoter driving tTAV-fluorescence fusion gene. In this construct, the *Drosophila* aly 5' UTR region replaced that of β2-tubulin promoter under the speculation that tTAV protein would then express earlier during spermatogenesis. Since the TurboGFP sequence was fused with the tTAV, sperm of OX3831 (FIG. 20) transgenic males should exhibit green fluorescence under the appropriate excitation filter. To test this, adult males from seven transgenic lines were dissected and observed under a fluorescence microscope. Although fluorescence expression was not readily visible in the testes of non-dissected males, in dissected testes of OX3831 (FIG. 20) adult males fluorescence expression was visible in the spermatid bundles. Some lines expressed stronger fluorescence than others but all spermatids in OX3831 (FIG. 20) strains displayed fluorescence testis-specific sperm marker expression.

OX3831-heterozygous flies were crossed with OX3866- and OX3867-heterozygous flies (FIGS. 14 and 15 respectively) (tetO-DsRed2 strains). More than 20 adult male progeny that had been raised on non-tetracycline food (i.e. permissive conditions for tetO-DsRed2 expression) in different crosses and at different times were dissected and observed under a high magnification fluorescence microscope. Only one male showed strong DsRed2 expression, which was visible in several spermatid bundles. In other males, no DsRed2 expression in any spermatid bundles was detected. A possible reason for only one male demonstrating strong DsRed2 expression is late transcription and translation of tTAV-fluorescence, driven by the Ccβ2-tubulin promoter. This late expression may mean that there is insufficient time for tTAV to bind to the tetO sequence and further induce enough DsRed2 transcripts before meiosis. According to our results, only by chance, some of the spermatocytes in some males have enough DsRed2 transcripts accumulated before meiosis and DsRed2 fluorescence can be detected in spermatid bundles. Reverse transcriptase PCR analysis on isolated testes and carcasses of OX3831 (FIG. 20) males, using tTAV specific primers, demonstrated the testis-specificity of the 5' UTR-aly Ccβ2-tubulin promoter.

It was apparent at this stage that an even earlier expression of tTAV was necessary in order to allow for adequate expression of the reporter gene in the male germ line. For this reason, we developed and tested construct OX4282 which contained the 5' UTR of the Hsp83 gene. Hsp83 is expressed strongly both in germline and somatic cells of the Mediterranean fruit fly *Ceratitis capitata* and is not considered to contain any delayed-translation signals. In construct OX4282, the reporter gene; TurboGFP, was not fused to the tTAV sequence but placed adjacent to the tetO sequence. Furthermore, the tetO-reporter and promoter-tTAV components were combined in a single plasmid in an attempt to assess the Hsp83 5' UTR at a more immediate fashion. tTAV should be expressed in the male germline of transformed individuals and, in the absence of tetracycline, by binding to tetO should induce expression of the adjacent TurboGFP marker gene. In other words, male testes of those strains carrying this construct should show TurboGFP expression when reared off tetracycline, and expression should be repressed by tetracycline. Testes dissection of adult males reared in the absence of tetracycline, revealed the presence of strong green (turboGFP) fluorescence in three out of 6 lines tested.

The fact that TurboGFP expression was not observed in the other lines is possibly due to positional effects of the transgene insertion. In the lines exhibiting TurboGFP fluorescence off tetracycline, expression was totally repressed by tetracycline (data not shown).

OX4282 males were crossed with OX3867 (tetO-protamine-DsRed2) (FIG. 15) females in each cage in order to further examine the ability of the promoter to drive adequate expression of the reporter gene; in this case DsRed2 using the "tet-off" bipartite conditional system.

TurboGFP expression can be detected at different stages of spermatogenesis (in both elongated spermatid and spermatocytes, although red fluorescence was only detected in elongated spermatids but not in early spermatocytes (FIG. 3). TurboGFP expression was detected in both the sperm head (where nucleus is located) and tail of the spermatids.

The above results indicate that there is a slight delay in the expression of the reporter gene (DsRed2 in this experiment)

compared to tTAV expression; as this is estimated by the amount of green fluorescence observed. Considering that red fluorescence was apparent in later stages of spermatogenesis (elongated spermatids), it is likely that the reporter is transcribed before meiosis but translated after meiosis.

Dmtopi is a testis-specific gene which encodes a testis-specific Zn-finger protein that physically interacts with Comr (Perezgasga, Jiang et al. 2004). Dmtopi is not required for the nuclear localisation of Aly or Comr, but is required for their accumulation on chromatin. In *Drosophila*, although all genes that depend on aly or comr for expression also depend on achi/vis and/or topi, there are a few genes, whose transcription depends on achi/vis and topi but not on aly or comr. (Perezgasga, Jiang et al. 2004). Perhaps more significantly, many of the aly-class genes seem to have arisen from gene duplications. Following duplication, one of the pair has assumed a somatic role and one a germline role. This has two limitations in respect of using these genes as a source of male germline promoters in a wide range of insects.

Firstly, the two genes may be quite similar, making it relatively difficult to identify the germline-specific version. Secondly, and much more significantly, many of these duplications appear to be quite recent. Most insects may therefore have the ancestral version, which is a single gene performing both germline and somatic functions, and hence no separate germline gene and promoter. topi is unusual in this respect in that it has no obvious somatic alternative, and it also seems more ancient than most of the aly-class duplications. It is therefore likely to provide a potential germline-specific promoter in a much wider range of insects than the other aly-class genes. One caveat for this is that the sequence conservation of topi is clear, but the functional conservation, and in particular the expression pattern, of topi in other insects is generally unknown. However, this reservation applies also to other male-germline genes. For these various reasons, topi was chosen for further investigation as a source of a male-germline promoter.

Before developing topi-based constructs in Medfly, the conservation of expression pattern of topi was first tested in the mosquito *Ae. aegypti*; availability of genome sequence meant that the topi homologue and putative promoter fragment could rapidly be isolated. RISH (RNA In Situ Hybridisation) results showed that *Ae. aegypti* topi (*Aetopi*) gene transcription starts from the primary spermatocyte stage; an expression profile that resembles that of Dmtopi in *Drosophila* testes (Perezgasga, Jiang et al. 2004). An *Ae. aegypti* transgenic strain (OX4286, FIG. 23), with tTA expression driven by a 1233-bp sequence, including 1168 bp of *Aetopi* promoter and 65 bp *Aetopi* 5'-UTR), was developed. After crossing 3 independent OX4286 (FIG. 23) lines with a tetO-reporter strain (OX3978, tetO Aehsp70 mini promoter-Amcyan, FIG. 24), clear Amcyan expression was seen in testes and spermatogenesis cells in all three crosses rearing on non-TET diet (data not shown). Expression was tetracycline-repressible.

After the *Ae. aegypti* topi promoter was shown to induce testis-specific expression of tTAV and, consequently, expression of a reporter gene, the expression pattern of *Ceratitis capitata* topi was analysed. Using the nucleotide sequence of this gene in Medfly, primers were designed to verify that Cctopi is a testis-specific gene in Medfly. Ten pairs of testes dissected from ten wild-type males were used to extract RNA (for dissection details see section 2.6.4.3). RNA was extracted from the remaining carcasses to provide non-testes controls. Reverse transcriptase analysis using the primers TopitestF1': and TopitestR' were used for these PCRs. The results confirmed that Cctopi expression is testis-specific. RISH also demonstrated that Cctopi is transcribed in Medfly testes (data not shown). This gene promoter was therefore chosen for use in new constructs for developing testes-specific expression in transgenic strains.

```
TopitestF1 primer:
                                 (SEQ ID NO: 55)
GTAACTCCCGTTCCTGAGACAACA TopitestR primer:
                                 (SEQ ID NO: 56)
CGATATGGAGTGGGTGAAACCTCA
```

Construct OX4275 (FIG. 25) comprises a putative promoter fragment (1178 bp) from Cctopi driving DsRed2 (SV40 3'UTR). Dissected testes from adult males of all strains obtained with this construct did not reveal any signs of DsRed2 expression (data not shown). To further test the Cctopi promoter, a construct with the same promoter sequence driving tTAV expression was developed (OX4254, FIG. 26). OX4254-heterozygous flies were crossed with OX3867 (tetO-DsRed2) (FIG. 15) heterozygous flies (tetO-DsRed2 strains) of the opposite sex and the adult male progeny of these crosses were dissected and assessed for red fluorescence. No DsRed2 expression in any spermatid bundles was detected in those male testes.

As the short length of the putative Cctopi promoter in OX4275 (FIG. 25) and OX4254 (FIG. 26) may have resulted in a lack of apparent function, a new construct—OX4371 (FIG. 27)—was made based on the following modifications. This construct contains a 1708-bp sequence from the putative Cctopi coding region, over 530 bp more than in previous constructs including a 484 bp possible coding sequence and a 55 bp intron in the retained portion of the coding region. As tTAV generally does not function after fusion with another protein at its N-terminus, a 228 bp ubiquitin gene sequence (sequence based on *Drosophila* ubiquitin but optimised for expression in a range of insects and synthesised by Geneart Ltd) was used between the Cctopi coding region and tTAV to separate the two gene products post-translationally via cleavage by the ubiquitin protease (Varshaysky 2005). This construct contains both the newly designed Cctopi promoter driving tTAV and a tetO-Dmhsp70 mini promoter-TurboGFP reporter. Therefore, expression of tTAV should be detected by fluorescence in testes of males reared without tetracycline in their larval diet. Weak TurboGFP expression in spermatogenesis cells was detected in dissected testes from OX4371 (FIG. 27) male adults reared off tetracycline in one of the two lines tested. No TurboGFP expression was detected in dissected testes of any males reared on tetracycline, indicating repressible expression.

Concurrent to the work with OX4371 (FIG. 27), OX4391 (FIG. 22) strains were generated and analysed. OX4391 (FIG. 22) differs from OX4371 (FIG. 27) in one aspect: the SV40 3' UTR of tTAV in OX4371 (FIG. 27) was replaced by the Cctopi endogenous 3' UTR in OX4391 (FIG. 22). As mentioned before, 3'-UTRs can influence the fate of a particular mRNA, for example transcript stability or level of translation (Mazumder, Seshadri et al. 2003). Considering that the 3' UTR has been shown to play an important role in mRNA processing, we hypothesised that the endogenous 3' UTR from Cctopi may confer the gene's desired expression patterns to our tTAV transgene. Reverse transcription PCR was used to amplify the Cctopi 3'-UTR. Testes from 2-3-day-old male adults reared off tetracycline from 6OX4391 (FIG. 22) strains were dissected. 3 strains showed strong TurboGFP expression in male germ line cells. Weak fluorescence was detected in the other three.

To further test the newly designed topi promoter sequence, we set up crosses with OX4391 (FIG. 22) males (reared on non-tetracycline diet) with wild type females and assessed the presence of fluorescence in dissected spermathecae. Examination of sperm stored in spermathecae under a fluorescence microscope demonstrated that TurboGFP was indeed detectable.

The above results indicate that our isolated topi promoter sequence (as described above) is expressed in the male germ line and adequately drives expression of tetO reporter genes in testes. Crosses with flies comprising tetO-nuclease transgenes are discussed later.

Example 2

Effector Proteins

The objective of this work is to produce sperm that are transferred to the female and will lead to a low or indeed none of the embryos—which the female would otherwise have produced—surviving. Same sperm should induce adequate refractoriness to remating in the female, while will do well in sperm competition if the female does remate. Our approach to this is to construct paternal-effect lethals, whereby the sperm can enter an egg but no viable zygote (capable of developing to a fertile adult) is formed. Ideally, this effect is generated by males with a single copy of the paternal-effect lethal, though the use of multiple copies is also envisioned. It is also preferred that the effector have a direct biochemical effect on the sperm, rather than merely using the sperm as a vehicle via which to enter the egg (and then to have an effect there). This is due to considerations of potential resistance. Nucleases are a preferable option for the purposes of this invention. Theoretically, if the genetic information carried by the sperm is damaged to the extent that some or (preferably) substantially all of the zygotes are non-viable, then this forms the basis for a suitable form of sterility through paternal-effect lethality. Different classes of nucleases have been explored in an attempt to induce sperm specific damage. All nucleases were tested as part of the "tet-off" bipartite conditional system; that is linked to a tetO sequence. This approach allows for the assessment of various effector proteins in combination with different germline specific promoter sequences, without the burden of creating new transformant strains. Furthermore, it provides a more realistic situation in terms of future application.

Zinc finger nucleases (ZFNs) have been described, wherein each zinc finger provides sequence-specific binding to a short nucleotide sequence, e.g. 3 nucleotides. Higher affinity and greater sequence specificity can be provided by combining multiple such zinc fingers into a single protein. If this is combined with a nuclease, e.g. the nuclease domain of the restriction endonuclease FokI, an artificial sequence-specific nuclease can be constructed, with arbitrary sequence specificity. We have tested the hypothesis that ZFNs can produce DNA breaks in elongated spermatids by crossing these lines to various male germ line specific promoters. Two (OX4103) (FIG. 18) and three (OX4104, FIG. 19) Zinc finger nuclease constructs were designed and tested. Previous assessment, by crossing to promoter-tTAV lines expressing in somatic tissues, indicated that the 3-Zn finger nuclease exhibits a greater "lethal" effect and the strongest of these lines was therefore used for the purposes of this work. This nuclease is therefore preferred.

Homing endonucleases are a type of restriction enzymes typically encoded by introns. They act on the cellular DNA of the cells that synthesize them and they tend to recognise relatively long (15-40 bp, though often accepting some mismatches to the nominal target sequence) nucleotide sequences which therefore occur rarely, if at all, in any given insect genome. The minimum number of acceptable recognition/cutting sites is one per diploid genome; one per haploid genome is preferred and recognising/cutting multiple sites per haploid genome is particularly preferred. One example of a homing endonuclease that cuts multiple sites per genome is IPpoI. Though this has a rather specific, long recognition site, it corresponds to a highly conserved sequence in an rDNA gene. Since multiple copies of this rDNA gene are present in all eukaryotic genomes, multiple target sites are available. A tetO-IPPO1 (OX4112, FIG. 17) construct was designed and tested.

Restriction endonucleases have recognition sites of 4-10 bp, which will typically cut a eukaryotic genome many times. Such nucleases have no substantial sequence specificity. FokI, which is not methylation sensitive and for which the nuclease domain is known to function in a range of cell types as well as in vitro, is particularly preferred for our aim. FokI nuclease domain combined with a DNA binding domain of little or no sequence specificity is of particular interest. Preferred examples of this class of effector are protamine-nuclease fusions. An advantage of the protamine-nuclease fusion is the need for dimerization (or polymerisation) either with itself (homodimer) or with at least one different protein (heterodimer) in order to cut DNA. An enzyme that does need to dimerise will typically have a non-linear dose-response function. Particularly for an enzyme that can bind at many sites in the genome, at low concentration it is unlikely that two enzyme molecules will meet in such a way as to be able to cut. This may be advantageous where, the conditional expression system is leaky—either through the promoter or through the conditional system itself, producing a low, non-zero level of effector in at least some cells other than the intended cells (e.g. other than in the male germline). A tetO-protamine-Fok1 construct (OX4458, FIG. 21) has been designed and tested.

Assessment of male sterility in the bipartite system mentioned before is referred to as "Egg hatch rate assays or experiments". A schematic representation of the design is illustrated in FIG. 1. Promoter lines drive expression of tTAV in the male germline, preferably with little or no expression elsewhere, while effector lines are linked to the tetO sequence, expression of which is correlated to tTAV, both temporally and spatially. Transformation markers in promoter and effector lines utilize different fluorescent genes for accurate evaluation of the results, i.e. promoter lines fluoresce green, while effector lines fluoresce red under appropriate excitation filters. Effector (E) and Promoter (P) lines are crossed without tetracycline, i.e. permissive (for expression) conditions. Eggs from these crosses are collected and divided into either permissive conditions (without tetracycline) or repressive conditions (with tetracycline) and reared accordingly. Pupae are screened for expression of line-specific fluorescent markers and double heterozygotes—with both markers—collected. These are checked for equal male to female ratio after ecclosion and males crossed to wild type females—again either on- or off-tet. Double-heterozygote females to wild type males crosses are used to test whether any observed effects are sex specific. Wild type control is included as the reference point for egg hatch rates.

Eggs from the crosses are collected and counted. Three days later counting is repeated and numbers of un-hatched eggs assessed.

FIG. 1.: Design of the egg hatch rate assay.

Results of a number of these crosses are shown below. All crosses presented here have followed the basic design described above.

OX4282 (PB-HrIE-AmCyan-SV40-TurboGFP-teto14-ccTubulin-hsp83-tTAV-SV40)×OX4104 (PB-YAFN-hsp83-tetO21-Hr5-IE1-Red) (FIG. 19)

FIG. 2. OX4282-OX4104 male sterility on and off Tetracycline. Three independent, autosomal insertion lines of OX4282 transposon carrying tetracycline repressible transactivator (tTAV) driven by the β2-tubulin promoter from *Ceratitis capitata* gene (I, L, G) were crossed to line OX4014 carrying a tetO-3Zn-finger effector. Progeny of these crosses was reared and bred either on a diet with (100 μg/ml; tet+) or without tetracycline (tet−). Males carrying both driver and effector alleles were crossed to the wild type females and the hatching rates of eggs obtained from these crosses were calculated (percentage of laid eggs that hatched). Two different egg collections of 100-150 eggs each were used for each cross. Wild type males crossed to wild type females in the presence or absence of tetracycline were used as controls. Crosses where highly significant male sterility was observed (chi-squared test, * represents P<0.01, ** represents P<0.001) are marked with asterisks.

Three OX4282 lines were crossed to a 3Zn-finger line (OX4104, FIG. 19) which has previously shown promising results when crossed to two generic promoters (Hsp83 and OP). No adverse effects were recorded for flies containing both plasmids, indicating that basal expression of the effector in somatic tissue was not high enough to show an adverse effect. Only 14% egg hatching was observed from line L and 27% from line I. There was no significant reduction in egg hatching from line G. Both lines L and I contain a single copy of the transgene in contrast to line G, which contains two (or more) copies. Results clearly indicate that the 5' Hsp83 UTR-Cctubulin-SV40 3' UTR promoter drives adequate expression of tTAV in the male germ line to induce sperm sterility, as indicated by the reduction of hatching larvae from the resulting progeny of these males. Additionally, no reduction in female fertility was observed indicating that the promoter acts in a male-germline specific fashion (data not shown). However, the fact that there was no significant reduction in the progeny of one OX4282 line points toward positional effects influencing the phenotype.

OX4282 (PB-HrIE-AmCyan-SV40-TurboGFP-teto14-ccTubulin-hsp83-tTAV-SV40)×OX4112 (PB-IPPO-1-hsp83-tetO21-Hr5-IE1-Red)

The same OX4282 lines were crossed to an I-Ppo1 line, which had demonstrated lethality when crossed to two promoters (Hsp83 and Opie2) active in somatic cells. Up to 50% sterility was observed compared to wild type and tetracycline controls, using this effector (data not shown). Results demonstrate that the sterility seen in this assay is the result of the activation of nuclease expression by tTAV and subsequent sperm DNA cleavage. Sterility levels indicate not enough penetrance. The fact that the same line exhibited a strong lethal effect when it was crossed to generic promoter lines may suggest that not enough molecules of this protein were produced in the male germline to cause a desirable effect. It is probable that the protein needs to exceed a certain threshold for a strong effect to occur which also increases the possibility of positional effects of the transgene influencing performance. This, together with the reduced numbers of pupae containing both transgenes that were observed during this assay, make I-Ppo1 a less appropriate, and therefore less preferred, candidate for developing sperm lethality.

OX4282 (PB-HrIE-AmCyan-SV40-TurboGFP-teto14-ccTubulin-hsp83-tTAV-SV40)×OX4458 (PB-AttP-Hr5-IE1-DsRed2-SV40-teto21-Dmprotamine-nuclease)

FIG. 3. OX4282-OX4458 male sterility on and off Tetracycline—Repressible male-specific sterility in transgenic Medflies.

Four independent, autosomal insertion lines of OX4458 (FIG. 21) transposon carrying a tetO-Protamine-FokI effector (B1, D1, D2,F2) were crossed to the OX4282L driver line carrying the tetracycline repressible transactivator (tTAV) driven by a promoter from *Ceratitis capitata* β2-tubulin gene. Progeny of these crosses was reared and bred either on a diet with (100 μg/ml; tet+) or without tetracycline (tet−). Males carrying both driver and effector alleles were crossed to the wild type females and the hatching rates of eggs obtained from these crosses were calculated (percentage of laid eggs that hatched). Four different egg collections of 200-500 eggs each were used for each cross. Wild type and OX4282L male crosses with wild type females in the presence or absence of tetracycline were used as controls. Crosses where highly significant male sterility was observed (chi-squared test, P<0.0001) are marked with asterisks.

OX4458 (FIG. 21) construct contains a single FokI cleavage domain fused to a *Drosophila* protamine under the transcriptional control of the tetO operator in a single ended piggyBac-derived vector with hr5-IE1-DsRed2 as a transformation marker. The OX4458 (FIG. 21) construct should not exert any effect on its own. Expression of the effector fusion protein occurs when OX4458 (FIG. 21) line is crossed to suitable tTAV expressing line, in double heterozygotic progeny, possessing both alleles, and in permissive conditions (without tTAV repressor—tetracycline).

Four lines with single, autosomal transgene insertion were crossed to the tTAV expressing line—OX4282L which exhibited higher promoter activity in previous experiments (see above). In all four double-heterozygote combinations a severe reduction was observed in the hatch rate of eggs from females mating transgenic males. The sex-specificity of the observed effect was confirmed using transgenic females carrying both transgenes crossed to wild type males (data not shown).

According to the results shown above, the combination of the "altered" tubulin promoter and the *Drosophila* protamine-Fok1 effector, seem to produce a male germ line specific lethal effect with minimal (or absent) adverse effects on the general fitness of the males in any other way than that tested. Additionally, females do not seem to be significantly affected by the expression of the transgenes, supporting the male germ line specificity of the sequences used. The next step would be to design a construct that will contain both promoter and effector sequences in a single plasmid (OX4353). Such a construct would provide a more realistic situation of the transposon to be used for the development of a paternal-effect lethal system.

OX4353 (PB-HrIE-AmCyan-SV40-teto14-Dmprotamine-nuclease-ccTubulin-hsp83-tTAVnew-SV40)

4 lines were considered to be single insertion events apart from line F which was thought to have two insertions, based on the inheritance pattern of the transformation marker. All lines were tested by crosses to wild type in the presence and absence of tetracycline as described before. Females from the same lines were also crossed to wild type males and their fertility was assessed in a similar way.

FIG. 4. Percentage of OX4353 male sterility on and off Tetracycline.

Five independent, autosomal insertion lines of OX4353 transposon carrying tetO-Protamine-FokI effector and tetracycline repressible transactivator (tTAV) driven by a β2-tubulin promoter from *Ceratitis capitata* were generated in Medflies (A, B, C, D, F). Progeny of these lines was reared and bred either on a diet with (100 μg/ml; tet+) or without tetracycline (tet−). Males were crossed to the wild type females and the hatching rates of eggs obtained from these crosses were calculated (percentage of laid eggs that hatched). Two egg collections of 100-150 eggs were used for each cross. Wild type male crossed to wild type females in the presence or absence of tetracycline were used as controls. Crosses where highly significant male sterility was observed (chi-squared test,  represents P<0.001, * represents P<0.0001) are marked with asterisks.

FIG. 5. Percentage of OX4353 female sterility on and off Tetracycline. Five independent, autosomal insertion lines of OX4353 transposon carrying tetO-Protamine-FokI effector and tetracycline repressible transactivator (tTAV) driven by the β2-tubulin promoter from *Ceratitis capitata* were generated in Medflies (A, B, C, D, F). Progeny of these lines was reared and bred either on a diet with (100 μg/ml; tet+) or without tetracycline (tet−). Females were crossed to wild type males and the hatching rates of eggs obtained from these crosses were calculated (percentage of laid eggs that hatched). Two egg collections of 100-150 eggs from each cross were used. Wild type males crossed to wild type females in the presence or absence of tetracycline were used as controls. No significant female sterility was observed (chi-squared test, P>0.05).

Results indicate that heterozygous OX4353 males were up to 100% sterile in the absence of tetracycline (permissive conditions) in the diet. However males of some lines were sub-fertile even in the presence of tetracycline and females from most lines showed a slight reduction of fertility in the absence of tetracycline. From the above results, we can conclude that expression of the transgene is operative in all 5 lines tested; in terms of inducing sperm lethality, however the fine tuning of achieving complete (or very close) sperm lethality with minimal effects on the general fitness of the insects that contain that transgene, seems to be greatly influenced by position effects (i.e. the location of the inserted sequences in the insect's genome and the regulatory elements in proximity).

The work described here shows that a 1030 bp Medfly β2-tubulin promoter fragment is enough to drive tTAV expression and further drive effector gene expression in spermatogenesis under the control of tetracycline. The OX4353 strain proved to be a functional, tetracycline-repressible sperm-lethal strain. Additionally, one can also conclude that the Dmprotamine retains at least one of its key properties when expressed in Medfly; that is binding to sperm DNA. The protamine sequence is not well conserved, thus the positive outcome was uncertain prior to these experiments. These results indicate promise for further use of this promoter/effector combination in relation to the bipartite "tet-off" system, with a view for Medfly population control.

OX4718 (PB4 Hrie1-AmC-MexMActPro-DsR-tetO21-Prota-mCh-FokI-CcBTubPro-tTAV2-Hrie1-ZsG)

OX4718 is an example of a single construct carrying both promoter and effector components, on Medfly. This plasmid was injected into pre-blastoderm *Ceratitis capitata* embryos. Pupae expressing both red and green fluorescent protein (4-ended pb construct containing different coloured pb ends (Dafaala et al., 2006)—signifying insertion of complete transposon—were found among G1 progeny in two Go crosses: V (1 pupa) and σ (47 pupae). The single pupa from OX4718-V line did not survive to adulthood. Pupae from OX4718-σ line displayed two clearly distinct phenotypes: stronger (30 pupae) and weaker (17 pupae) and were named σ1 and σ2 respectively. These were propagated, mostly as single male or female crosses to wild type and at this stage are considered two independent insertion events. OX4718-σ1(b) and OX4718-σ2(b) lines were discontinued at G2 stage. Phenotypic analysis of G2 pupae indicated multiple insertions in each of these lines. Further analysis of lines at the G3 stage confirmed that both σ1(a) and σ1(c) lines are single, autosomal insertions. OX4718-σ2(a) carries a single insertion on X chromosome—as suggested by the alternating absence or presence of the transgene in males of different generations and has not been further analysed for the purposes of this study.

OX4718-σ1(a) and OX4718-σ1(c) lines were reared and bred either on a diet with (100 μg/ml; tet+) or without tetracycline (tet−) and were crossed to wild type. Wild type to wild type and OX4718 female crosses with wild type males in the presence or absence of tetracycline were used as controls. Fresh—not older than 24 hours—eggs from these crosses were collected on day 4 after setting up cages. Three collections per cross/cage were performed. Total number of eggs was compared with the number of eggs that had failed to hatch after four days. Hatching rates were calculated as the mean percentage of laid eggs that hatched; these data showed significant sterility of OX4718-σ1 males in the absence of tetracycline. Results are shown on FIG. 6. OX4718-σ1 (a) and X4718-σ1(c) lines reared in the presence or the absence of tetracycline were crossed to the wild type females and the hatching rates of eggs obtained from these crosses were calculated (percentage of laid eggs that hatched). Wild type to wild type and OX4718 female crosses with wild type males were used as controls. Crosses where highly significant male sterility was observed (chi-squared test, P<0.0001) are marked with asterisks.

The above results demonstrate successful development of conditional male-specific sterility in *Ceratitis capitata* in a format suitable for field use; i.e. individual promoter and effector molecules were assembled in a single construct.

FIGS. 7 and 8 Percentage of OX4705 male and female sterility on and off Tetracycline in Olive Fly.

OX4705 (PBMexMActPro-DsR-tetO21-Prota-mCh-FokI-CcBTubPro-tTAV2)

This provides another example of a single construct containing both promoter and effector components, in this case in olive fly.

Based on the encouraging results obtained in Medfly (*Ceratitis capitata*), similar plasmids were developed for a relative Tephritid; *Bactrocera oleae*, commonly referred to as olive fly. Plasmid OX4705 incorporates the altered form of $B_2$ tubulin driving expression of tTAV in the male germline and subsequently that of tetO and DroProtamine-FokI fusion effector. The plasmid also incorporates a novel Mexfly (*Anastrepha ludens*) muscle actin promoter which drives the expression of DsRed2 fluorescent protein as a transformation marker.

Micro-injection of plasmid OX4705 on olive fly pre-blastoderm embryos generated 10 independent insertion events. All strains exhibited a strong fluorescent phenotype (fluorescent marker expression) under a microscope with the appropriate excitation filter and were single insertions according to Mendelian laws of inheritance. Nine insertions were autosomal while one was on the X chromosome. All strains were tested for male and female sterility in the presence and absence of tetracycline from the larval medium. Wild type crosses provided additional control. Results are shown on FIGS. 7 and 8.

FIG. 7 shows the percentage of OX4705 olive fly male sterility on and off tetracycline. 9 independent, autosomal insertion lines of OX4605 transposon carrying tetO-Protamine-FokI effector and tetracycline repressible transactivator (tTAV) driven by an altered form of β2-tubulin promoter from *Ceratitis capitata* were generated in olive fly (A, A1, A2, A3, B, B1, F, F1, P). Progeny of these lines was reared and bred either on a diet with (100 µg/ml; tet+) or without tetracycline (tet−). Males were crossed to wild type females and the hatching rates of eggs obtained from these crosses were calculated (percentage of laid eggs that hatched). Three egg collections of 100-150 eggs were used for each cross to provide statistical significance. Wild type males crossed to wild type females in the presence or absence of tetracycline were used as controls.

FIG. 8 shows the percentage of OX4705 olive fly female sterility on and off tetracycline. 9 independent, autosomal insertion of OX4705 transposon carrying tetO-Protamine-FokI effector and tetracycline repressible transactivator (tTAV) driven by the β2-tubulin promoter from *Ceratitis capitata* were generated in olive fly (A, A1, A2, A3, B, B1, F, F1, P). Progeny of these lines was reared and bred either on a diet with (100 µg/ml; tet+) or without tetracycline (tet−). Females were crossed to wild type males and the hatching rates of eggs obtained from these crosses were calculated (percentage of laid eggs that hatched). Two egg collections of 100-150 eggs from each cross were used. Wild type males crossed to wild type females in the presence or absence of tetracycline were used as controls. No significant female sterility was observed.

Data strongly indicates formidable OX4705 olive fly male sterility when males are reared in the presence of tetracycline in the larval diet, with no reduction in male fertility in the absence of tetracycline from the larval diet, as compared to wild type controls (FIG. 7). Female fertility (FIG. 8) and general fitness of males were unaffected suggesting a male germline specific expression of the "paternal lethal cassette".

FIG. 9 Percentage of OX4466 male and female sterility on and off Tetracycline Following the success of paternally transmitted lethal effect in *Ceratitis capitata*, and *Bactrocera oleae*, the focus was shifted to another Diptera of economic importance; *Aedes aegypti*. The examples below provide evidence of significant male sterility on this species utilising similar promoter and effector sequences as in *C. capitata*. Slight alterations occurred in some constructs utilising genomic sequences of this organism to achieve maximum results.

OX4466 (PB-hr5IE1-DsRed-Aeprot-tGFP-EcoRI)

This also provides an example of another effector; Aepro-EcoRI. OX4466 was injected in pre-blastoderm *Aedes aegypti* embryos. The components of this construct are constitutively expressed rather than inducible by the tet-off system. 4 independent insertion events were generated. Males and females from each strain were backcrossed to wild type mosquitoes of the opposite sex. Wild type insects were used as control. Females were allowed to oviposit on wet filter papers for 24 hours. Survival of progeny was assessed. Results are shown in FIG. 9. The chart shows the percentage of collected embryos that hatched from each test cross. The inside table presents actual recorded numbers. The experiment demonstrates a significant reduction in the number of hatched eggs when these were fathered by OX4466 males; reduction in embryo viability was less apparent in line D, probably due to positional effects. Results confirm the expected sex-specificity of embryo lethality; embryos from transgenic females are equally viable to these of the wild type control cross.

The *Aedes*-protamine-nuclease effector DNA sequence (EcoRI) of construct OX4466 was fused to a fluorescent gene (turboGFP) so that expression of the nuclease should co-exist with expression of the fluorescent protein in the sperm. Fluorescent microscopy of sperm isolated from dissected testis in a number of OX4466 males, showed strong GFP co-localization with nucleus/sperm heads. This is an example of nuclease function fused to fluorescent expression.

FIG. 10 Percentage of OX4467 male and female sterility on and off Tetracycline OX4467 (PB-hr5IE1-DsRed-Aeprot-tGFP-FokICD)

OX4467 is identical to plasmid OX4466, the only difference being that the nuclease effector is Fok1 rather than EcoRI.

Injection of this plasmid to pre-blastoderm *Aedes aegypti* embryos resulted in 3 independent insertion events. Two of these events were lost in generation G1 through transgenic G0 males; indicating very strong expression of the paternal lethal effect. The remaining strain was analysed as previously. Results are shown in FIG. 10. The chart shows the percentage of collected embryos that hatched from each test cross. The inside table presents actual recorded numbers. The experiment demonstrates a significant reduction in the number of hatched eggs when these were fathered by OX4467 males. Results confirm the expected sex-specificity of embryo lethality; embryos from transgenic females are equally viable to these of the wild type control crosses.

As in OX4466 plasmid, the *Aedes*-protamine-nuclease effector DNA sequence (Fok1) was fused to a fluorescent gene (turboGFP) so that expression of the nuclease should co-exist with expression of the fluorescent protein in the sperm. Fluorescent microscopy of sperm isolated from dissected testis in a number of OX4467-E1 males, showed strong GFP co-localization with nucleus/sperm heads. This is another example of nuclease function fused to fluorescent expression.

OX4286 (PB-AeTopi-tTAV-K10-3xP3-DsR)

OX4286 (FIG. 23) is a piggyBac transposon based construct that contains tTAV driven by *Aedes aegypti* derived topi promoter and topi 5'UTR. OX4286 (FIG. 23) employs 3xP3 driven DsRed as a transformation marker. 3xP3 is an artificial, eye-specific promoter, responsive to the evolutionary conserved Pax-6 transcription factor and is active during embryonic, larval and pupal stages. To test the activity of the Topi promoter, a reporter line, OX3979-Ae, was used. The OX3979-Ae contains an AmCyan coding sequence under the control of tetO operator, integrated into a genomic docking site using the phage C31 system. It expresses hr5IE1 driven DsRed as the transformation marker. Double heterozygotes carrying both Topi-tTAV and tetO-AmCyan, generated by crossing together OX4628B and OX3979 lines, showed clear expression of AmCyan in *Aedes aegypti* testis from later larval stages.

OX4635 (PB-HrIE-AmCyan-SV40-Aebeta2tubulin-hsp83-tTAV-SV40)

To test the suitability of the B2 tubulin promoter for use in a conditional male sterility system in *Aedes aegypti* mosquitoes, OX4635, a piggyBac-based construct was built. Smith et al., in their 2007 paper described cloning and characterization of the *Aedes aegypti* B2-tubulin promoter and defined its 959 bp fragment as sufficient for driving DsRed expression in mosquito testis—in stage and tissue-specific manner similar to endogenous promoter. This represented successful direct expression of a reporter gene and was similar in terms of design to our previously tested constitutive male sterile system. To adapt the promoter for use in our conditional expression system we decided to remove as far as possible the transcribed sequences of B2-tubulin, reasoning that these were likely to mediate the translational delay typical of B2-tubulin which would be highly undesirable for the proposed bipartite expression system. The 5'UTR, along with first 36 bp of ORF present in the sequence used by Smith et al (2007), was removed and replaced with an hsp83 minimal promoter from Mediterranean fruit fly. This altered promoter was employed to drive tTAV expression in construct OX4635. OX4635 contains hr5IE1—driven AmCyan as the transformation marker.

Conditional Male Sterility in Aedes Aegytpi

FIG. 11 OX4282-OX4627 Topi-tTAV-driven expression of tetO-Ae-Protamine-FokI-CD (OX4286-B×OX4458) OX4627 (PB-AeProt-FokI-sv40-polyA-hrIE1-DsRed)

For the second part of the conditional sterility system; the nuclease effector protein, construct OX4627 was built in a similar fashion as OX4458 (FIG. 21) (used with success in C. capita); the main difference being that the protamine sequence utilised originated from Aedes aegypti and not D. melanogaster for optimal results.

Strain OX4282B was crossed to four different OX4627 strains. Double-heterozygous males were crossed to wild type females and resulting embryos were scored for hatching rates. Wild type, OX4627 alone, and female controls were included. Significant (up to 100%) reduction of embryonic hatch rate was observed in all 4 samples of males carrying both alleles reared on a diet without tetracycline. Results are shown in FIG. 11. Progeny of crosses between OX4286B and OX4627 lines was reared either on a diet with (tet+) or without tetracycline (tet−). Males carrying both driver and effector alleles were crossed to the wild type females and the hatching rates of eggs obtained from these crosses were calculated (percentage of laid eggs that hatched). Wild type males' crosses with wild type females were used as controls. Crosses where highly significant male sterility was observed (chi-squared test) are marked with asterisks.

FIG. 12 OX4635-OX4627 β2-tub-tTAV-driven expression of tetO-Ae-Protamine-FokI-CD (OX4635×OX4627)

Two OX4635 strains were crossed to four different OX4627 strains. Double-heterozygous males were crossed to wild type females and resulting embryos scored for hatch rate. A wild type cross was used as control. Significant reduction of embryonic hatch rate was observed in some heterozygous males (for each allele) carrying both alleles reared on a diet without tetracycline. The fact that not all samples demonstrated the same rate of sperm sterility is believed to be due to positional effects of the various transgene insertions. Results are shown in FIG. 12. Progeny of crosses between OX4635 and OX4627 lines was reared either on a diet with (tet+) or without tetracycline (tet−). Males carrying both driver and effector alleles were crossed to the wild type females and the hatching rates of eggs obtained from these crosses were calculated (percentage of laid eggs that hatched). Wild type males' crosses with wild type females were used as controls. Crosses where highly significant male sterility was observed (chi-squared test) are marked with asterisks.

A stronger overall sterilisation effect was seen in crosses where nuclease expression was driven by Topi promoter, compared to B2-tubulin, in Aedes aegypti. Nevertheless, significant male sterility was observed in both cases, rendering both topi and the altered form of B2-tubulin suitable promoters for the "paternal lethality effect" in the mosquito species Aedes aegypti. The stronger effect exerted by Topi promoter could be however, related to more than one insertion of Topi-tTAV allele. According to a phenotype segregation data, there are several Topi-tTAV insertions in OX4286B line—some of them being linked to the male sex determination locus. Aedes aegypti lack sexually dimorphic chromosomes, instead sex is determined by the presence or absence of male sex-determination locus (M).

The nuclease effector fusion protein; protamine-Fok1, is fully functional in three different diptera species tested so far, namely C. capita, B. oleae and Aedes aegypti.

Male Sterile and Female Lethal Strains Crossed Together

In order to examine how the sperm lethal technology may interact with the female lethal RIDL technology and the possible effects on the general performance of a final product containing both transgenes, an experiment was set up where Medfly females of OX4353 (two lines were selected B and F) were crossed to males of a Medfly female lethal line (OX3864A and OX3647Q). The use of RIDL technology was first described in WO 01/39599. Individuals containing both insertions were selected according to their fluorescent phenotypes and sterility and female lethality assays were in place. In the absence of tetracycline, the progeny of these crosses should be male only and sterile. Male fertility and female lethality were assessed in the presence and absence of tetracycline (100 ng/μl). Results confirmed that no female progeny was produced in the absence of tetracycline in any of the crosses, whereas a normal 50:50 male to female ratio was obtained when larvae were grown on food containing tetracycline. Males containing both insertions were back crossed to wild type females and male sterility was assessed as in previous crosses. Results are presented in FIG. 13. Data indicates that the male sterility of the OX4353 strains tested remained unaffected by the presence of the female lethal positive feedback or indeed it has been reduced slightly further although this can be attributed to stochastic variation. Importantly so, these crosses strongly suggest that the presence of female and sperm lethal plasmids can co-exist in a single organism without any adverse effects on performance of either insertion.

Role of the 5' and 3' UTR in the Ccβ2-tubulin Promoter in Sperm-Lethal Strains

The Ccβ2-tubulin promoter as described elsewhere in literature (Catteruccia et al., 2005; Smith et al., 2007; Scolari et al., 2008; Nirmala et al., 2009) did not drive DsRed2 expression in all sperm in OX3671 (FIG. 16) strains, possibly related to the late transcription or translation of the Ccβ2-tubulin gene. Late expression may result in insufficient tTAV protein binding to tetO repeats for activation of the function of either a reporter gene or a lethal gene in the transgenic strain. Constructs with a modified 5'UTR—OX3831, OX4282 and OX4353—showed higher levels of fluorescence or lethality in sperm, which illustrates the importance of the 5'UTR in gene expression in spermatogenesis.

In D. melanogaster most genes are expressed before meiosis and the products are stored in the developing germline cells, only a few genes are transcribed after meiosis (White-Cooper 2009). The timing of transcription and translation, and the stability of RNA and protein products, are vital for developing sperm-lethal transgenic Medfly strains. The importance of this may vary from one type of effector to another. Indeed Windbichler et al speculate that part of their problem was that the nuclease was too stable, and persisted into the embryo (Windbichler et al. 2008). On the other hand, for sperm labelling with a fluorescent protein, it is clearly essential that the fluorescent protein survives into the mature sperm. Unmodified Ccβ2-tubulin is expressed in the male germline, as confirmed by using promoters from this gene to drive a reporter gene expression in spermatocyte cells. However, this Ccβ2-tubulin promoter in its normal configuration, i.e. combined with 5'UTR sequences derived from the same gene, may drive translation of tTAV very late, and just before meiosis. In which case, there is not enough time for the tTAV protein to bind to tetO sequences and further induce sufficient expression of the adjacent reporter gene, when crossed to a tetO-reporter strain. With the unmodified Ccβ2-tubulin promoter, only one in 20 testes showed reporter (DsRed2) expression in a few spermatid bundles. On the other hand, 5' UTR replacement resulted in greater fluorescence expression in early spermatocytes and spermatids of dissected male testis in strains OX3831 (FIG. 20) and OX4282. The 3'UTR contains sequences that regulate translation efficiency and mRNA stability, therefore replacing the 3' UTR of the tubulin gene with a sequence that is known to function in a wide range of species; one possibly eliminates the regulatory elements responsible for late translation of the tubulin gene.

OX4371 (PB-HrIE-AmCyan-SV40-TurboGFP-teto14-Topi-ubi-tTAV2-SV40)

OX4112 (PB-IPPO-1-hsp83-tetO21-Hr5-IE1-Red)

By inheritance pattern, OX4371 (FIG. 27) lines appeared to have a single copy of the transgene. When crossed to line OX4112 (FIG. 17), which contains the effector IPpo1, there was a slight reduction in the number of individuals containing both plasmids (as compared to wild type pupae of the same cross). However, there was no significant reduction in the number of hatched eggs in most lines with the exception of line E which exhibited a 40% reduction in male fertility.

OX4371 (PB-HrIE-AmCyan-SV40-TurboGFP-teto14-Topi-ubi-tTAV2-SV40)

OX4104 (PB-YAFN-hsp83-tetO21-Hr5-IE1-Red) (FIG. 19).

When OX4371 (FIG. 27) lines were crossed to the 3-Zn finger line, flies containing both plasmids were totally viable and healthy. There was no reduction in male fertility of line F; however there was a 45% and 40% reduction in lines B and E respectively.

OX4391 (PB-HrIE-AmCyan-SV40-TurboGFP-teto14-Topi-ubi-tTAV2-Topi3'UTR)

OX4104 (PB-YAFN-hsp83-tetO21-Hr5-IE1-Red) (FIG. 19)

Lines OX4391 G, C and D were estimated to have a single insertion while lines B and H seemed to have two copies of the transgene each. When OX4391 (FIG. 22) lines were crossed to the tetO-3zn-finger line (OX4104, FIG. 19), there did not seem to be any adverse effect on the viability of the individuals containing both plasmids. This indicates that there was very low (if any) basal expression of the transgenes in somatic tissue. Out of all 5 lines analysed, B had a 70% reduction in the ability of sperm to produce viable progeny, while line H was only 40% fertile. There was no significant difference in egg viability on and off T in the rest of the lines. Results strongly indicate that the presence of two copies in this particular combination significantly decreases the fertility of the males tested.

OX4391 (PB-HrIE-AmCyan-SV40-TurboGFP-teto14-Topi-ubi-tTAV2-Topi3'UTR)

OX4112 (PB-IPPO-1-hsp83-tetO21-Hr5-IE1-Red)

When the same OX4391 (FIG. 22) lines were crossed to the IPPO1 line, the number of progeny containing both plasmids in the absence of T was reduced compared to progeny containing either of the two plasmids or neither.

Egg viability was assessed as described in similar experiments. There was no significant reduction in the number of larvae hatched when compared to the wild type control in lines B, C, F and G. There was a 50% embryo viability reduction in line H.

Both *Aetopi* and Cctopi promoters have shown ability to direct testis-specific expression of a reporter gene and tTAV, which subsequently induced testis-specific expression of a reporter gene or a lethal gene. Specifically, a 1233-bp sequence, including 1168 bp of *Aetopi* promoter and 65 bp *Aetopi* 5'-UTR, was shown to drive testes-specific expression of the tTAV-DsRed fusion protein in *Ae. aegypti* (data not shown), and tTAV expression can further induce testes-specific AmCyan reporter gene expression. A 1178 bp putative Cctopi promoter did not show evidence of testes-specific activity in Medfly. A larger (1708 bp) Cctopi fragment sequence was found to be sufficient to drive testes-specific tTAV expression.

From an applied genetic engineering perspective, the Cctopi putative promoter fragment used was validated as a new male germline-specific promoter in Medfly, with earlier expression than the previously characterised β-2-tubulin promoter.

REFERENCES

Alphey, L. (2007). "Engineering insects for the Sterile Insect Technique", in M. Vreysen, A. Robinson, and J. Hendrichs, (eds.), *Area -wide control of insect pests: from research to field implementation*. Dordrecht, The Netherlands, Springer, pp. 51-60.

Alphey, L., Beard, B., Billingsley, P., Coetzee, M., Crisanti, A., Curtis, C. F., Eggleston, P., Godfray, C., Hemingway, J., Jacobs-Lorena, M., James, A., Kafatos, F., Mukwaya, L., Paton, M., Powell, J., Schneider, W., Scott., T., Sine, B., Sinden, R., Sinkins, S., Spielman, A., Touré, Y., and Collins, F. (2002). "Malaria control with genetically modified vectors." *Science*, 298, pp. 119-121.

Arama, E., Agapita, J., and Steller, H. (2003). "Caspase activity and a specific cytochrome C are required for sperm differentiation in *Drosophila.*" *Developmental Cell*, 4, pp. 687-697.

Barreau, C., Benson, E., Gudmannsdottir, E., Newton, F., and White-Cooper, H. (2008). "Post-meiotic transcription in *Drosophila* testes." *Development*, 135, pp. 1897-1902.

Bauer DuMont, V., Flores, H., Wright, M., and Aquadro, C. (2007). "Recurrent positive selection at Bgcn, a key determinant of germ line differentiation, does not appear to be driven by simple coevolution with its partner protein Bam." *Mol. Biol. Evol.*, 24(1), pp. 182-191.

Beall, E., Lewis, P., Bell, M., Rocha, M., Jones, D., and Botchan, M. (2007). "Discovery of tMAC: a *Drosophila* testis-specific meiotic arrest complex paralogous to Myb-Muv B." *Genes Dev.*, 21, pp. 904-919.

Beumer, K., Bhattacharyya, G., Bibikova, M., Trautman, and Carroll, D. (2006). "Efficient gene targeting in *Drosophila* with Zinc-finger nucleases." *Genetics*, 172, pp. 2391-2403.

Bibikova, M., Golic, M., Golic, K., and Carroll, D. (2002). "Targeted chromosomal cleavage and mutagenesis in *Drosophila* using Zinc-finger nucleases." *Genetics*, 161, pp. 1169-1175.

Brand, A., Manoukian, A., and Perrimon, N. (1994). "Ectopic expression in *Drosophila.*" *Meth. Cell Biol.*, 44, pp. 635-654.

Brand, A., and Perrimon, N. (1993). "Targeted gene expression as a means of altering cell fates and generating dominant phenotypes." *Development*, 118, pp. 401-415.

Burt, A. (2003). "Site-specific selfish genes as tools for the control and genetic engineering of natural populations." *Proc. Biol. Sci.*, 270, pp. 921-928.

Burt, A., and Trivers, R. (2006). *Genes in conflict: The biology of selfish genetic elements*, Cambridge, Belknap Press, Harvard University Press.

Cagan, R. (2003). "Spermatogenesis: Borrowing the apoptotic machinery." *Current Biology*, 13, pp. R600-R602.

Catteruccia, F., Benton, J., and Crisanti, A. (2005). "An *Anopheles* transgenic sexing strain for vector control." *Nature Biotechnology*, 23(11), pp. 1414-1417.

Catteruccia, F., Crisanti, A., and Wimmer, E. (2009). "Transgenic technologies to induce sterility." *Malaria Journal*, 8(Suppl 2), pp. S7.

Chintapalli, V., Wang, J., and Dow, J. (2007). "Using Fly-Atlas to identify better *Drosophila* models of human disease." *Nature Genetics*, 39, pp. 715-720.

Deredec, A., Burt, A., and Godfray, H. (2008). "Population genetics of using homing endonuclease genes in vector and pest management." *Genetics*, 179, pp. 2013-2026.

Dhillon, M., Singh, R., Naresh, J., and Sharma, H. (2005). "The melon fruit fly, *Bactrocera cucurbitae*: a review of its biology and management." *Journal of Insect Science*, 5, pp. 40.

Dyck, V. A., Hendrichs, J., and Robinson, A. S. (2005). "Sterile Insect Technique: Principles and practice in Area-Wide Integrated Pest Management". City: Springer: The Netherlands, pp. 801.

Franz, G. (2005). "Genetic sexing strains in mediterranean fruit fly, an example for other species amenable to large-scale rearing for the sterile insect technique", in V. A. Dyck, J. Hendrichs, and A. S. Robinson, (eds.), *Sterile Insect Technique. Principles and practice in area-wide integrated pest management*. The Netherlands, Springer, pp. 427-451.

Fu, G., Condon, K. C., Epton, M. J., Gong, P., Jin, L., Condon, G. C., Morrison, N. I., Dafa'alla, T. H., and Alphey, L. (2007). "Female-specific insect lethality engineered using alternative splicing." *Nature Biotechnology*, 25(3), pp. 353-357.

Fuller, M. (1993). "Spermatogenesis", in M. Bate and A. Martinez Arias, (eds.), *The development of Drosophila melanogaster*. Cold Spring Harbor, N.Y., Cold Spring Harbor Laboratory Press, pp. 71-147.

Fussenegger, M. (2001). "The impact of mammalian gene regulation concepts on functional genomic research, metabolic engineering, and advanced gene therapies." *Biotechnol. Prog.*, 17, pp. 1-51.

Fussenegger, M., Morris, R., von Stockar, B., Fux, C., Timann, M., Thompson, C., and Bailey, J. (2000). "Novel Streptogramin-based gene regulation systems for mammalian cells." *Nat. Biotech.*, 18, pp. 1203-8.

Gonczy, P., Matunis, E., and DiNardo, S. (1997). "bag-of-marbles and benign gonial cell neoplasm act in the germline to restrict proliferation during *Drosophila* spermatogenesis." *Development*, 124, pp. 4361-4371.

Gong, P., Epton, M., Fu, G., Scaife, S., Hiscox, A., Condon, K., Kelly, D., Dafa'alla, T., Coleman, P., and Alphey, L. (2005). "A dominant lethal genetic system for autocidal control of the Mediterranean fruitfly." *Nat. Biotech.*, 23, pp. 453-456.

Gong, W., and Golic, K. (2003). "Ends-out, or replacement, gene targeting in *Drosophila*." *Proc. Nat. Acad. Sci.* (USA), 100, pp. 2556-2561.

Gossen, M., and Bujard, H. (1992). "Tight control of gene expression in mammalian cells by tetracycline-responsive promoters." *Proc Natl Acad Sci USA*, 89(12), pp. 5547-51.

Gossen, M., and Bujard, H. (2002). "Studying gene function in eukaryotes by conditional gene inactivation." *Annu. Rev. Genet.*, 36, pp. 153-173.

Hiller, M., Chen, X., Pringle, M., Suchorolski, M., Sancak, Y., Viswanathan, S., Bolival, B., Lin, T. Y., Marino, S., and Fuller, M. (2004). "Testis-specific TAF homologs collaborate to control a tissue-specific transcription program." *Development*, 131, pp. 5297-5308.

Hockemeyer, D., Wang, H., Kiani, S., Lai, C. S., Gao, Q., Cassady, J. P., Cost, G. J., Zhang, L., Santiago, Y., Miller, J. C., Zeitler, B., Cherone, J. M., Meng, X., Hinkley, S. J., Rebar, E. J., Gregory, P. D., Urnov, F. D., and Jaenisch, R. (2011). "Genetic engineering of human pluripotent cells using TALE nucleases." *Nat Biotech*, 29(8), pp. 731-734.

Horn, C., Wimmer, A. E., (2003) "A transgene-based, embryo-specific lethality system for insect pest management". Nature Biotechnology, 1, pp. 64-70

Jattani, R., Patel, U., Kerman, B., and Myat, M. M. (2009). "Deficiency screen identifies a novel role for beta 2 tubulin in salivary gland and myoblast migration in the *Drosophila* embryo." *Developmental Dynamics*, 238(4), pp. 853-863.

Jiang, J., Benson, E., Bausek, N., Doggett, K., and White-Cooper, H. (2007). "Tombola, a tesmin/TSO1 family protein, regulates transcriptional activation in the *Drosophila* male germline and physically interacts with Always early." *Development*, 134(1549-1559).

Jiang, J., and White-Cooper, H. (2003). "Transcriptional activation in *Drosophila* spermatogenesis involves the mutually dependent function of aly and a novel meiotic arrest gene cookie monster." *Development*, 130, pp. 563-573.

Kawase, E., Wong, M., Ding, B., and Xie, T. (2004). "Gbb/Bmp signaling is essential for maintaining germline stem cells and for repressing bam transcription in the *Drosophila* testis." *Development*, 131, pp. 1365-1375.

Kim, Y.-G., Cha, J., and Chandrasegaran. (1996). "Hybrid restriction enzymes: Zinc finger fusions to FokI cleavage domain." *Proc. Nat. Acad. Sci.* (USA), 93, pp. 1156-1160.

Klassen, W., and Curtis, C. F. (2005). "History of the sterile insect technique", in V. A. Dyck, J. Hendrichs, and A. S. Robinson, (eds.), *Sterile Insect Technique. Principles and practice in area-wide integrated pest management*. The Netherlands, Springer, pp. 3-36.

Knipling, E. F. (1955). "Possibilities of insect control or eradication through the use of sexually sterile males." *J Econ Entomol*, 48, pp. 459-469.

Mahfouz, M. M., Li, L., Shamimuzzaman, M., Wibowo, A., Fang, X., and Zhu, J.-K. (2011). "De novo-engineered transcription activator-like effector (TALE) hybrid nuclease with novel DNA binding specificity creates double-strand breaks." *Proceedings of the National Academy of Sciences*.

Malacrida, A., Scolari, F., Schetelig, M., Bertin, S., Gasperi, G., and Wimmer, E. (2007). "A transgenic sperm marking system in the medfly, as a tool for pest control strategies and sperm use analysis." *Entomological Research*, 37, pp. (Suppl. 1): A56.

Maynard-Smith, L., Chen, L.-C., Banaszynski, L., Ooi, A., and Wandless, T. (2007). "A directed approach for engineering conditional protein stability using biologically silent small molecules." *Journal of Biological Chemistry*, 282(34), pp. 24866-24872.

Miller, J., Holmes, M., Wang, J., Guschin, D., Lee, Y.-L., Rupniewski, I, Beausejour, C., Waite, A., Wang, N., Kim, K., Gregory, P., Pabo, C., and Rebar, E. (2007). "An improved zinc-finger nuclease architecture for highly specific genome editing." *Nature Biotechnology*, 25(7), pp. 778-785.

Miller, J. C., Tan, S., Qiao, G., Barlow, K. A., Wang, J., Xia, D. F., Meng, X., Paschon, D. E., Leung, E., Hinkley, S. J., Dulay, G. P., Hua, K. L., Ankoudinova, I., Cost, G. J., Urnov, F. D., Zhang, H. S., Holmes, M. C., Zhang, L., Gregory, P. D., and Rebar, E. J. (2011). "A TALE nuclease architecture for efficient genome editing." *Nat Biotech*, 29(2), pp. 143-148.

Nielsen, M., Turner, F., Hutchens, J., and Raff, E. (2001). "Axoneme-specific β-tubulin specialization: a conserved C-terminal motif specifies the central pair." *Current Biology*, 11, pp. 529-533.

Osterwalder, T., Yoon, K., White, B., and Keshishian, H. (2001). "A conditional tissue-specific transgene expression system using inducible GAL4." *Proc. Nat. Acad. Sci. (USA)*, 98(22), pp. 12596-12601.

Perezgasga, L., Jiang, J., Bolival, B., Hiller, M., Benson, E., Fuller, M., and White-Cooper, H. (2004). "Regulation of transcription of meiotic cell cycle and terminal differentiation genes by the testis-specific Zn-finger protein *matotopetli*." *Development*, 131, pp. 1691-1702.

Phuc, H. K., Andreasen, M. H., Burton, R. S., Vass, C., Epton, M. J., Pape, G., Fu, G., Condon, K. C., Scaife, S., Donnelly, C. A., Coleman, P. G., White-Cooper, H., and Alphey, L. (2007). "Late-acting dominant lethal genetic systems and mosquito control." *BMC Biology*, 5, pp. 11.

Raja, S., and Renkawitz-Pohl, R. (2005). "Replacement by *Drosophila melanogaster* protamines and Mst77F of histones during chromosome condensation in late spermatids and role of Sesame in the removal of these proteins from the male pronucleus." *Molecular and Cellular Biology*, 25(14), pp. 6165-6177.

Rendón, P., McInnis, D., Lance, D., and Stewart, J. (2004). "Medfly (Diptera:Tephritidae) genetic sexing: large-scale field comparison of males-only and bisexual sterile fly releases in Guatemala." *Journal of Economic Entomology*, 97(5), pp. 1547-1553.

Robinson, A. S. (2005). "Genetic basis of the sterile insect technique", in V. A. Dyck, J. Hendrichs, and A. S. Robinson, (eds.), *Sterile Insect Technique. Principles and practice in area-wide integrated pest management*. The Netherlands, Springer, pp. 95-114.

Rong, Y., and Golic, K. (2000). "Gene targeting by homologous recombination in *Drosophila*." *Science*, 288(5473), pp. 2013-8.

Rong, Y., and Golic, K. (2001). "A targeted gene knockout in *Drosophila*." *Genetics*, 157, pp. 1307-1312.

Rong, Y., Titen, S., Xie, H., Golic, M., Bastiani, M., Bandyopadhyay, P., Olivera, B., Brodsky, M., Rubin, G., and Golic, K. (2002). "Targeted mutagenesis by homologous recombination in *Drosophila melanogaster*." *Genes Dev.*, 16, pp. 1568-1581.

Santel, A., Winhauer, T., Blümer, N., and Renkawitz-Pohl, R. (1997). "The *Drosophila* don Juan (dj) gene encodes a novel sperm specific protein component characterized by an unusual domain of a repetitive amino acid motif." *Mechanisms of Development*, 64, pp. 19-30.

Schetelig, M. F., Handler, M. A. (2012) "strategy for enhanced transgenic strain development for embryonic conditional lethality in *Anastrepha suspensa*". PNAS, 109 (24), pp. 9348-9353

Thomas, D. D., Donnelly, C. A., Wood, R. J., and Alphey, L. S. (2000). "Insect population control using a dominant, repressible, lethal genetic system." *Science*, 287(5462), pp. 2474-2476.

Urnov, F., Miller, J., Lee, Y.-L., Beausejour, C., Rock, J., Augustus, S., Jamieson, A., Porteus, M., Gregory, P., and Holmes, M. (2005). "Highly efficient endogenous human gene correction using designed zinc-finger nucleases." *Nature*, 435, pp. 646-651.

Victorinová, I., and Wimmer, E. (2007). "Comparative analysis of binary expression systems for directed gene expression in transgenic insects." *Insect Biochem. Mol. Biol.*, 37, pp. 246-254.

White-Cooper, H., Leroy, D., MacQueen, A., and Fuller, M. (2000). "Transcription of meiotic cell cycle and terminal differentiation genes depends on a conserved chromatin associated protein, whose nuclear localisation is regulated." *Development*, 127, pp. 5463-5473.

Wilson, C., Bellen, H. J., and Gehring, W. J. (1990). "Position effects on eukaryotic gene expression." *Annu Rev Cell Biol*, 6, pp. 679-714.

Wilson, K., Fitch, K., Bafus, B., and Wakimoto, B. (2006). "Sperm plasma membrane breakdown during *Drosophila* fertilization requires sneaky, an acrosomal membrane protein." *Development*, 133(24), pp. 4871-4879.

Windbichler, N., Menichelli, M., Papathanos, P. A., Thyme, S. B., Li, H., Ulge, U. Y., Hovde, B. T., Baker, D., Monnat, R. J., Burt, A., and Crisanti, A. (2011). "A synthetic homing endonuclease-based gene drive system in the human malaria mosquito." *Nature*, 473(7346), pp. 212-215.

Windbichler, N., Papathanos, P., Catteruccia, F., Ranson, H., Burt, A., and Crisanti, A. (2007). "Homing endonuclease mediated gene targeting in *Anopheles gambiae* cells and embryos." *Nucl Acids Res*, 35, pp. 5922-5933.

Windbichler, N., Papathanos, P. A., and Crisanti, A. (2008). "Targeting the X chromosome during spermatogenesis induces Y chromosome transmission ratio distortion and early dominant embryo lethality in *Anopheles gambiae*." *PLoS Genet*, 4(12), pp. e1000291.

SEQUENCES

The following relate to SEQ ID NOs: 1-56 provided hereafter.

SEQ ID NOS: 1-5 Full Beta-2 Tubulin Sequences—Different Insects

SEQ ID NO: 1
>gi|167822003|gb|EU386342.1| *Ceratitis capitata* beta-2 tubulin mRNA, complete cds SEQ ID NO: 2
>gi|158742|gb|M20420.1|DROTUBB2A *D.melanogaster* beta-2 tubulin mRNA, complete cds SEQ ID NO: 3
>gi|111035017|gb|DQ833526.1|*Aedes aegypti* beta-2 tubulin (B2t) gene, complete cds SEQ ID NO: 4
>gi|219815271|gb|EU938673.1| Bactrocera *dorsalis* beta-2 tubulin gene, complete cds SEQ ID NO: 5
>gi|219815267|gb|EU938671.1| *Anastrepha suspensa* beta-2 tubulin gene, complete cds SEQ ID NOS: 6-10: Beta-2 Tubulin 5' UTR Sequences—Different Insects
  SEQ ID NO: 6
  >gi|167822003|gb|EU386342.1| *Ceratitis capitata* beta-2 tubulin 5'UTR
  SEQ ID NO: 7
  >gi|1158742|gb|M20420.1|DROTUBB2A *D.melanogaster* beta-2 tubulin 5' UTR
  SEQ ID NO: 8
  >gi|219815271|gb|EU938673.1| *Bactrocera dorsalis* beta-2 tubulin 5' UTR
  SEQ ID NO: 9
  >gi|111035017|gb|DQ833526.1| *Aedes aegypti* beta-2 tubulin (B2t) 5' UTR
  SEQ ID NO: 10
  >gi|219815267|gb|EU938671.1| *Anastrepha suspensa* beta-2 tubulin 5' UTR
SEQ ID NOS: 11-15: Beta-2 Tubulin 3' UTR Sequences—Different Insects
  SEQ ID NO: 11
  >gi|167822003|gb|EU386342.1| *Ceratitis capitata* beta-2 tubulin 3' UTR
  SEQ ID NO: 12
  >gi|1158742|gb|M20420.1|DROTUBB2A *D.melanogaster* beta-2 tubulin mRNA 3' UTR
  SEQ ID NO: 13
  >gi|111035017|gb|DQ833526.1| *Aedes aegypti* beta-2 tubulin (B2t) gene 3' UTR
  SEQ ID NO: 14
  >gi|219815271|gb|EU938673.1| *Bactrocera dorsalis* beta-2 tubulin gene 3' UTR
  SEQ ID NO: 15
  >gi|219815267|gb|EU938671.1| *Anastrepha suspensa* beta-2 tubulin gene 3' UTR
tTAV and Variants
  SEQ ID NO: 16: Open reading frame of tTAV
  SEQ ID NO: 17: Protein sequence of tTAV
  SEQ ID NO: 18: Open reading frame of tTAV2
  SEQ ID NO: 19: Protein sequence of tTAV2
  SEQ ID NO: 20: Open reading frame of tTAV3
  SEQ ID NO: 21: Protein sequence of tTAV3
  SEQ ID NO: 22—5' UTR Beta-2 tubulin from *D. melanogaster*
  SEQ ID NO: 23-24—b2 tubulin promoter sequence of *drosophila melanogaster* (SEQ ID NO 24) aligned with the mRNA sequence of Dm b2-tubulin (5'UTR is included in the alignment) (SEQ ID NO 23)
  SEQ ID NO: 25—ORF of Hsp83 Medfly
  SEQ ID NO: 26—5' UTR as given by genebank
  SEQ ID NO: 27—Hsp83 5' UTR from 4353
  SEQ ID NO: 28—Amino acid sequence of Hsp83 medfly
  SEQ ID NO: 29—Dm Aly 5'UTR from OX3831
  SEQ ID NO: 30—Dm Aly promoter
  SEQ ID NO: 31—TETR
  SEQ ID NO: 32—VP16
  TETR and VP16 sequences combined make the tTAV sequence.
  SEQ ID NO: 33—DmTopi cDNA
  SEQ ID NO: 34—Dm promoter sequence as found on fly base
  SEQ ID NO: 35—#OX4254 Cc topi promoter
  SEQ ID NO: 36—#OX4275 Cc topi promoter
  SEQ ID NO: 37—#OX4371 Cc topi promoter
  SEQ ID NO: 38-40—Alignment of LA4254 (SEQ ID NO 38) cf LA4275 (SEQ ID NO 39) cf LA4371 (SEQ ID NO 40)
  SEQ ID NO: 41—*Aedes topi* promoter from 4286
  SEQ ID NO: 42—Ae topi 5'UTR from 4286
  SEQ ID NO: 43—Topi *Drosophila melanogaster* ORF (coding region)
  SEQ ID NO: 44—Aly ORF from *Drosophila melanogaster* (coding region)
  SEQ ID NO: 45—LA 3671 B2 tubulin promoter and 5'UTR
  SEQ ID NO: 46—LA 4353 B2 tubulin promoter
  SEQ ID NO: 47—LA 4353 hsp83 5' UTR
  SEQ ID NO: 48—B2 tubulin 5'UTR
  SEQ ID NO: 49—AeProtamine
  SEQ ID NO: 50—SG4
  SEQ ID NO: 51—Fok1 cleavage domain
  SEQ ID NO: 52—Aeprotamine-SG4-Fok1
  SEQ ID NO: 53—Medfly B2 tubulin promoter forward primer
  SEQ ID NO: 54—Medfly B2 tubulin promoter reverse primer
  SEQ ID NO: 55—TopitestF1 primer
  SEQ ID NO: 56—Topitest R primer

```
b2 tubulin promoter sequence of drosophila melanogaster aligned with the
mRNA sequence of Dm b2-tubulin (5'UTR is included in the alignment)
                                                           SEQ ID NO: 23-24
extended   TCCTTTATTGAGATTAACGGTCAAATCAATAGATAAAAGAAAACTTATTACATATTTAAA
dro        ------------------------------------------------------------ extended   GAATGATGAAATTTTTAAAATTCATTGTATCATATGTTATTCGGCCACTGTAACCGAAAT
dro        ------------------------------------------------------------ extended   CAACCATTTTTGGCGGATGCTGTGTGTTTGTTTTGCTGACAACTATCGATTTTGTCAGAC
dro        ------------------------------------------------------------ extended   GCAGCATCTTTAACTGAACGAAAAAGGCGCGTGGTGCAAAATATATTAATTGATTATAGA
dro        ------------------------------------------------------------ extended   TCGTAGTGATTATATTTGAGACTATATGATGAAGCGACAGAATGTCCGTACCCTTTCCCT
dro        ------------------------------------------------------------ extended   GGTGGTATGCACTTTCACCTATCTTTTAATTGGAGCCGCCGTGTTCGATTCCCTGGAGTC
dro        ------------------------------------------------------------ extended   ACCAACGGAGGCCAAAAGATGGGAATTCCTACAGAGTGAGAAGCTTGTTGATTTATTAAC
dro        ------------------------------------------------------------ extended   CTAATTTCTTAGTAATGAATTTATTTAATCAATTGTAGCCGTTAAGAACAACTTTGTTAG
dro        ------------------------------------------------------------
```

```
extended    AAAGTACAATGTGACTGACGAGGATTTCCGTGTGATGGAAATCGTCATCATTGAAAATAA
dro         ------------------------------------------------------------ extended    GCCCCACAAGGCCGGACCTCAGTGGAAATTCGCTGGAGCTTTCTATTTCAGCACGGTTGT
dro         ------------------------------------------------------------ extended    ACTGGCAATGATAGGTAAATTAATTATCTATTAAATATGATTTATTGAATAGATTATAAT
dro         ------------------------------------------------------------ extended    TCTGTTGTAACTTTCTTTAGGATATGGTCATTCTACGCCAGTTACAATTCCGGGAAAAGC
dro         ------------------------------------------------------------ extended    ATTTTGTATGGGCTATGCTATGGTAAGTGAACTTACAATCCCAATTTCCAGTCTTCTAAA
dro         ------------------------------------------------------------ extended    GATATTCCCTTATTAGGTGGGCATCCCGCTGGGTCTGGTGATGTTCCAGTCTATCGGAGA
dro         ------------------------------------------------------------ extended    ACGTCTGAATAAGTTTGCATCCGTGATAATAAGGCGGGCAAAGAGAGCCAGTGGAGCTCG
dro         ------------------------------------------------------------ extended    CTGTACGGATGCCACCGAAATGAATCTCATGTTGGCCACCGGAATGCTCTCCTCCATAAT
dro         ------------------------------------------------------------ extended    AATCACCACTGGAGCAGCAGTCTTTTCCCGATACGAGGGTTGGAGCTACTTCGATAGCTT
dro         ------------------------------------------------------------ extended    CTACTATTGTTTTGTCACCTTGACGACAATTGGTTTCGGCGATTATGTGGCATTGCAGAA
dro         ------------------------------------------------------------ extended    CGACCAAGCTCTAACTAATAAGCCTGGCTATGTGGCGCTGAGCTTGGTCTTCATCCTATT
dro         ------------------------------------------------------------ extended    CGGCTTGGCCGTGGTGGCCGCCAGTATCAATCTATTGGTGCTCCGATTCATGACCATGTG
dro         ------------------------------------------------------------ extended    AGTCCATGTTCTATTGCAGGAAATATCTTATTTAATGGATTTTTAATCACAGGCAAGCAG
dro         ------------------------------------------------------------ extended    AGGATGCCAAGAGAGATGAGCAGGATGCTCAGAACTTGGCTGGAAATGCCCAGCCGGTGA
dro         ------------------------------------------------------------ extended    CCTTCGATGATGAGTCCACGTACAATATGCACGGCAAGCTGCTGGAGAACAACTACACAA
dro         ------------------------------------------------------------ extended    CGGAGAACGATGAGACCGCCTCCCTGTGTTCCTGCACCTGCATGGGTGGCACCAGGTGCC
dro         ------------------------------------------------------------ extended    TGAATCATGAGCAGTTCGTGGACCCGGACTTTCAGCCTACCGACATTATCGAGAGCACCT
dro         ------------------------------------------------------------ extended    TGTGCCTGAAGCGAGCCTCCGTCTGATATCCGTACAGCCAGCTGTGGGACTCCTCATTGT
dro         ------------------------------------------------------------ extended    AGGAGCCAGAGCCAATGGATCACCAAATCGTAGTTACAATCCTGTAGAGAACCATCCGCC
dro         ------------------------------------------------------------ extended    GCCAAAATTTGGTTGTTAGACAAACCTTCCTCCCTACGTAGATTTTAAACCAGGATGGG
dro         ------------------------------------------------------------ extended    TCATAATACATATAAGTTTGGAGAGCAAGGTTAATAGTCTTTAAAAGGCAGTTTTTGCTT
dro         ------------------------------------------------------------ extended    AAGAAATAATCGACCCATCCCATTATACACCCATATAAACATTTACAAAGGAGTAAAATC
dro         ------------------------------------------------------------ extended    CAGGACATCCATGTCAATATCAATCGTATCATCTGGTCGGTAGCCTTGGAATCCTCTATT
dro         ------------------------------------------------------------ extended    GCTTCCAAGGCACCGCCAAATCCATCCCATCTCGAATTTTAGCCGTATATTCGTTTATCT
dro         ------------------------------------------------------------ extended    ATGTAAGTACTATTAAAGTTTGTGCTCAAAACGGAGAACTGAGTTTTCTGAAATCGGGGT
dro         ------------------------------------------------------------ extended    GTGTGAAATGTGTCGAAGTCGGAAATCGTAGTAGCCTATTTGTGAACATTCGGTGTAGTA
dro         -------------------GGAAATCGTAGTAGCCTATTTGTGAACATTCGGTGTAGTA
                               ****************************************
```

```
extended  ATCCAAGCCAGGTTCAGTTCACCTCAGTATCAGCTAGCACGTACACGACTAAAATCTAAA
dro       ATCCAAGCCAGGTTCAGTTCACCTCAGTATCAGCTAGCACGTACACGACTAAAATCTAAA
          ************************************************************ extended  CCTGAAAAATTATACGTTTAAATATTCAGTCTTTTGCCGATTTTTGCCCCACTCAGACTG
dro       CCTGAAAAATTATACGTTTAAATATTCAGTCTTTTGCCGATTTTTGCCCCACTCAGACTG
          ************************************************************ extended  TTTTAAAAGCTCGATTTTTTTTGTACCATTTTTTCGGTGTGAAAAAGGGGCCCTAACTT
dro       TTTTAAAAGCTCGATTTTTTTTGTACCATTTTTTCGGTGTGAAAAAGGGGCCCTACTT
          ********************************************      **** extended  TACTATCAAAATGCGTGAAATTGTACACATTCAGGCCGGTCAATGCGGTAACCAGATCGG
dro       TACTATCAAAATGCGTGAAATTGTACACATTCAGGCCGGTCAATGCGGTAACCAGATCGG
          ************************************************************ extended  TGGTAAATTCTGGGAGGTAATCTCGGATGAGCACTGTATAGATGCGACCGGAACGTACTA
dro       TGGTAAATTCTGGGAGGTAATCTCGGATGAGCACTGTATAGATGCGACCGGAACGTACTA
          ************************************************************ extended  CGGCGATAGTGATCTCCAGCTGGAGCGCATCAATGTATACTACAATGAAGCCACCGGTGC
dro       CGGCGATAGTGATCTCCAGCTGGAGCGCATCAATGTATACTACAATGAAGCCACCGGTGC
          ************************************************************ extended  CAAGTATGTGCCACGCGCAATTCTCGTGGACCTGGAGCCCGGCACCATGGATTCGGTTCG
dro       CAAGTATGTGCCACGCGCAATTCTCGTGGACCTGGAGCCCGGCACCATGGATTCGGTTCG
          ************************************************************ extended  TTCTGGCGCCTTTGGCCAGATCTTCCGGCCGGACAATTTTGTGTTTGGCCAATCGGGAGC
dro       TTCTGGCGCCTTTGGCCAGATCTTCCGGCCGGACAATTTTGTGTTTGGCCAATCGGGAGC
          ************************************************************ extended  AGGCAACAACTGGGCCAAGGGTCATTACACCGAGGGTGCTGAACTGGTGGATTCCGTCTT
dro       AGGCAACAACTGGGCCAAGGGTCATTACACCGAGGGTGCTGAACTGGTGGATTCCGTCTT
          ************************************************************ extended  GGATGTGGTGCGAAAGGAGTCCGAGGGATGCGATTGCCTTCAGGTAAGTTTTGGGGGTTT
dro       GGATGTGGTGCGAAAGGAGTCCGAGGGATGCGATTGCCTTCAGG----------------
          ******************************************** extended  GGGAATTTATCTGAAAAAGTTTACCCTACTTTTCTCCAACAGGGCTTCCAGCTGACCCAC
dro       -----------------------------------------GCTTCCAGTCGACCCAC
                                                   *****  ***** extended  TCGCTGGGTGGCGGCACTGGCTCCGGCATGGGAACCCTGCTGATCTCGAAGATCCGCGAG
dro       TCGCTGGGTGGCGGCACTGGCTCCGGCATGGGAACCCTGCTGATCTCGAAGATCCGCGAG
          ************************************************************ extended  GAGTACCCGGACCGCATCATGAACACCTTCTCGGTGGTGCCCTCGCCCAAGGTGTCCGAT
dro       GAGTACCCGGACCGCATCATGAACACCTTCTCGGTGGTGCCCTCGCCCAAGGTGTCCGAT
          ************************************************************ extended  ACGGTGGTGGAGCCCTACAATGCCACCCTGAGTGTGCATCAGCTGGTGGAGAACACCGAT
dro       ACGGTGGTGGAGCCCTACAATGCCACCCTGAGTGTGCATCAGCTGGTGGAGAACACCGAT
          ************************************************************ extended  GAGACGTACTGCATCGACAACGAGGCGTTGTATGACATCTGCTTCCGCACACTGAAGCTG
dro       GAGACGTACTGCATCGACAACGAGGCGTTGTATGACATCTGCTTCCGCACACTGAAGCTG
          ************************************************************ extended  ACCACGCCCACCTACGGTGACCTGAACCATCTGGTTTCGGCCACCATGTCTGGTGTGACG
dro       ACCACGCCCACCTACGGTGACCTGAACCATCTGGTTTCGGCCACCATGTCTGGTGTGACG
          ************************************************************ extended  ACCTGCCTGCGCTTCCCTGGCCAGCTGAACGCTGATCTTCGCAAGCTGGCCGTGAACATG
dro       ACCTGCCTGCGCTTCCCTGGCCAGCTGAACGCTGATCTTCGCAAGCTGGCCGTGAACATG
          ************************************************************ extended  GTACCCTTCCCCCGGCTGCACTTCTTCATGCCCGGATTCGCACCGCTCACCTCGCGAGGA
dro       GTACCCTTCCCCCGGCTGCACTTCTTCATGCCCGGATTCGCACCGCTCACCTCGCGAGGA
          ************************************************************ extended  TCGCAACAATACCGGGCCCTTACCGTTCCGGAGCTGACCCAGCAGATGTTCGATGCCAAG
dro       TCGCAACAATACCGGGCCCTTACCGTTCCGGAGCTGACCCAGCAGATGTTCGATGCCAAG
          ************************************************************ extended  AACATGATGGCTGCGTGCGATCCGCGACATGGTCGCTATCTGACCGTCGCCGCCATCTTC
dro       AACATGATGGCTGCGTGCGATCCCCGACATGGTCGCTATCTGACCGTCGCCGCCATCTTC
          *********************** ************************************
```

```
extended  CGTGGCCGCATGTCCATGAAGGAGGTGGACGAGCAGATGCTCAACATTCAGAACAAGAAC
dro       CGTGGCCGCATGTCCATGAAGGAGGTGGACGAGCAGATGCTCAACATTCAGAACAAGAAC
          ************************************************************ extended  AGCAGCTTCTTCGTGGAATGGATCCCGAATAACTGCAAGACAGCGGTGTGCGATATTCCG
dro       AGCAGCTTCTTCGTGGAATGGATCCCGAATAACTGCAAGACAGCGGTGTGCGATATTCCG
          ************************************************************ extended  CCCAGAGGTCTCAAGATGTCGGCCACCTTCATTGGCAACTCCACCGCCATTCAGGAGCTA
dro       CCCAGAGGTCTCAAGATGTCGGCCACCTTCATTGGCAACTCCACCGCCATTCAGGAGCTA
          ************************************************************ extended  TTCAAACGGGTTTCGGAGCAGTTCACCGCCATGTTCCGAAGGAAGGCCTTCTTGCATTGG
dro       TTCAAACGGGTTTCGGAGCAGTTCACCGCCATGTTCCGAAGGAAGGCCTTCTTGCATTGG
          ************************************************************ extended  TACACCGGCGAGGGAATGGACGAAATGGAATTCACAGAGGCCGAGAGCAACATGAACGAC
dro       TACACCGGCGAGGGAATGGACGAAATGGAATTCACAGAGGCCGAGAGCAACATGAACGAC
          ************************************************************ extended  TTGGTTTCTGAATATCAGCAGTACCAGGAGGCGACTGCCGATGAGGAGGGCGAATTCGAT
dro       TTGGTTTCTGAATATCAACAGTACCAGGAGGCGACTGCCGATGAGGAGGGCGAATTCGAT
          *************** **************************************** extended  GAAGACGAAGAGGGTGGCGGCGATGAATAATAGGATTAACTTCCCACTCAAGATCACACA
dro       GAAGACGAAGAGGGTGGCGGCGATGAATAATAGGATTAACTTCCCACTCAAGATCACACA
          ************************************************************ extended  TGAACACCAAAACAGGCTAGCAGGGGAACCCATTAGGAAGGCACAACACATTGGATCTTT
dro       TGAACACCAAAACAGGCTAGCAGGGGAACCCATTAGGAAGGCACAATACATTGGATCTTT
          ******************************************** *********** extended  GGGCCTTAGCATATTGTGCTTCGAGGCCCGTCGGTTGTACATATTTCCTATATGGATTCT
dro       GGGCCTTAGCATATTGTGCTTCGAGGCCCGTCGGTTGTACATATTTCCTATATGGATTCT
          ************************************************************ extended  TCACTGTTCGATTATTTATCATTCACACACGTACAGAAGAAATATGTCCACCTTTGTTAA
dro       TCACTGTTCGATTATTTATCATTCACACACGTACAGAAGAATTATGTCCAC-TTTGTTAA
          *************************************** **** ****** extended  GCTCATGTTGCAATTGCTGTGATTTCTGGGTTACGAATAAATGTTGATTTATAAGCAGAC
dro       GCTCATGTTGCAATTGCTGTGATTTCTGGGTTACGAATAAATGTTGATTTATAAGCAGAC
          ************************************************************ extended  AAGATTACCAACAGCATTTTGCATATTTTTATACCGTTCAAAAGGCATTGCATAAACCTA
dro       AAGATTACCAACAGCATTTTGCATATTTTT------------------------------
          ******************************

Alignment of LA4254 (SEQ ID NO 38) cf LA4275 (SEQ ID NO 39) cf
LA4371 (SEQ ID NO 40):
                                                         SEQ ID NO: 38-40
4254   GCCGTTCAGTCAAATGTGATATTCACAACTATTGAGCAGAGAATTCCATTAATGTACATA   60
4275   GCCGTTCAGTCAAATGTGATATTCACAACTATTGAGCAGAGAATTCCATTAATGTACATA   60
4371   ------------------------------------------------------------

4254   TGTATTTTGATTGCTGCAACAAAAAATATTAAAATGGTTTAGCAAGGTTAATTAAGTGTA  120
4275   TGTATTTTGATTGCTGCAACAAAAAATATTAAAATGGTTTAGCAAGGTTAATTAAGTGTA  120
4371   ------------------------------------------------------------

4254   AATGACAGATTTTTTTTACATACACCACCTTCGCCCTGTAGCTAGTTGCGAGTTTACTT  180
4275   AATGACAGATTTTTTTTACATACACCACCTTCGCCCTGTAGCTAGTTGCGAGTTTACTT  180
4371   ------------------------------------------------------------

4254   CAGTTTCTATCTAATTCGTTTGAATCCATATGGCAGAATTACAGTGTAATGGACGCTCTC  240
4275   CAGTTTCTATCTAATTCGTTTGAATCCATATGGCAGAATTACAGTGTAATGGACGCTCTC  240
4371   ---------CTAATTCGTTTGAATCCATATGGCAGAATTACAGTGTAATGGACGCTCTC   50
                ****************************************************

4254   TTACTTTTTTAGGCTTAAAAAACACATTAAAGATCAATTAATTTTAAGGAATAAGCAAAT  300
4275   TTACTTTTTTAGGCTTAAAAAACACATTAAAGATCAATTAATTTTAAGGAATAAGCAAAT  300
4371   TTACTTTTTTAGGCTTAAAAAACACATTAAAGATCAATTAATTTTAAGGAATAAGCAAAT  110
       ************************************************************

4254   AAAATTACTCCGGCGTTCAGATATTGGAAATATAGAATAATGTAACATTTAAAATAAGGC  360
4275   AAAATTACTCCGGCGTTCAGATATTGGAAATATAGAATAATGTAACATTTAAAATAAGGC  360
4371   AAAATTACTCCGGCGTTCAGATATTGGAAATATAGAATAATGTAACATTTAAAATAAGGC  170
       ************************************************************
```

-continued

```
4254   CTAATATTTATCAATTATCAAGACATATGTATATACATGATTCATGCAAAAGGTATTCAT   420
4275   CTAATATTTATCAATTATCAAGACATATGTATATACATGATTCATGCAAAAGGTATTCAT   420
4371   CTAATATTTATCAATTATCAAGACATATGTATATACATGATTCATGCAAAAGGTATTCAT   230
       ************************************************************

4254   TTTTAATAATGCAGGGAAAAACTACAGCTAAACAACAACGTAATCAATTCCTACTTGGTA   480
4275   TTTTAATAATGCAGGGAAAAACTACAGCTAAACAACAACGTAATCAATTCCTACTTGGTA   480
4371   TTTTAATAATGCAGGGAAAAACTACAGCTAAACAACAACGTAATCAATTCCTACTTGGTA   290
       ************************************************************

4254   TTTCTTCGTTTCCCTTTAACATTTTTTCATAACAGTAGGTTTTCAATATTTTAGATGTAA   540
4275   TTTCTTCGTTTCCCTTTAACATTTTTTCATAACAGTAGGTTTTCAATATTTTAGATGTAA   540
4371   TTTCTTCGTTTCCCTTTAACATTTTTTCATAACAGTAGGTTTTCAATATTTTAGATGTAA   350
       ************************************************************

4254   ATGAAAAATGTACGGTTTCCGTGGCAAGCTTAACTTGCCATTCTTCTGAACAATTTAATC   600
4275   ATGAAAAATGTACGGTTTCCGTGGCAAGCTTAACTTGCCATTCTTCTGAACAATTTAATC   600
4371   ATGAAAAATGTACGGTTTCCGTGGCAAGCTTAACTTGCCATTCTTCTGAACAATTTAATC   410
       ************************************************************

4254   TAATAATTTTTCATTATCTAAGGCGTCAATTTAAATGGCAAAGTATTAATATTCTTGATG   660
4275   TAATAATTTTTCATTATCTAAGGCGTCAATTTAAATGGCAAAGTATTAATATTCTTGATG   660
4371   TAATAATTTTTCATTATCTAAGGCGTCAATTTAAATGGCAAAGTATTAATATTCTTGATG   470
       ************************************************************

4254   GTTGCCTAAATTTTAGAAATAAACACTGAATGCTATTAACTAAGGAAGTTGAGGTAAAAG   720
4275   GTTGCCTAAATTTTAGAAATAAACACTGAATGCTATTAACTAAGGAAGTTGAGGTAAAAG   720
4371   GTTGCCTAAATTTTAGAAATAAACACTGAATGCTATTAACTAAGGAAGTTGAGGTAAAAG   530
       ************************************************************

4254   TTTTGTTTAAATTCCACATATGTTGGAATATCGTCATCAAAAATAAATGTGTCCTGTAAT   780
4275   TTTTGTTTAAATTCCACATATGTTGGAATATCGTCATCAAAAATAAATGTGTCCTGTAAT   780
4371   TTTTGTTTAAATTCCACATATGTTGGAATATCGTCATCAAAAATAAATGTGTCCTGTAAT   590
       ************************************************************

4254   TAATATGTTTATCGTTTAGTTTTAAAATTAAAATTAATTTAAGTTAACTGTAATGGGTGT   840
4275   TAATATGTTTATCGTTTAGTTTTAAAATTAAAATTAATTTAAGTTAACTGTAATGGGTGT   840
4371   TAATATGTTTATCGTTTAGTTTTAAAATTAAAATTAATTTAAGTTAACTGTAATGGGTGT   650
       ************************************************************

4254   ACTCAATCGTTGGATTAGAAATTGAAAGCGGAGGCAAATATAATTTTTCGGTGTTGGGTA   900
4275   ACTCAATCGTTGGATTAGAAATTGAAAGCGGAGGCAAATATAATTTTTCGGTGTTGGGTA   900
4371   ACTCAATCGTTGGATTAGAAATTGAAAGCGGAGGCAAATATAATTTTTCGGTGTTGGGTA   710
       ************************************************************

4254   AGTGTTACAATTCGAACAGTTTTAAATTAGAACTAATTAAATATATGAAAATGCATTAAA   960
4275   AGTGTTACAATTCGAACAGTTTTAAATTAGAACTAATTAAATATATGAAAATGCATTAAA   960
4371   AGTGTTACAATTCGAACAGTTTTAAATTAGAACTAATTAAATATATGAAAATGCATTAAA   770
       ************************************************************

4254   ATCAAAAATATCCATGATTAAATCATATTTAAAATGTAGAAATTAATAACACTAAAATAT   1020
4275   ATCAAAAATATCCATGATTAAATCATATTTAAAATGTAGAAATTAATAACACTAAAATAT   1020
4371   ATCAAAAATATCCATGATTAAATCATATTTAAAATGTAGAAATTAATAACACTAAAATAT   830
       ************************************************************

4254   TTTGGTAAATTAAGACACTATCAAAAAACTCGAAAAAAGTAGGCTAGCTTTCTATGTCAA   1080
4275   TTTGGTAAATTAAGACACTATCAAAAAACTCGAAAAAAGTAGGCTAGCTTTCTATGTCAA   1080
4371   TTTGGTAAATTAAGACACTATCAAAAAACTCGAAAAAAGTAGGCTAGCTTTCTATGTCAA   890
       ************************************************************

4254   GGCGCCATTTTTAAAGAACAATAGATCTAGAAATACTGCAGAGTCCGCAAAATTTTGAA   1140
4275   GGCGCCATTTTTAAAGAACAATAGATCTAGAAATACTGCAGAGTCCGCAAAATTTTGAA   1140
4371   GGCGCCATTTTTAAAGAACAATAGATCTAGAAATACTGCAGAGTCCGCAAAATTTTGAA   950
       ************************************************************

4254   TTTATTTTTATAAATATAAACTAAATTAAATCCACTAG----------------------   1178
4275   TTTATTTTTATAAATATAAACTAAATTAAATCCACTAG----------------------   1178
4371   TTTATTTTTATAAATATAAACTAAATTAAATCCACTAGTATGAATACAAGTGAAGAAGAA   1010
       *************************************

4254   ------------------------------------------------------------
4275   ------------------------------------------------------------
4371   TTTTCGAATTCCGATGCGTGGCTATCCGAGCAACTGTTTGCTCMATTAAAAGAATTTAAT   1070

4254   ------------------------------------------------------------
4275   ------------------------------------------------------------
4371   TCAGATTATAGAGAAAAGTCGGTTGGTGATGCATCGACMACATTTGTATTTCCTTCCGGT   1130

4254   ------------------------------------------------------------
4275   ------------------------------------------------------------
4371   AGTCTCAGCTGTTTGCCTGAAGGAGAACCTCACGACTTAACAAAATCACGACTTGAAAAC   1190
```

-continued

```
4254   ------------------------------------------------------------
4275   ------------------------------------------------------------
4371   TACGAGCCTGTTTTCAAATTATCTACACCAACTAATATATCTTCTTTCGATCTGAACGAT  1250

4254   ------------------------------------------------------------
4275   ------------------------------------------------------------
4371   GTGTTGGATTTAACTAATATTACTGGCAGATGTAACGATTCAGCGCTGCTGGATTTGGTT  1310

4254   ------------------------------------------------------------
4275   ------------------------------------------------------------
4371   GGGACAGTTCCATTAACTCCATTTGTAACTCCCGTTCCTGAGACAACATTAATGGTAAAT  1370

4254   ------------------------------------------------------------
4275   ------------------------------------------------------------
4371   GAGACAGTGAAACAAACGGCTGAATCATCCTTTGATGTAACAGAAGAGGAATTAAAGCTT  1430

4254   ------------------------------------------------------------
4275   ------------------------------------------------------------
4371   TTGAAATTTTTGGAGTCACAGCCAACTACTAATCAGTTTGGTGTGTATTGTATATCGGAT  1490

4254   ------------------------------------------------------------
4275   ------------------------------------------------------------
4371   ATACTTAATAATATCTAATTTCTTGATCTTTTCAGACACAAAATCATATGTTCAAACTGA  1550

4254   ------------------------------------------------------------
4275   ------------------------------------------------------------
4371   GGTTTCACCCACTCCATATCGTATTGTCAAGTGTTCAAATTGCAATGTTCTCTTTGATTT  1610

4254   ------------------------------------------------------------
4275   ------------------------------------------------------------
4371   AATGTCTTTCCAAACACATATTTGTGATTATGACGAACACCACAATCTAATTGCTCCACC  1670

4254   ------------------------------------------------------------
4275   ------------------------------------------------------------
4371   AATAACATCAACACCTCTCAGCAAACCAATAAAAGAAGAACCATTACTACCAGTAGAACC  1730

4254   --------------------------------------------------
4275   --------------------------------------------------
4371   TGCATGTATTCGTTTATTGCGTGAAAATCAAATTCGAATCCGACGACCTAGCTCG       1785
```

---

The invention claimed is:

1. An arthropod male germline gene expression system suitable for conditional expression of an effector gene in an arthropod male germline, the system comprising:
   a first expression unit comprising an effector gene and a promoter therefor operably linked thereto; and
   a second expression unit comprising a coding sequence for a transcription factor and an upstream regulatory element operably linked thereto, the transcription factor being capable of acting upon the promoter in the first expression unit to drive expression of the effector gene, the upstream regulatory element comprising:
      a promoter for the transcription factor, wherein the promoter is from the topi, aly, or β-2 tubulin gene, or a homologue thereof; and
      a 5' UTR adjacent to a start site for the transcription factor coding sequence, wherein the 5' UTR is from topi, aly, or hsp83, or a homologue thereof,
   the upstream regulatory element driving sufficient expression of the transcription factor such that the transcription factor protein in turn drives transcription of the effector gene before meiosis.

2. The gene expression system according to claim 1, wherein the transcription factor is a transcriptional activator.

3. The gene expression system according to claim 1, wherein the effector is a nuclease.

4. The gene expression system according to claim 1, wherein the promoter of the first expression unit is a minimal promoter.

5. The gene expression system according to claim 1, wherein the expression system comprises a Gal4-UAS system, and the transcription factor is GAL4.

6. The gene expression system according to claim 1, wherein the system is an inducible system, where induction occurs by provision or absence of a chemical entity.

7. The gene expression system according to claim 6, wherein the transcription factor in the second expression unit is tTA or a variant thereof selected from the group consisting of tTAV, tTAV2, and tTAV3.

8. The gene expression system according to claim 1, wherein the transcription factor of the second expression unit is tTA or a variant thereof, and the first expression unit comprises the tet operator (tetO).

9. The gene expression system according to claim 1, wherein the arthropod is an insect.

10. The gene expression system according to claim 1, wherein the effector is a nuclease and confers or imparts a paternal lethality effect.

11. A method of expressing an effector protein in a gonad or sperm of an arthropod, comprising transforming the gonad with the expression system according to claim 1.

12. A method of determining the mating status of a female arthropod, comprising:
   allowing a transgenic male population comprising the expression system according to claim 1 to mate with the female arthropod, wherein said system comprises a marker detectable in the sperm of said transgenic male population; and
   assaying for the presence of said marker in the female, the presence of the marker being indicative that the female has mated with a transgenic male carrying the system.

13. The gene expression system according to claim 2, wherein the transcriptional activator is tTA or GAL4 or a variant thereof.

14. The gene expression system according to claim 3, wherein the nuclease is a 3-Zn finger nuclease or a restriction endonuclease.

15. The gene expression system according to claim 1, wherein the 5' UTR is from a homologue of hsp83 found in the target anthropod.

16. The gene expression system according to claim 1, wherein the 5' UTR is from hsp83 of a Medfly.

17. The gene expression system according to claim 6, wherein the chemical entity is a tetracycline or an analogue thereof.

18. The gene expression system according to claim 17, wherein the tetracycline analogue is doxycycline.

19. The gene expression system according to claim 9, wherein the insect is a dipteran.

20. The gene expression system according to claim 19, wherein the dipteran is a Tephritidae.

21. The gene expression system according to claim 20, wherein the Tephritidae is a Medfly or an Olive fly.

22. The gene expression system according to claim 1, wherein the promoter of the upstream regulatory element of the second expression unit is from topi or a homologue thereof.

23. The gene expression system according to claim 22, wherein the 5' UTR of the upstream regulatory element of the second expression unit is from topi or a homologue thereof.

24. The gene expression system according to claim 1, wherein the promoter of the upstream regulatory element of the second expression unit is from β-2 tubulin or a homologue thereof.

25. The gene expression system according to claim 24, wherein the 5' UTR of the upstream regulatory element of the second expression unit is from aly or a homologue thereof.

26. The gene expression system according to claim 24, wherein the 5' UTR of the upstream regulatory element of the second expression unit is from hsp83 or a homologue thereof.

27. The gene expression system according to claim 1, wherein the 5' UTR of the upstream regulatory element of the second expression unit is from hsp83 or a homologue thereof.

* * * * *